(12) United States Patent
Lee et al.

(10) Patent No.: US 11,459,316 B2
(45) Date of Patent: Oct. 4, 2022

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Hanill Lee, Suwon-si (KR); Hyung Sun Kim, Suwon-si (KR); Chang Ju Shin, Suwon-si (KR); Dongkyu Ryu, Suwon-si (KR); Jiah Yoon, Suwon-si (KR); Seungjae Lee, Suwon-si (KR); Suyong Lim, Suwon-si (KR); Sung-Hyun Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 293 days.

(21) Appl. No.: 16/887,114

(22) Filed: May 29, 2020

(65) Prior Publication Data

US 2020/0377489 A1 Dec. 3, 2020

(30) Foreign Application Priority Data

May 30, 2019 (KR) ........................ 10-2019-0064010

(51) Int. Cl.
*C07D 407/14* (2006.01)
*C07D 409/14* (2006.01)
*H01L 51/00* (2006.01)

(52) U.S. Cl.
CPC ......... *C07D 407/14* (2013.01); *C07D 409/14* (2013.01); *H01L 51/0067* (2013.01);
(Continued)

(58) Field of Classification Search
CPC ............ H01L 51/0067; H01L 51/0072; H01L 51/0073; H01L 51/0074
See application file for complete search history.

(56) References Cited

U.S. PATENT DOCUMENTS

| 5,061,569 | A  | 10/1991 | VanSlyke |
| 8,541,112 | B2 | 9/2013  | Otsu et al. |
| 9,978,952 | B2 | 5/2018  | Nakano et al. |

FOREIGN PATENT DOCUMENTS

| JP | 1993-009471 | 1/1993 |
| JP | 1995-126615 | 5/1995 |

(Continued)

*Primary Examiner* — Anthony Ho
(74) *Attorney, Agent, or Firm* — Lee IP Law, P.C.

(57) ABSTRACT

A compound for an organic optoelectronic device, a composition for an organic optoelectronic device including the same, an organic optoelectronic device, and a display device, the being represented by Chemical Formula 1:

[Chemical Formula 1]

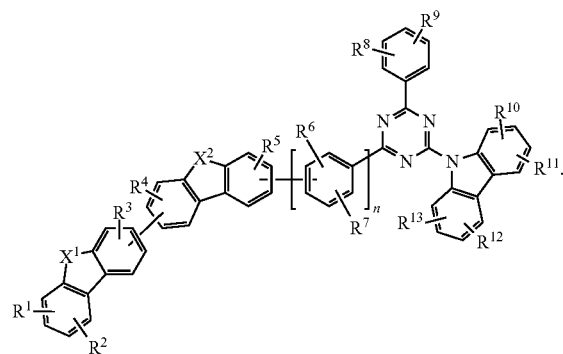

19 Claims, 1 Drawing Sheet

(52) U.S. Cl.
CPC ...... *H01L 51/0072* (2013.01); *H01L 51/0073* (2013.01); *H01L 51/0074* (2013.01)

(56) References Cited

FOREIGN PATENT DOCUMENTS

| | | |
|---|---|---|
| JP | 1998-095973 | 4/1998 |
| JP | 5181676 B2 | 1/2013 |
| KR | 10-2015-0042335 A | 4/2015 |
| KR | 10-2015-0070860 A | 6/2015 |
| KR | 10-2015-0083385 A | 7/2015 |
| KR | 10-2015-0117173 A | 10/2015 |
| KR | 10-2017-0026359 A | 3/2017 |
| KR | 10-2017-0120413 A | 10/2017 |
| KR | 10-1788094 B1 | 10/2017 |
| KR | 10-2018-0061076 A | 6/2018 |
| KR | 10-2019-0010350 A | 1/2019 |
| KR | 10-1947747 B1 | 2/2019 |
| KR | 10-1959821 B1 | 3/2019 |
| KR | 10-2019-0038108 A | 4/2019 |
| KR | 10-2019-0079340 A | 7/2019 |
| WO | WO 1995-009147 | 4/1995 |
| WO | WO 2013/035275 A1 | 3/2013 |
| WO | WO 2013/077362 A1 | 5/2013 |

COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

CROSS-REFERENCE TO RELATED APPLICATION

Korean Patent Application No. 10-2019-0064010, filed on May 30, 2019, in the Korean Intellectual Property Office, and entitled: "Compound for Organic Optoelectronic Device, Composition for Organic Optoelectronic Device, Organic Optoelectronic Device, and Display Device," is incorporated by reference herein in its entirety.

BACKGROUND

1. Field

Embodiments relate to a compound for an organic optoelectronic device, a composition for an organic optoelectronic device, an organic optoelectronic device, and a display device.

2. Description of the Related Art

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device include an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and performance of an organic light emitting diode may be affected by organic materials disposed between electrodes.

SUMMARY

The embodiments may be realized by providing a compound for an organic optoelectronic device, the compound being represented by Chemical Formula 1:

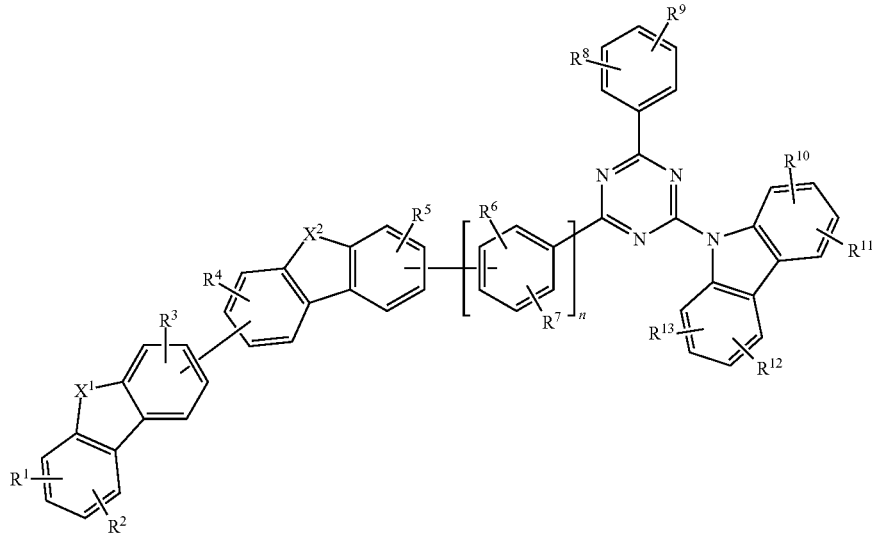

[Chemical Formula 1]

wherein, in Chemical Formula 1, $X^1$ and $X^2$ are independently O or S, $R^1$ to $R^{13}$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof, $R^{10}$ to $R^{13}$ are separate or adjacent groups are linked to each other to provide a substituted or unsubstituted aliphatic, aromatic, or heteroaromatic monocyclic ring or a substituted or unsubstituted aliphatic, aromatic, or heteroaromatic polycyclic ring, and n is 0 or 1.

The embodiments may be realized by providing a composition for an organic optoelectronic device, the composition comprising a first compound and a second compound, wherein the first compound is the compound according to an embodiment, the second compound is represented by Chemical Formula 2; or a combination of Chemical Formula 3 and Chemical Formula 4:

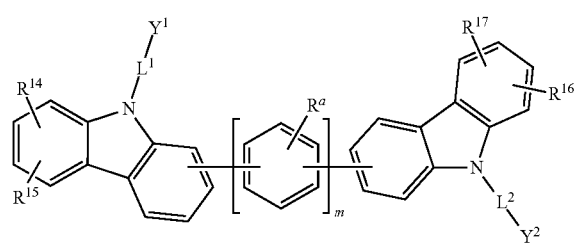

[Chemical Formula 2]

wherein, in Chemical Formula 2, $Y^1$ and $Y^2$ are independently a substituted or unsubstituted C6 to C20 aryl group or a substituted or unsubstituted C2 to C30 heterocyclic group, $L^1$ and $L^2$ are independently a single bond or a substituted or unsubstituted C6 to C20 arylene group, $R^a$ and $R^{14}$ to $R^{17}$ are independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, and m is an integer of 0 to 2;

[Chemical Formula 3]

[Chemical Formula 4]

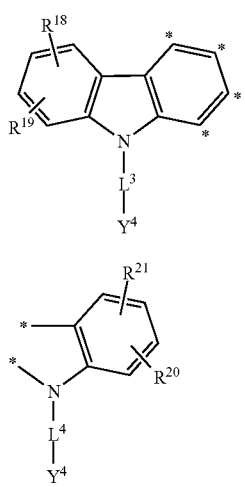

wherein, in Chemical Formulae 3 and 4, $Y^3$ and $Y^4$ are independently a substituted or unsubstituted C6 to C20 aryl group, or a substituted or unsubstituted C2 to C30 heterocyclic group, two adjacent *s of Chemical Formula 3 are linked at *s of Chemical Formula 4, the other *s of Chemical Formula 3 not linked to Chemical Formula 4 are independently C-$L^a$-$R^b$, $L^a$, $L^3$, and $L^4$ are independently a single bond or a substituted or unsubstituted C6 to C20 arylene group, and $R^b$ and $R^{18}$ to $R^{21}$ are independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

The embodiments may be realized by providing an organic optoelectronic device including an anode and a cathode facing each other, at least one organic layer between the anode and the cathode, wherein the at least one organic layer includes the compound according to an embodiment.

The embodiments may be realized by providing an organic optoelectronic device including an anode and a cathode facing each other, at least one organic layer between the anode and the cathode, wherein the at least one organic layer includes the composition according to an embodiment.

The embodiments may be realized by providing a display device including the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
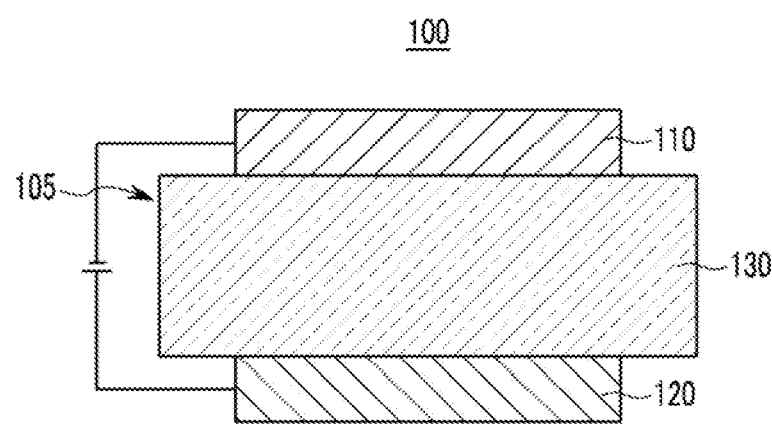
FIGS. 1 and 2 are cross-sectional views showing organic light emitting diodes according to embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, "substituted" refers to replacement of at least one hydrogen of a substituent or a compound by deuterium, a cyano group, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, or a combination thereof.

In one example, the "substituted" refers to replacement of at least one hydrogen of a substituent or a compound by deuterium, a cyano group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in a specific example, the "substituted" refers to replacement of at least one hydrogen of a substituent or a compound by deuterium, a cyano group, a C1 to C20 alkyl group, or a C6 to C30 aryl group. In addition, in a specific example, the "substituted" refers to replacement of at least one hydrogen of a substituent or a compound by deuterium, a cyano group, a C1 to C5 alkyl group, or a C6 to C18 aryl group. In addition, in a specific example, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

In the present specification, the description of adjacent groups being linked to each other to provide a substituted or unsubstituted aliphatic, aromatic, or heteroaromatic monocyclic or a substituted or unsubstituted aliphatic, aromatic, or heteroaromatic polycyclic ring means that any two adjacent substituents directly substituting to an aromatic ring or an aromatic heterocyclic ring with a single bond without a linking group are linked to provide an additional ring.

For example, adjacent groups may be linked to each other to provide a substituted or unsubstituted aromatic monocyclic or aromatic polycyclic additional ring and specific examples may be a substituted or unsubstituted aromatic monocyclic additional ring.

For example, any two substituents directly substituting to the benzene ring of the carbazole are linked to each other to provide an additional ring, and thus, together with the benzene ring of the carbazole, a substituted or unsubstituted benzocarbazole group or a substituted or unsubstituted dibenzocarbazole group may be provided.

As used herein, when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example, a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

A compound for an organic optoelectronic device according to an embodiment may be represented by Chemical Formula 1.

dibenzothiophene, dibenzofuran and dibenzothiophene, or dibenzothiophene and dibenzofuran are continuously bonded with a triazine moiety that is substituted with a phenyl group and a 9-carbazolyl group.

In the structure, 9-carbazole may be introduced on one side of the triazine, and at least two dibenzofuran, at least two dibenzothiophene, dibenzofuran and dibenzothiophene, or dibenzothiophene and dibenzofuran may be introduced on another side thereof, and thereby bipolar properties may be realized.

The introduction of at least two dibenzofuran, at least two dibenzothiophene, dibenzofuran and dibenzothiophene, or dibenzothiophene and dibenzofuran may have higher electron/hole mobility compared with carbazole, and thereby, the device to which the compound is applied may have low driving characteristics.

[Chemical Formula 1]

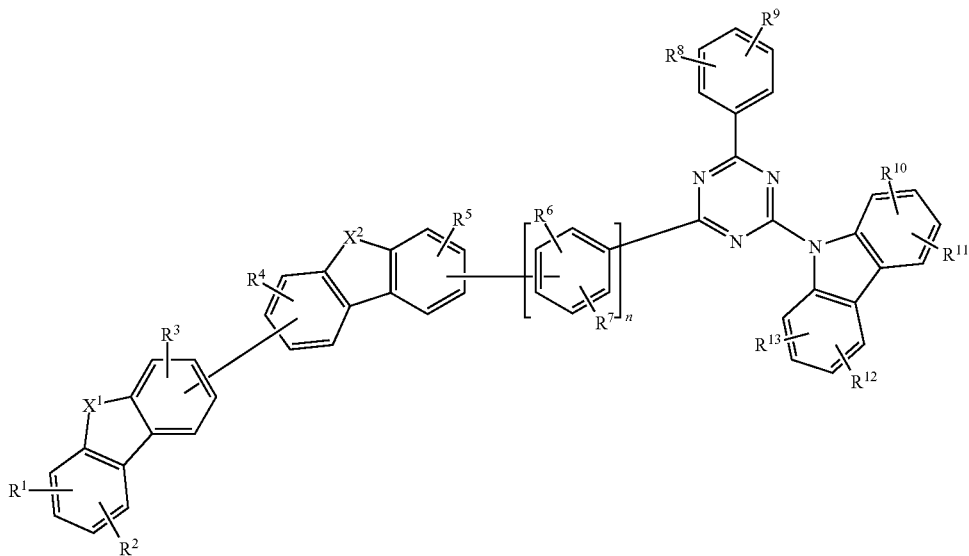

In Chemical Formula 1, $X^1$ and $X^2$ may each independently be, e.g., O or S, $R^1$ to $R^{13}$ may each independently be or include, e.g., hydrogen, deuterium, a cyano group, a halogen, a substituted or unsubstituted C1 to C10 alkyl group, a C6 to C12 aryl group, a C2 to C20 heterocyclic group, or a combination thereof. In an implementation, $R^{10}$ to $R^{13}$ may be separate or adjacent groups are linked to each other to provide a substituted or unsubstituted aliphatic, aromatic, or heteroaromatic monocyclic ring or a substituted or unsubstituted aliphatic, aromatic, or heteroaromatic polycyclic ring. n may be, e.g., 0 or 1.

The compound represented by Chemical Formula 1 has a structure in which at least two dibenzofuran, at least two In an implementation, the at least two dibenzofuran, at least two dibenzothiophene, dibenzofuran and dibenzothiophene, or dibenzothiophene and dibenzofuran may be introduced in a directly bonded form without a linking group, and a boundary of the HOMO/LUMO electron clouds in the molecule may be clearly divided. Accordingly, the compound may have a high T1 value, so that a high-efficiency and long life-span device may be realized when it is applied.

In an implementation, the compound represented by Chemical Formula 1 may be represented by one of Chemical Formula 1-1 to Chemical Formula 1-4 (e.g., according to the specific linking point between dibenzofuran or dibenzothiophene bound to triazine and another dibenzofuran or dibenzothiophene).

[Chemical Formula 1-1]
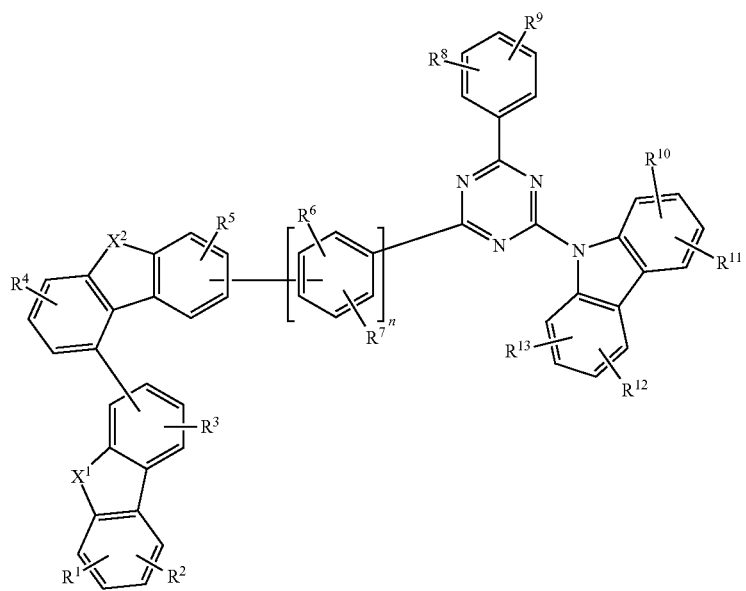
[Chemical Formula 1-2]
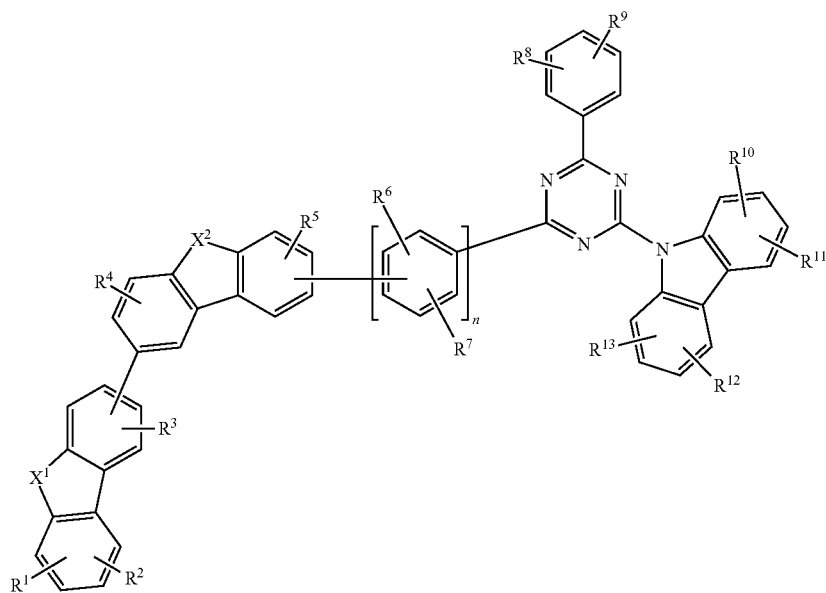
[Chemical Formula 1-3]
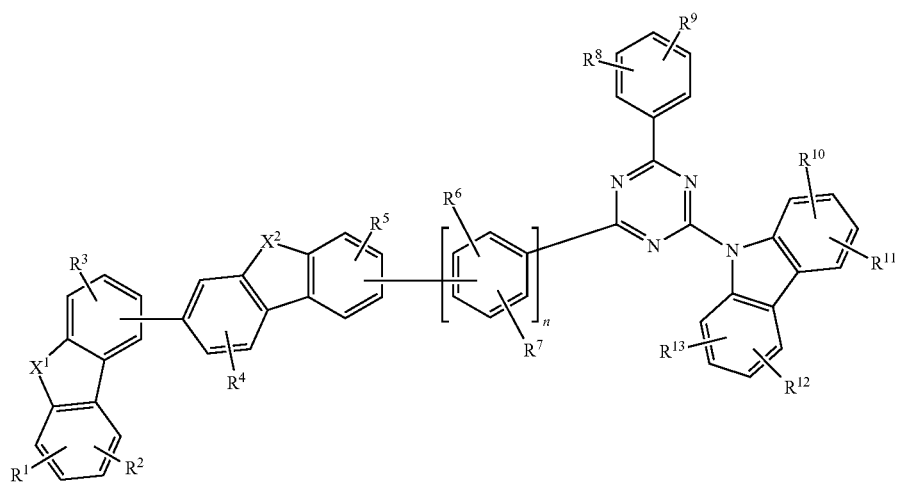

[Chemical Formula 1-4]

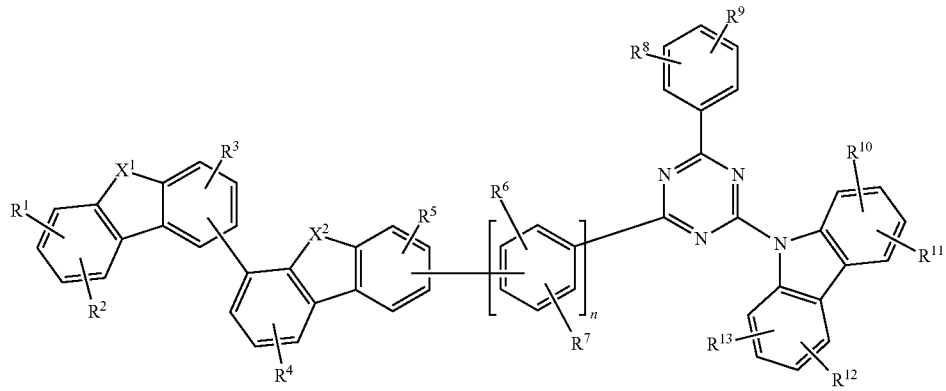

In Chemical Formula 1-1 to Chemical Formula 1-4, $X^1$, $X^2$, n, and $R^1$ to $R^{13}$ may be the same as described above.

In an implementation, Chemical Formula 1-1 may be represented by one of Chemical Formula 1-1a to Chemical Formula 1-1d (e.g., according to the specific linking point between the dibenzofuran or dibenzothiophene and triazine).

[Chemical Formula 1-1a]

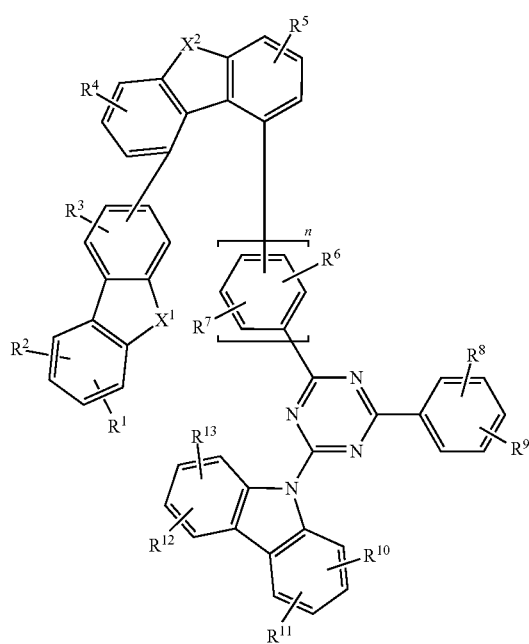

[Chemical Formula 1-1b]

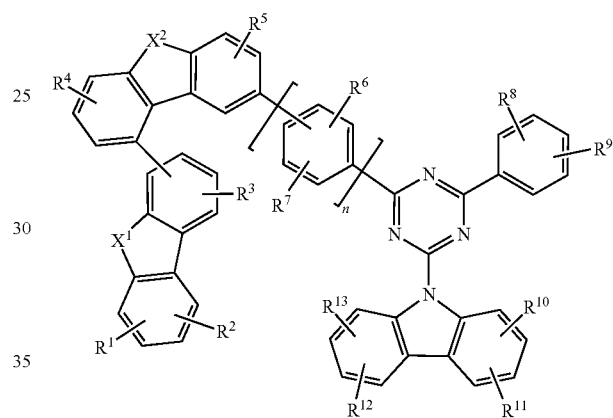

[Chemical Formula 1-1c]

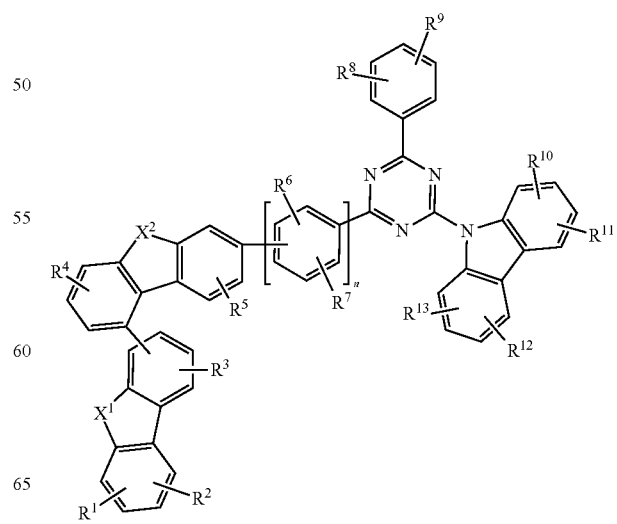

[Chemical Formula 1-1d]

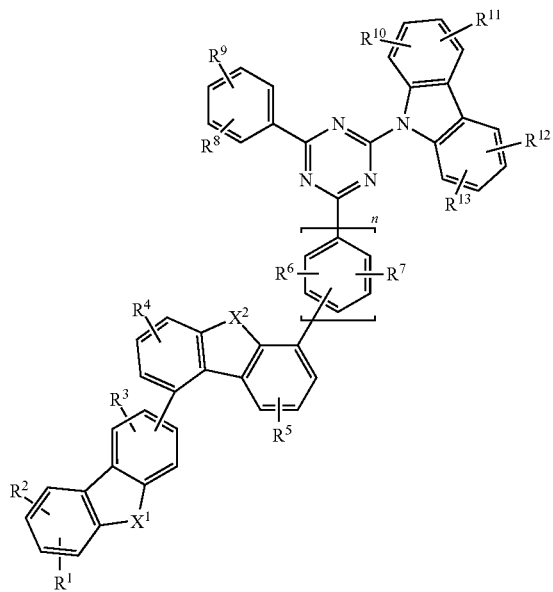

[Chemical Formula 1-1a-II]

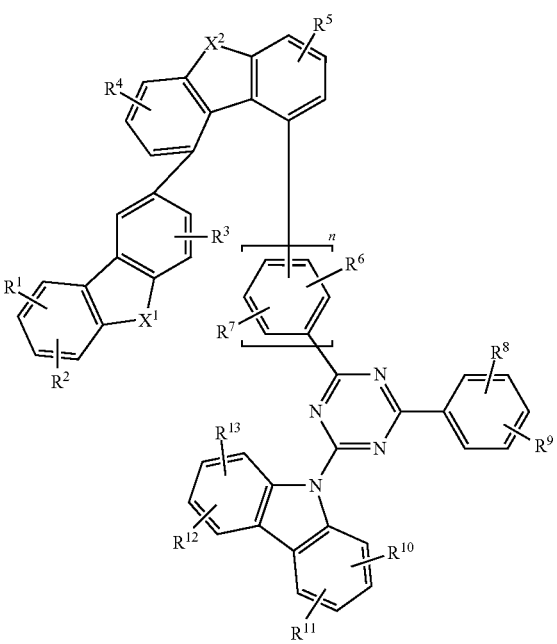

In Chemical Formula 1-1a to Chemical Formula 1-1d, $X^1$, $X^2$, n, and $R^1$ to $R^{13}$ may be the same as described above.

In an implementation, the compound represented by Chemical Formula 1-1a may be represented by one of Chemical Formula 1-1a-I to Chemical Formula 1-1a-IV (e.g., according to the specific linking point between dibenzofuran or dibenzothiophene bound to triazine and another dibenzofuran or dibenzothiophene).

[Chemical Formula 1-1a-I]

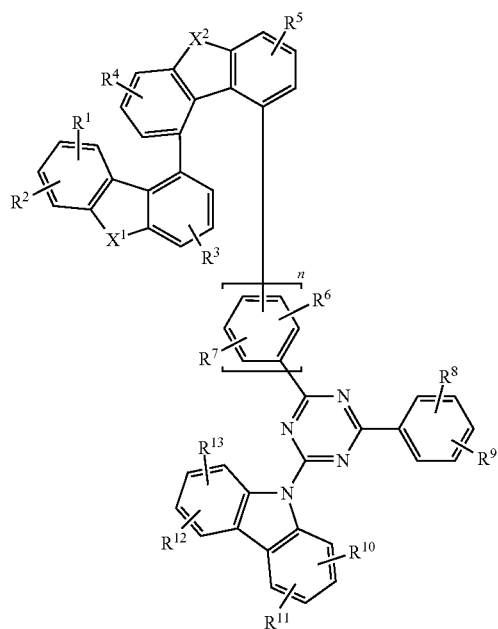

[Chemical Formula 1-1a-III]

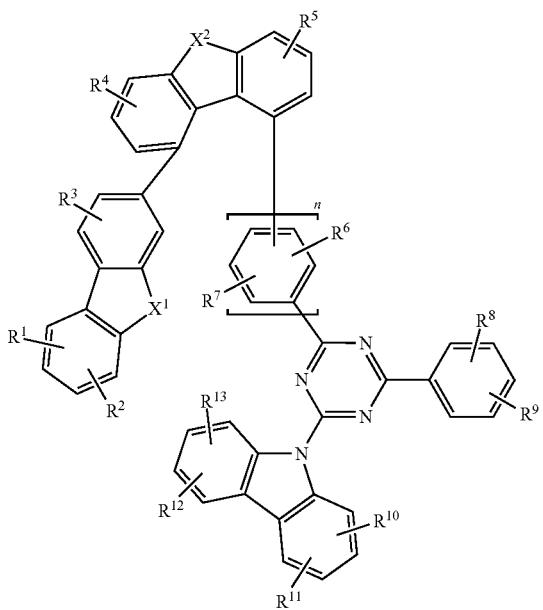

-continued

[Chemical Formula 1-1a-IV]

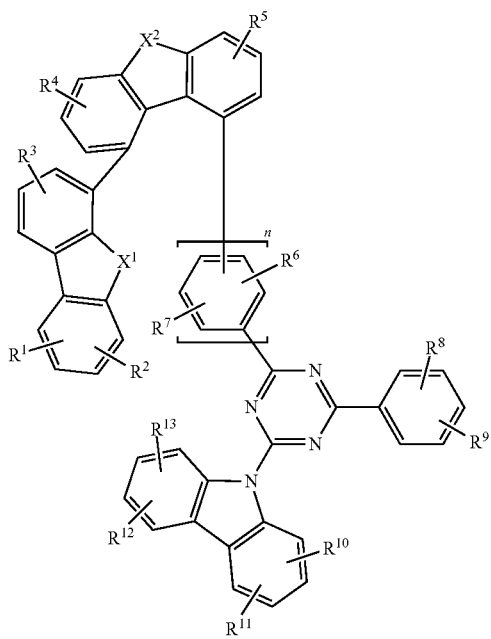

In Chemical Formula 1-1a-I to Chemical Formula 1-1a-IV, $X^1$, $X^2$, n, and $R^1$ to $R^{13}$ may be the same as described above.

In an implementation, the compound represented by Chemical Formula 1-1b may be represented by one of Chemical Formula 1-1b-I to Chemical Formula 1-1b-IV (e.g., according to the specific linking point between dibenzofuran or dibenzothiophene bound to triazine and another dibenzofuran or dibenzothiophene).

[Chemical Formula 1-1b-I]

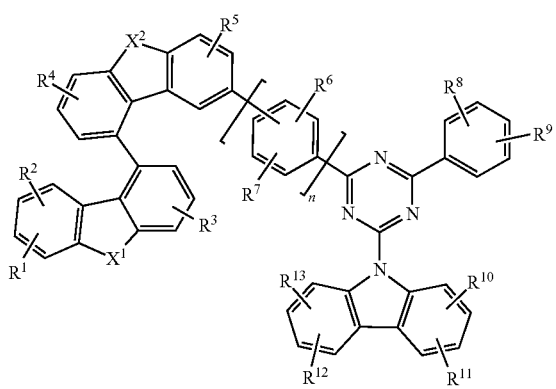

[Chemical Formula 1-1b-II]

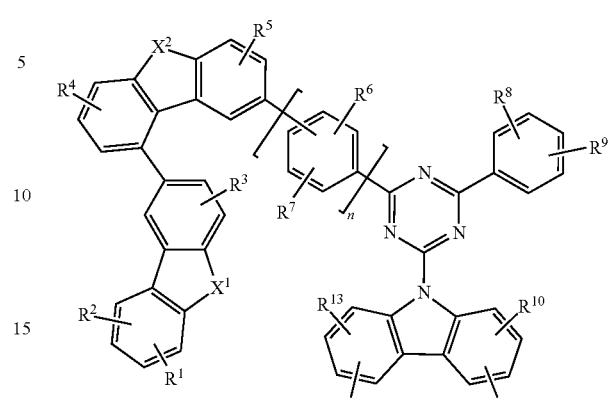

[Chemical Formula 1-1b-III]

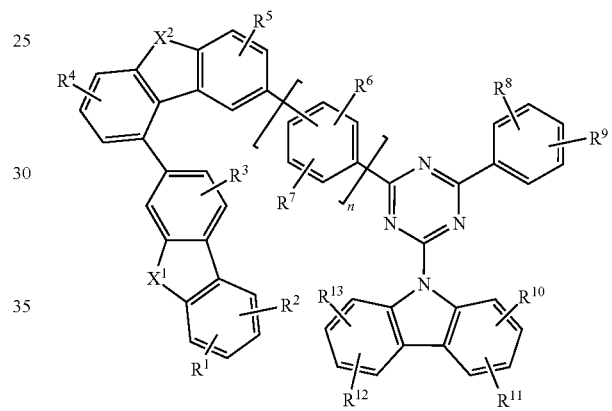

[Chemical Formula 1-1b-IV]

In Chemical Formula 1-1b-I to Chemical Formula 1-1b-IV, $X^1$, $X^2$, n, and $R^1$ to $R^{13}$ may be the same as described above.

In an implementation, the compound represented by Chemical Formula 1-1c may be represented by one of Chemical Formula 1-1c-I to Chemical Formula 1-1c-IV (e.g., according to the specific linking point between dibenzofuran or dibenzothiophene bound to triazine and another dibenzofuran or dibenzothiophene).

[Chemical Formula 1-1c-I]

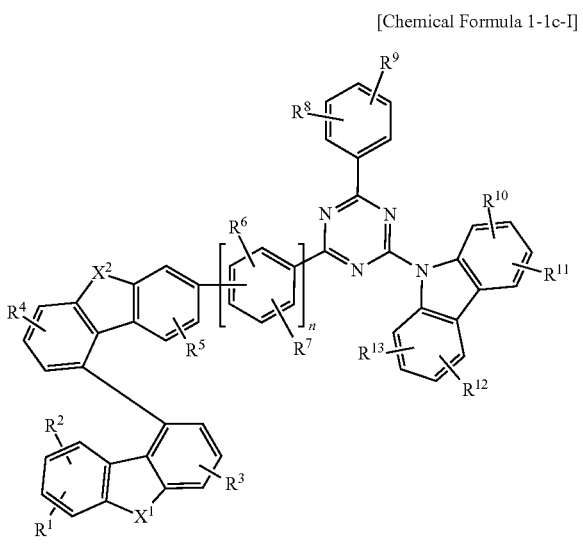

[Chemical Formula 1-1c-II]

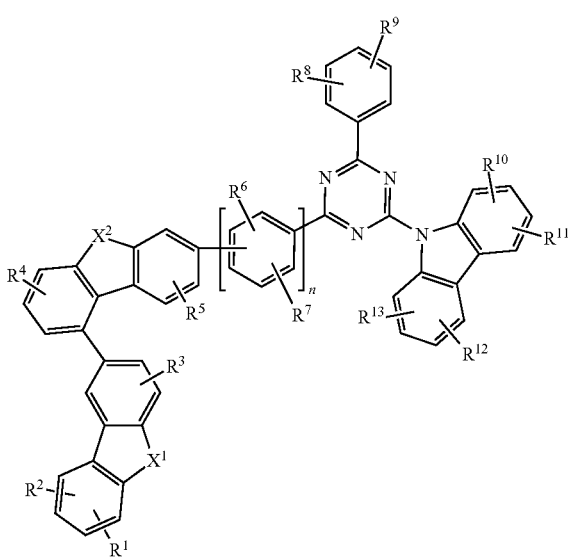

[Chemical Formula 1-1c-III]

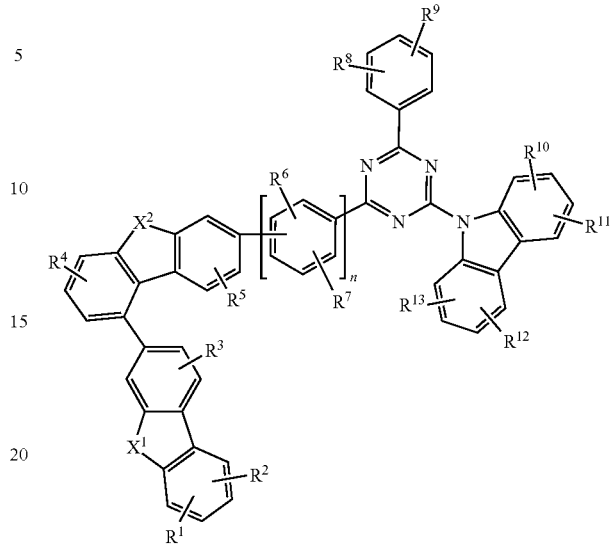

[Chemical Formula 1-1c-IV]

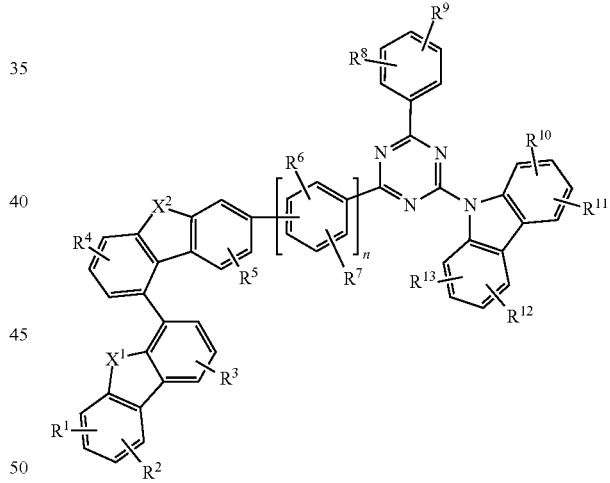

In Chemical Formula 1-1c-I to Chemical Formula 1-1c-IV, $X^1$, $X^2$, n, and $R^1$ to $R^{13}$ may be the same as described above.

In an implementation, the compound represented by Chemical Formula 1-1d may be represented by one of Chemical Formula 1-1d-I to Chemical Formula 1-1d-IV (e.g., according to the specific linking point between dibenzofuran or dibenzothiophene bound to triazine and another dibenzofuran or dibenzothiophene).

[Chemical Formula 1-1d-I]

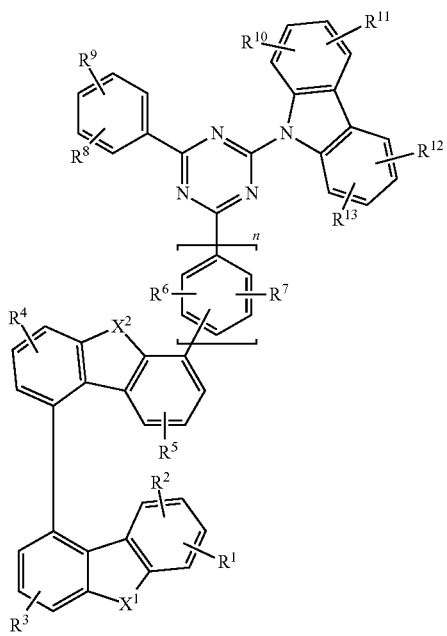

[Chemical Formula 1-1d-II]

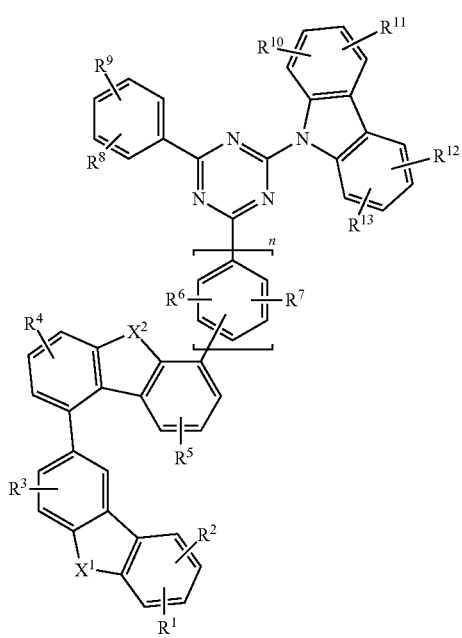

[Chemical Formula 1-1d-III]

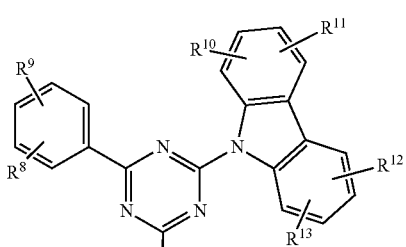

[Chemical Formula 1-1d-IV]

In Chemical Formula 1-1d-I to Chemical Formula 1-1d-IV, $X^1$, $X^2$, n, and $R^1$ to $R^{13}$ may be the same as described above.

In an implementation, the compound represented by Chemical Formula 1-2 may be represented by one of Chemical Formula 1-2a to Chemical Formula 1-2d (e.g., according to the specific linking point between dibenzofuran or dibenzothiophene and triazine).

[Chemical Formula 1-2a]
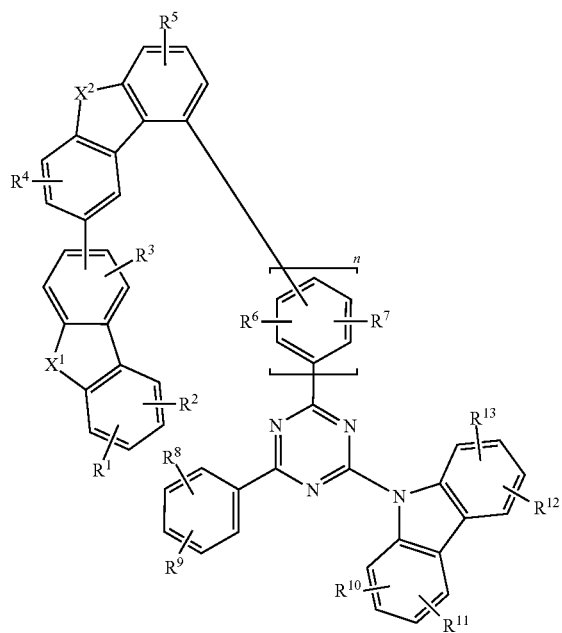
[Chemical Formula 1-2b]
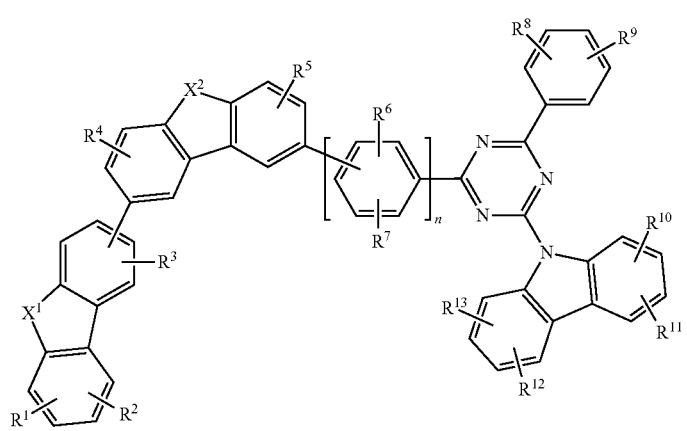

[Chemical Formula 1-2c]
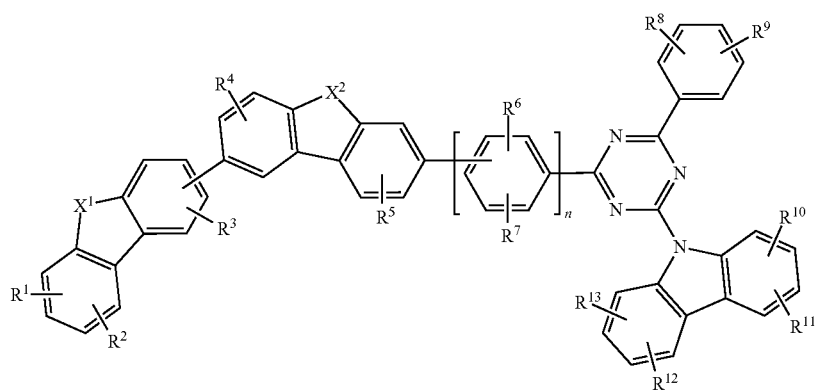
[Chemical Formula 1-2d]
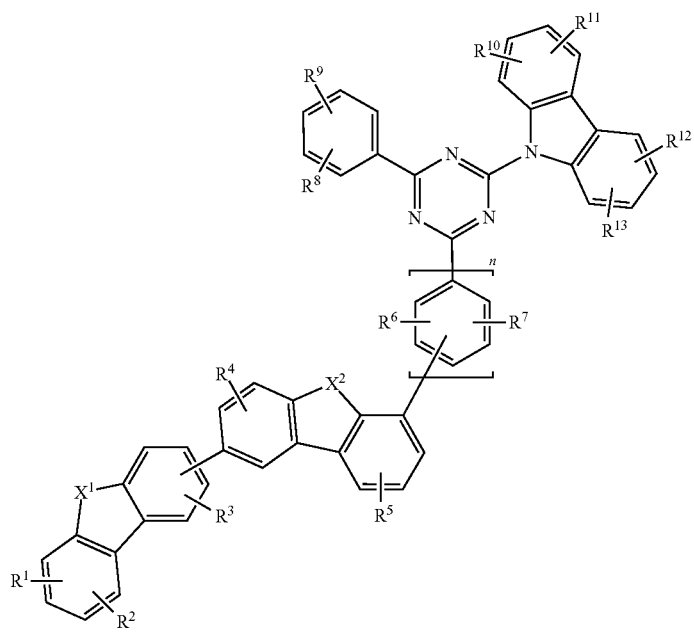

In Chemical Formula 1-2a to Chemical Formula 1-2d, $X^1$, $X^2$, n, and $R^1$ to $R^{13}$ may be the same as described above.

In an implementation, the compound represented by Chemical Formula 1-2a may be represented by one of Chemical Formula 1-2a-I to Chemical Formula 1-2a-IV (e.g., according to the specific linking point between dibenzofuran or dibenzothiophene bound to triazine and another dibenzofuran or dibenzothiophene).

[Chemical Formula 1-2a-I]

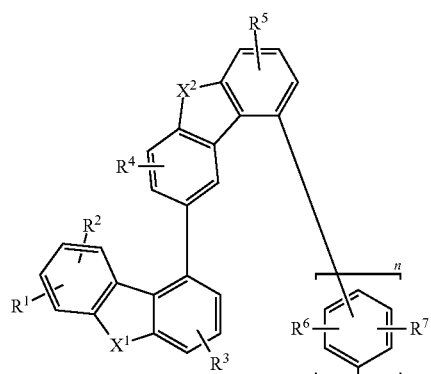

[Chemical Formula 1-2a-II]

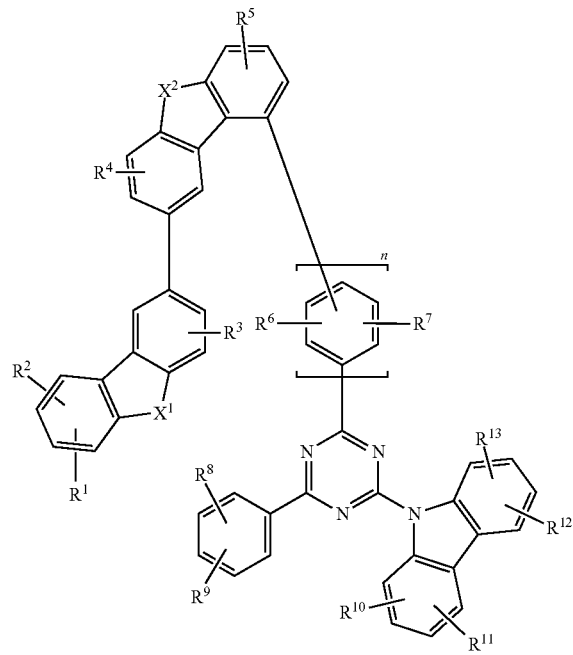

[Chemical Formula 1-2A-III]

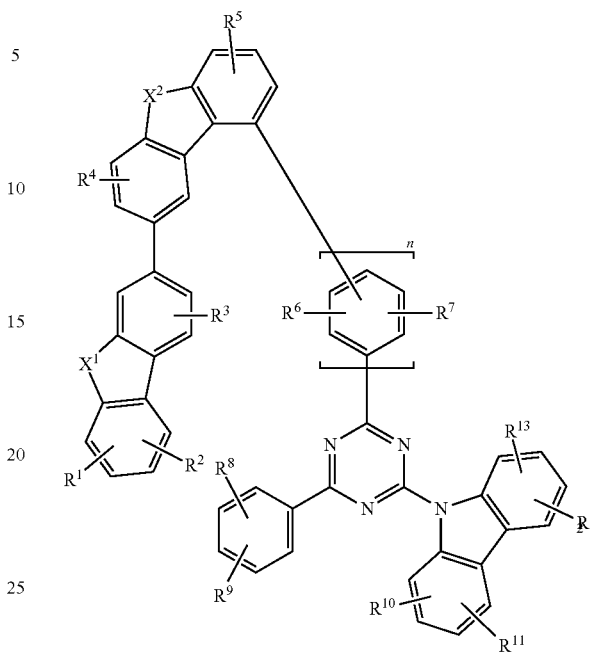

[Chemical Formula 1-2a-IV]

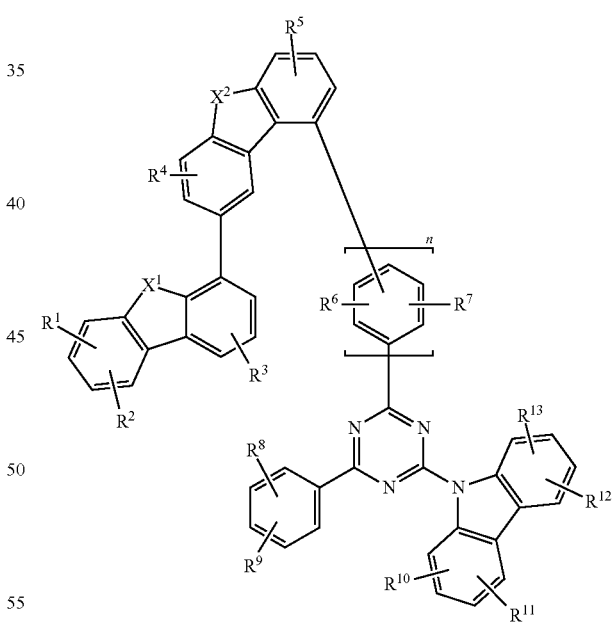

In Chemical Formula 1-2a-I to Chemical Formula 1-2a-IV, $X^1$, $X^2$, n, and $R^1$ to $R^{13}$ may be the same as described above.

In an implementation, the compound represented by Chemical Formula 1-2b may be represented by one of Chemical Formula 1-2b-I to Chemical Formula 1-2b-IV (e.g., according to the specific linking point between dibenzofuran or dibenzothiophene bound to triazine and another dibenzofuran or dibenzothiophene).

[Chemical Formula 1-2b-I]
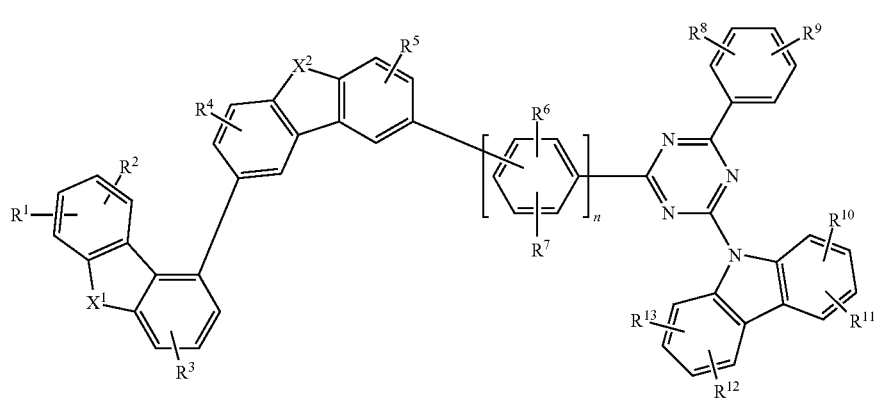
[Chemical Formula 1-2b-II]
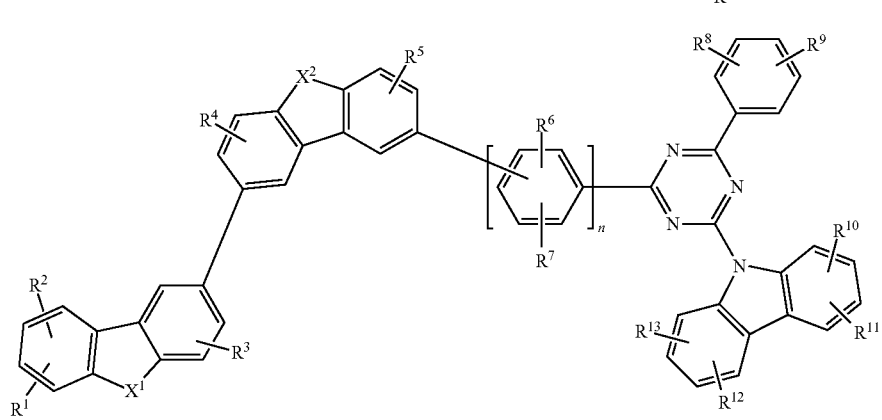
[Chemical Formula 1-2b-III]
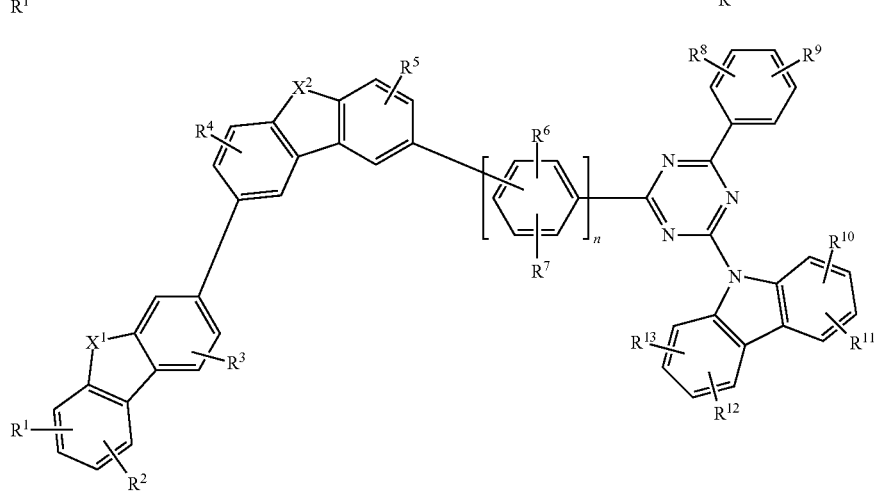
[Chemical Formula 1-2b-IV]
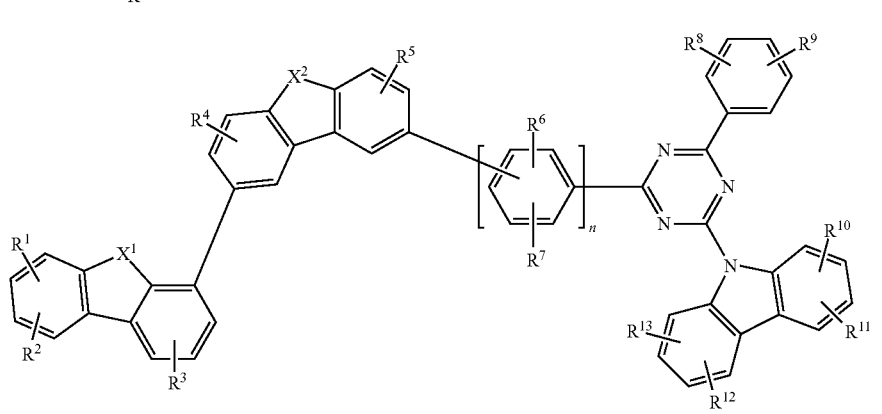

In Chemical Formula 1-2b-I to Chemical Formula 1-2b-IV, $X^1$, $X^2$, n, and $R^1$ to $R^{13}$ may be the same as described above.

In an implementation, the compound represented by Chemical Formula 1-2c may be represented by one of Chemical Formula 1-2c-I to Chemical Formula 1-2c-IV (e.g., according to the specific linking point between dibenzofuran or dibenzothiophene bound to triazine and another dibenzofuran or dibenzothiophene).

[Chemical Formula 1-2c-I]

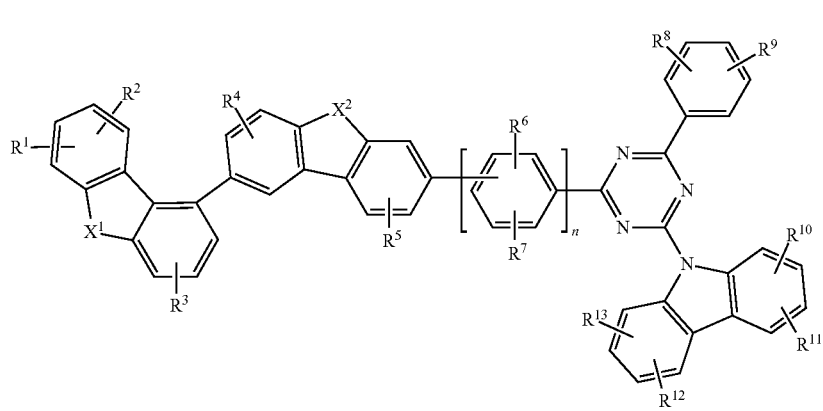

[Chemical Formula 1-2c-II]

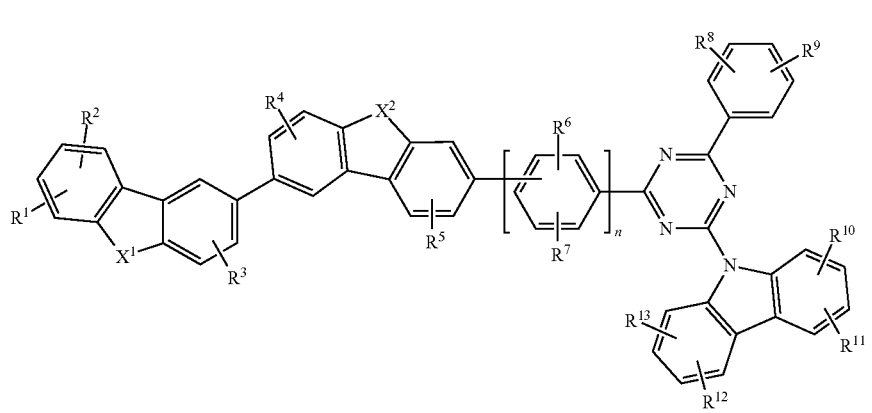

[Chemical Formula 1-2c-III]

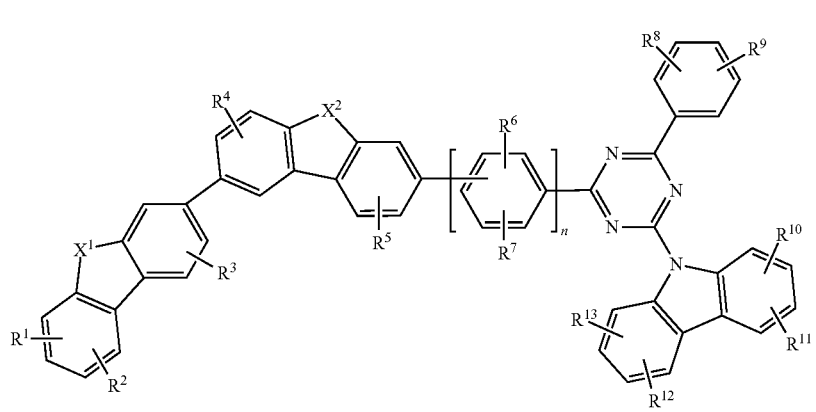

-continued

[Chemical Formula 1-2c-IV]

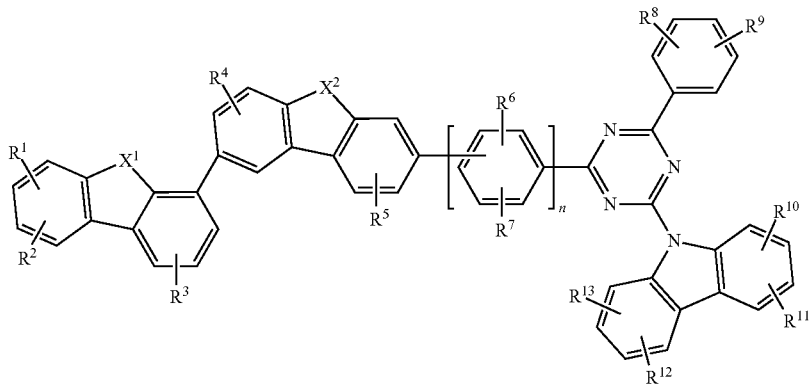

In Chemical Formula 1-2c-I to Chemical Formula 1-2c-IV, $X^1$, $X^2$, n, and $R^1$ to $R^{13}$ may be the same as described above.

In an implementation, the compound represented by Chemical Formula 1-2d may be represented by one of Chemical Formula 1-2d-I to Chemical Formula 1-2d-IV (e.g., according to the specific linking point between dibenzofuran or dibenzothiophene bound to triazine and another dibenzofuran or dibenzothiophene).

[Chemical Formula 1-2d-I]

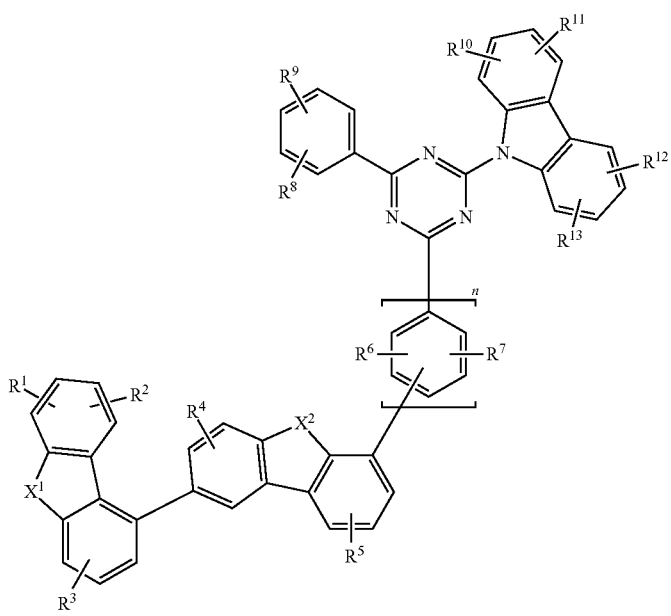

[Chemical Formula 1-2d-II]
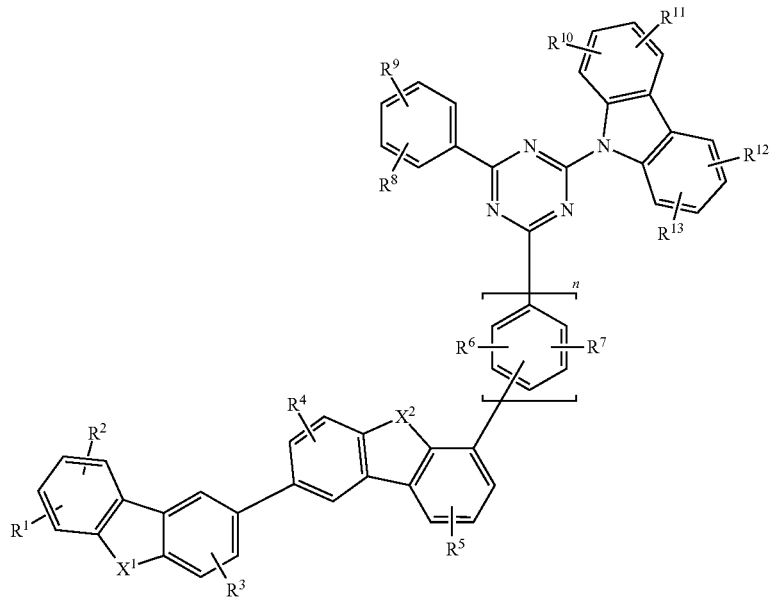
[Chemical Formula 1-2d-III]
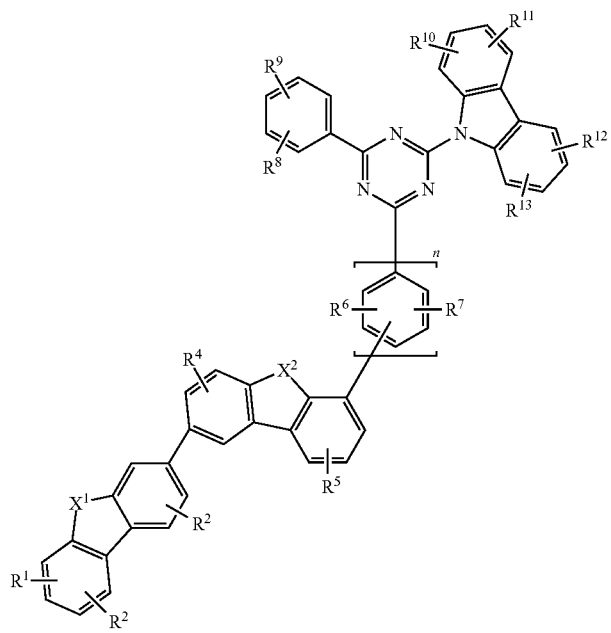

[Chemical Formula 1-2d-IV]

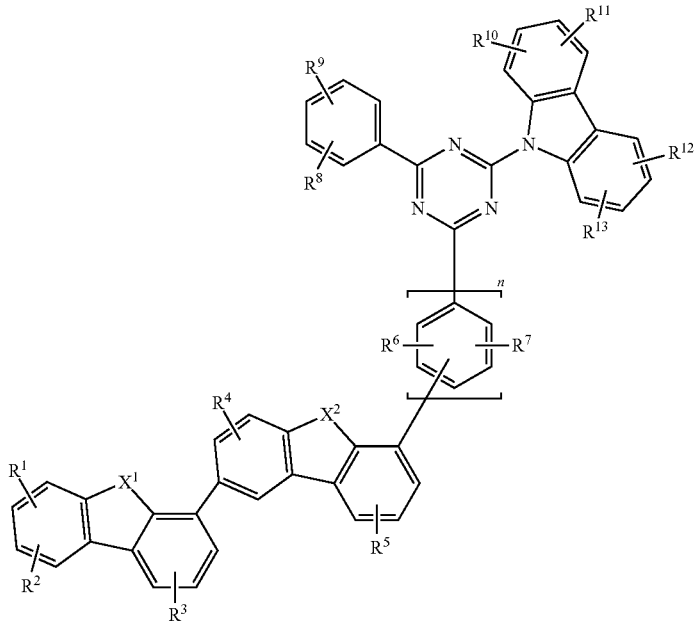

In Chemical Formula 1-2d-I to Chemical Formula 1-2d-IV, $X^1$, $X^2$, n, and $R^1$ to $R^{13}$ may be the same as described above.

In an implementation, the compound represented by Chemical Formula 1-3 may be represented by one of Chemical Formula 1-3a to Chemical Formula 1-3d (e.g., according to the specific linking point between dibenzofuran or dibenzothiophene and triazine).

[Chemical Formula 1-3a]

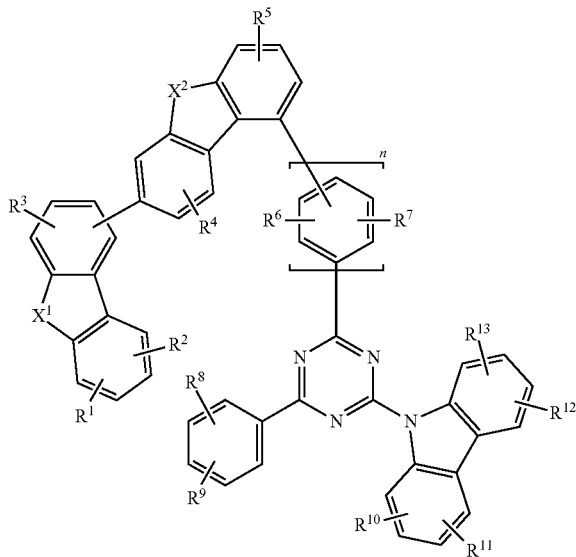

37 38
-continued
[Chemical Formula 1-3b]
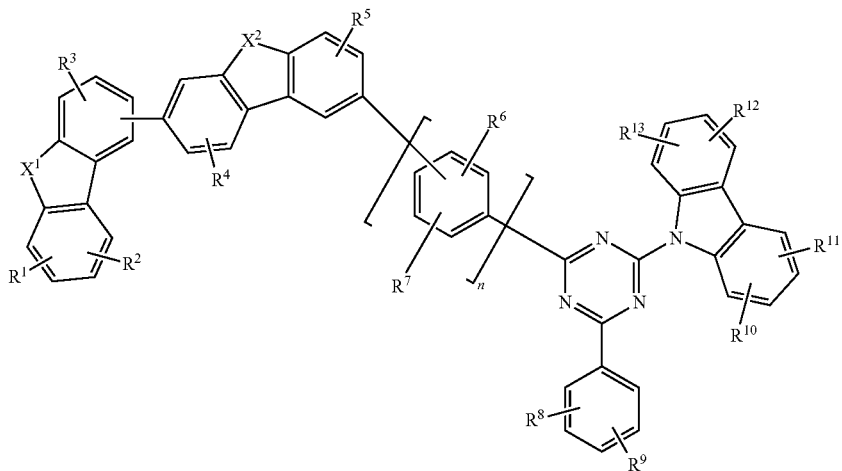
[Chemical Formula 1-3c]
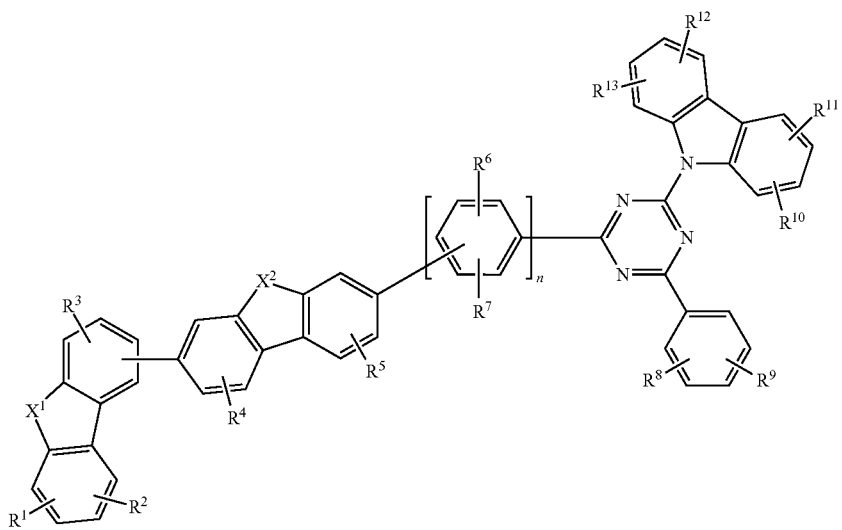
[Chemical Formula 1-3d]
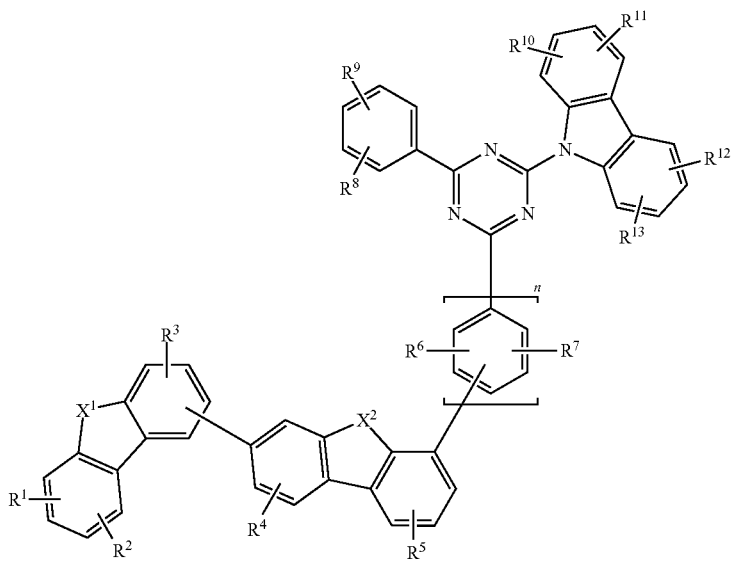

In Chemical Formula 1-3a to Chemical Formula 1-3d, $X^1$, $X^2$, n, and $R^1$ to $R^{13}$ may be the same as described above.

In an implementation, the compound represented by Chemical Formula 1-3a may be represented by one of Chemical Formula 1-3a-I to Chemical Formula 1-3a-IV (e.g., according to the specific linking point between dibenzofuran or dibenzothiophene bound to triazine and another dibenzofuran or dibenzothiophene).

[Chemical Formula 1-3a-I]

[Chemical Formula 1-3a-II]

[Chemical Formula 1-3a-III]

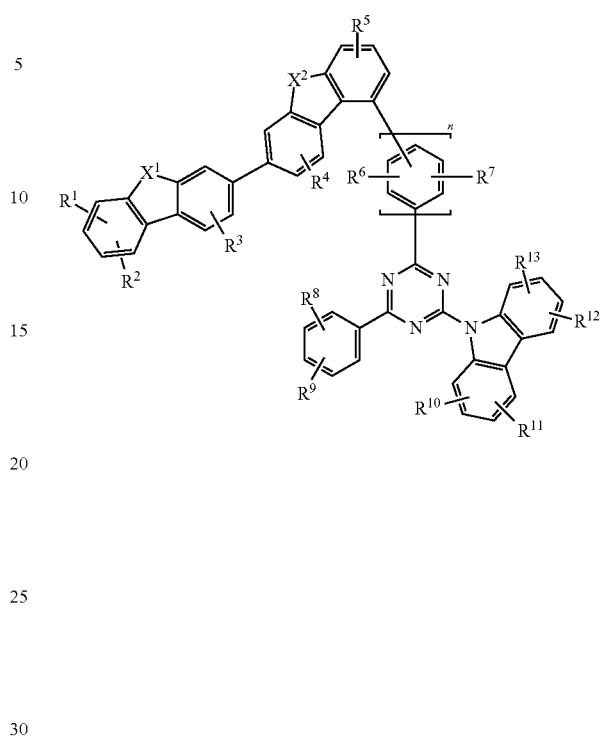

[Chemical Formula 1-3a-IV]

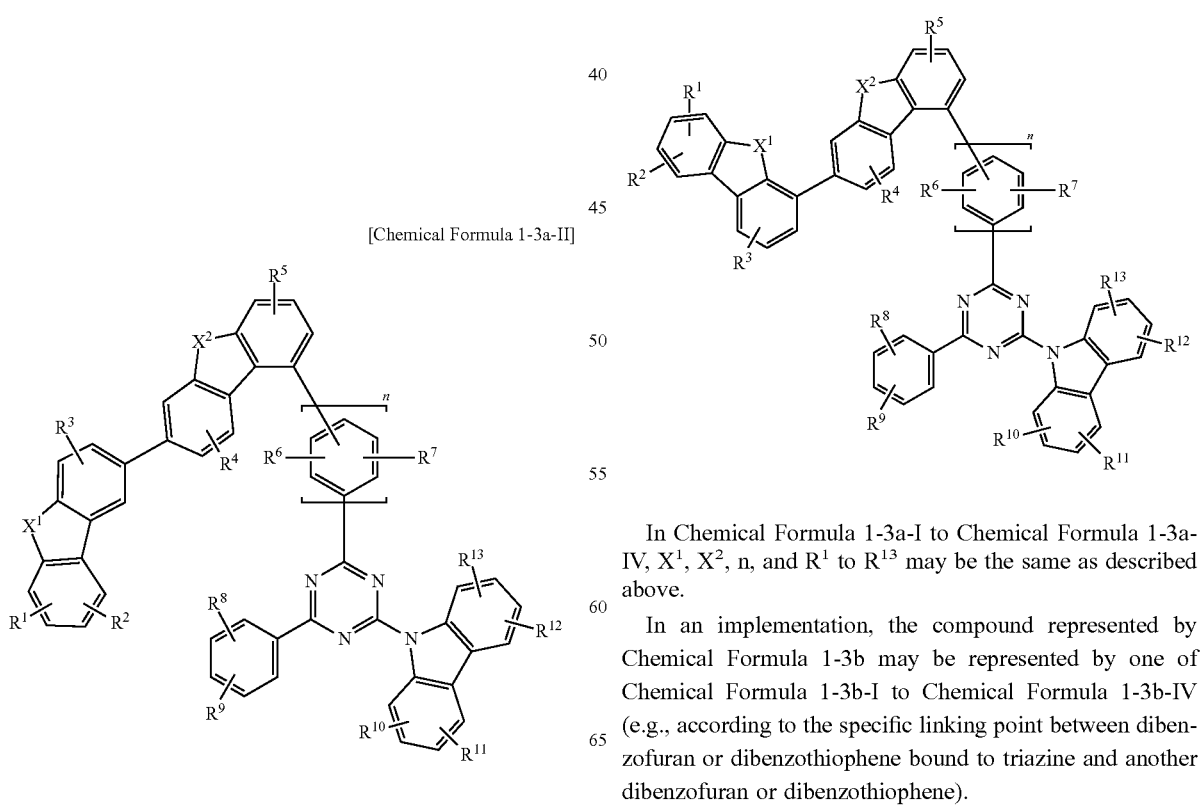

In Chemical Formula 1-3a-I to Chemical Formula 1-3a-IV, $X^1$, $X^2$, n, and $R^1$ to $R^{13}$ may be the same as described above.

In an implementation, the compound represented by Chemical Formula 1-3b may be represented by one of Chemical Formula 1-3b-I to Chemical Formula 1-3b-IV (e.g., according to the specific linking point between dibenzofuran or dibenzothiophene bound to triazine and another dibenzofuran or dibenzothiophene).

[Chemical Formula 1-3b-I]
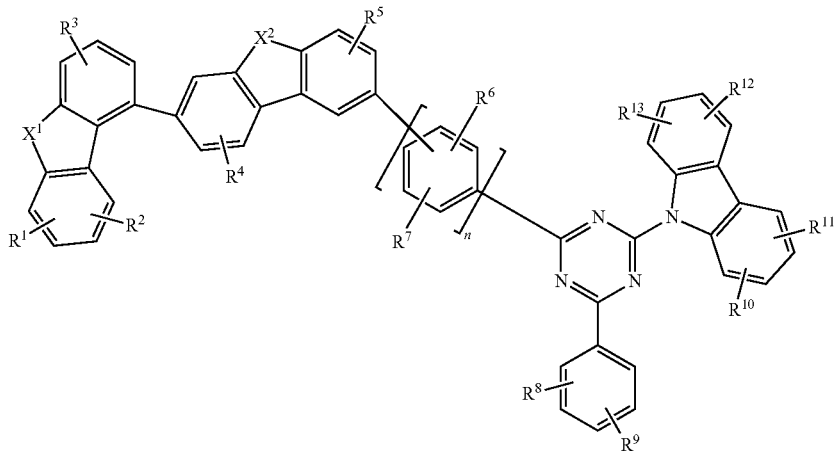
[Chemical Formula 1-3b-II]
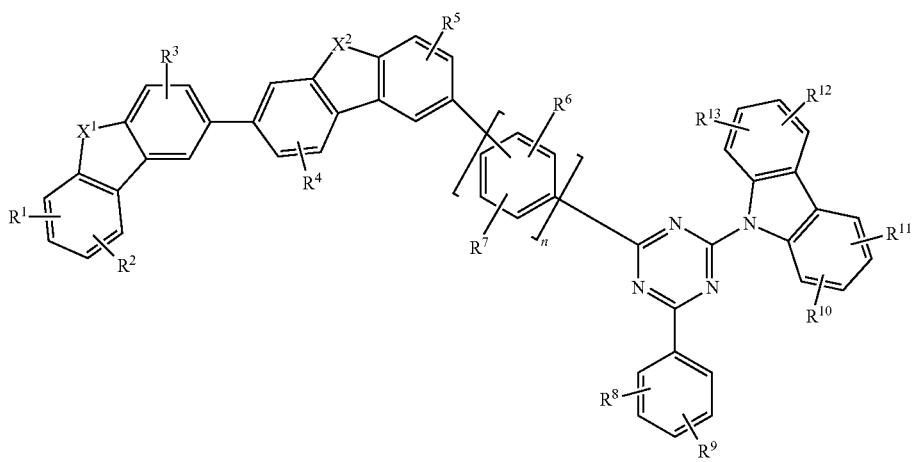
[Chemical Formula 1-3b-III]
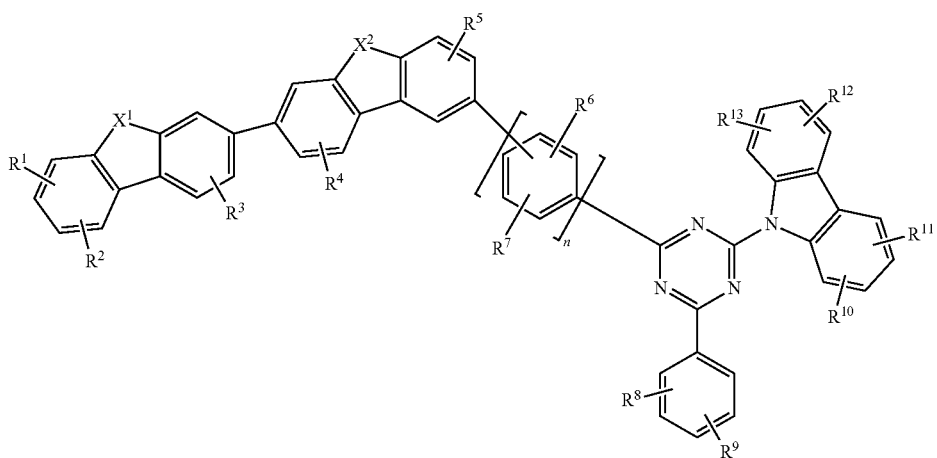

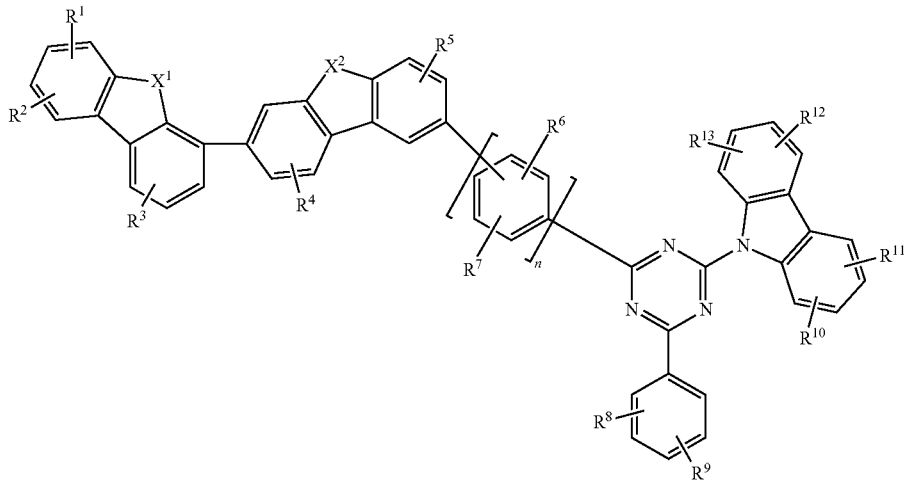

[Chemical Formula 1-3b-IV]

In Chemical Formula 1-3b-I to Chemical Formula 1-3b-IV, $X^1$, $X^2$, n, and $R^1$ to $R^{13}$ may be the same as described above.

In an implementation, the compound represented by Chemical Formula 1-3c may be represented by one of Chemical Formula 1-3c-I to Chemical Formula 1-3c-IV (e.g., according to the specific linking point between dibenzofuran or dibenzothiophene bound to triazine and another dibenzofuran or dibenzothiophene).

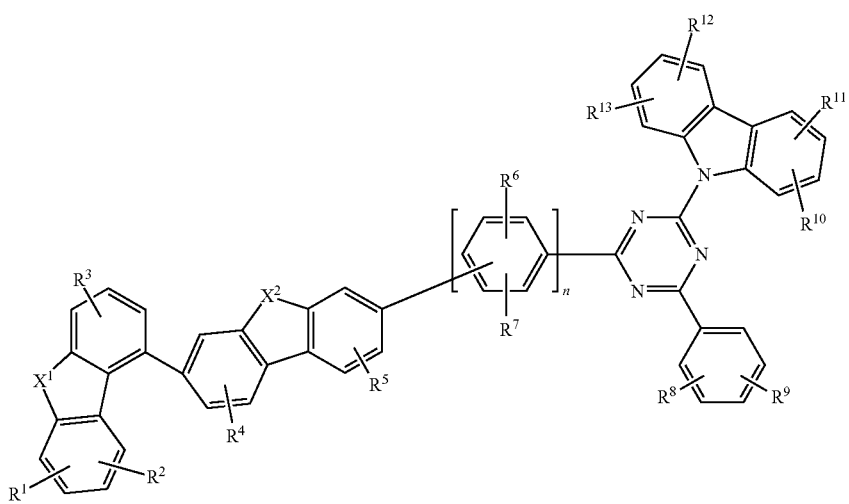

[Chemical Formula 1-3c-I]

-continued
[Chemical Formula 1-3c-II]
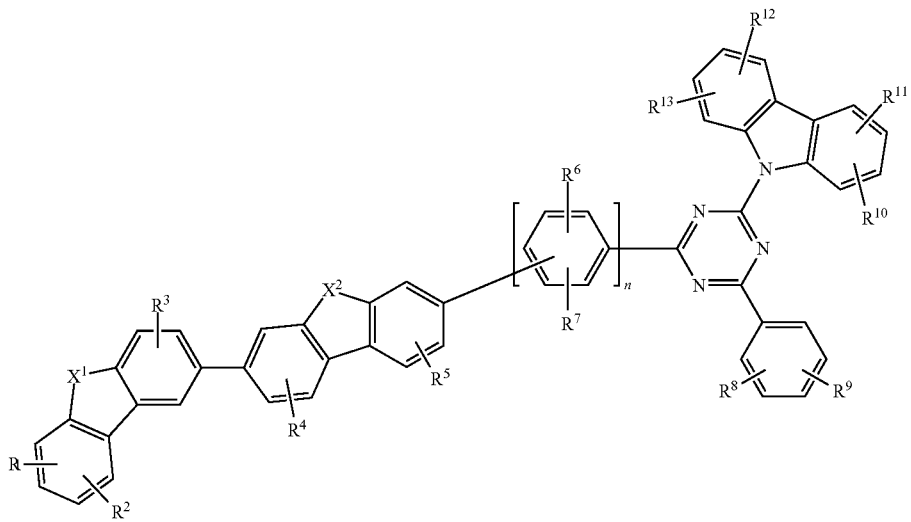
[Chemical Formula 1-3c-III]
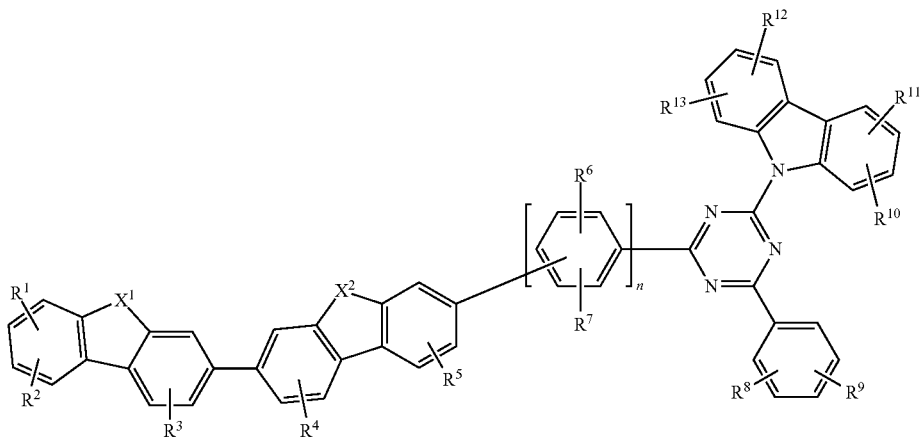
[Chemical Formula 1-3c-IV]
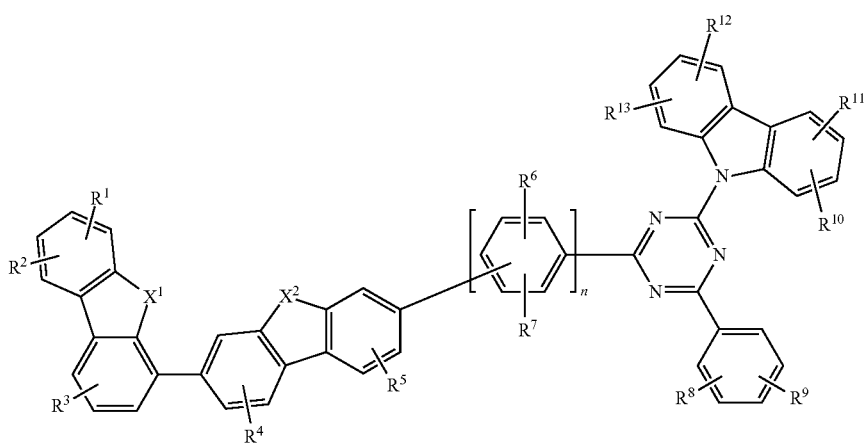

In Chemical Formula 1-3c-I to Chemical Formula 1-3c-IV, $X^1$, $X^2$, n, and $R^1$ to $R^{13}$ may be the same as described above.

In an implementation, the compound represented by Chemical Formula 1-3d may be represented by one of Chemical Formula 1-3d-I to Chemical Formula 1-3d-IV (e.g., according to the specific linking point between dibenzofuran or dibenzothiophene bound to triazine and another dibenzofuran or dibenzothiophene).

[Chemical Formula 1-3d-I]

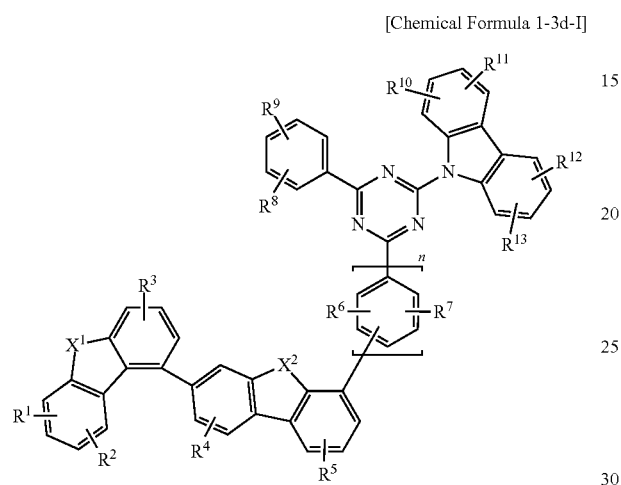

[Chemical Formula 1-3d-II]

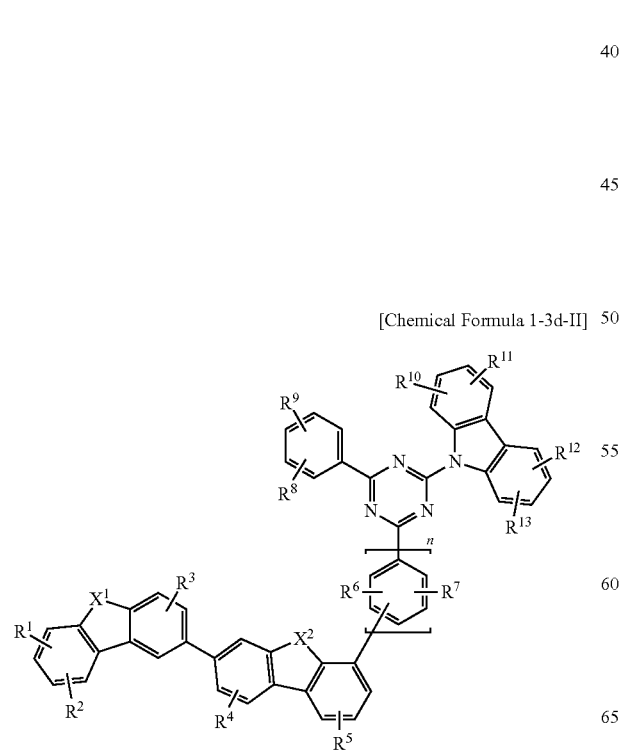

[Chemical Formula 1-3d-III]

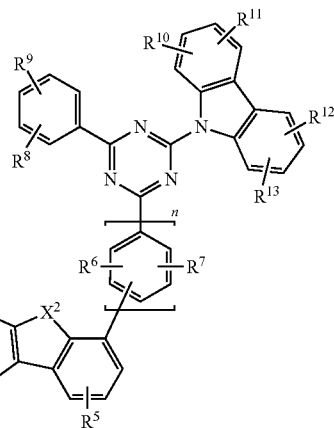

[Chemical Formula 1-3d-IV]

In Chemical Formula 1-3d-I to Chemical Formula 1-3d-IV, $X^1$, $X^2$, n, and $R^1$ to $R^{13}$ may be the same as described above.

In an implementation, the compound represented by Chemical Formula 1-4 may be represented by one of Chemical Formula 1-4a to Chemical Formula 1-4d (e.g., according to the specific linking point between dibenzofuran or dibenzothiophene and triazine).

[Chemical Formula 1-4a]
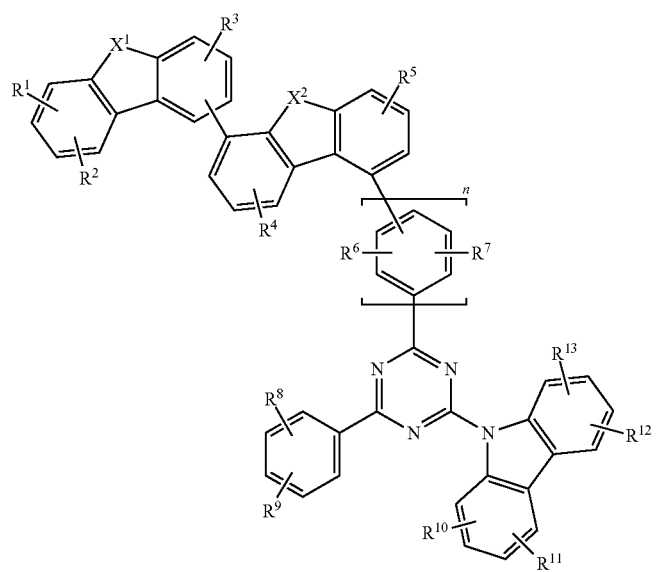
[Chemical Formula 1-4b]
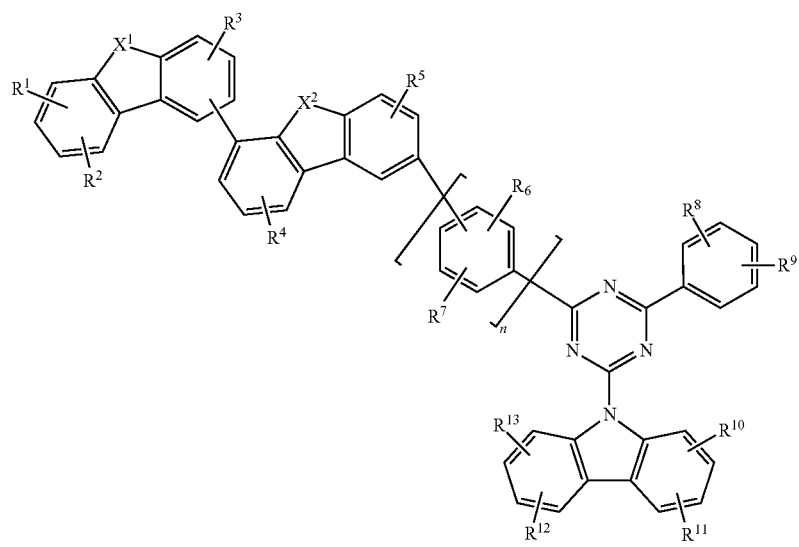

[Chemical Formula 1-4c]

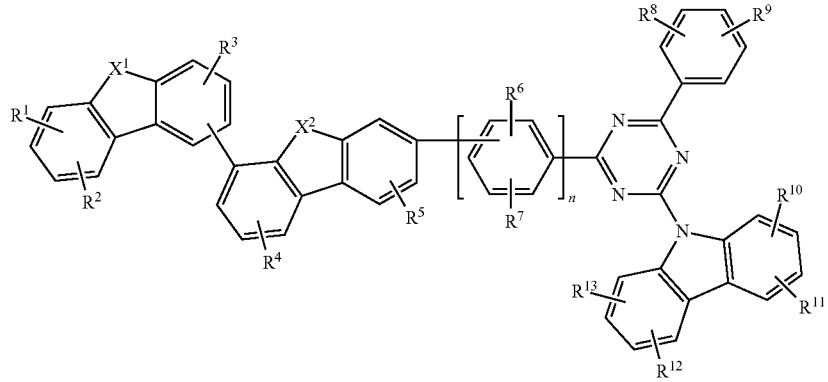

[Chemical Formula 1-4d]

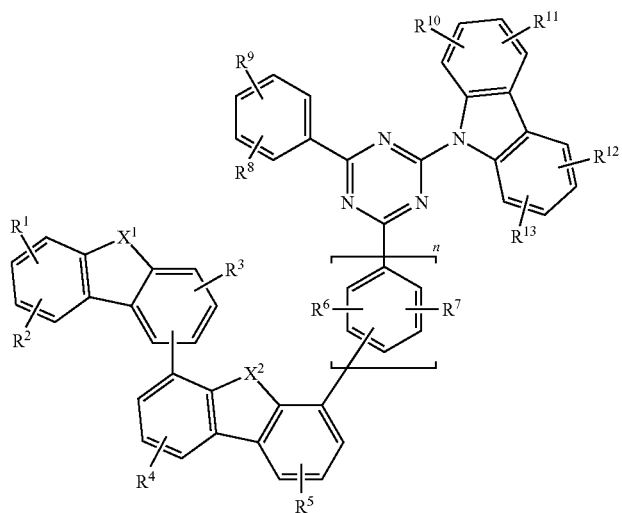

In Chemical Formula 1-4a to Chemical Formula 1-4d, $X^1$, $X^2$, n, and $R^1$ to $R^{13}$ may be the same as described above.

In an implementation, the compound represented by Chemical Formula 1-4a may be represented by one of Chemical Formula 1-4a-I to Chemical Formula 1-4a-IV (e.g., according to the specific linking point between dibenzofuran or dibenzothiophene bound to triazine and another dibenzofuran or dibenzothiophene).

[Chemical Formula 1-4a-I]

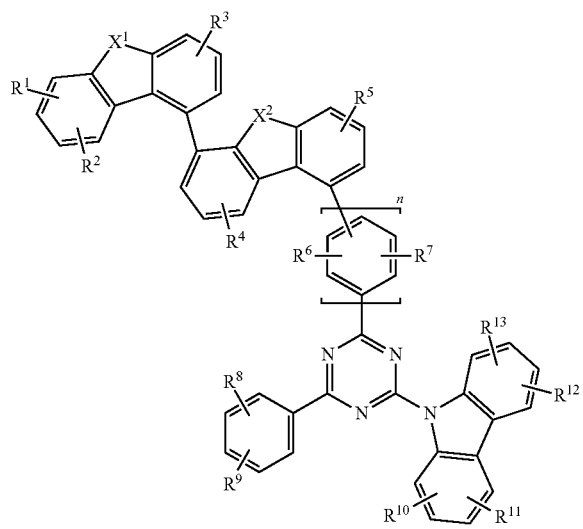

[Chemical Formula 1-4a-II]

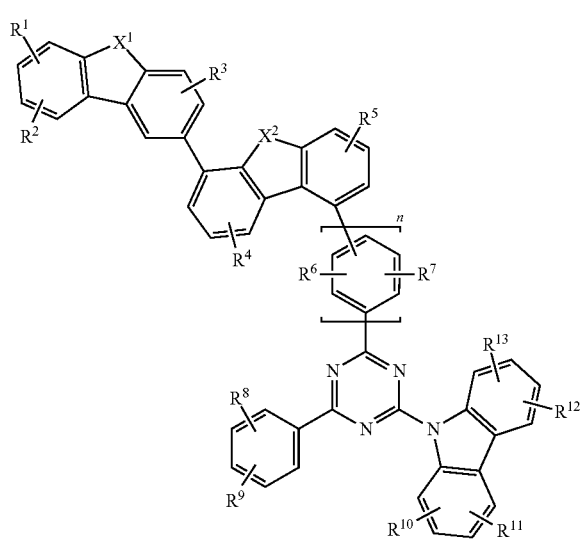

[Chemical Formula 1-4a-III]

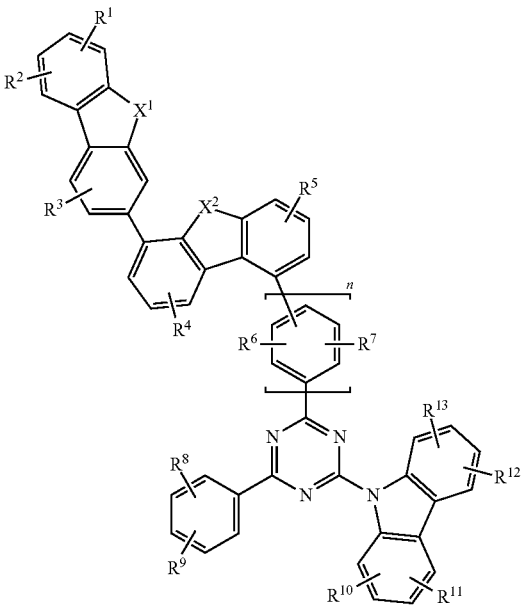

[Chemical Formula 1-4a-IV]

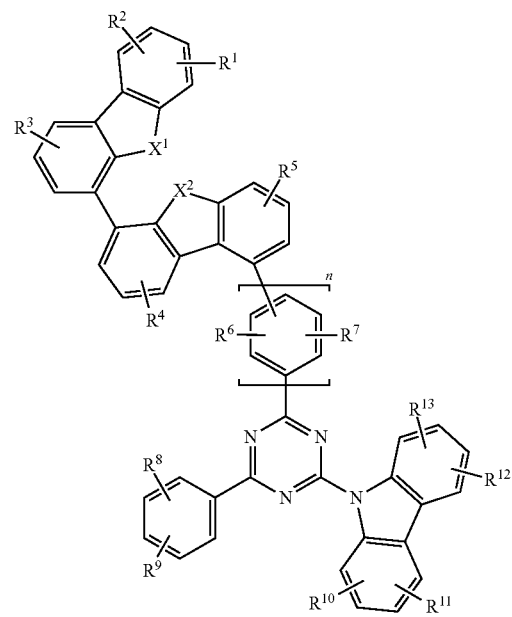

In Chemical Formula 1-4a-I to Chemical Formula 1-4a-IV, $X^1$, $X^2$, n, and $R^1$ to $R^{13}$ may be the same as described above.

In an implementation, the compound represented by Chemical Formula 1-4b may be represented by one of Chemical Formula 1-4b-I to Chemical Formula 1-4b-IV (e.g., according to the specific linking point between dibenzofuran or dibenzothiophene bound to triazine and another dibenzofuran or dibenzothiophene).

[Chemical Formula 1-4b-I]
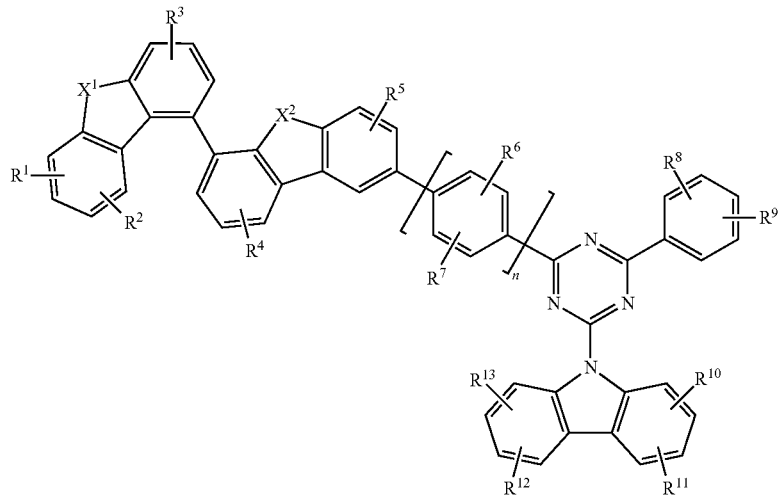
[Chemical Formula 1-4b-II]
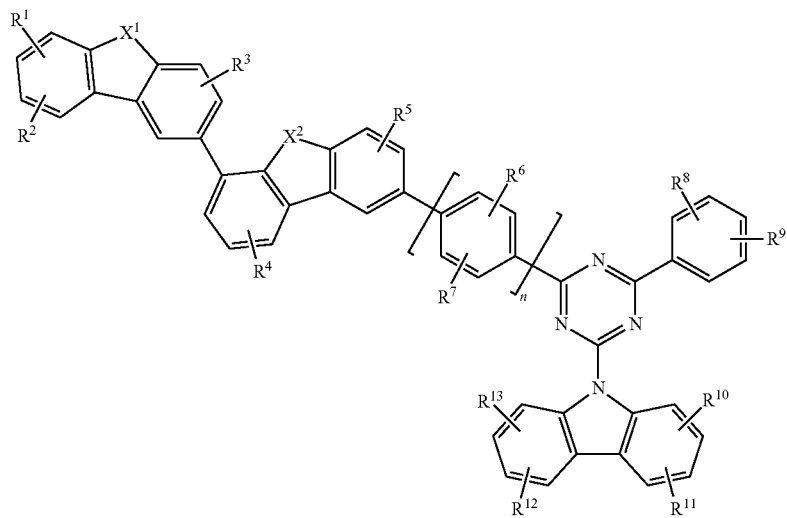
[Chemical Formula 1-4b-III]
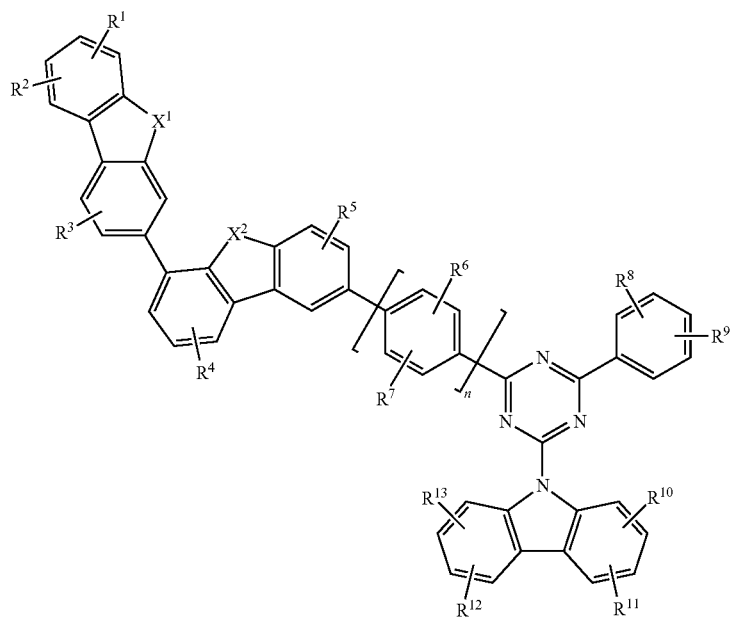

-continued

[Chemical Formula 1-4b-IV]

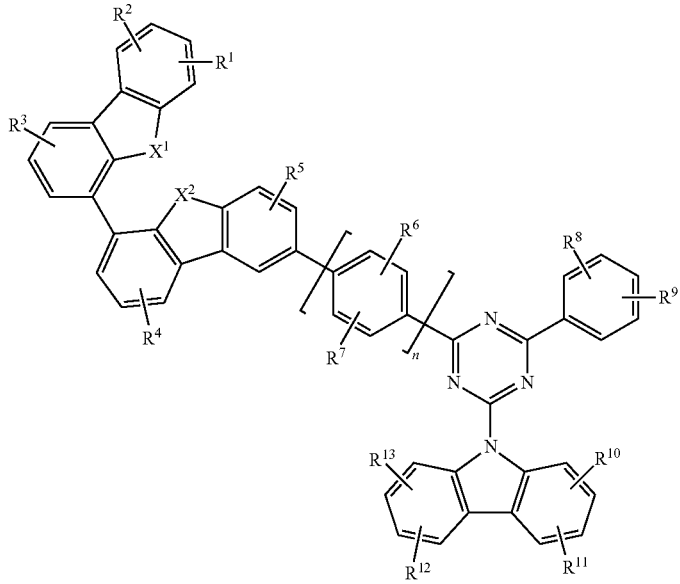

In Chemical Formula 1-4b-I to Chemical Formula 1-4b-IV, $X^1$, $X^2$, n, and $R^1$ to $R^{13}$ may be the same as described above.

In an implementation, the compound represented by Chemical Formula 1-4c may be represented by one of Chemical Formula 1-4-I to Chemical Formula 1-4c-IV (e.g., according to the specific linking point between dibenzofuran or dibenzothiophene bound to triazine and another dibenzofuran or dibenzothiophene).

[Chemical Formula 1-4c-I]

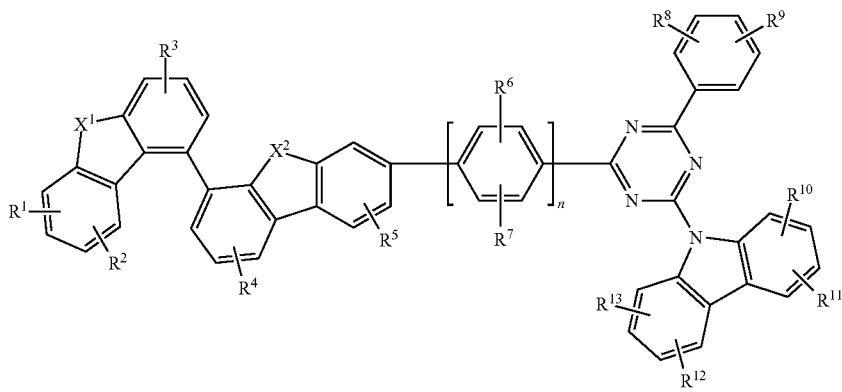

[Chemical Formula 1-4c-II]

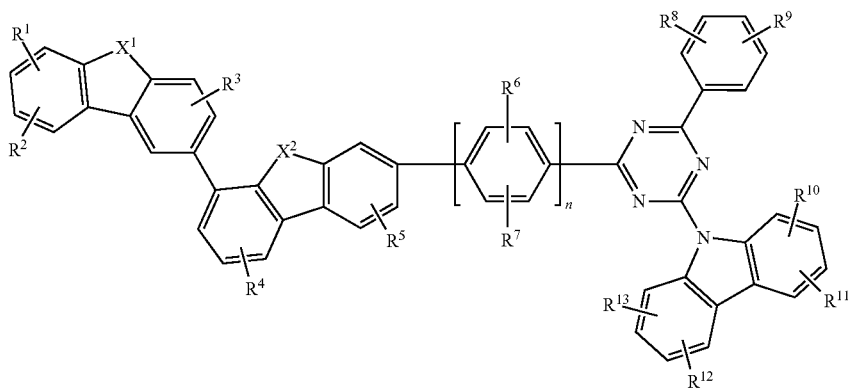

[Chemical Formula 1-4c-III]

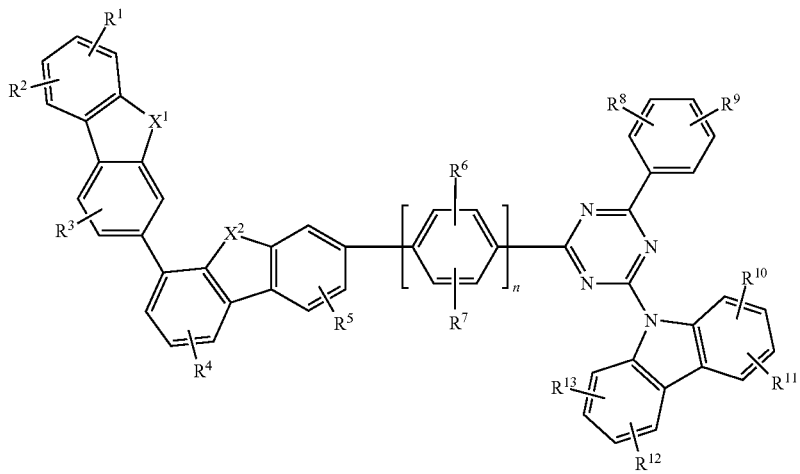

[Chemical Formula 1-4c-IV]

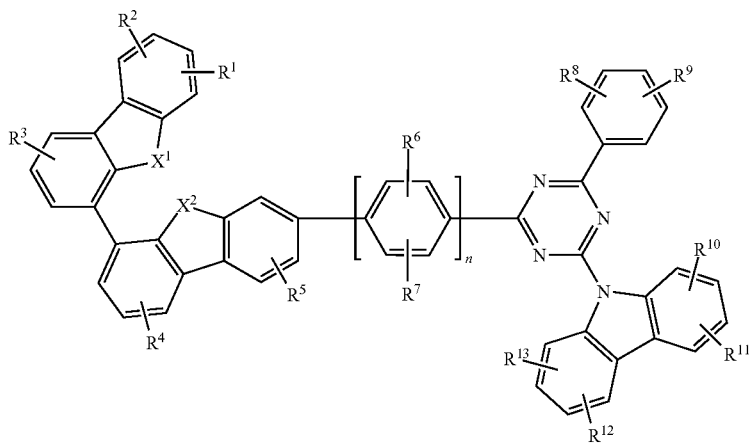

In Chemical Formula 1-4c-I to Chemical Formula 1-4c-IV, $X^1$, $X^2$, n, and $R^1$ to $R^{13}$ may be the same as described above.

In an implementation, the compound represented by Chemical Formula 1-4d may be represented by one of Chemical Formula 1-4d-I to Chemical Formula 1-4d-IV (e.g., according to the specific linking point between dibenzofuran or dibenzothiophene bound to triazine and another dibenzofuran or dibenzothiophene).

[Chemical Formula 1-4d-I]

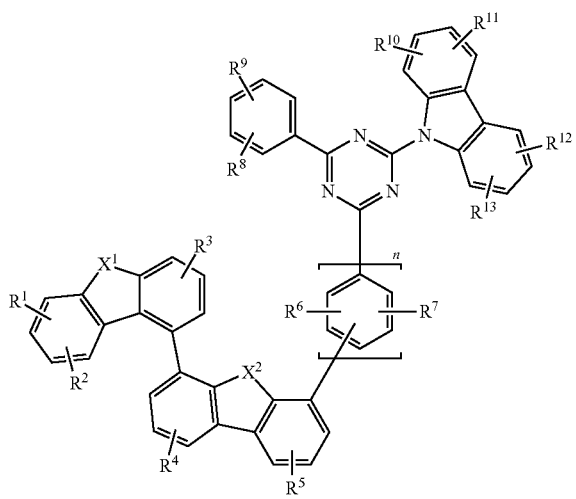

[Chemical Formula 1-4d-II]

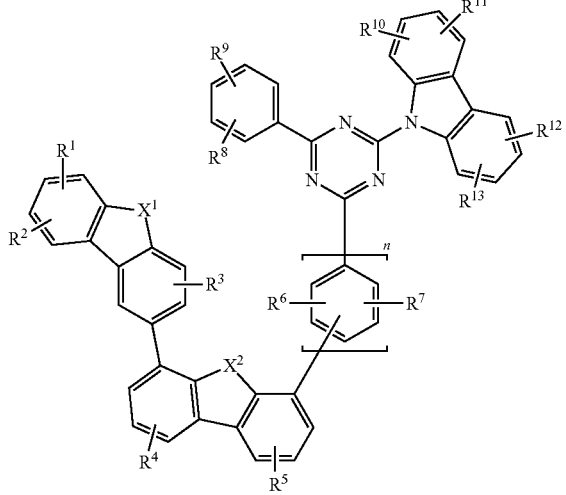

[Chemical Formula 1-4d-III]

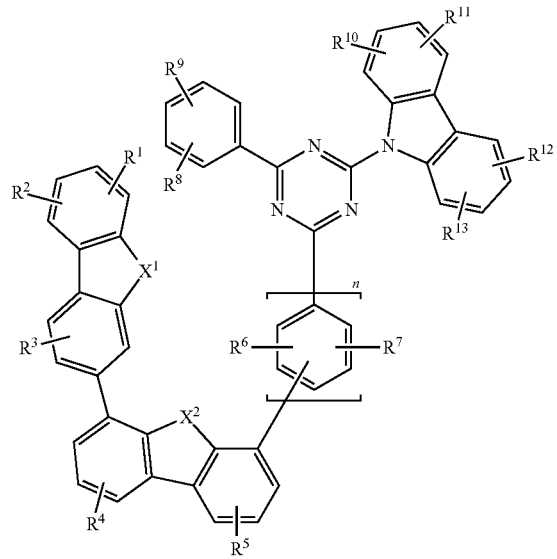

[Chemical Formula 1-4d-IV]

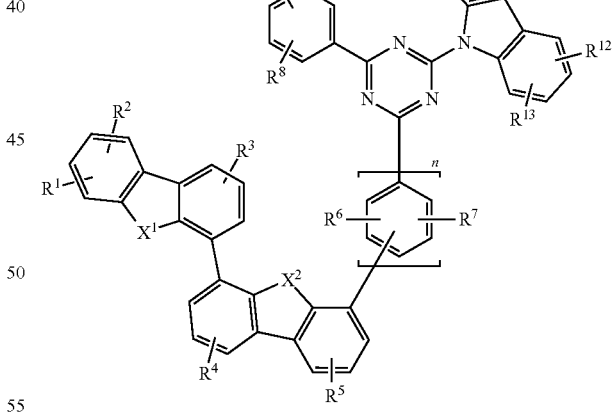

In Chemical Formula 1-4d-I to Chemical Formula 1-4d-IV, $X^1$, $X^2$, n and $R^1$ to $R^{13}$ may be the same as described above.

In an implementation, the compound represented by Chemical Formula 1 may be represented by one of Chemical Formula 1A to Chemical Formula 1D (e.g., depending on the presence or absence of a linking group between triazine to dibenzofuran or dibenzothiophene, and the linking point of the linking group).

[Chemical Formula 1A]
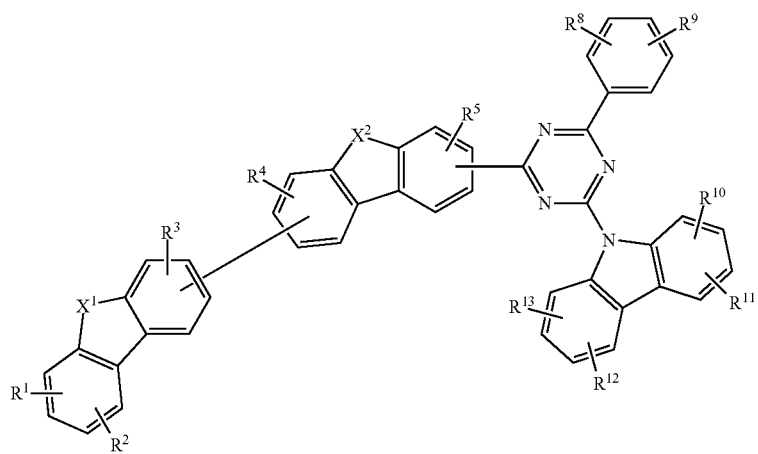
[Chemical Formula 1B]
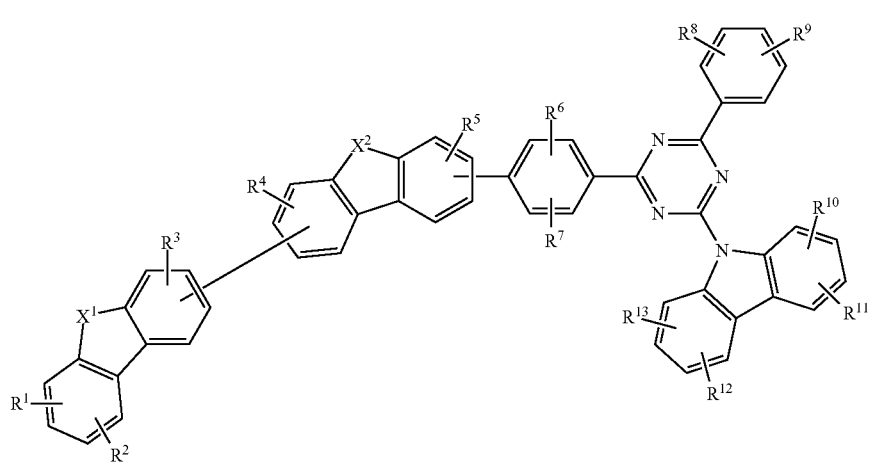
[Chemical Formula 1C]
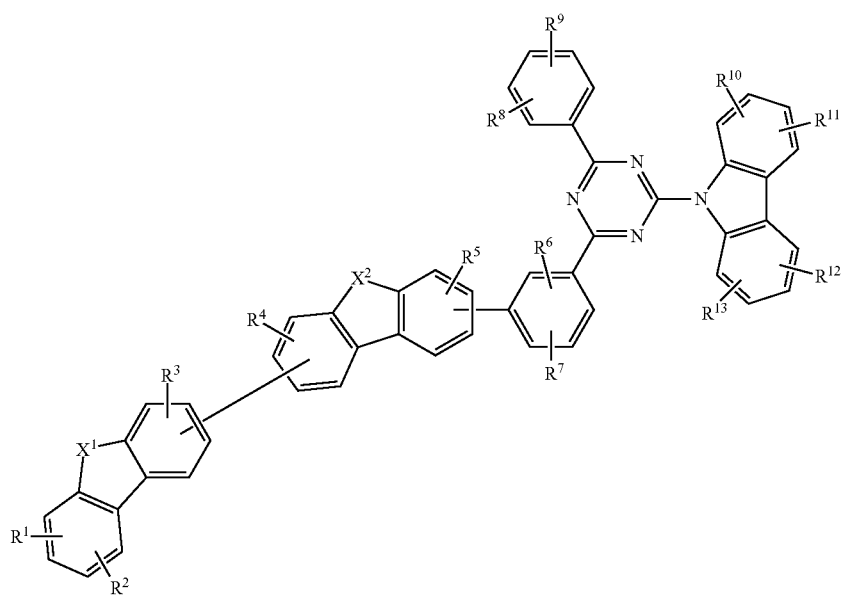

[Chemical Formula 1D]

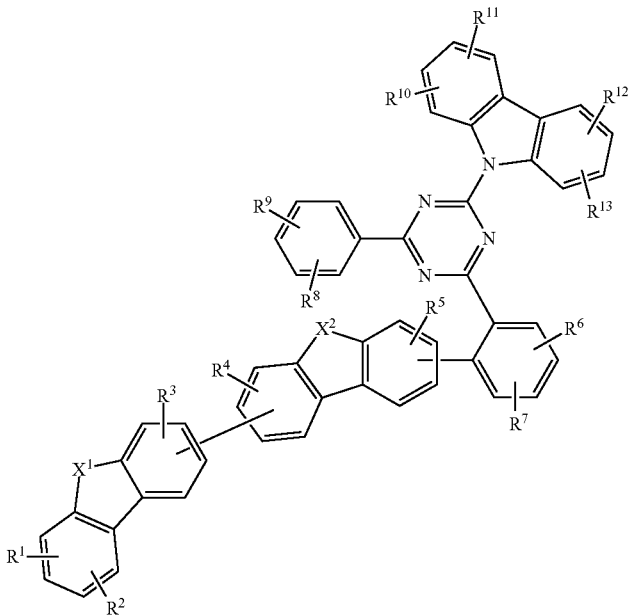

In Chemical Formula 1A to Chemical Formula 1D, $X^1$, $X^2$, n, and $R^1$ to $R^9$ may be the same as described above.

In an implementation, $R^{10}$ to $R^{13}$ may each independently be or include, e.g., hydrogen, deuterium, a cyano group, a halogen, a C1 to C10 alkyl group, a C6 to C12 aryl group, a C2 to C20 heterocyclic group, or a combination thereof.

In an implementation, the compound represented by Chemical Formula 1 may be represented by, e.g., Chemical Formula 1-1a, Chemical Formula 1-2b, Chemical Formula 1-3c, Chemical Formula 1-4c, or Chemical Formula 1-4d.

In an implementation, the compound represented by Chemical Formula 1 may be represented by, e.g., Chemical Formula 1-1a-IV, Chemical Formula 1-2b-IV, Chemical Formula 1-3c-III, Chemical Formula 1-4c-I, Chemical Formula 1-4c-III, Chemical Formula 1-4c-IV, Chemical Formula 1-4d-II, or Chemical Formula 1-4d-IV.

In an implementation, the compound represented by Chemical Formula 1 may be represented by, e.g., Chemical Formula 1A, Chemical Formula 1B, or Chemical Formula 1C.

In an implementation, $X^1$ and $X^2$ may be each "O."
In an implementation, $X^1$ and $X^2$ may be each "S."
In an implementation, $X^1$ may be "O" and $X^2$ may be "S."
In an implementation, $X^1$ may be "S" and $X^2$ may be "O."
In an implementation, $R^1$ to $R^5$ may each independently be or include, e.g., a cyano group, a C1 to C10 alkyl group, a C6 to C12 aryl group, or a combination thereof. In an implementation, all may be hydrogen or at least one of $R^1$ to $R^5$ may be, e.g., a cyano group or a C1 to C5 alkyl group.

In an implementation, $R^6$ and $R^7$ may be hydrogen.

In an implementation, $R^8$ and $R^9$ may each independently be or include, e.g., a cyano group, a C1 to C10 alkyl group, a C6 to C12 aryl group, or a combination thereof. In an implementation, $R^1$ and $R^9$ may be all hydrogen or at least one of $R^6$ and $R^7$ may be, e.g., a cyano group, a C1 to C5 alkyl group, or a phenyl group.

In an implementation, $R^{10}$ to $R^{13}$ may be separate, or adjacent groups thereof may be linked to each other to provide a substituted or unsubstituted aliphatic, aromatic, or heteroaromatic monocyclic ring or a substituted or unsubstituted aliphatic, aromatic, or heteroaromatic polycyclic ring.

When $R^{10}$ to $R^{13}$ are separate, $R^{10}$ to $R^{13}$ may each independently be or include, e.g., a cyano group, a C1 to C10 alkyl group, a C6 to C12 aryl group, or a combination thereof. In an implementation, $R^{10}$ to $R^{13}$ may be all hydrogen or at least one of $R^{10}$ and $R^{13}$ may be, e.g., a cyano group, a C1 to C5 alkyl group, a phenyl group, or a biphenyl group and may be for example represented by one of Chemical Formula 1A to Chemical Formula 1D.

In an implementation, when adjacent groups of $R^{10}$ to $R^{13}$ are linked to each other to provide a substituted or unsubstituted aliphatic, aromatic, or heteroaromatic monocyclic ring or a substituted or unsubstituted aliphatic, aromatic, or heteroaromatic polycyclic ring, e.g. the adjacent groups of $R^{10}$ to $R^{13}$ are linked to each other to provide a substituted or unsubstituted aromatic monocyclic or a substituted or unsubstituted aromatic polycyclic ring, and may be, e.g., represented by one of Chemical Formula 1E to Chemical Formula 1G.

[Chemical Formula 1E]
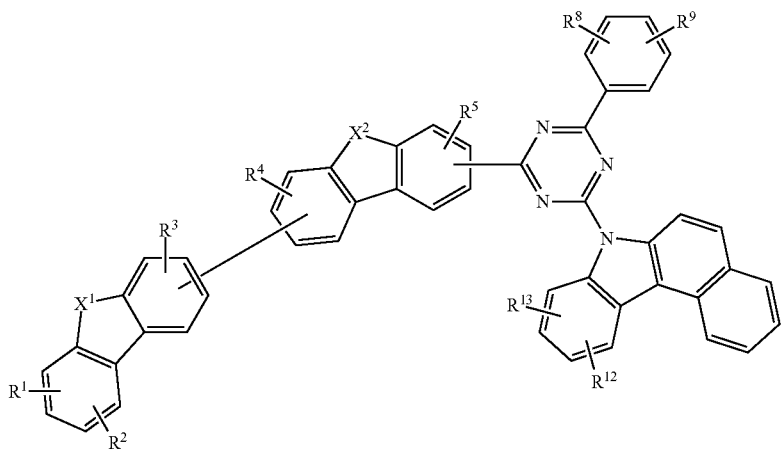
[Chemcal Formula 1F]
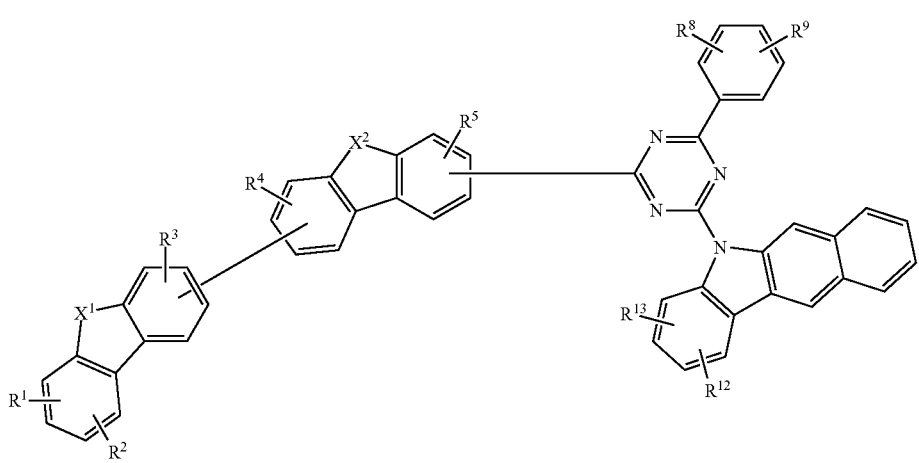
[Chemcal Formula 1G]
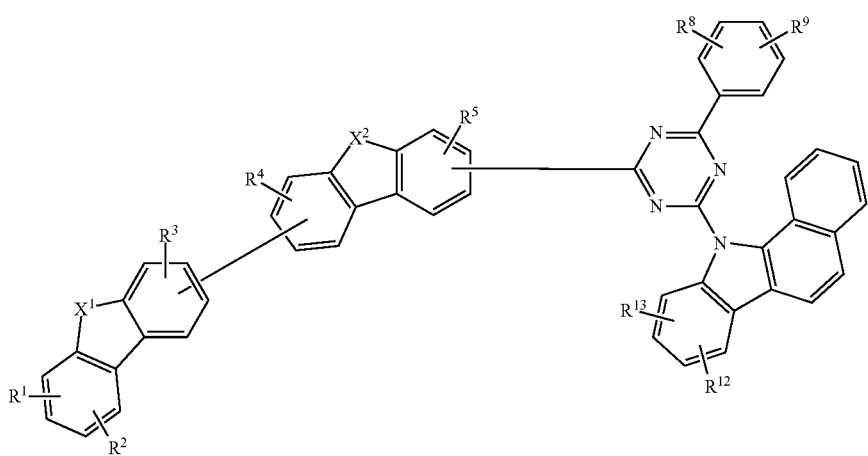
In Chemical Formula 1E to Chemical Formula 1G, $X^1$, $X^2$ and $R^1$ to $R^{10}$, $R^{12}$ and $R^{13}$ may be the same as described above.
In an implementation, the compound for the organic optoelectronic device represented by Chemical Formula 1 may be, e.g., a compound of Group 1.

[Group 1]
1
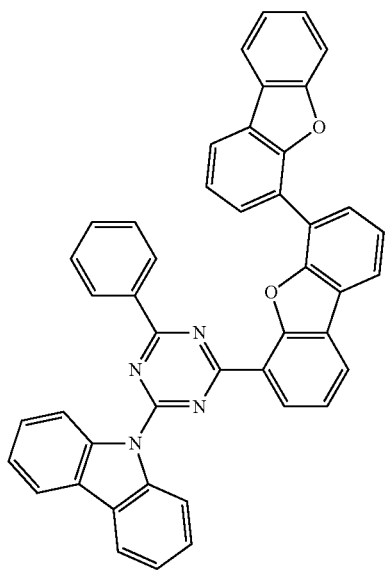
2
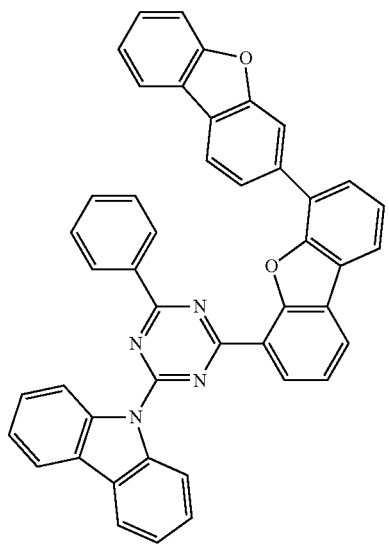
3
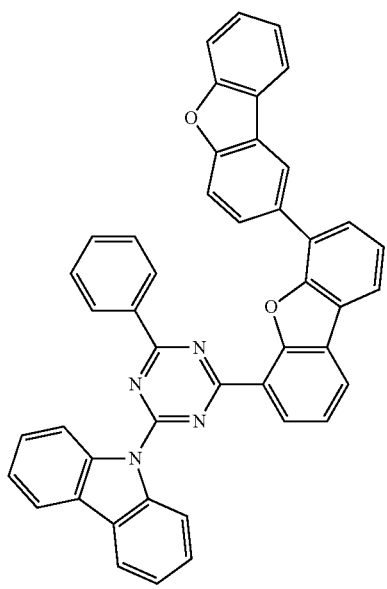
4
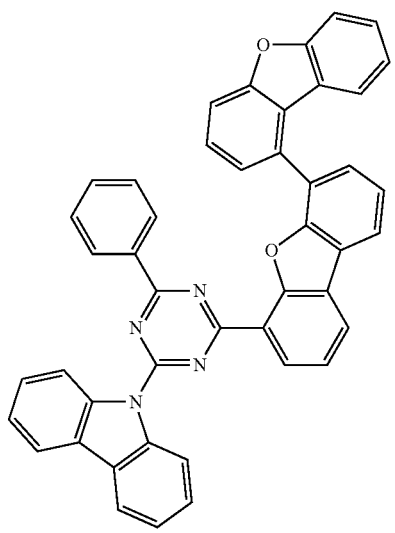

5
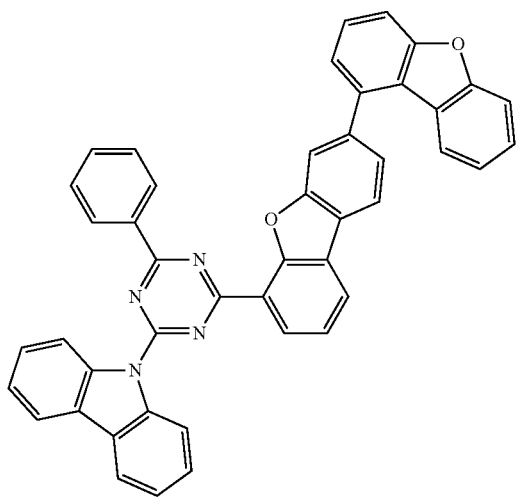
6
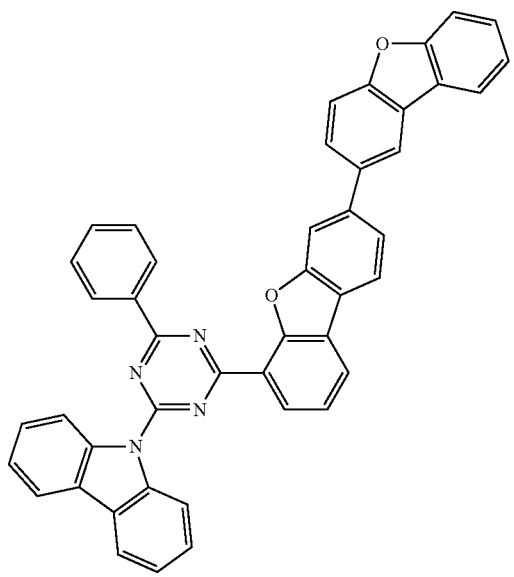
7
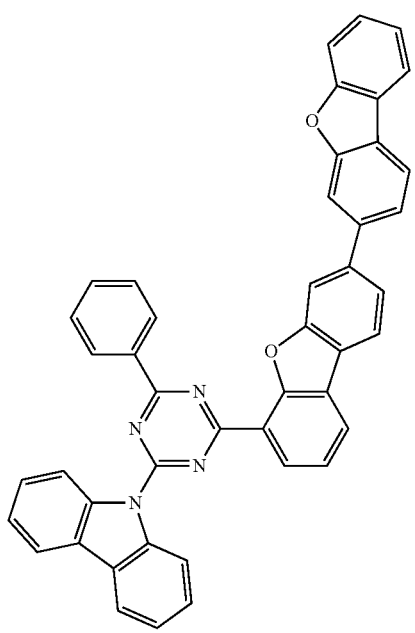
8
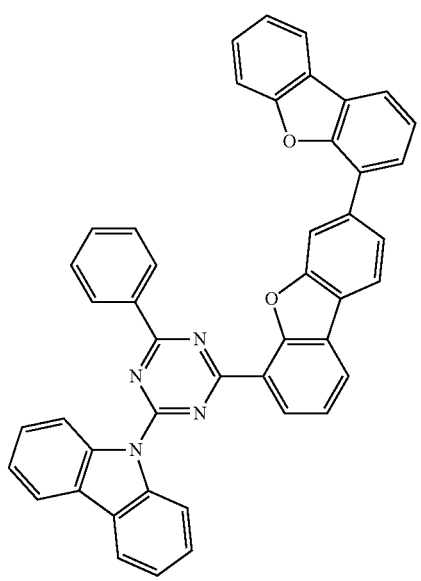

9
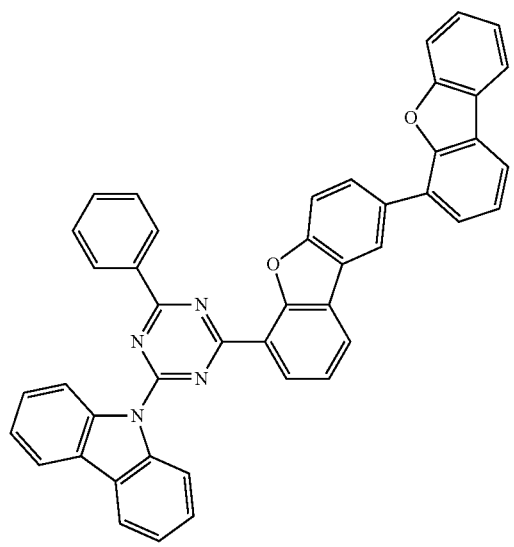
10
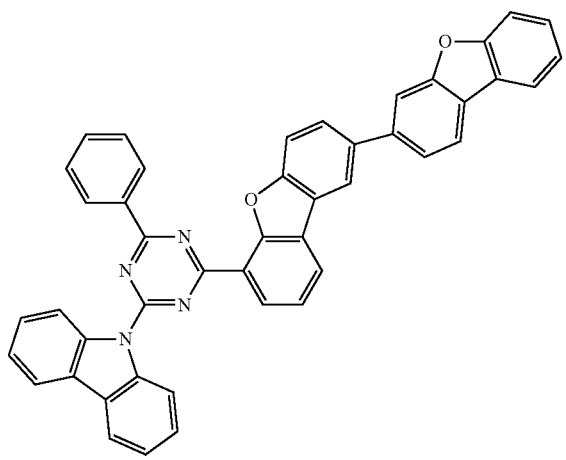
11
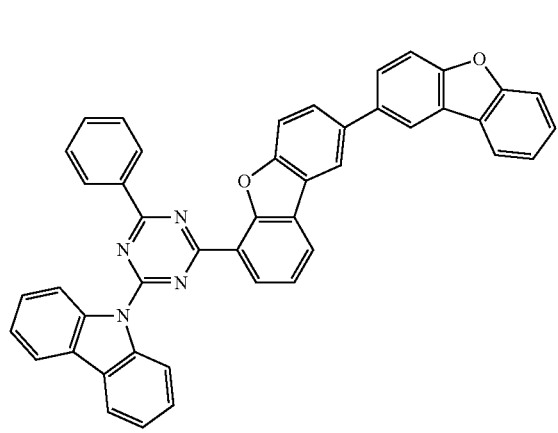
12
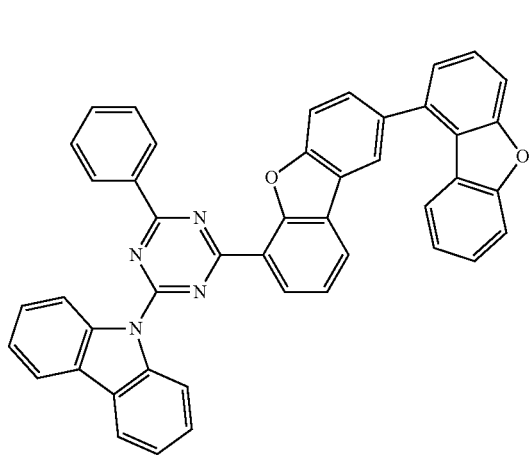
13
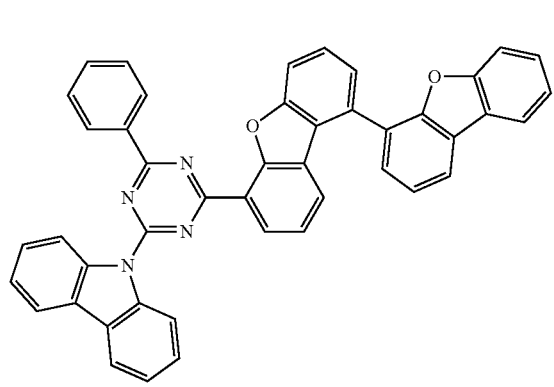
14
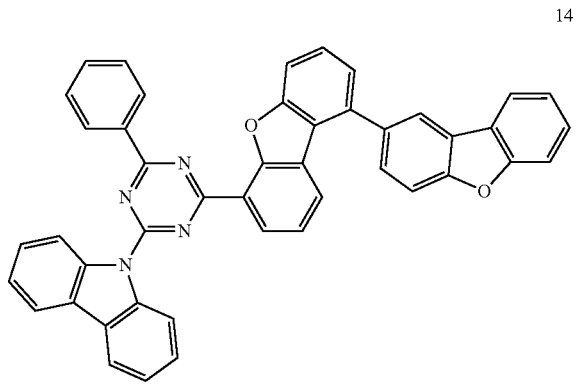

-continued
15
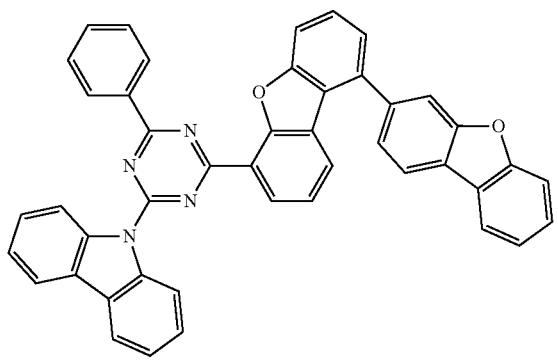
16
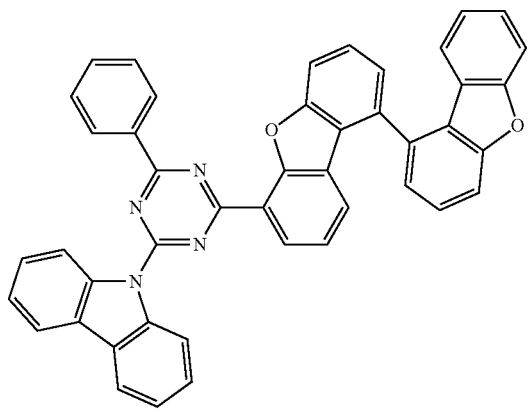
17
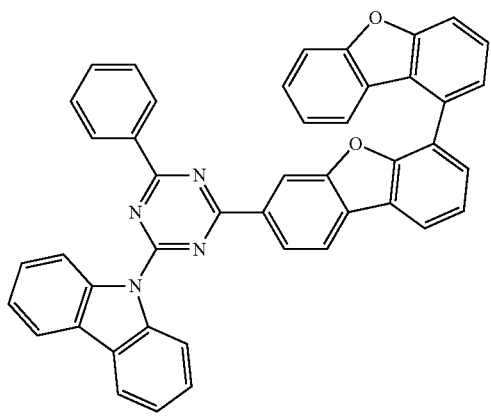
18
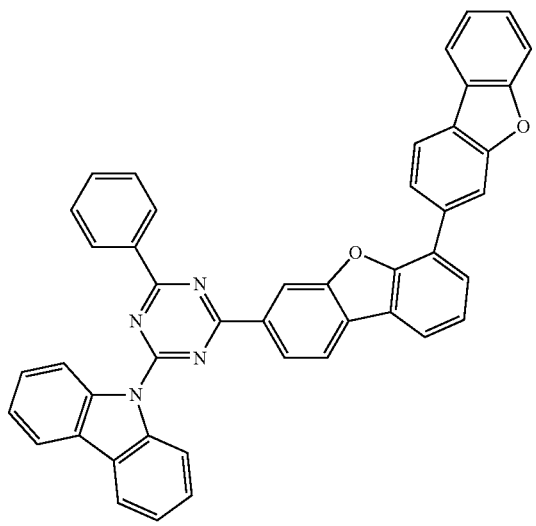
19
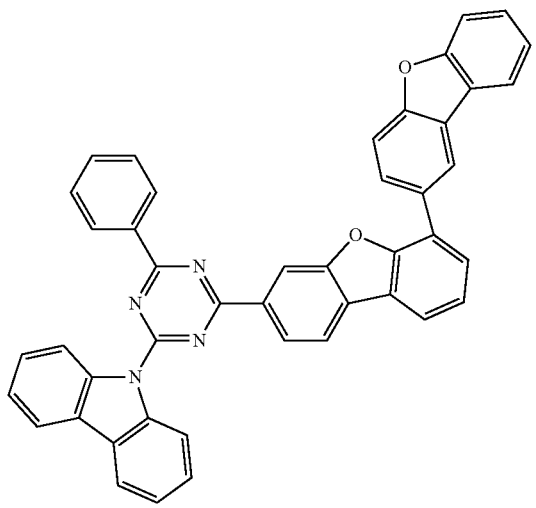
20
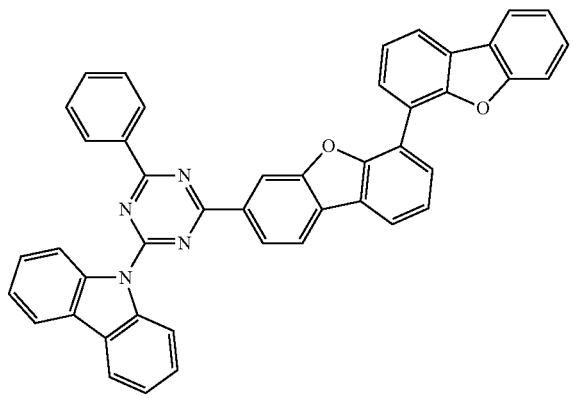

-continued
21
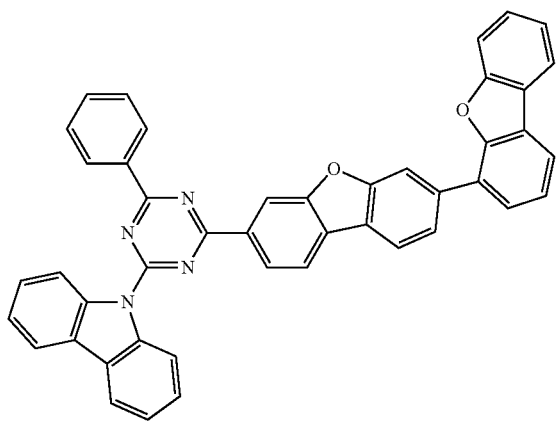
22
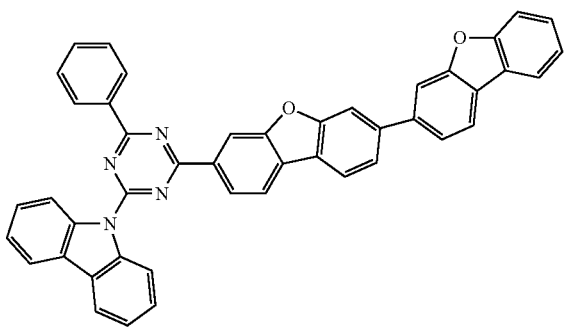
23
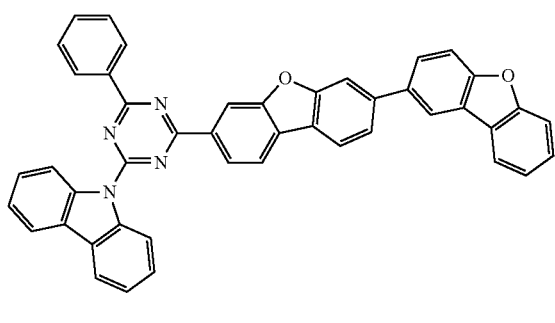
24
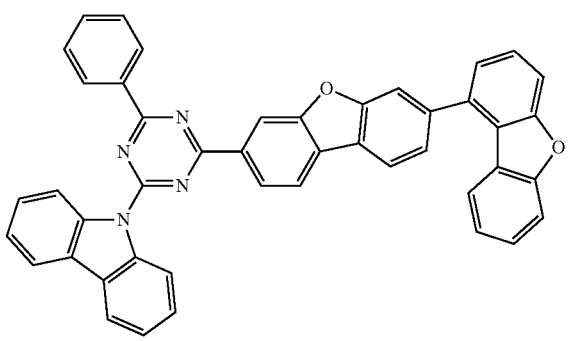
25
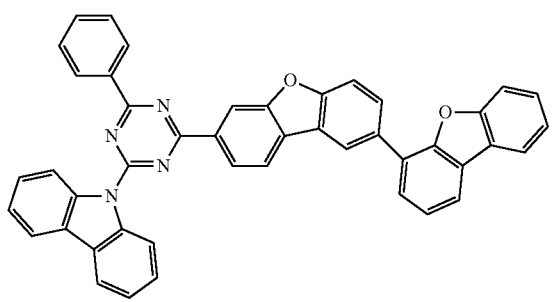
26
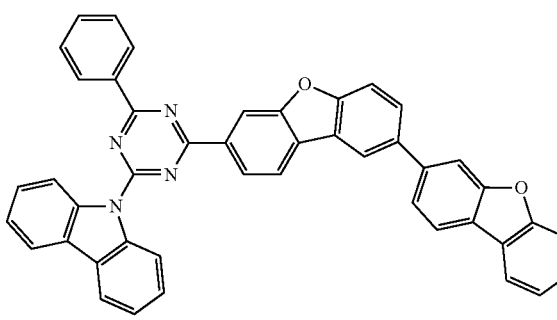
27
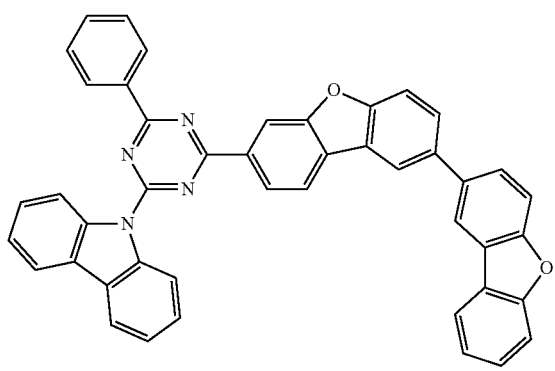
28
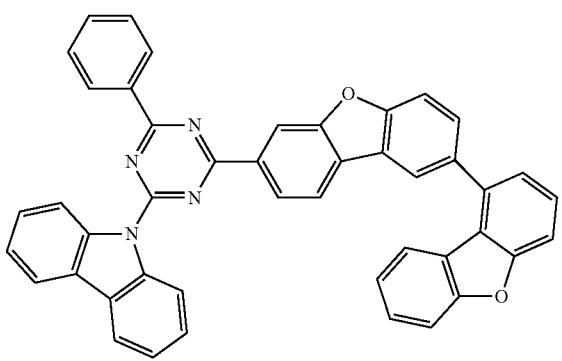

-continued
29
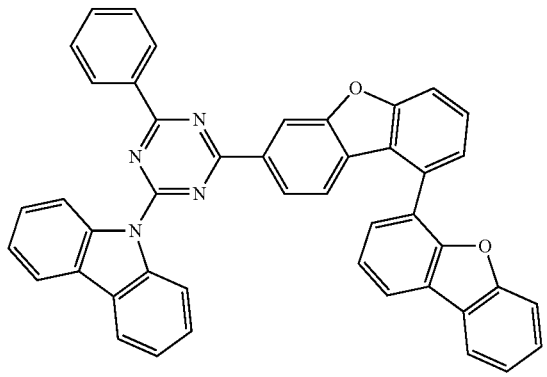
30
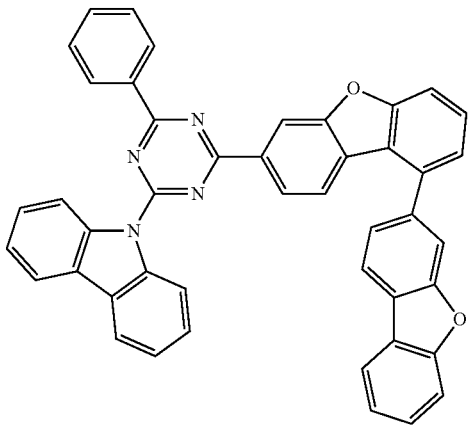
31
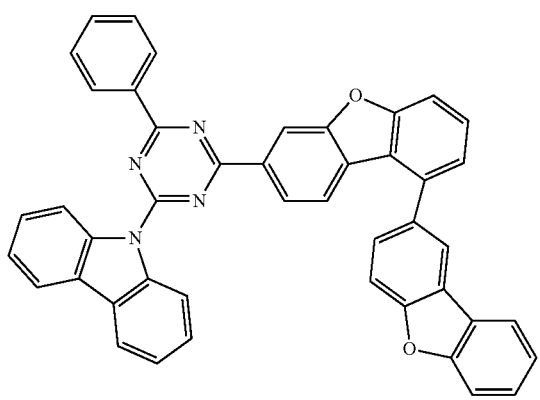
32
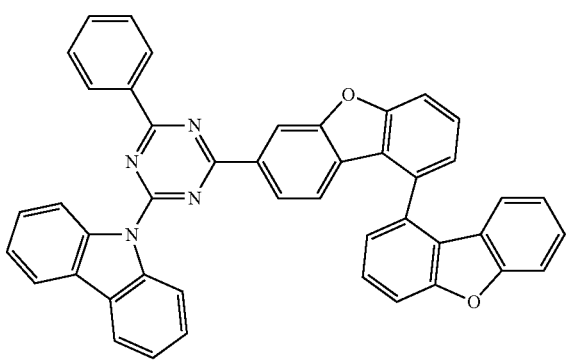
33
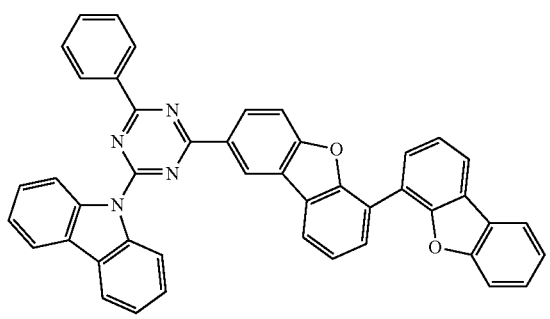
34
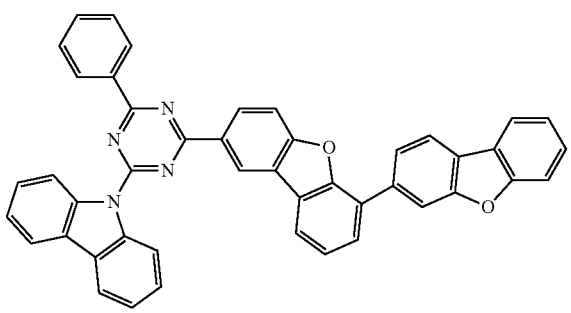
35
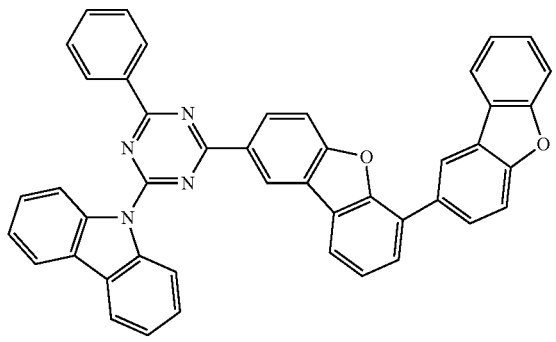
36
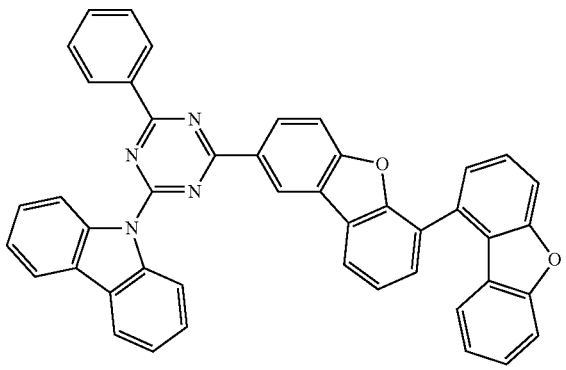

37
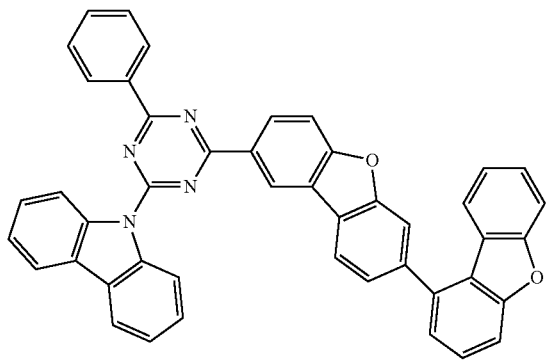
38
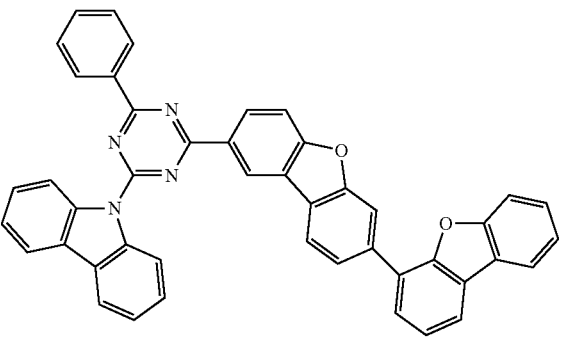
39
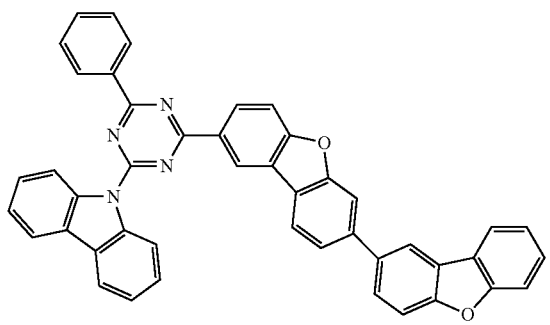
40
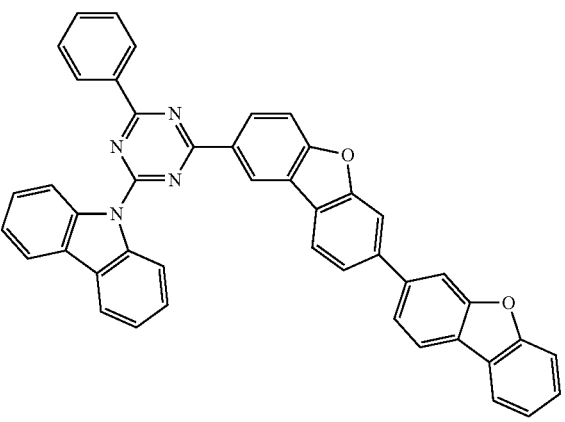
41
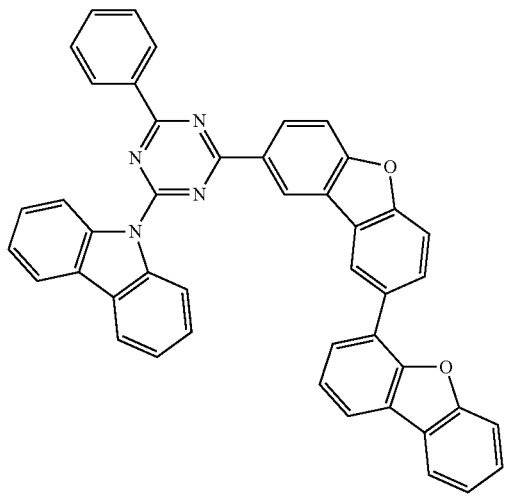
42
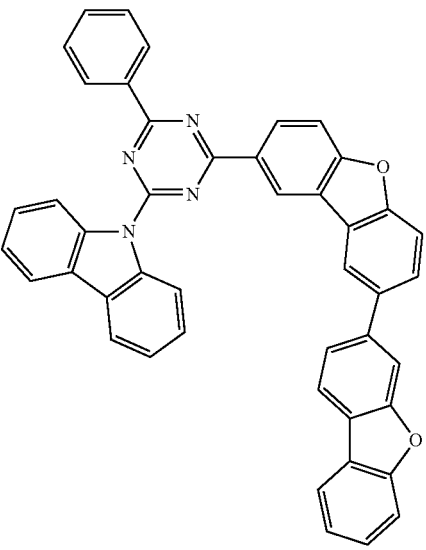

43
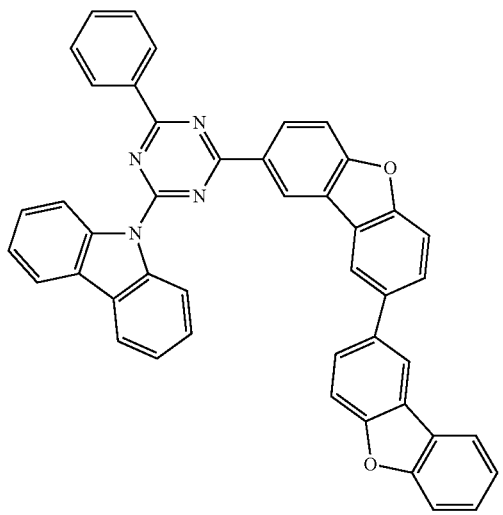
44
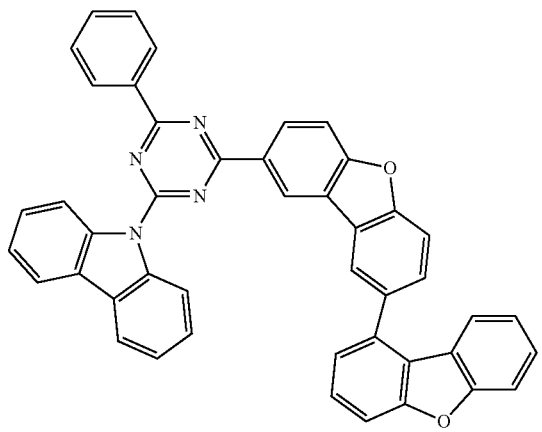
45
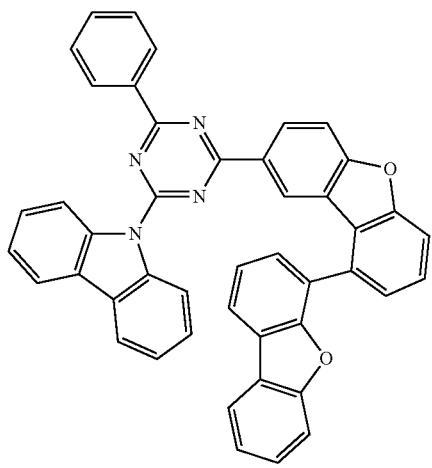
46
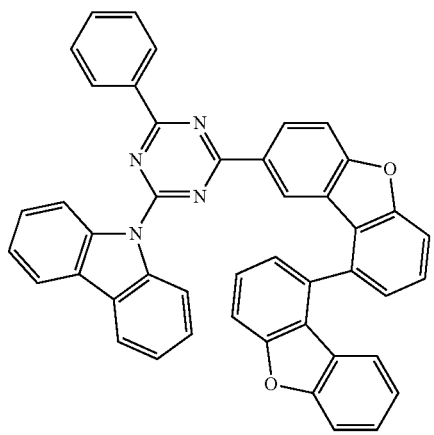
47
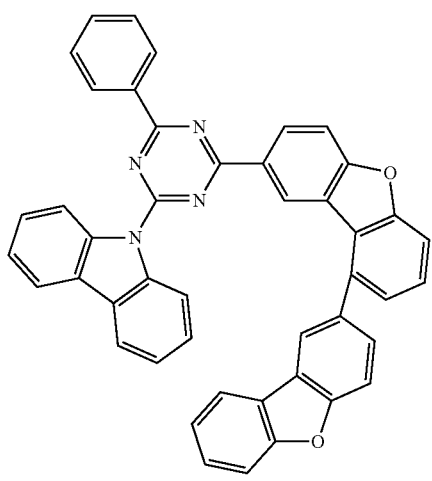
48
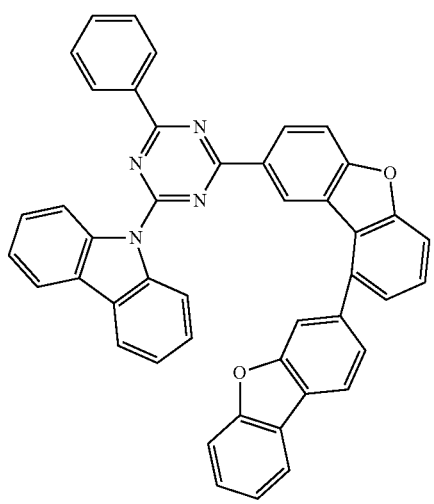

-continued
49
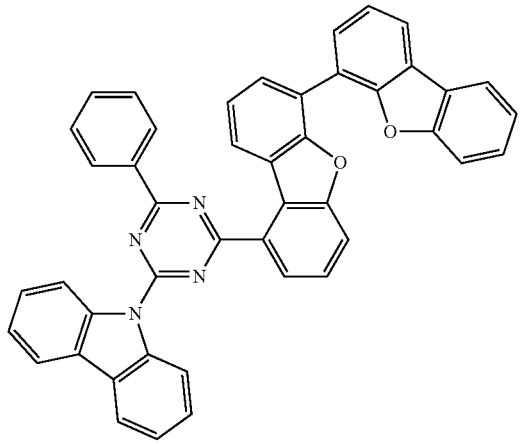
50
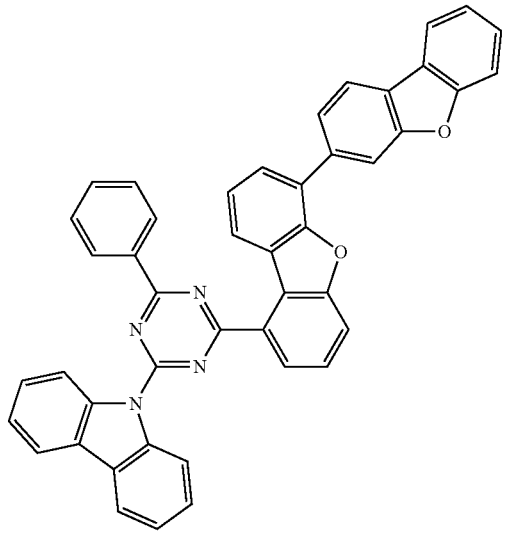
51
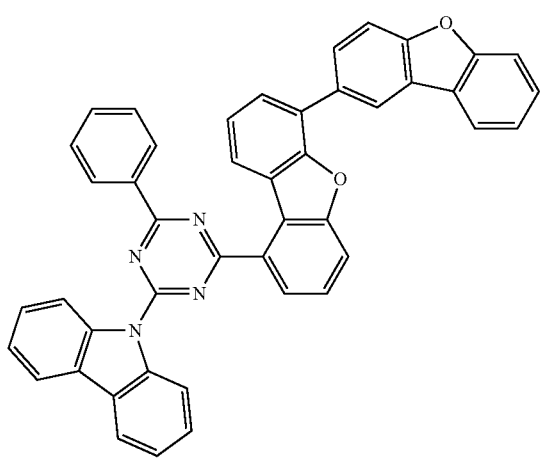
52
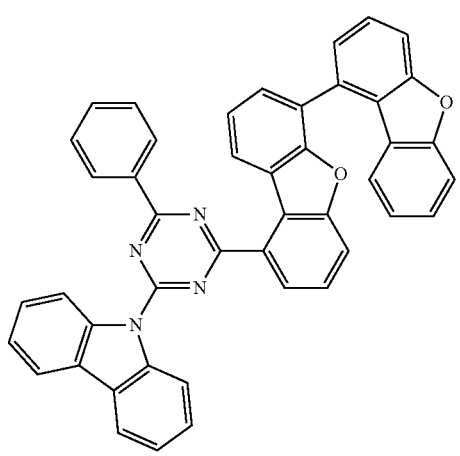
53
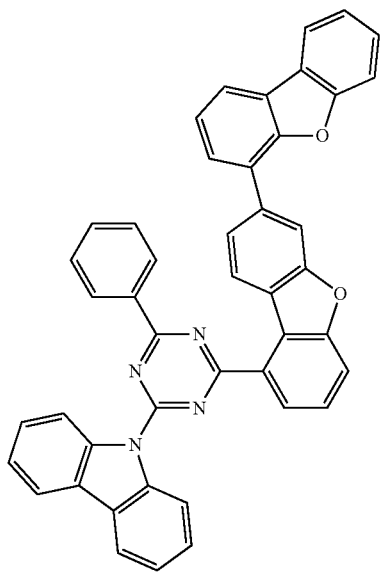
54
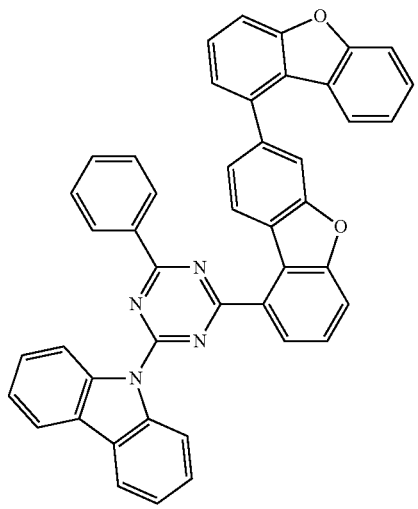

55
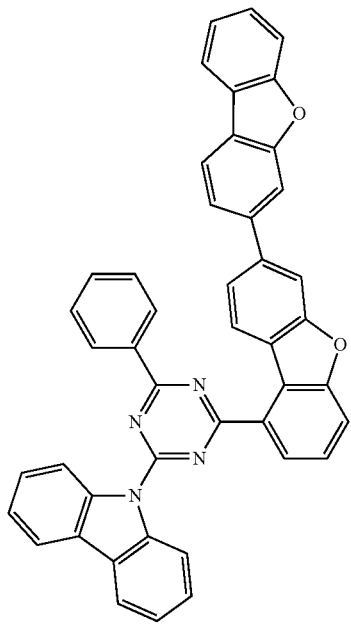
56
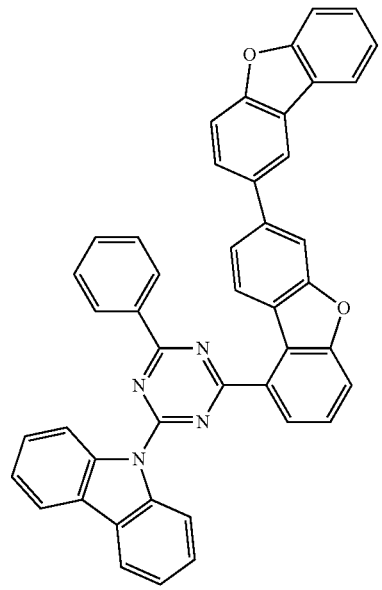
-continued
57
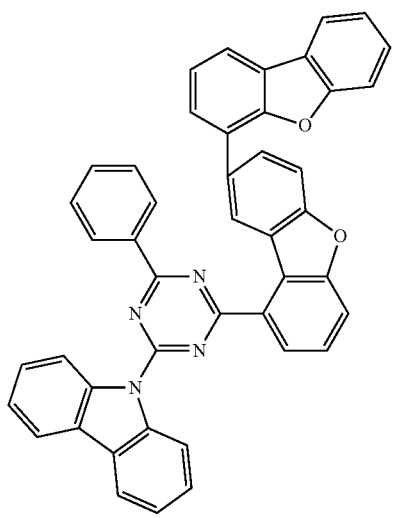
58
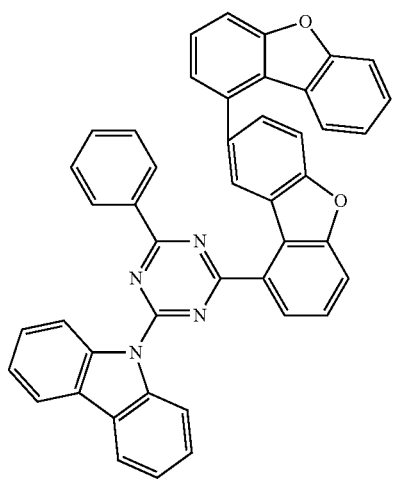

59
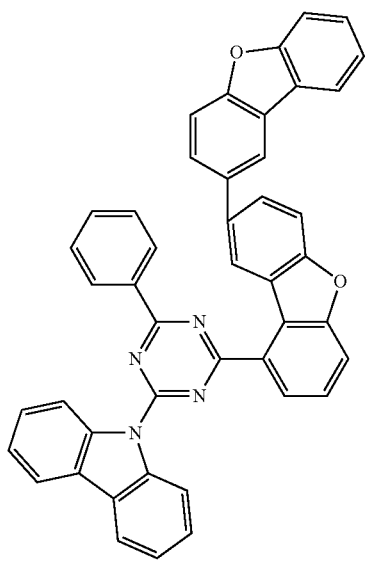
60
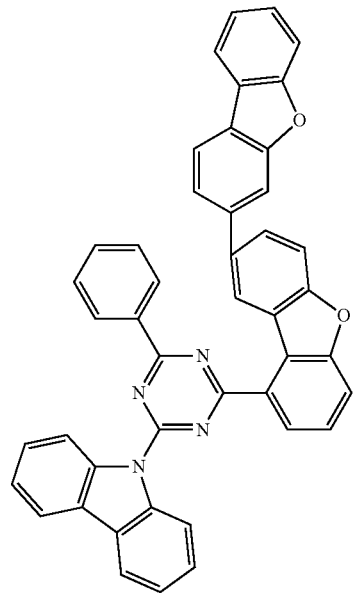
61
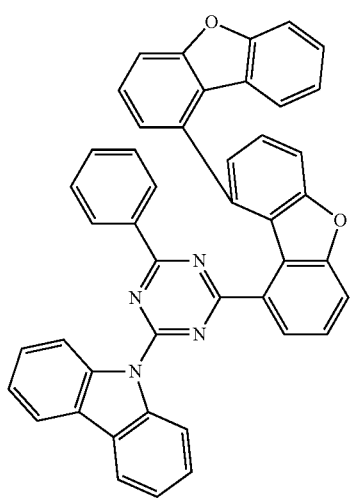
62
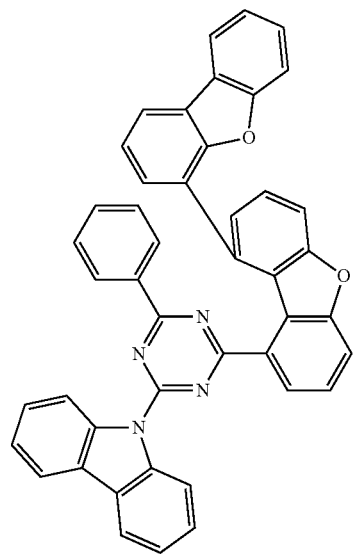

-continued
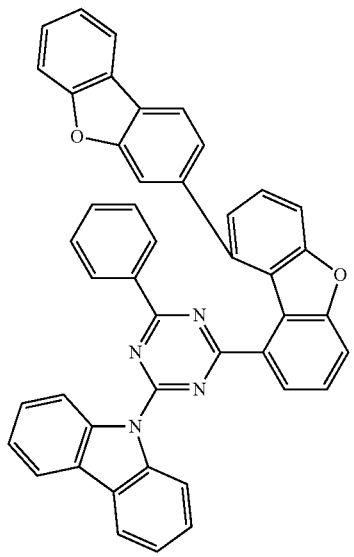
63
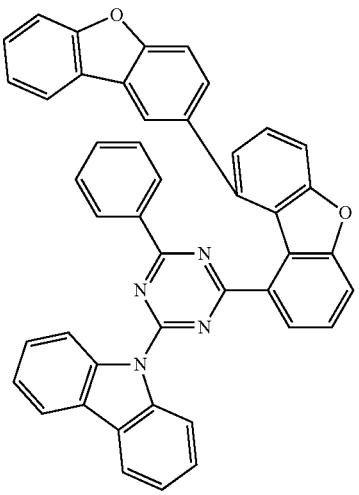
64
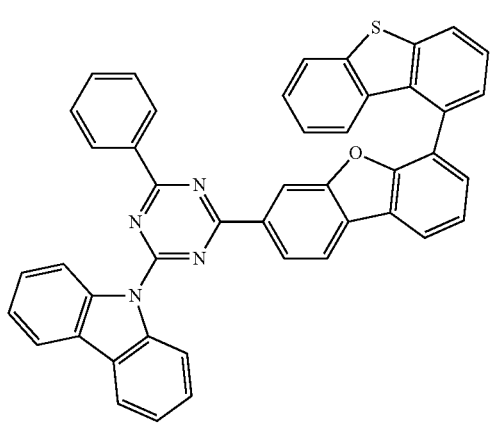
65
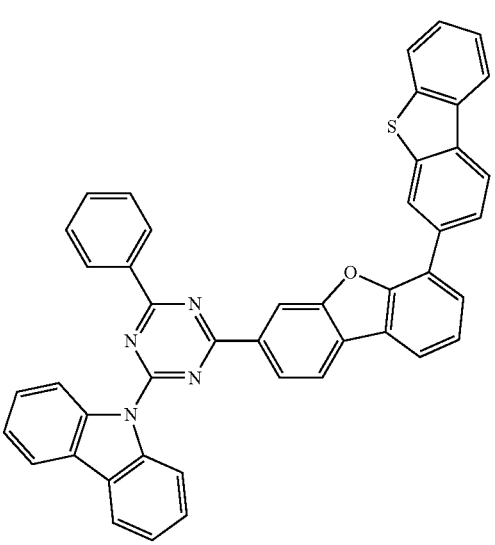
66
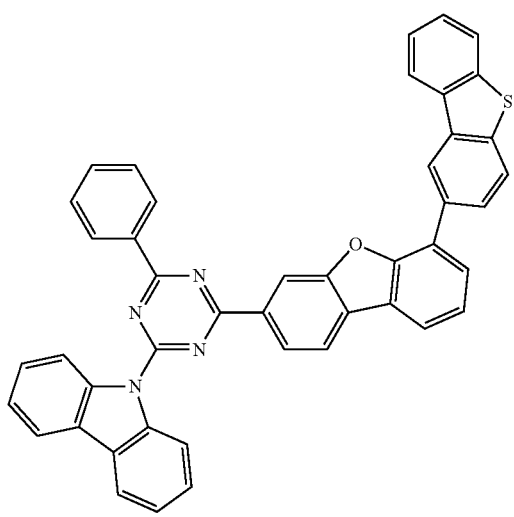
67
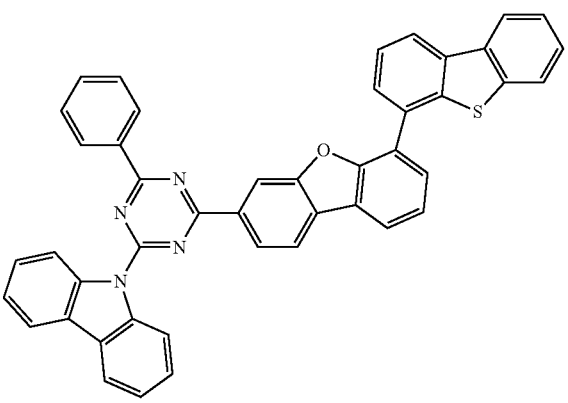
68

-continued
69
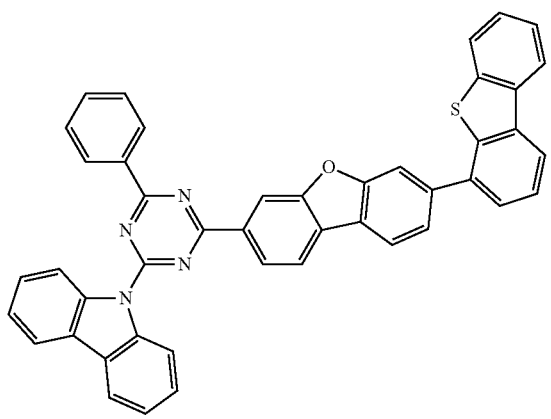
70
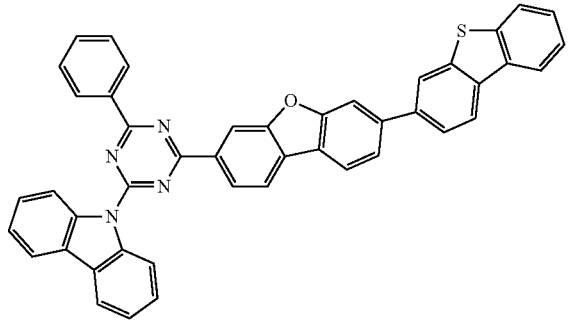
71
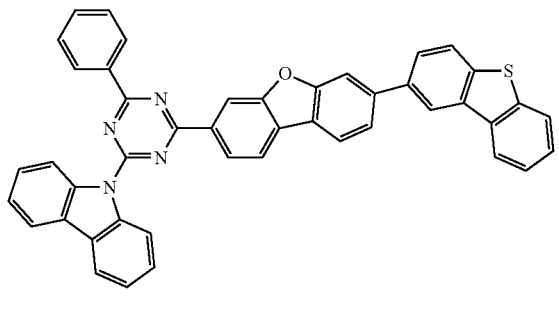
72
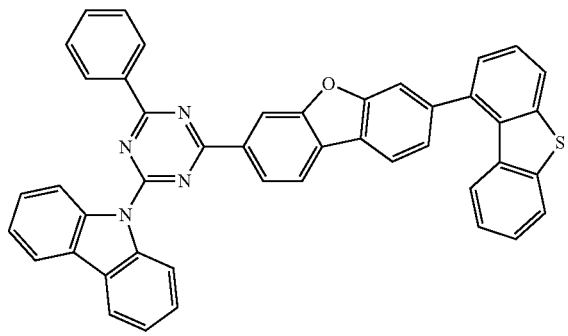
73
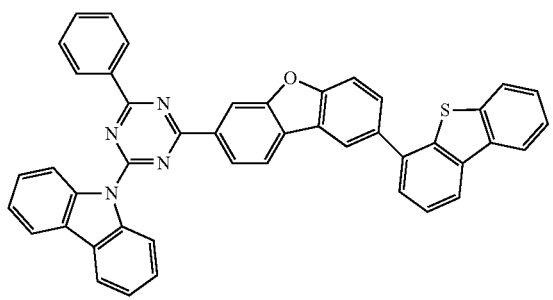
74
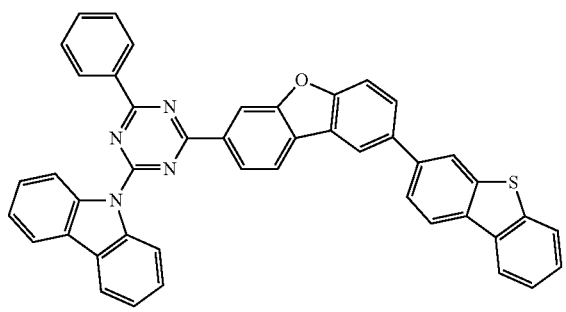
75
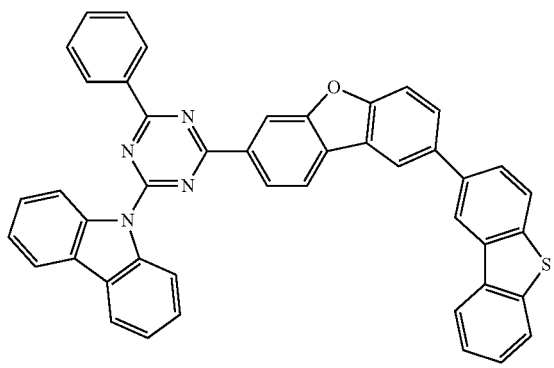
76
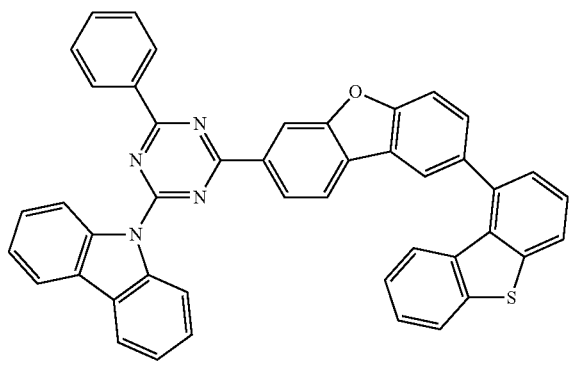

-continued
77
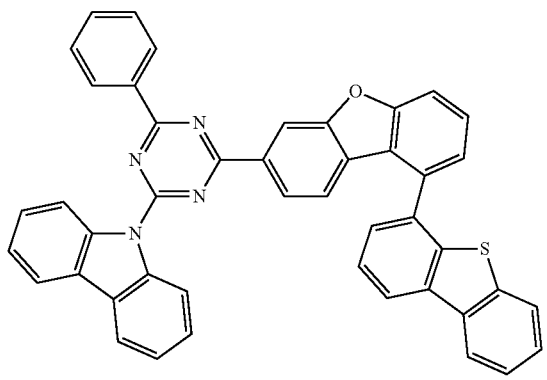
78
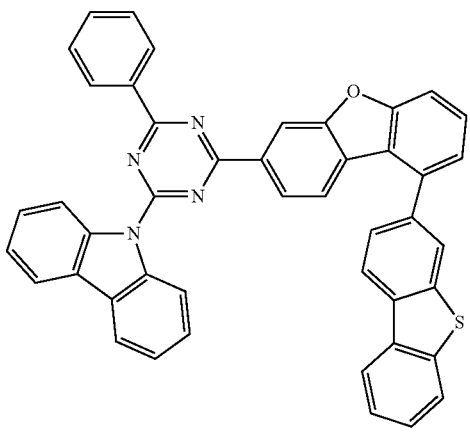
79
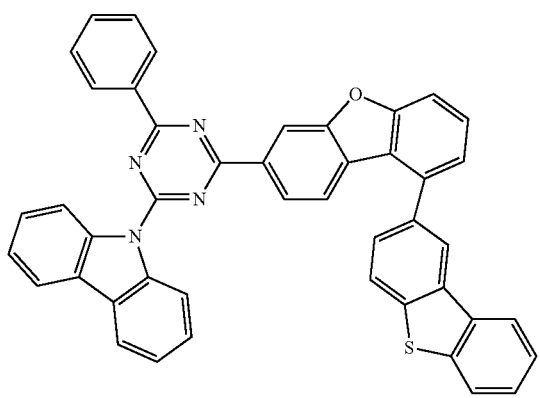
80
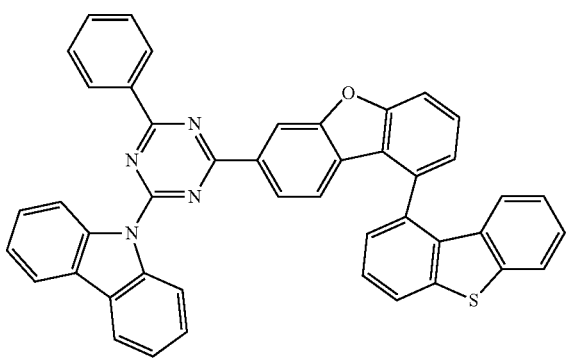
81
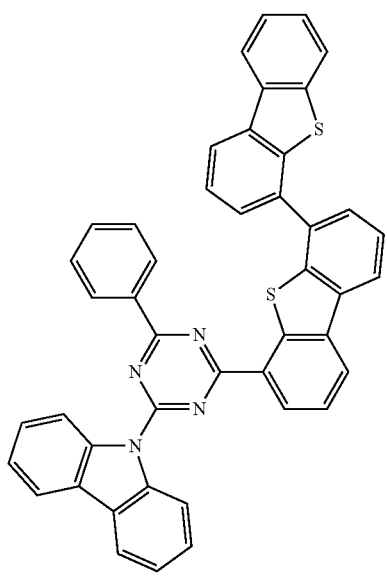
82
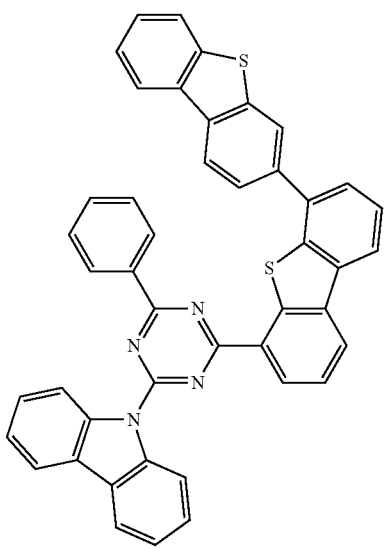

83
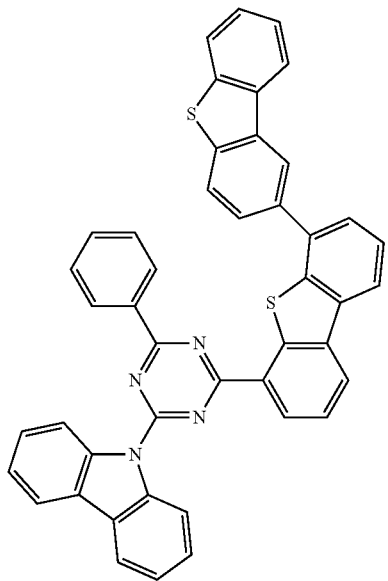
84
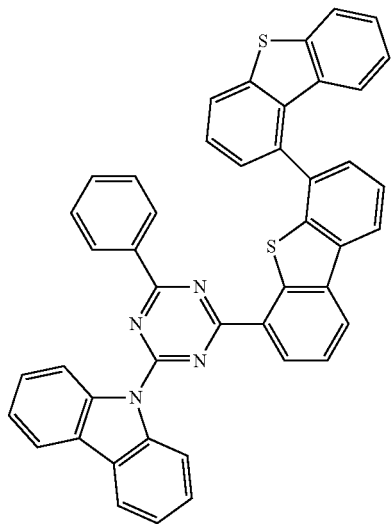
85
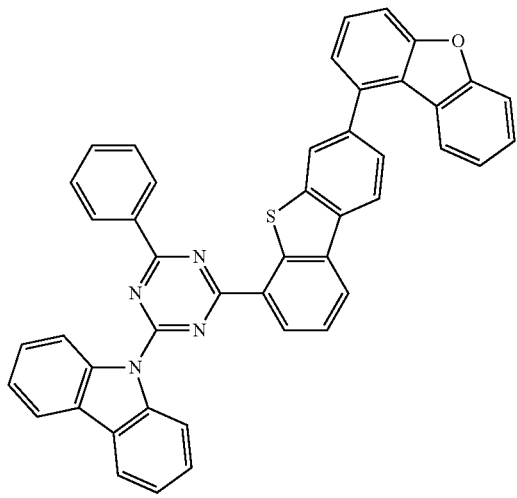
86
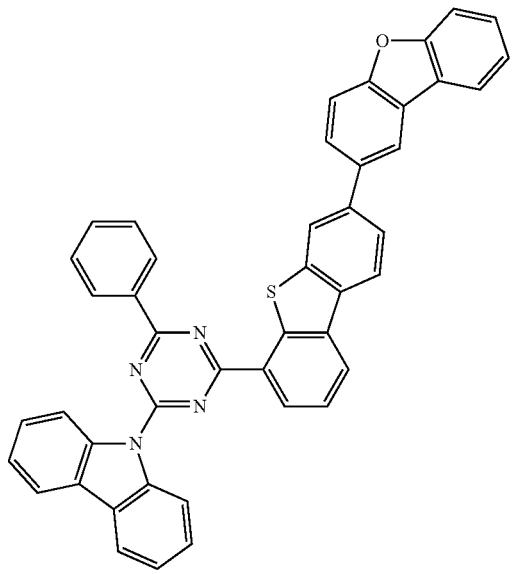

-continued
87
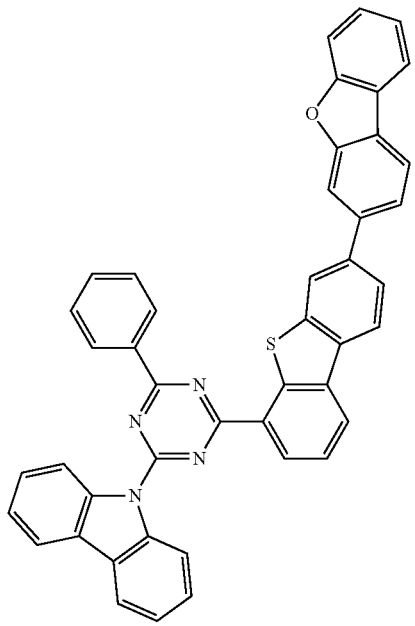
88
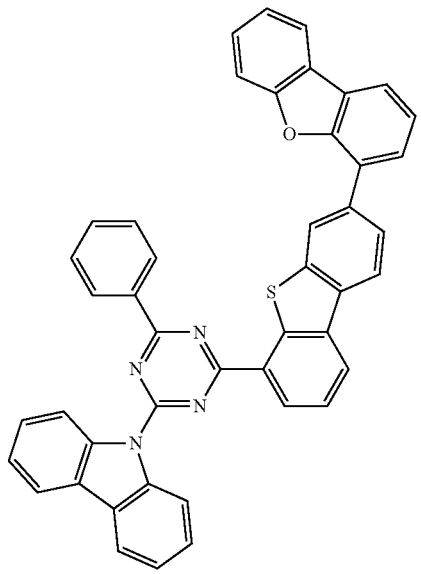
89
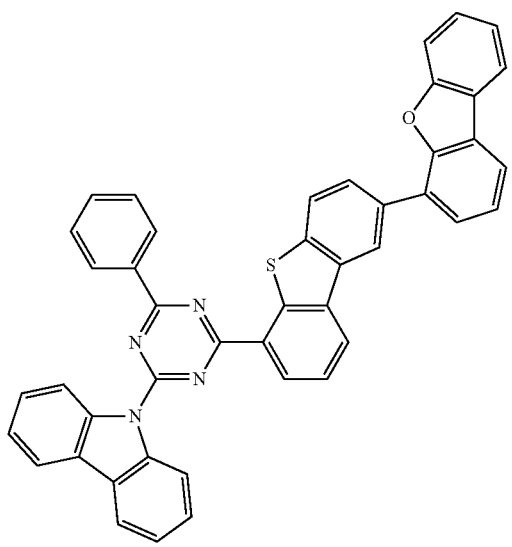
90
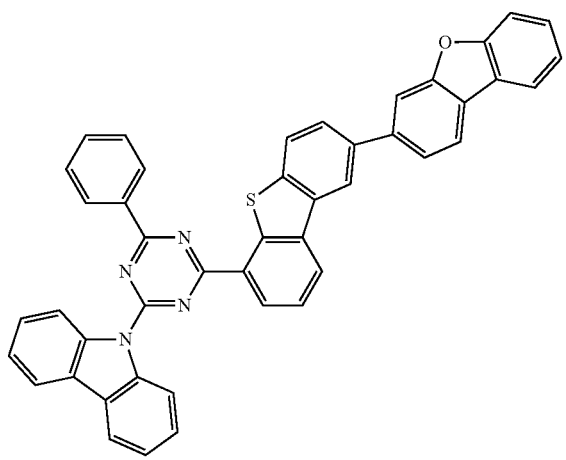
91
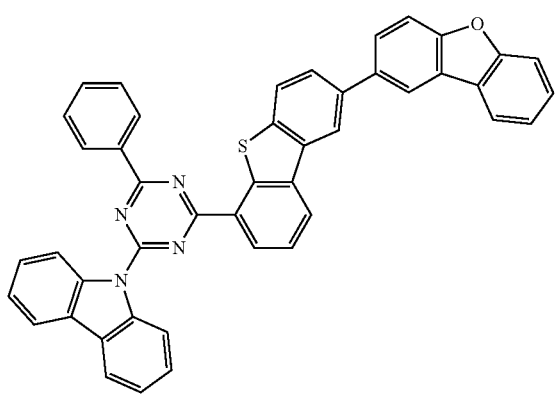
92
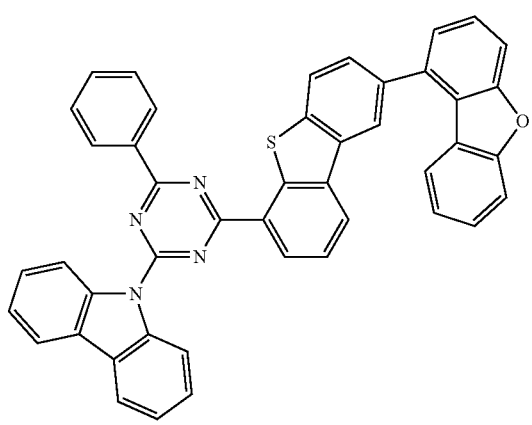

-continued
93
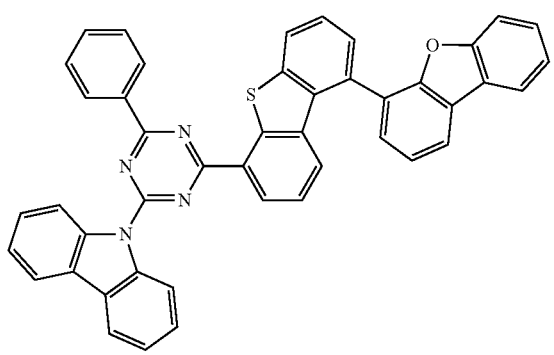
94
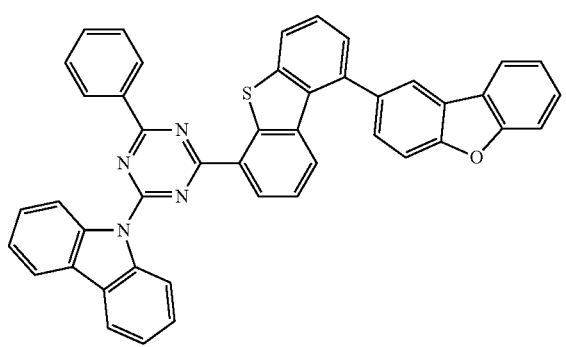
95
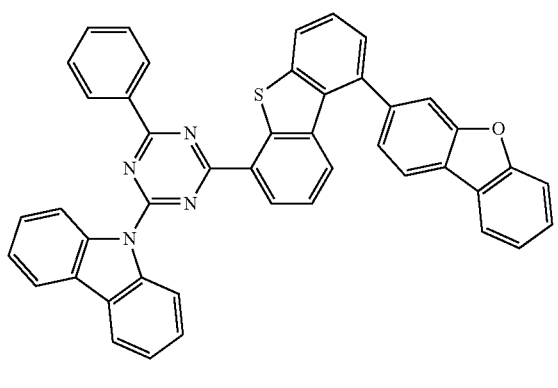
96
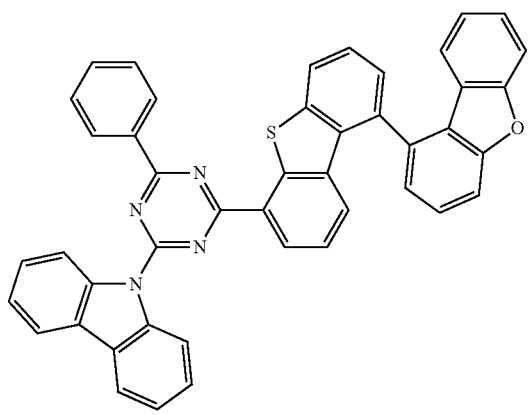
97
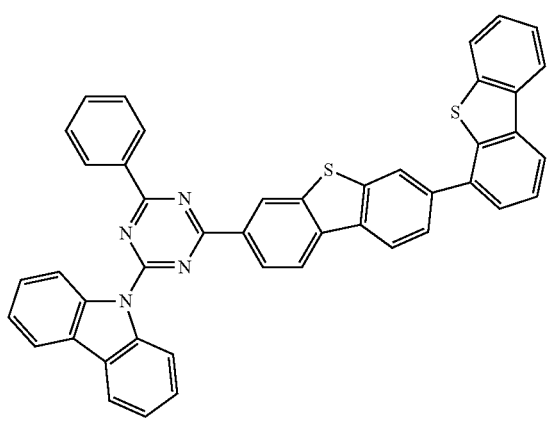
98
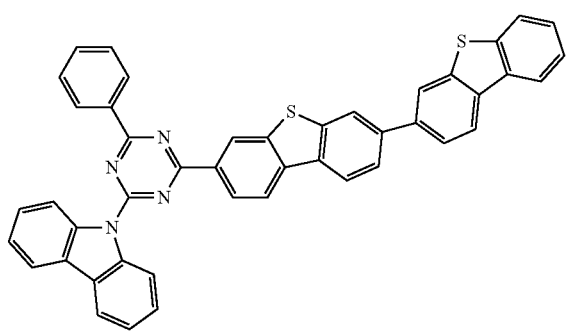
99
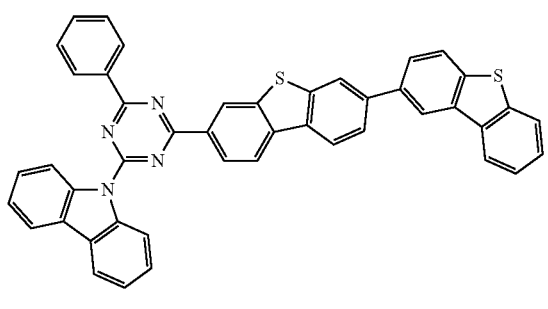
100
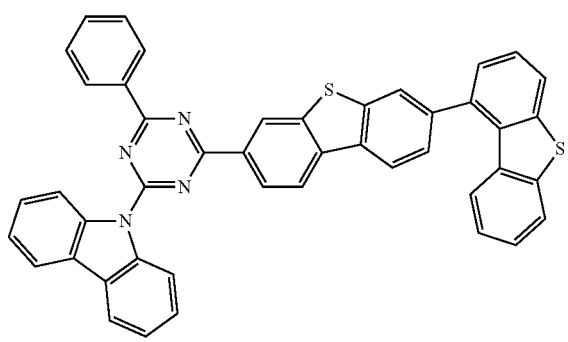

-continued
101
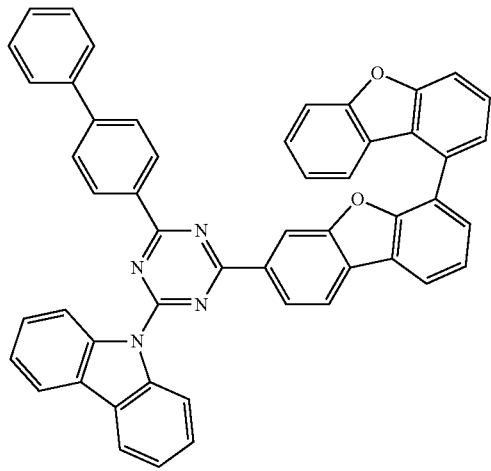
102
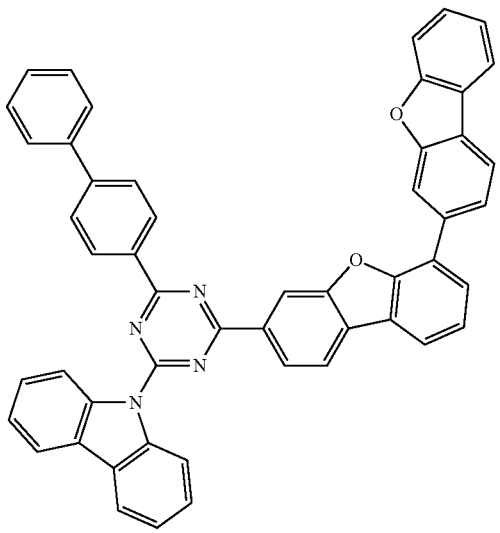
103
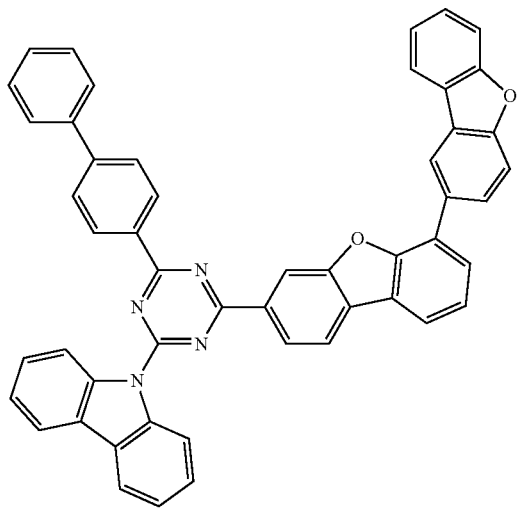
104
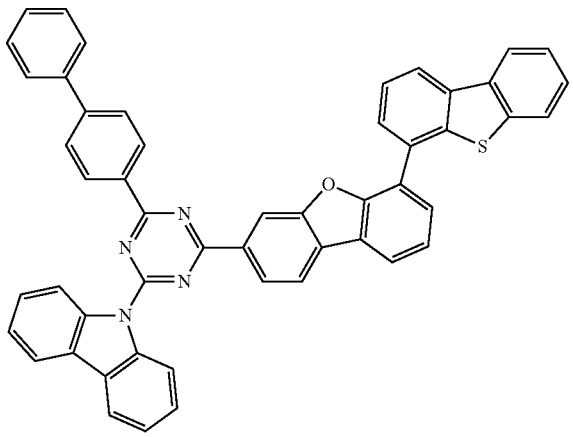
105
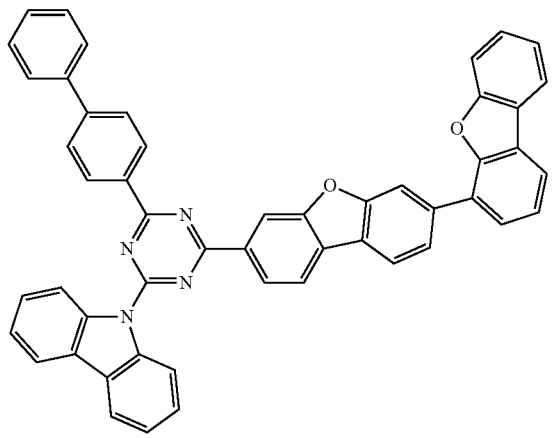
106
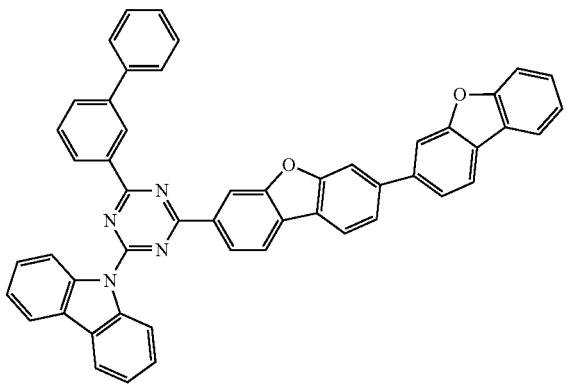

107
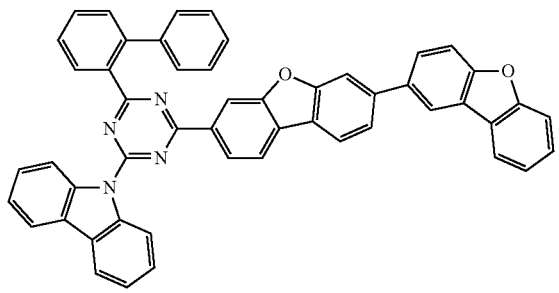
108
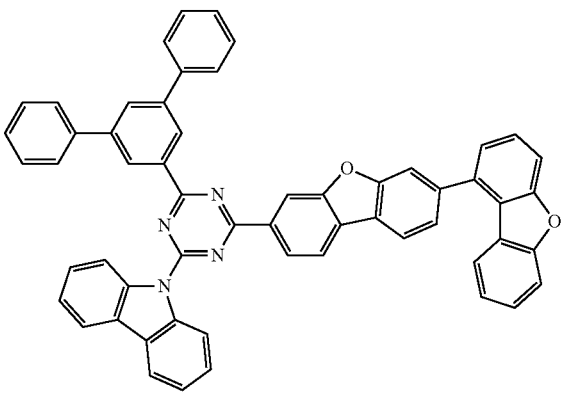
109
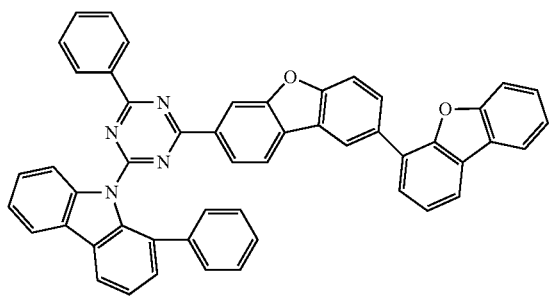
110
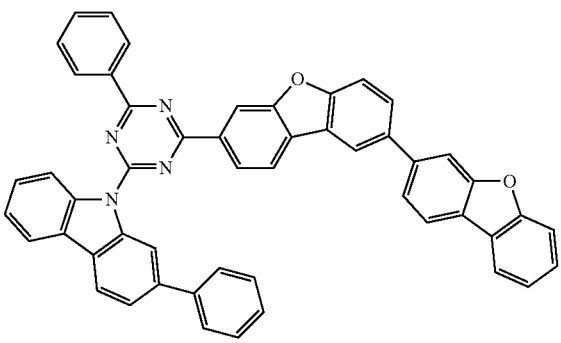
111
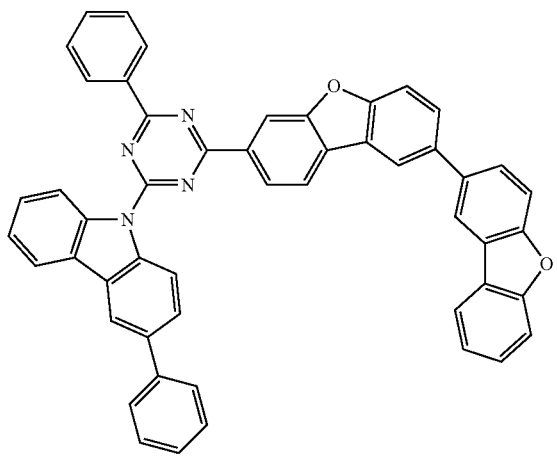
112
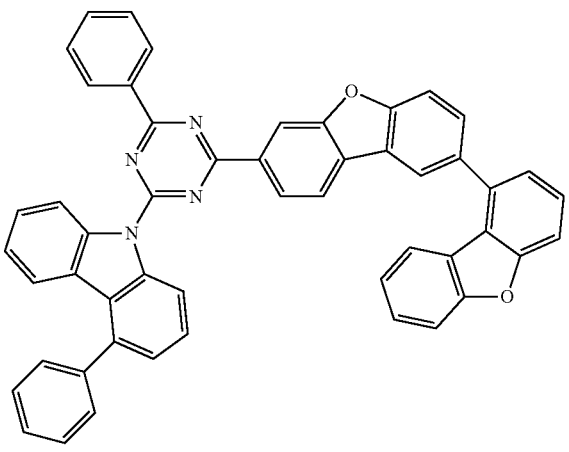

-continued
113
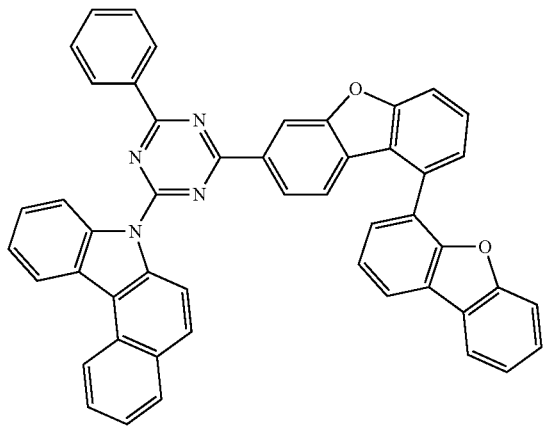
114
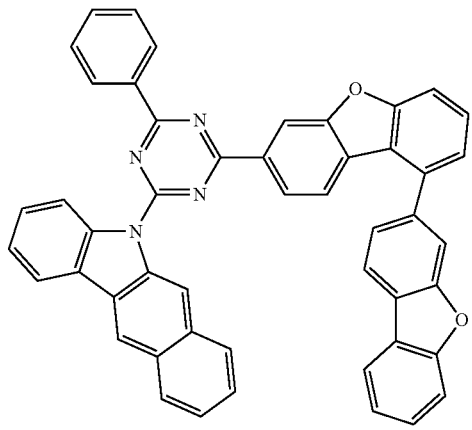
115
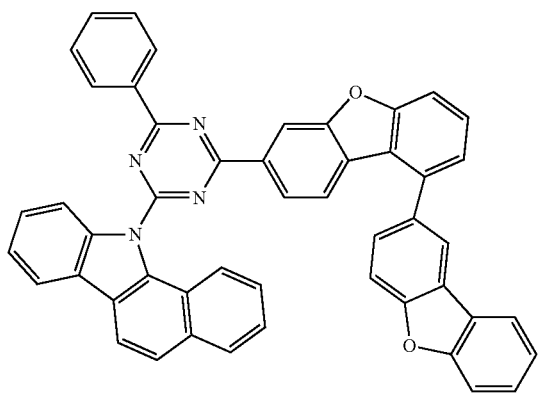
116
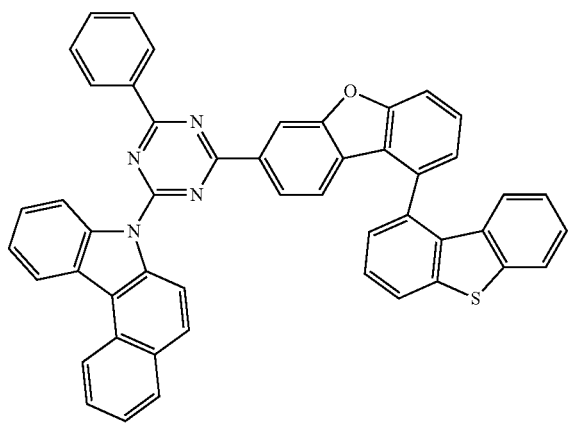
117
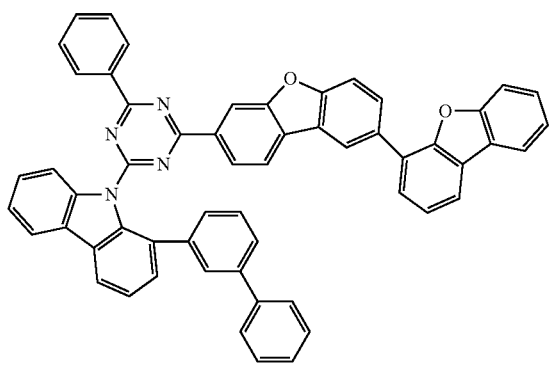
118
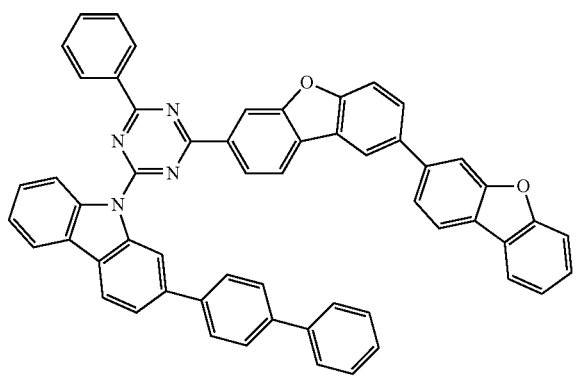

-continued
119
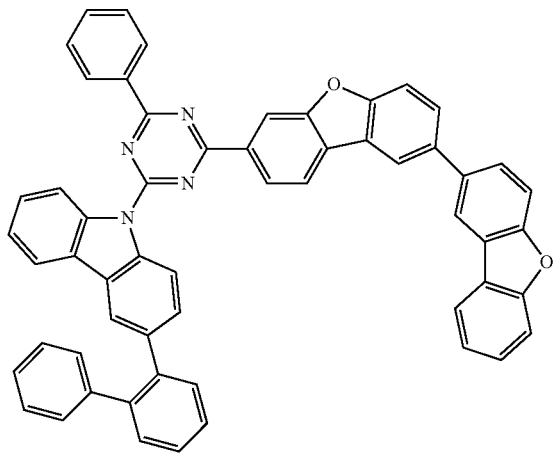
120
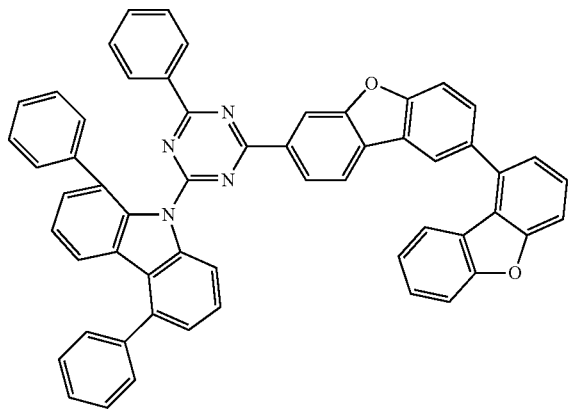
121
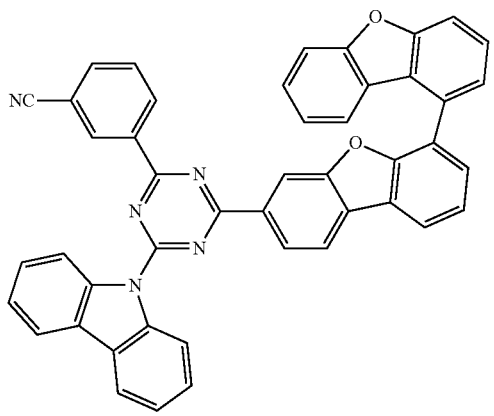
122
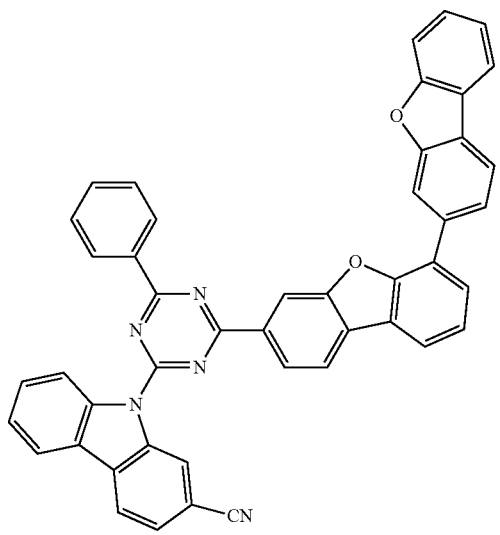
123
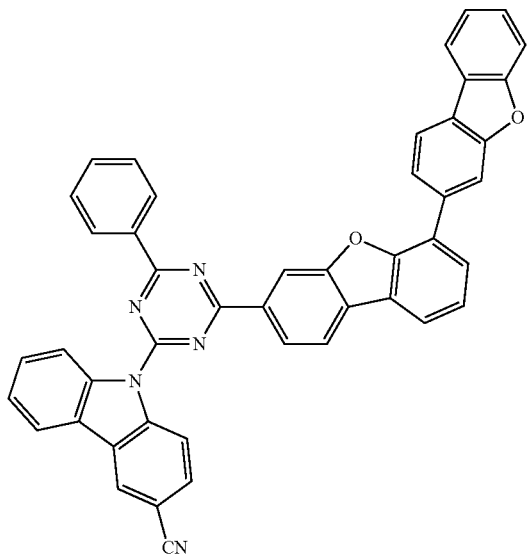
124
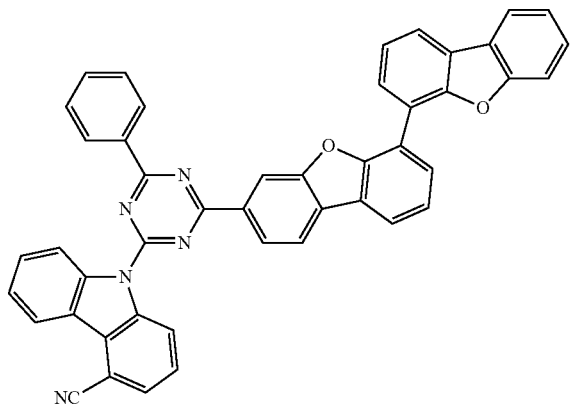

-continued
125
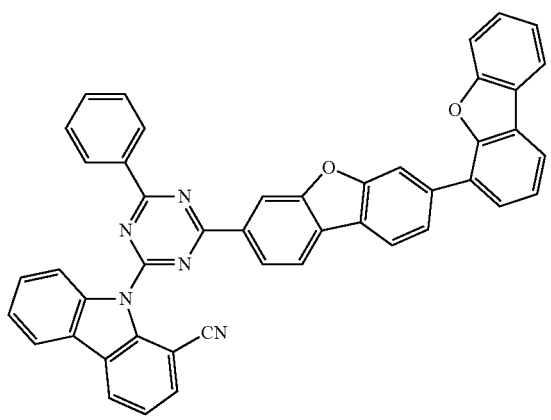
126
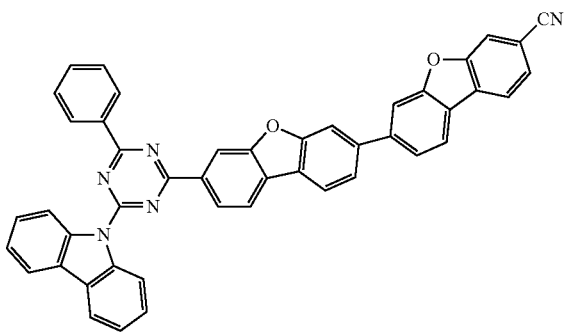
127
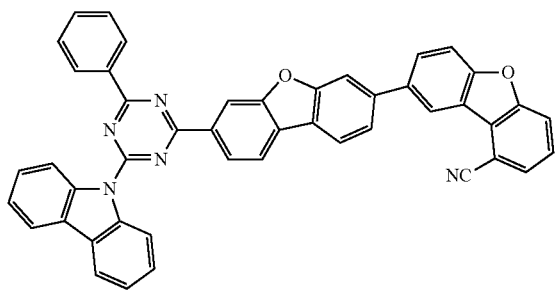
128
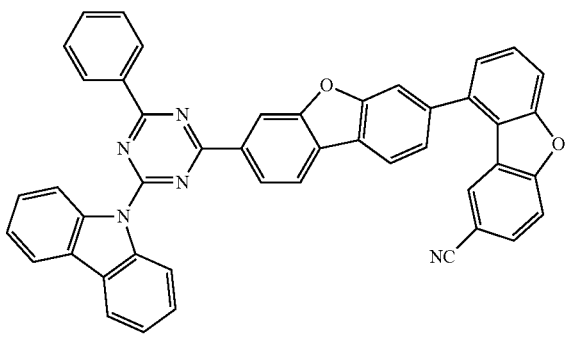
129
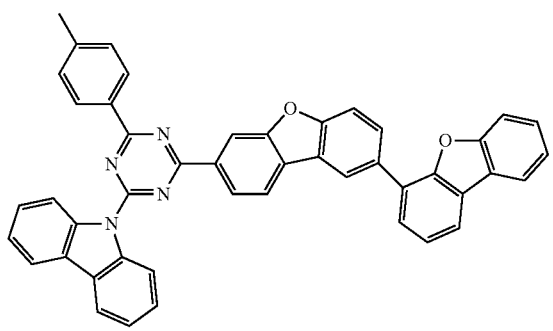
130
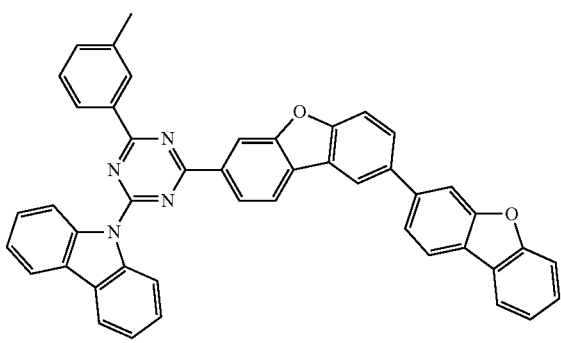
131
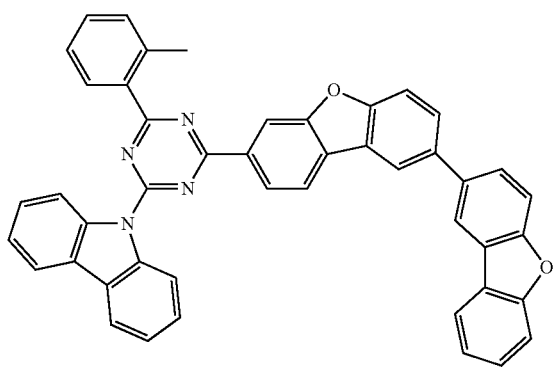
132
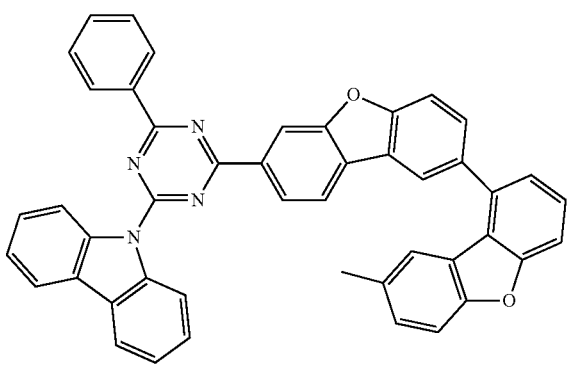

133
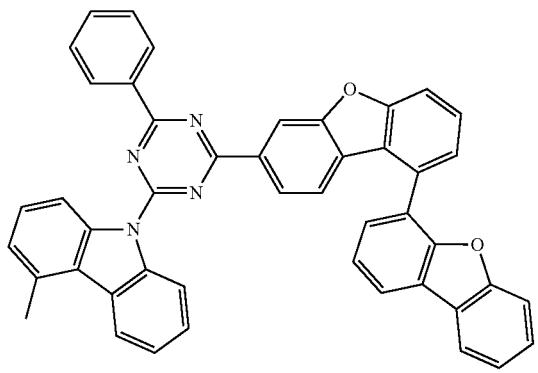
134
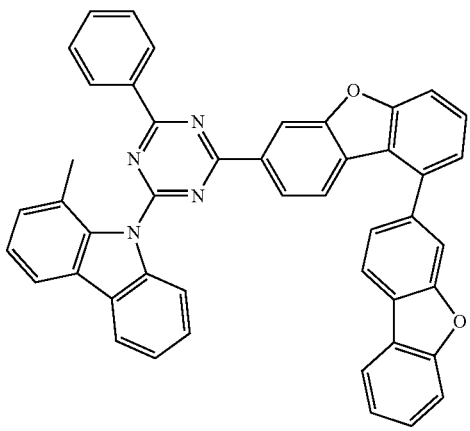
135
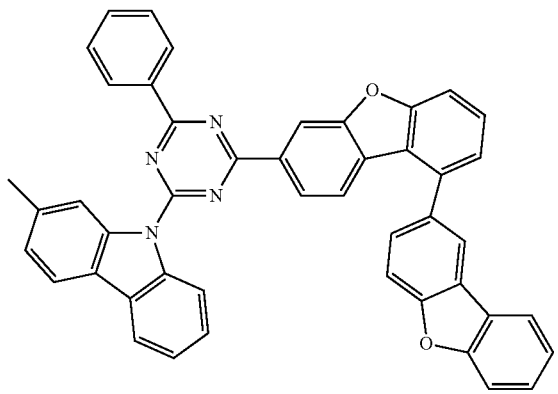
136
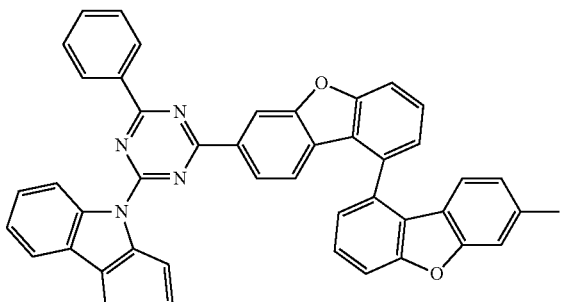
137
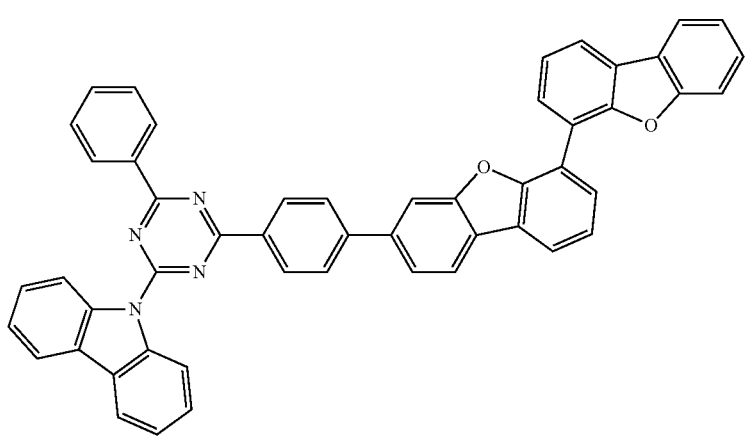

-continued
138
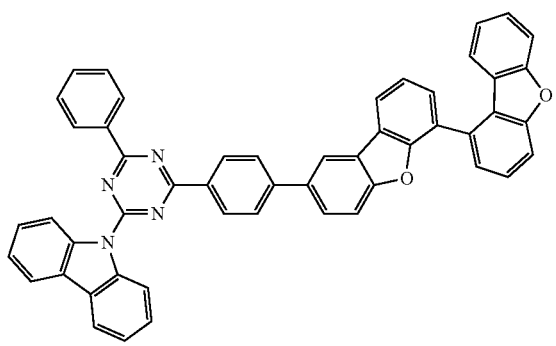
139
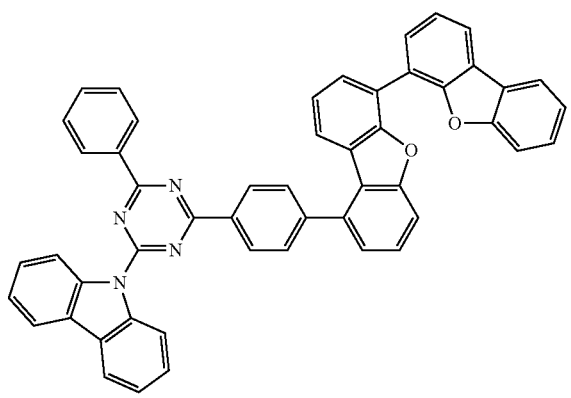
140
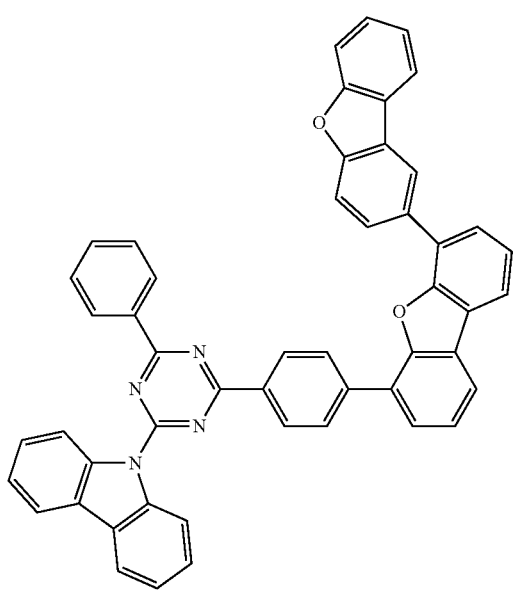
141
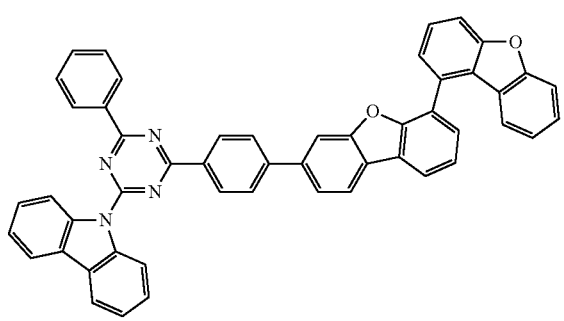
142
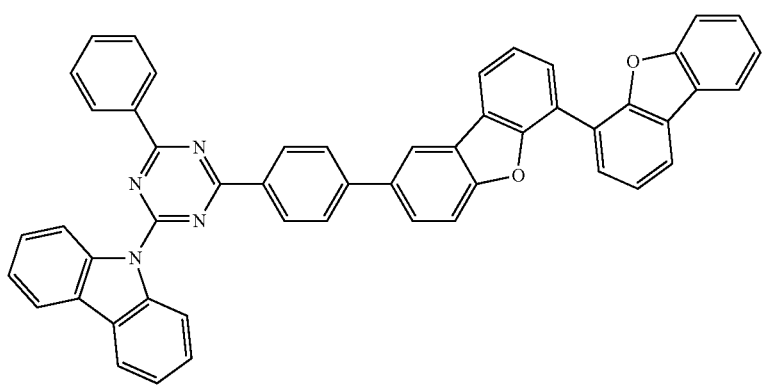

143
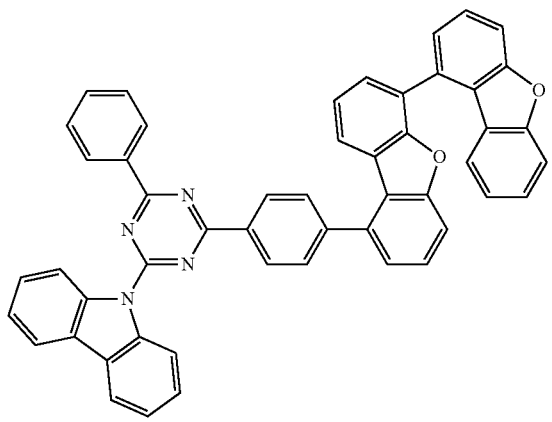
144
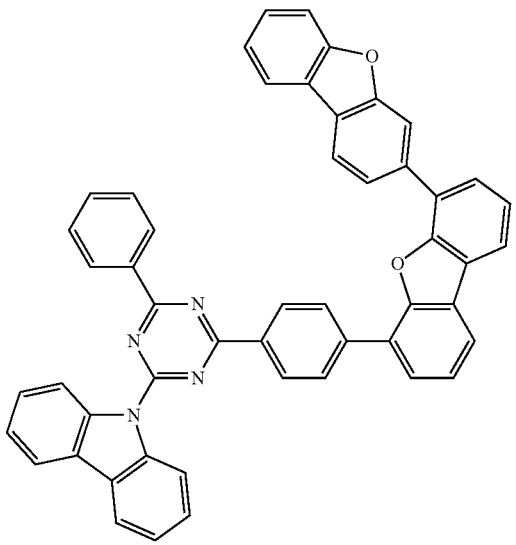
145
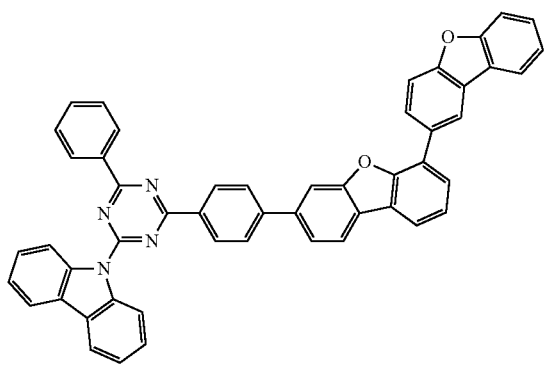
146
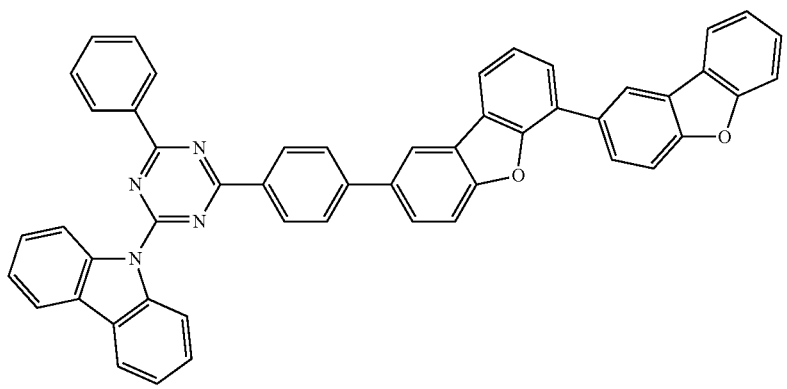

-continued
147
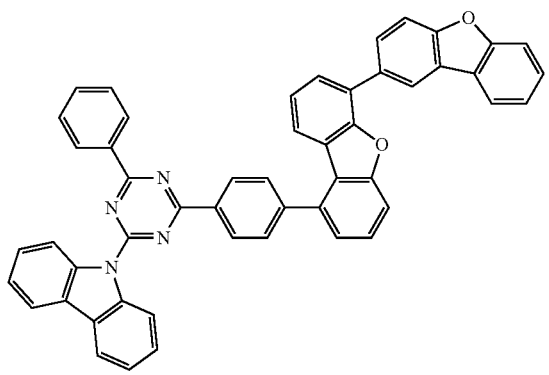
148
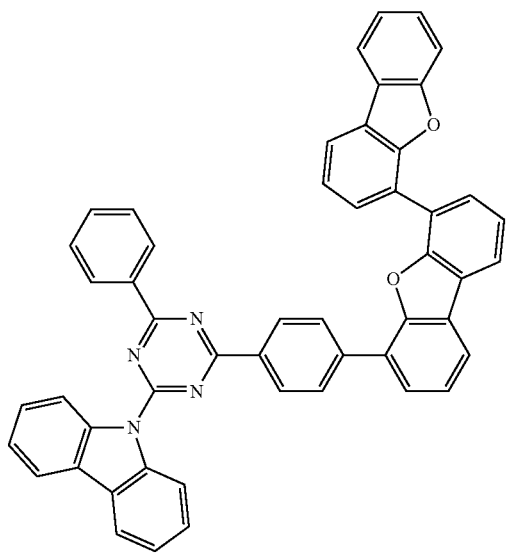
149
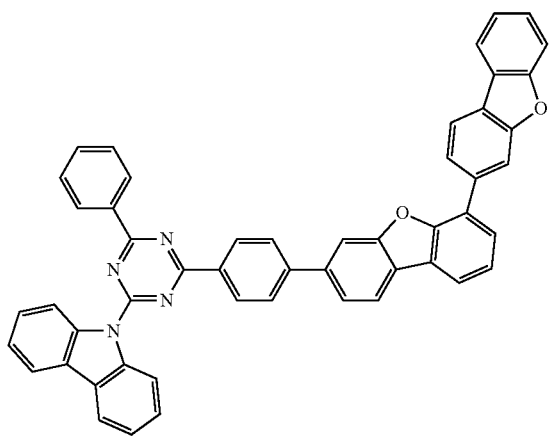
150
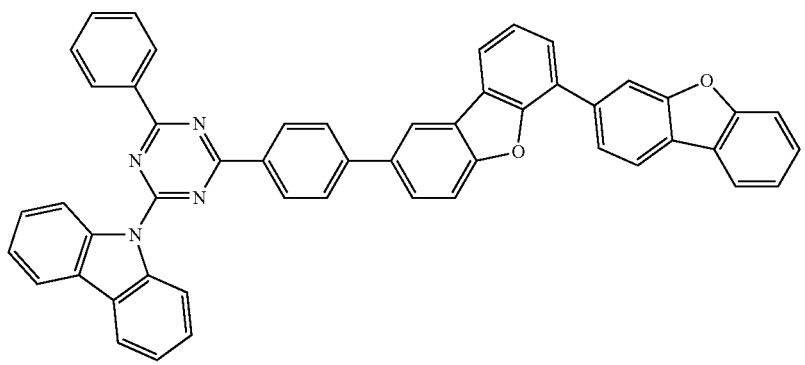

-continued
151
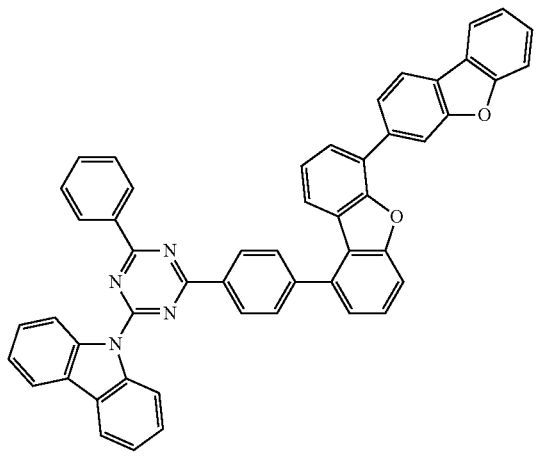
152
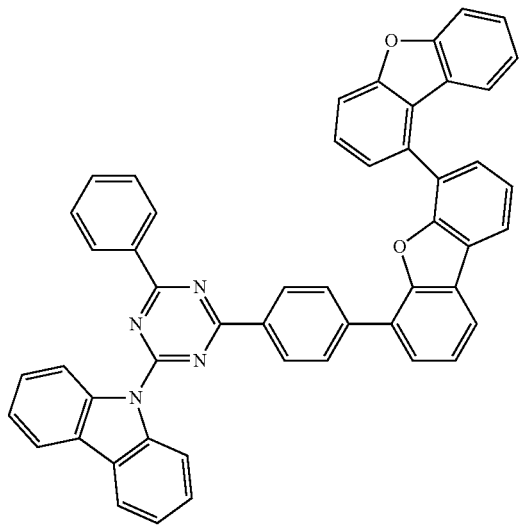
153
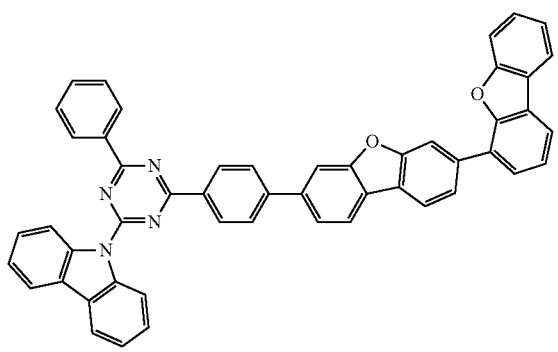
154
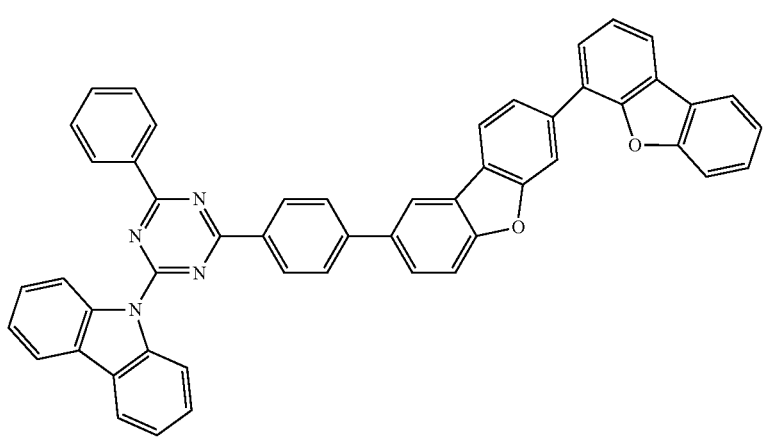

-continued
155
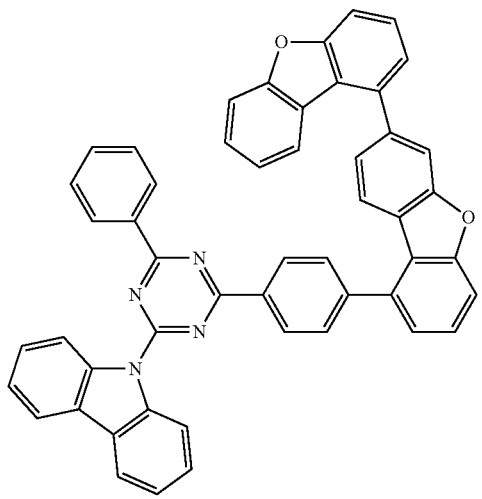
156
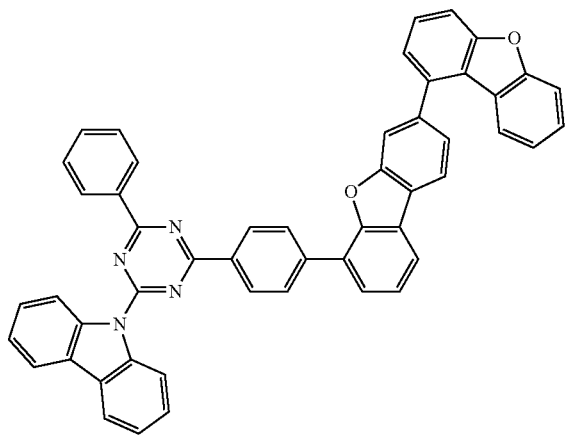
157
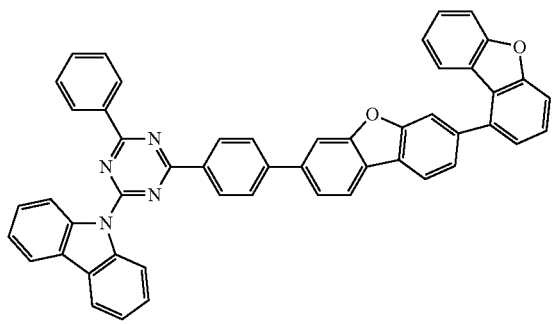
158
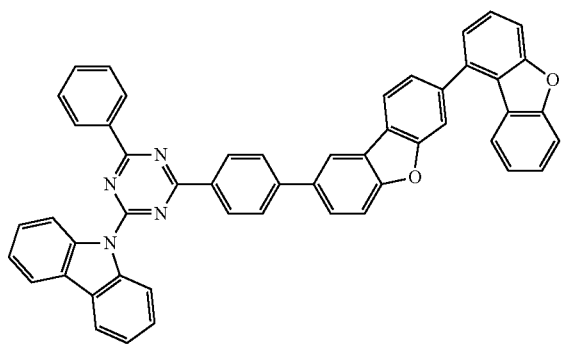
159
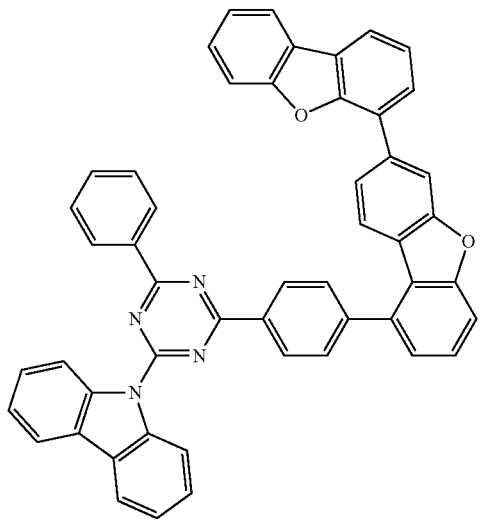
160
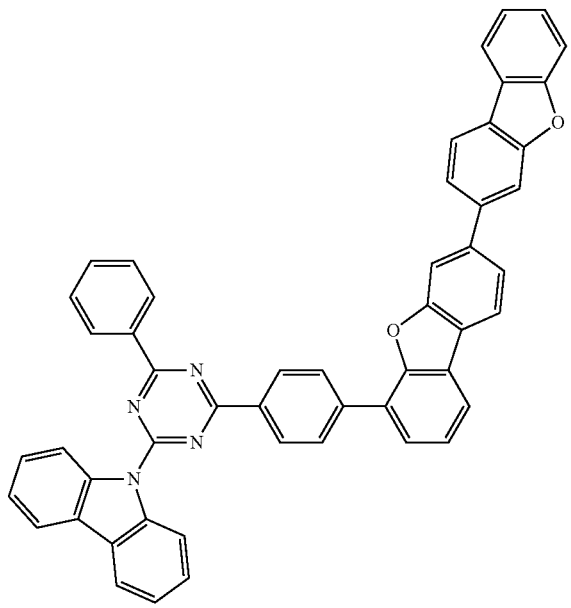

161
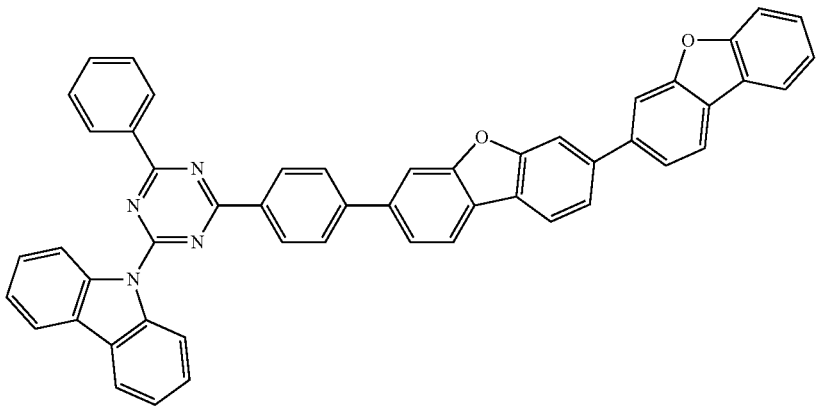
162
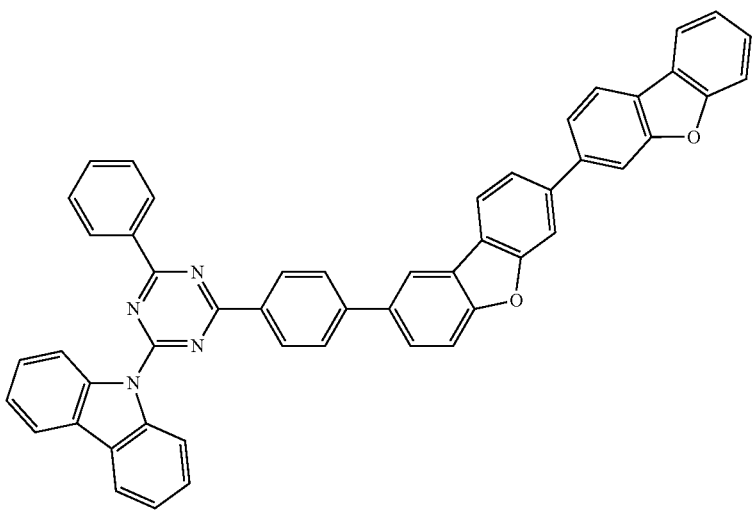
163
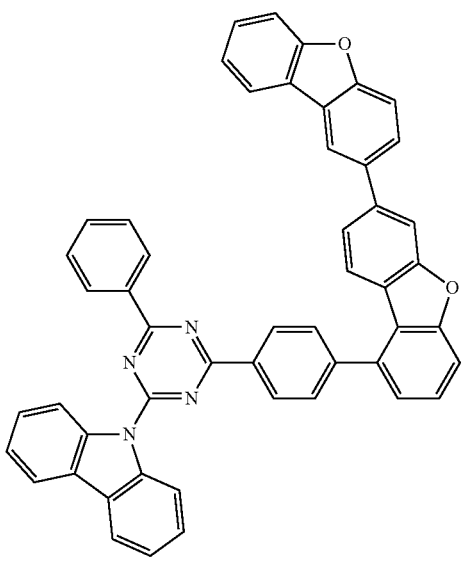
164
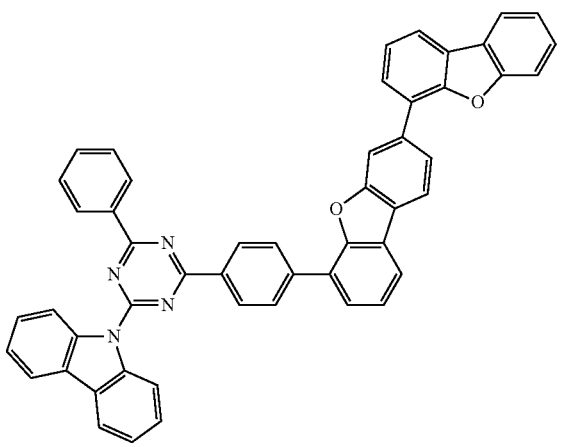

165
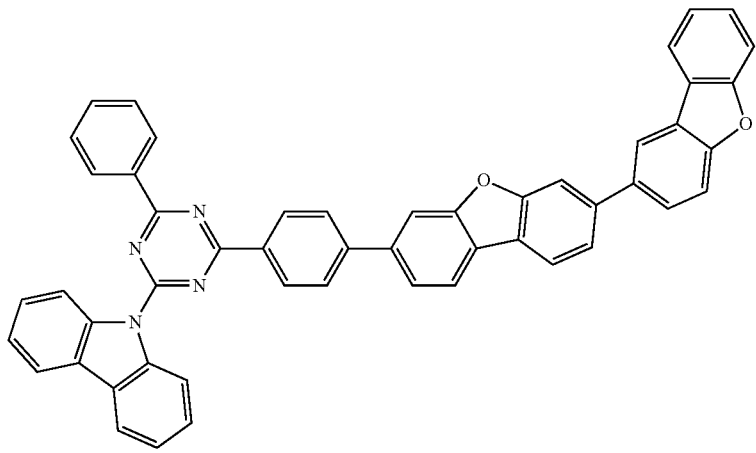
166
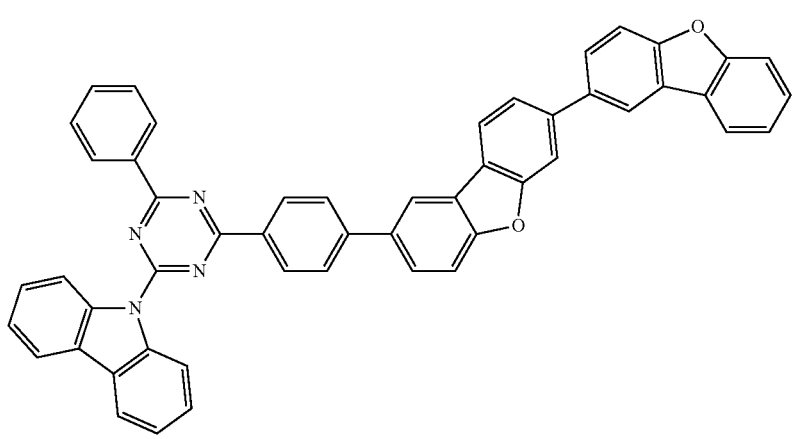
167
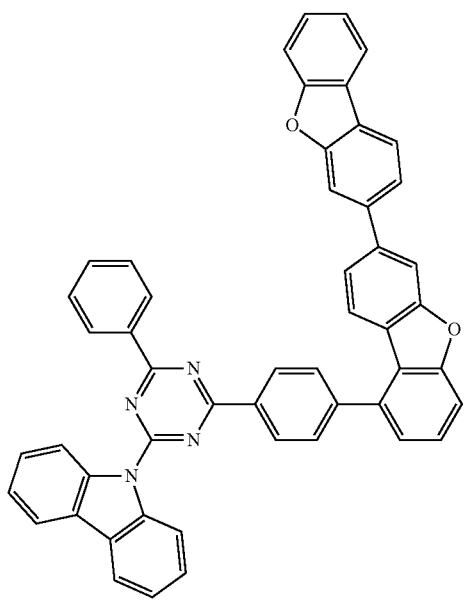
168
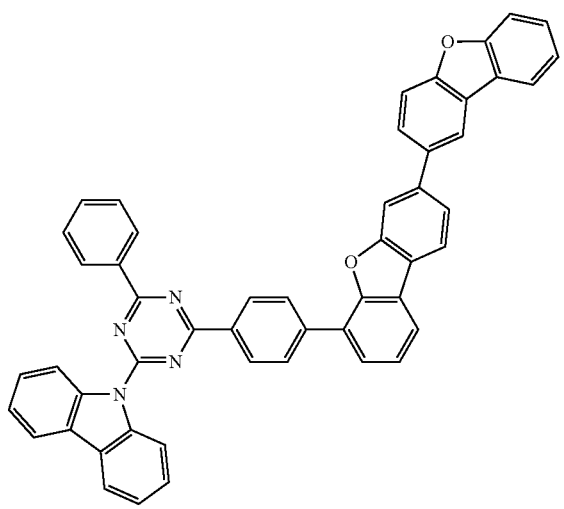

-continued
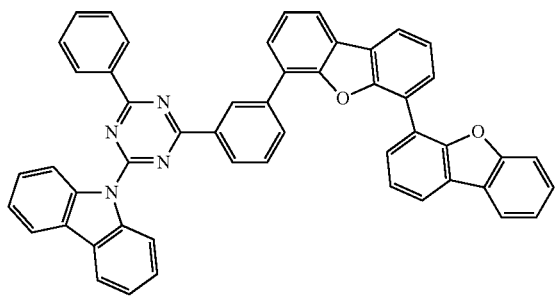
169
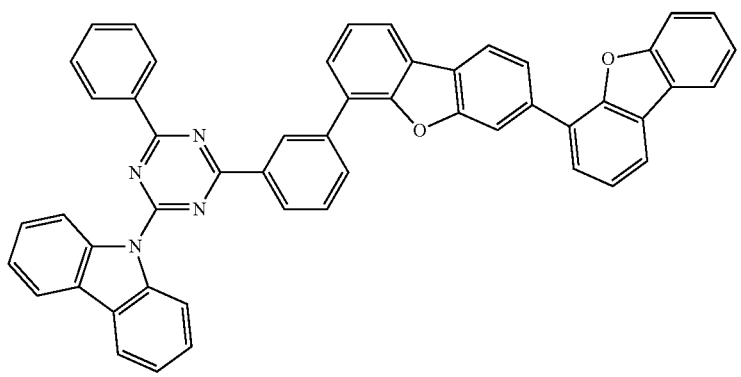
170
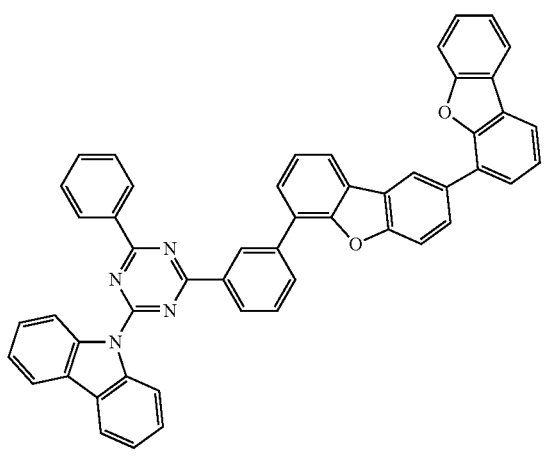
171
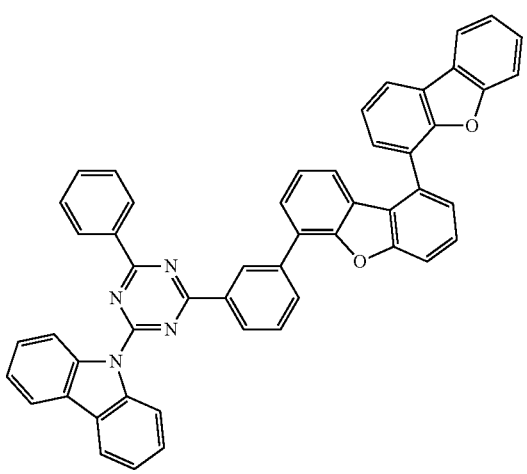
172
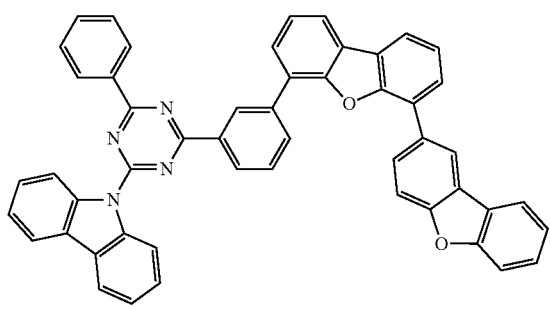
173
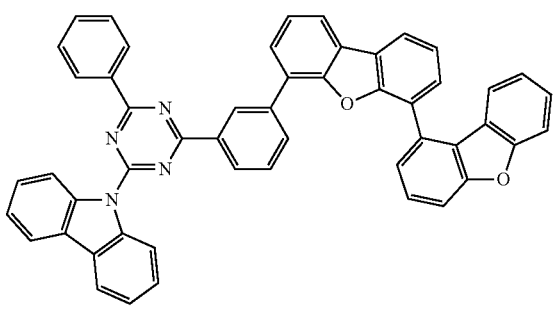
174

175
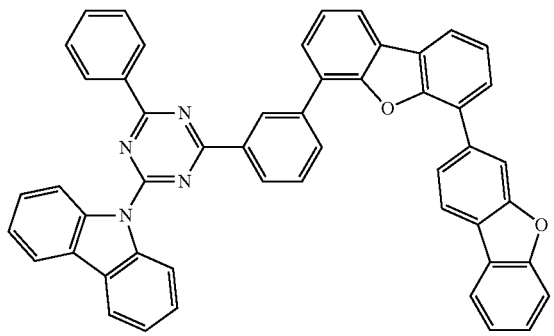
176
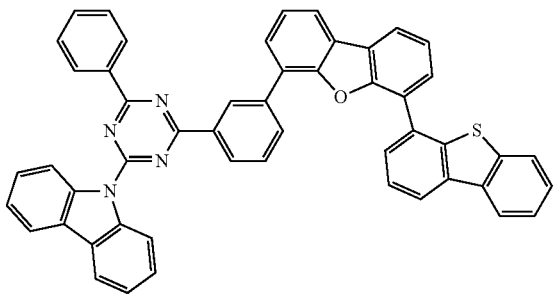
177
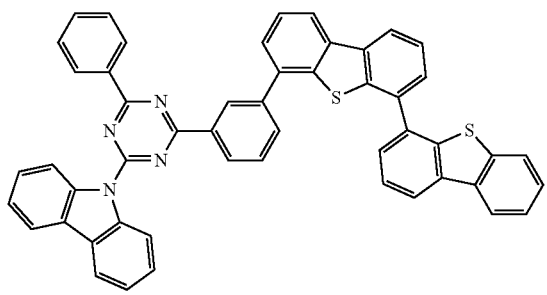
178
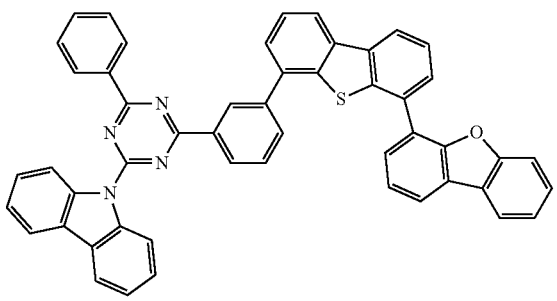
179
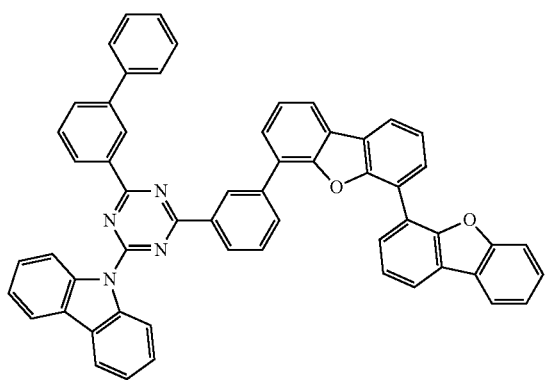
180
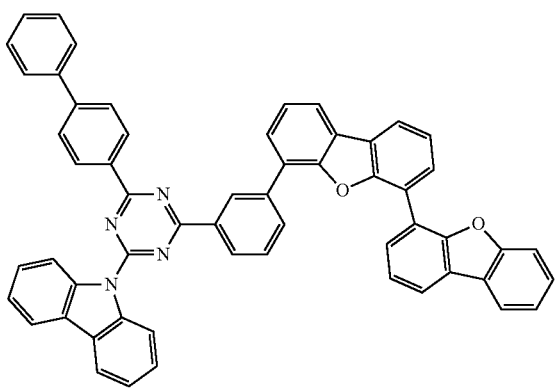
181
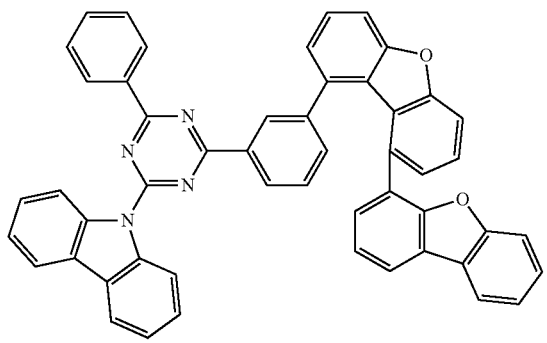
182
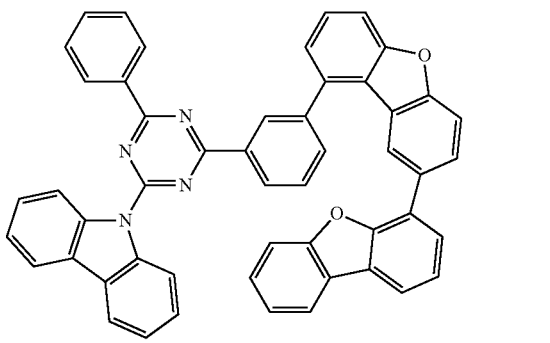

183
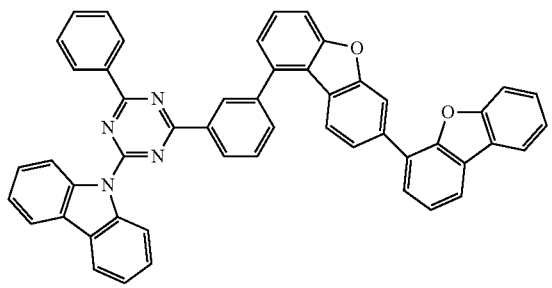
184
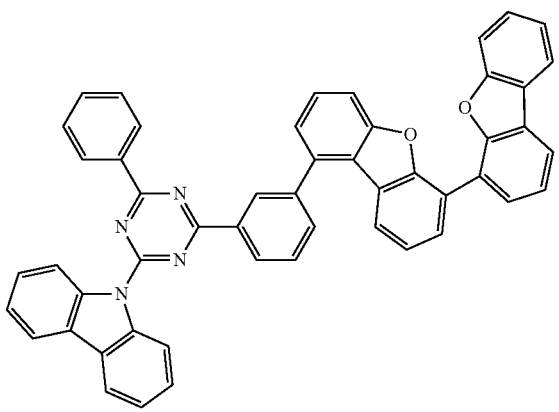
185
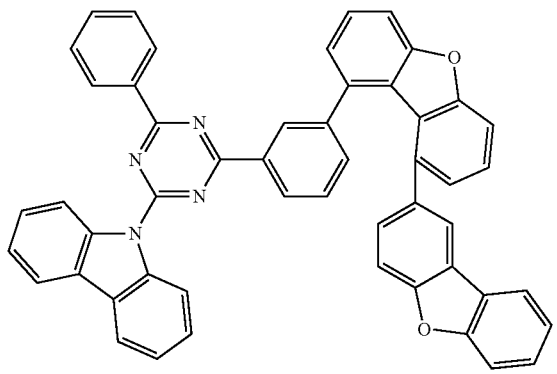
186
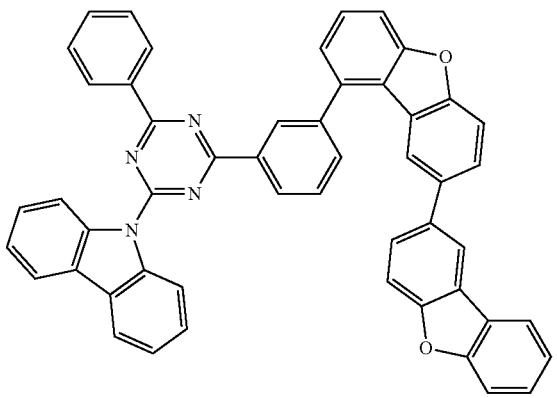
187
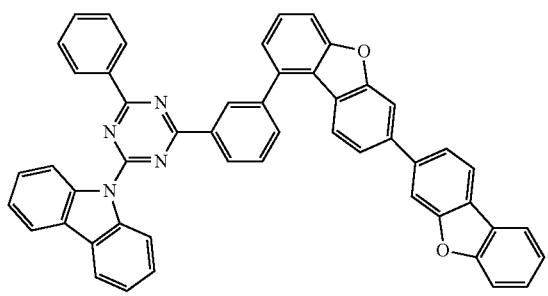
188
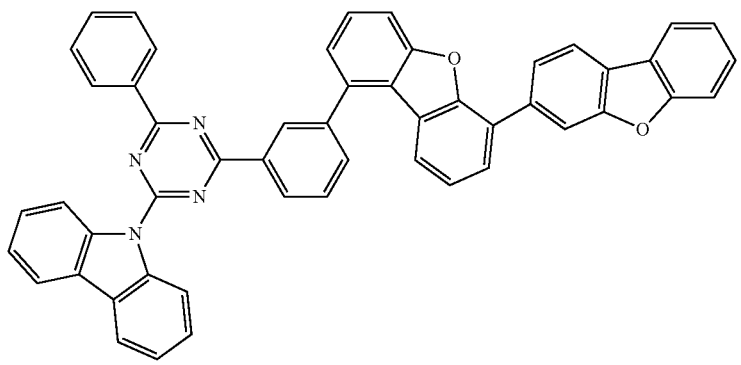

-continued
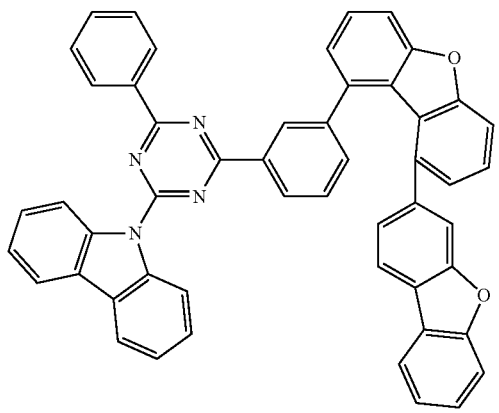
189
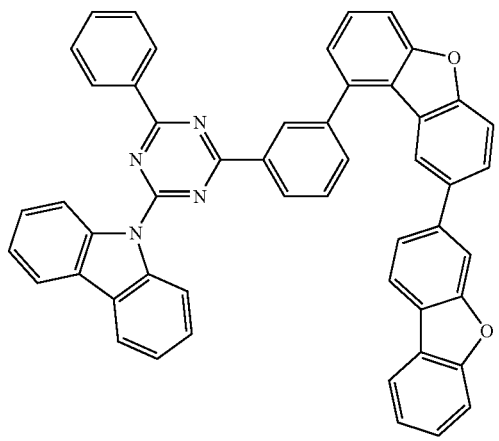
190
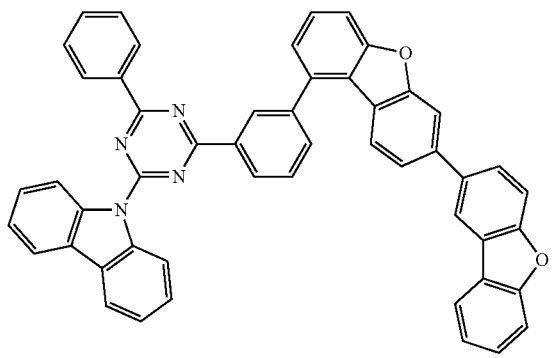
191
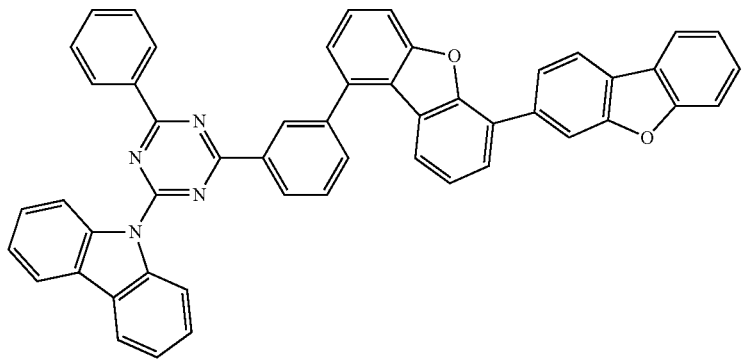
192
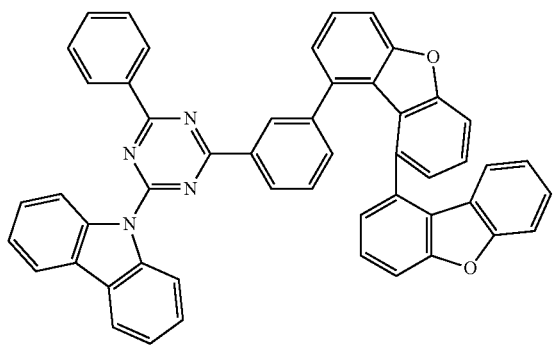
193
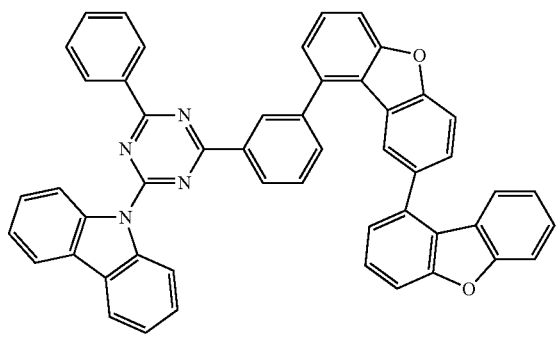
194

195
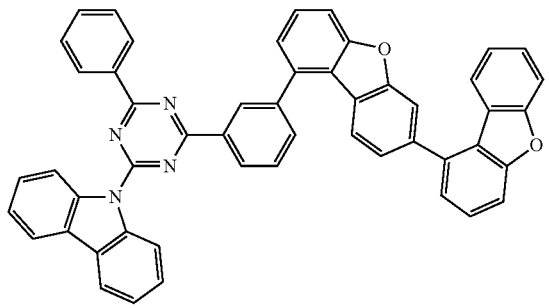
196
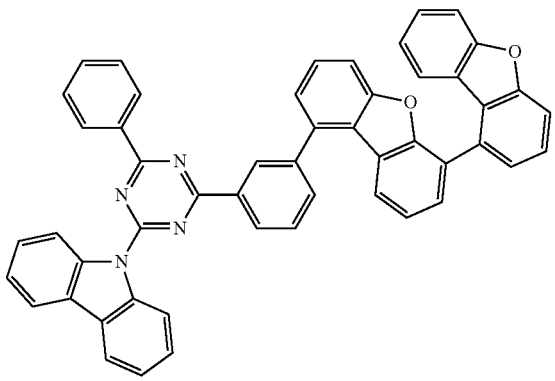
197
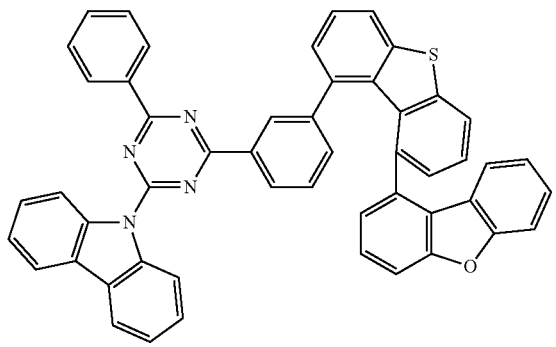
198
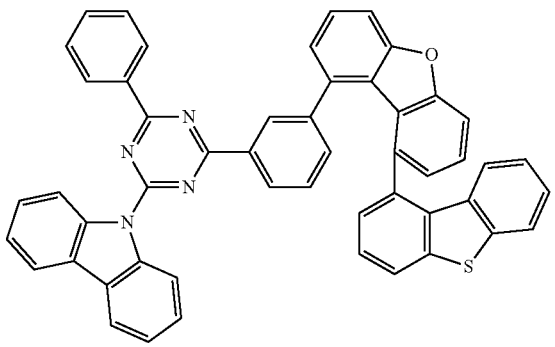
199
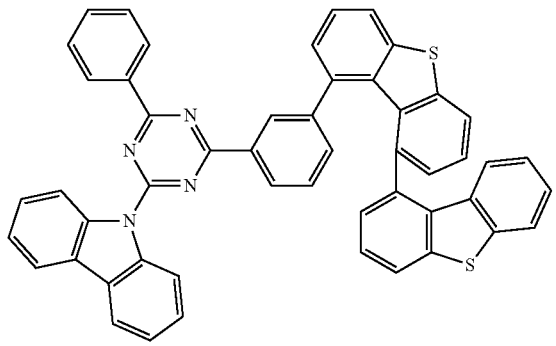
200
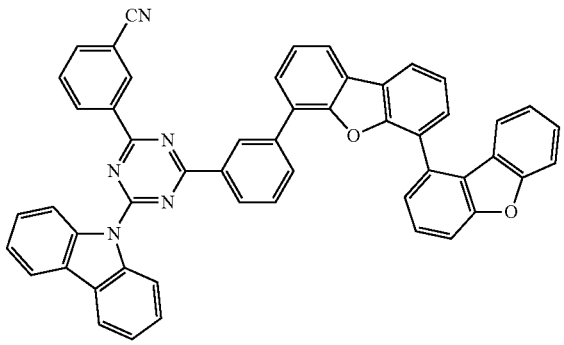
201
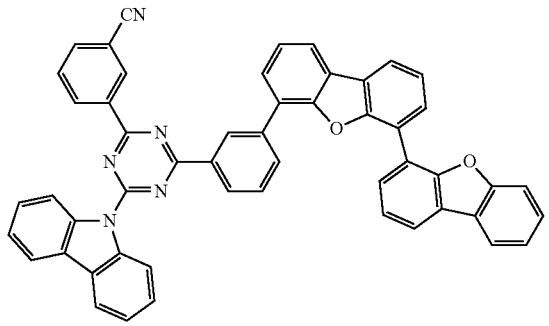
202
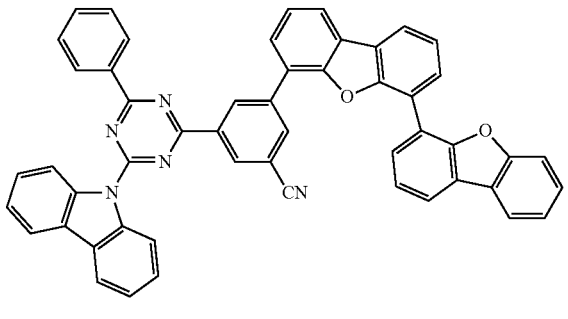

-continued

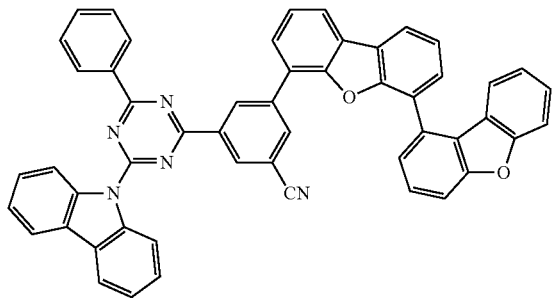
203

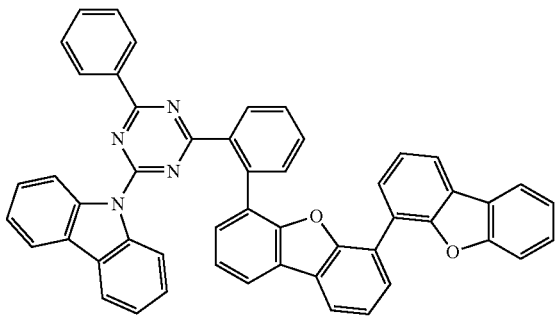
204

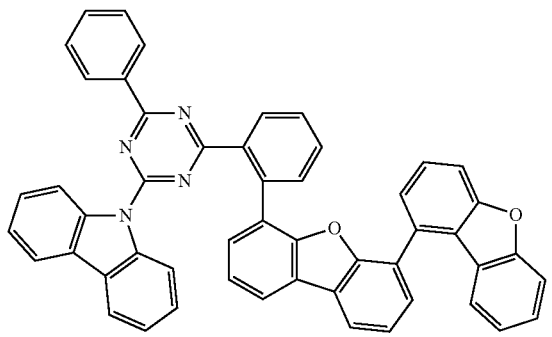
205

A composition for an organic optoelectronic device according to an embodiment may include, e.g., a first compound for an organic optoelectronic device and a second compound for an organic optoelectronic device (e.g., different from the first compound). In an implementation, the first compound may be represented by Chemical Formula 1 and the second compound may be represented by Chemical Formula 2; or a combination of Chemical Formula 3 and Chemical Formula 4.

[Chemical Formula 2]

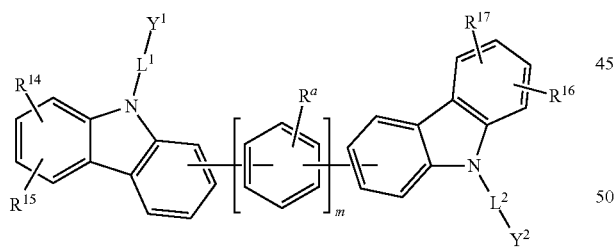

In Chemical Formula 2, $Y^1$ and $Y^2$ may each independently be or include, e.g., a substituted or unsubstituted C6 to C20 aryl group, or a substituted or unsubstituted C2 to C30 heterocyclic group, $L^1$ and $L^2$ may each independently be or include, e.g., a single bond or a substituted or unsubstituted C6 to C20 arylene group, $R^a$ and $R^{14}$ to $R^{17}$ may each independently be or include, e.g., hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, and m may be, e.g., an integer of 0 to 2.

[Chemical Formula 3]

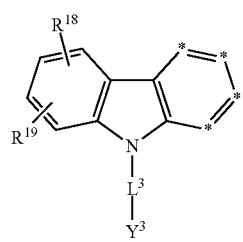

[Chemical Formula 4]

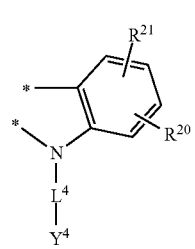

In Chemical Formulae 3 and 4, $Y^3$ and $Y^4$ may each independently be or include, e.g., a substituted or unsubstituted C6 to C20 aryl group or a substituted or unsubstituted C2 to C30 heterocyclic group, two adjacent *s of Chemical Formula 3 are linked to, e.g., are linking points for, the *s of Chemical Formula 4, the other *s of Chemical Formula 3 (e.g., not linked to Chemical Formula 4) may each independently be, e.g., $C-L^a-R^b$, $L^a$, $L^3$, and $L^4$ may each independently be or include, e.g., a single bond or a substituted or unsubstituted C6 to C20 arylene group, and $R^b$ and $R^{18}$ to $R^{21}$ may each independently be or include, e.g., hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group.

The second compound may be used in the light emitting layer together with the first compound to help improve the luminous efficiency and life-span characteristics by increasing mobility of charges and increasing stability.

In an implementation, $Y^1$ and $Y^2$ of Chemical Formula 2 may each independently be or include, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, a substituted or unsubstituted fluorenyl group, or a substituted or unsubstituted pyridinyl group, $L^1$ and $L^2$ of Chemical Formula 2 may each independently be or include, e.g., a single bond, a substituted or unsubstituted phenylene group, or a substituted or unsubstituted biphenylene group, $R^{14}$ to $R^{17}$ of Chemical Formula 2 may each independently be or include, e.g., hydrogen, deuterium, or a substituted or unsubstituted C6 to C12 aryl group, and m may be, e.g., 0 or 1.

For example, "substituted" of Chemical Formula 2 means replacement of at least one hydrogen by deuterium, a C1 to C4 alkyl group, a C6 to C18 aryl group, or a C2 to C30 heteroaryl group.

In an implementation, the compound represented by Chemical Formula 2 may be represented by one of Chemical Formula 2-1 to Chemical Formula 2-15.

[Chemical Formula 2-1]

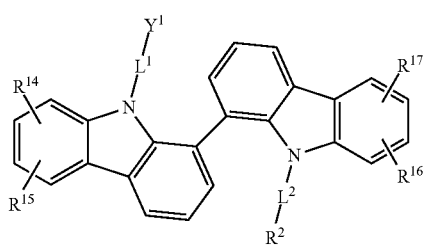

[Chemical Formula 2-2]

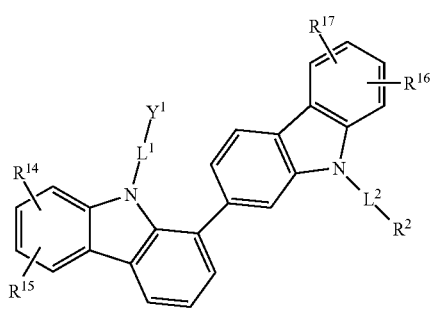

[Chemical Formula 2-3]

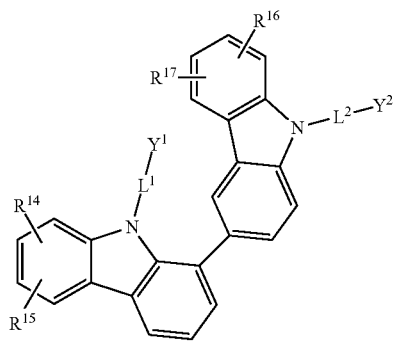

[Chemical Formula 2-4]

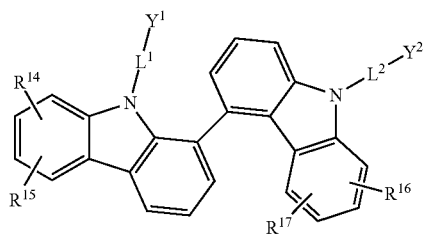

[Chemical Formula 2-5]

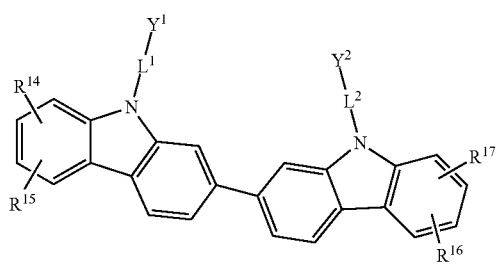

[Chemical Formula 2-6]

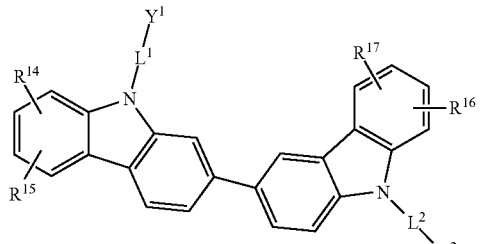

[Chemical Formula 2-7]

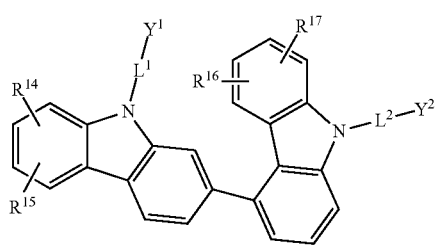

[Chemical Formula 2-8]

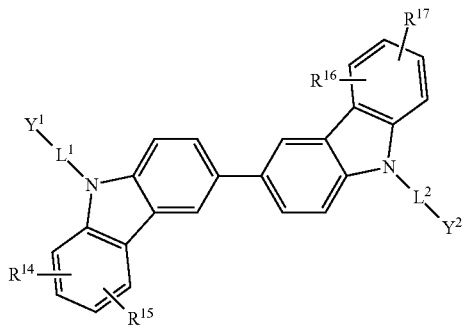

[Chemical Formula 2-9]

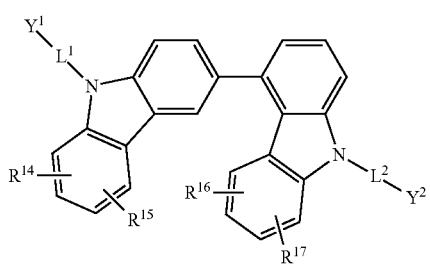

[Chemical Formula 2-10]

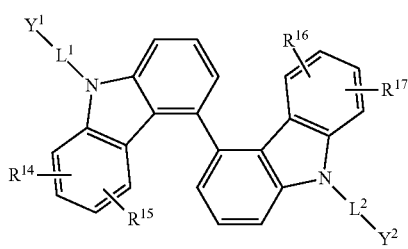

[Chemical Formula 2-11]

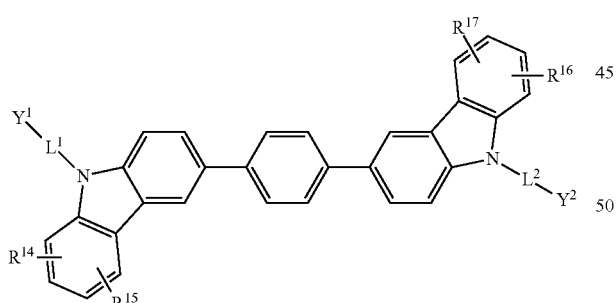

[Chemical Formula 2-12]

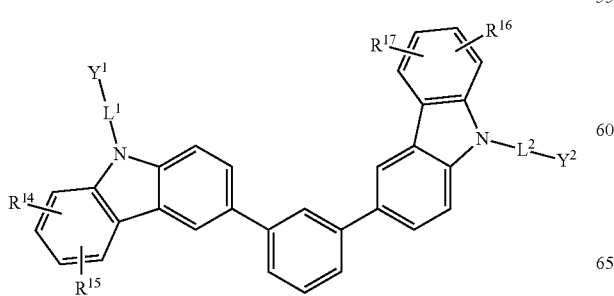

[Chemical Formula 2-13]

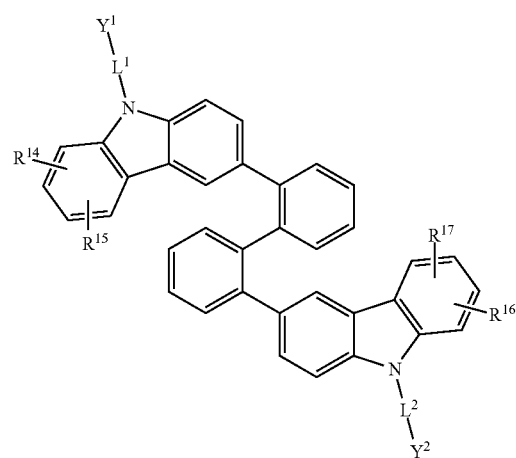

[Chemical Formula 2-14]

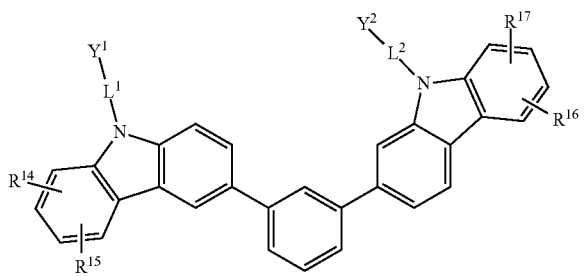

[Chemical Formula 2-15]

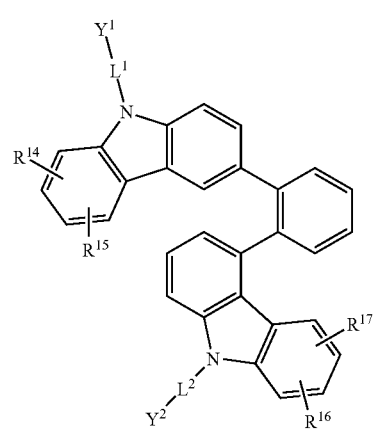

In Chemical Formula 2-1 to Chemical Formula 2-15, $R^{14}$ to $R^{17}$ may each independently be or include, e.g., hydrogen or a substituted or unsubstituted C6 to C12 aryl group. In an implementation, the moieties *-$L^1$-$Y^1$ and *-$L^2$-$Y^2$ may each independently be a moiety of Group II.

[Group II]

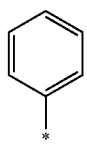

B-1

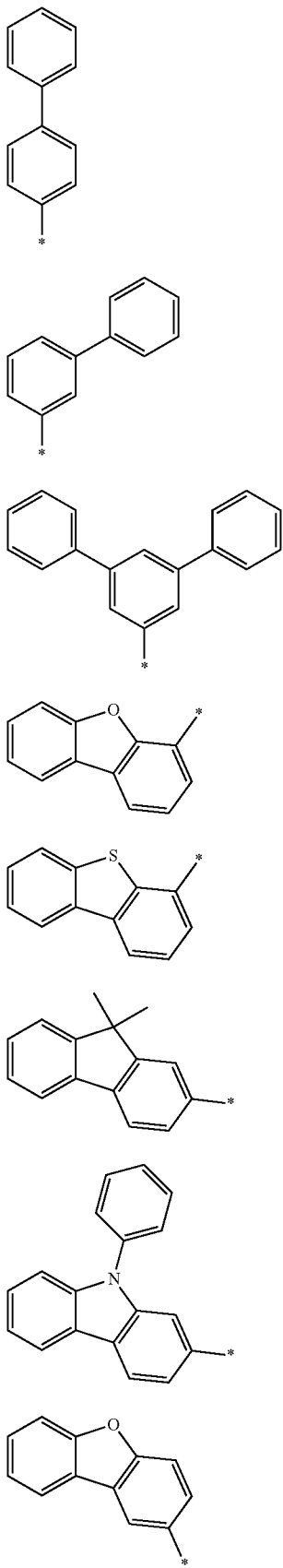
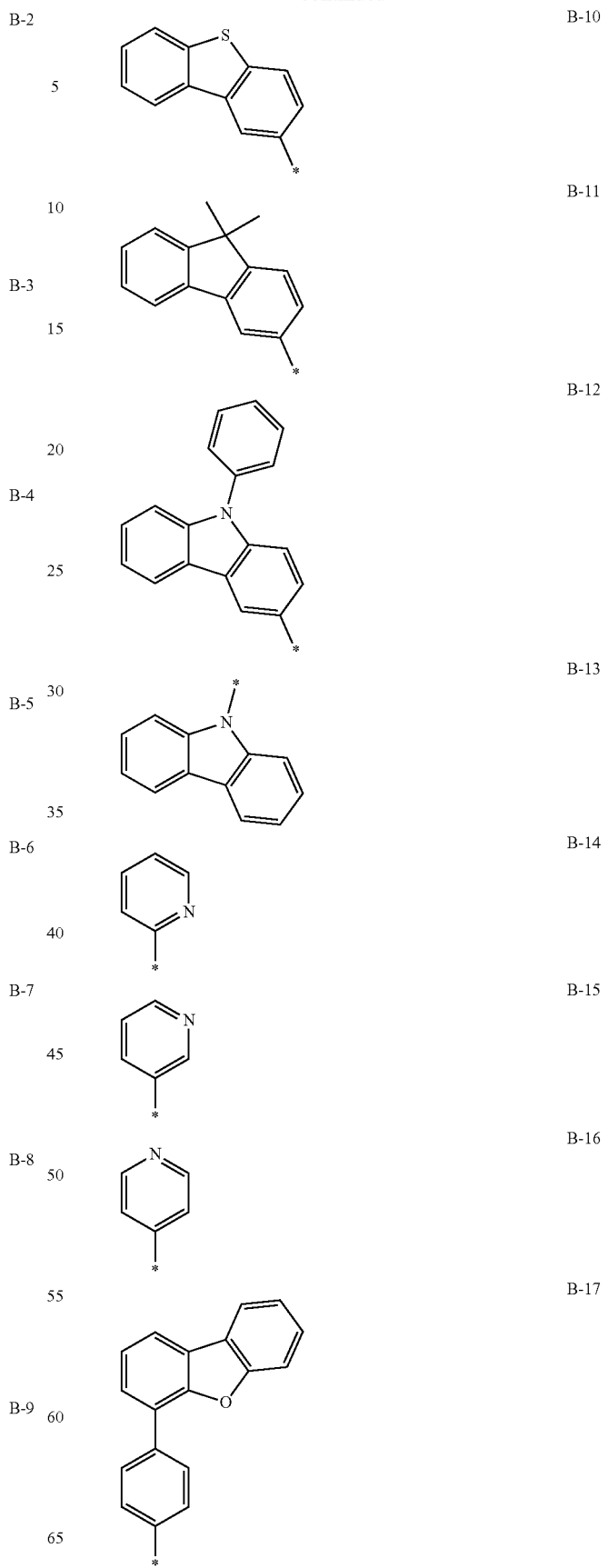

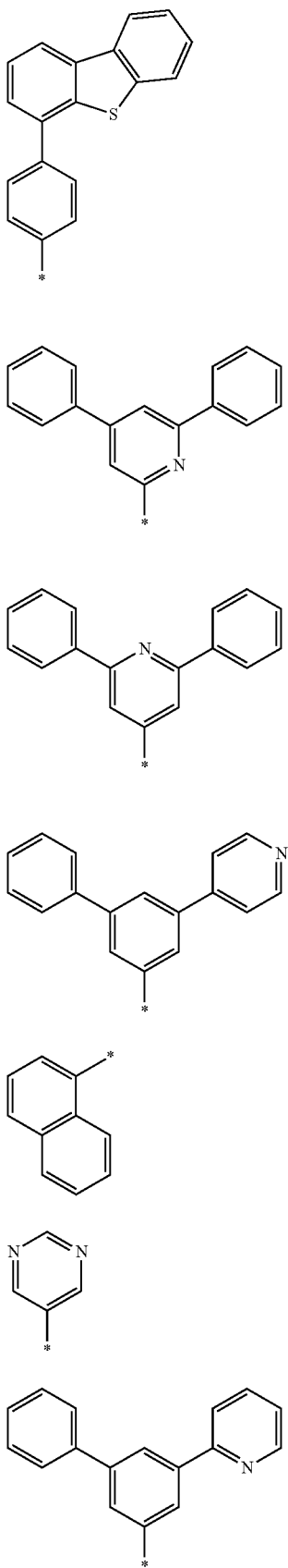
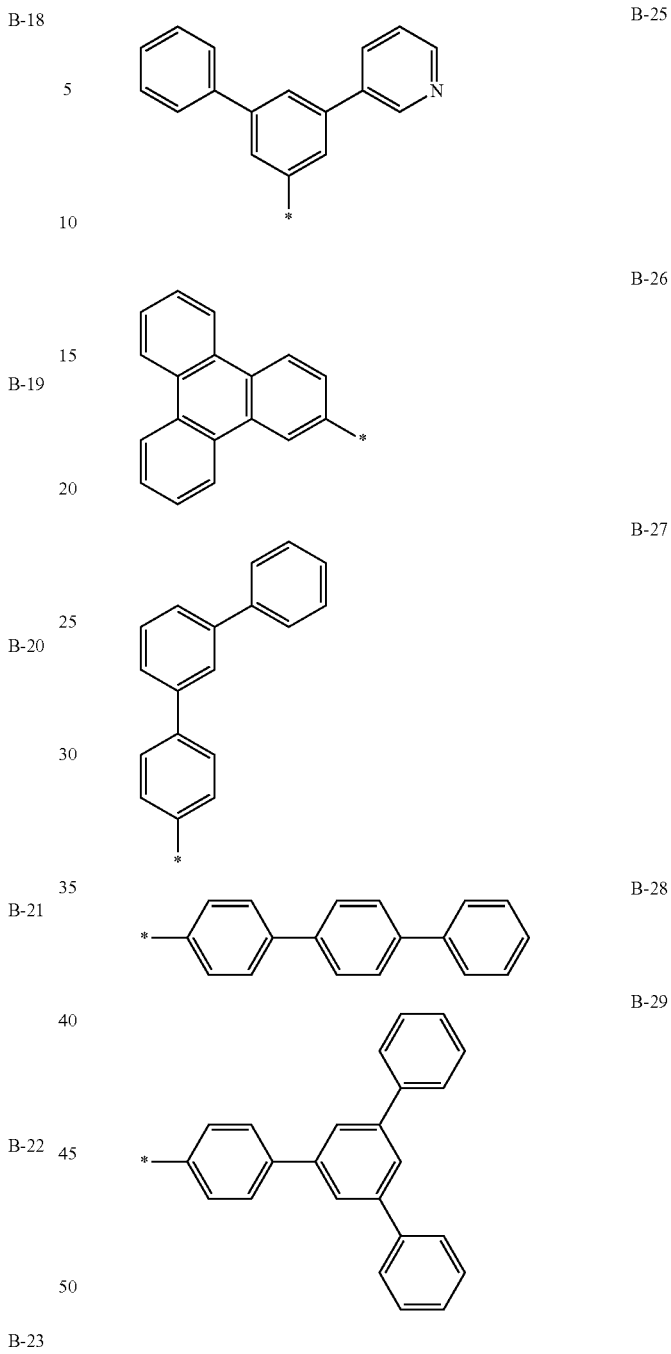

The * indicates a linking point (e.g., to N of Chemical Formulae 2-1 to 2-15.

In an implementation, the compound represented by Chemical Formula 2 may be represented by Chemical Formula 2-8.

In an implementation, the moieties *-$L^1$-$Y^1$ and *-$L^2$-$Y^2$ of Chemical Formula 2-8 may each independently be a moiety of Group II, e.g., B-1, B-2, B-3, B-19, or B-26.

In an implementation, the second compound represented by a combination of Chemical Formula 3 and Chemical Formula 4 may be represented by one of Chemical Formula 3A, Chemical Formula 3B, Chemical Formula 3C, Chemical Formula 3D, and Chemical Formula 3E.

[Chemical Formula 3A]

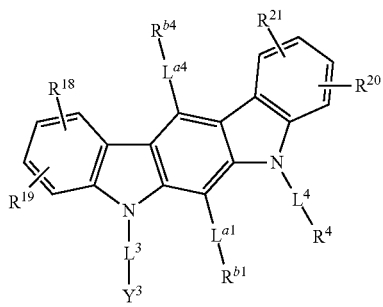

[Chemical Formula 3B]

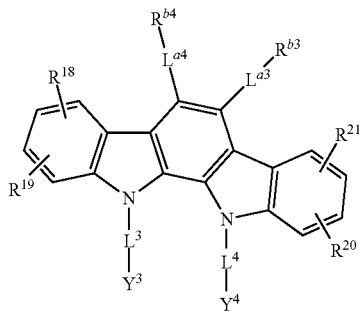

[Chemical Formula 3C]

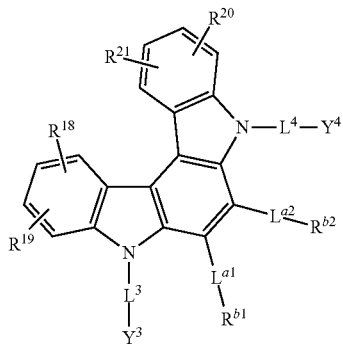

[Chemical Formula 3D]

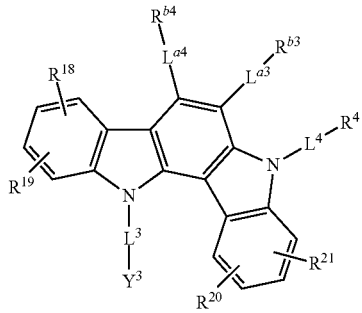

[Chemical Formula 3E]

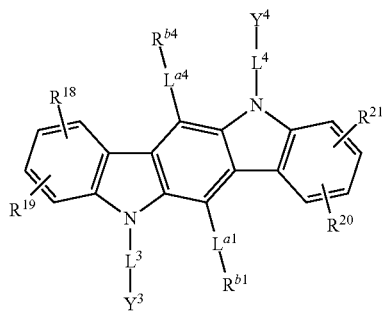

In Chemical Formula 3A to Chemical Formula 3E, $Y^3$ and $Y^4$, $L^3$ and $L^4$, and $R^{18}$ to $R^{21}$ may be the same as described above, $L^{a1}$ to $L^{a4}$ may be defined the same as $L^3$ and $L^4$, and $R^{b1}$ to $R^{b4}$ may be defined the same as $R^{18}$ to $R^{21}$.

In an implementation, $Y^3$ and $Y^4$ of Chemical Formulae 3 and 4 may each independently be or include, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, and $R^{b1}$ to $R^{b4}$ and $R^{18}$ to $R^{21}$ may each independently be or include, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $Y^3$ and $Y^4$ of Chemical Formulae 3 and 4 may each independently be, e.g., a group of Group III.

[Group III]

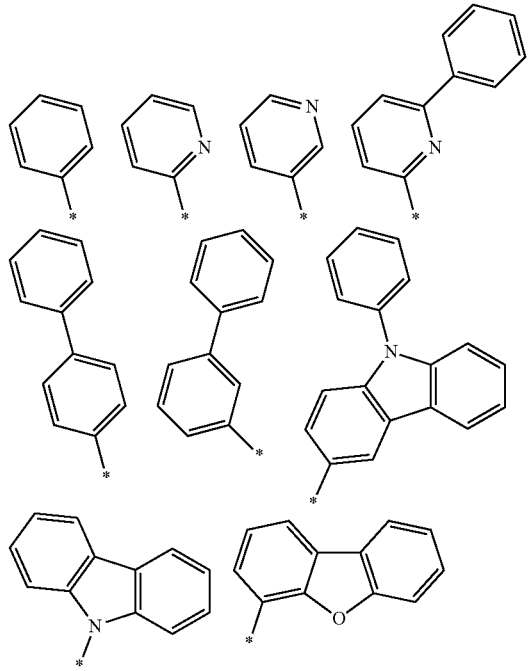

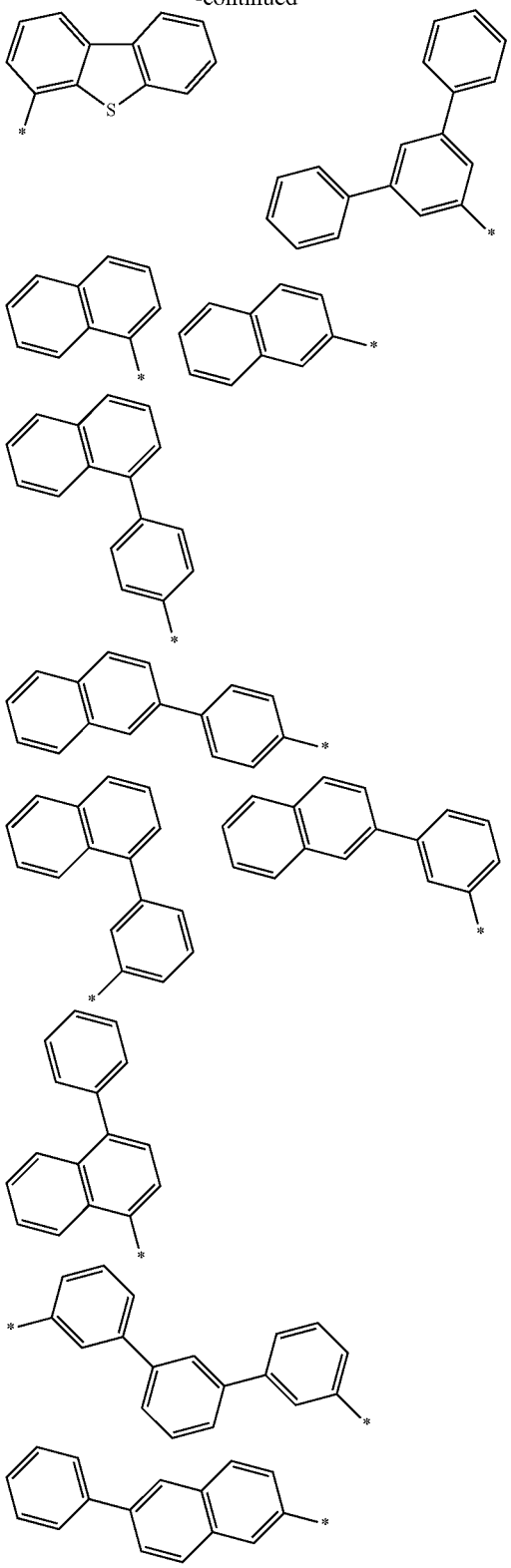

In Group III, each * is a linking point with $L^3$ or $L^4$.

In an implementation, $R^{b1}$ to $R^{b4}$ and $R^{18}$ to $R^{21}$ may each independently be or include, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{b1}$ to $R^{b4}$ and $R^{18}$ to $R^{21}$ may each independently be or include, e.g., hydrogen, deuterium, a cyano group, or a substituted or unsubstituted phenyl group.

In an implementation, $R^{b1}$ to $R^{b4}$ may each be hydrogen and $R^{18}$ to $R^{21}$ may each independently be or include, e.g., hydrogen or a phenyl group.

In an implementation, the second compound may be represented by, e.g., Chemical Formula 2-8, Chemical Formula 3A, Chemical Formula 3C, or Chemical Formula 3D.

In an implementation, $Y^1$ to $Y^4$ of Chemical Formula 2-8 and Chemical Formula 3A, Chemical Formula 3C and Chemical Formula 3D may each independently be or include, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, $L^1$ to $L^4$, and $L^{a1}$ to $L^{a4}$ may each independently be or include, e.g., a single bond or a substituted or unsubstituted C6 to C20 arylene group, and $R^{b1}$ to $R^{b4}$ and $R^{14}$ to $R^{21}$ may each independently be or include, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, the second compound may be, e.g., a compound of Group 2.

[Group 2]

[B-1]

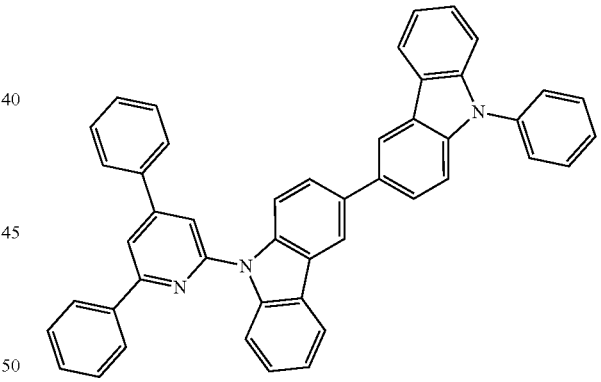

[B-2]

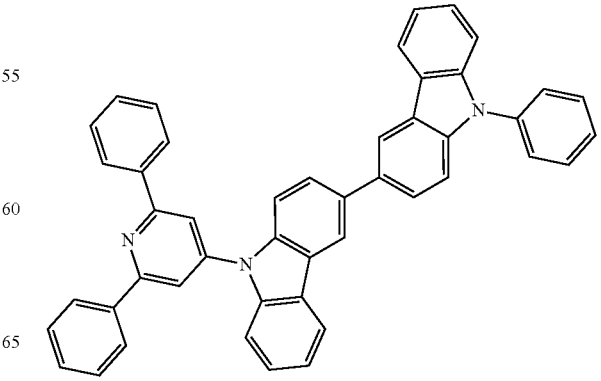

[B-3]
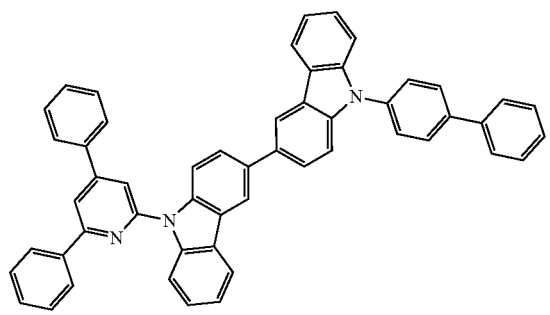
[B-7]
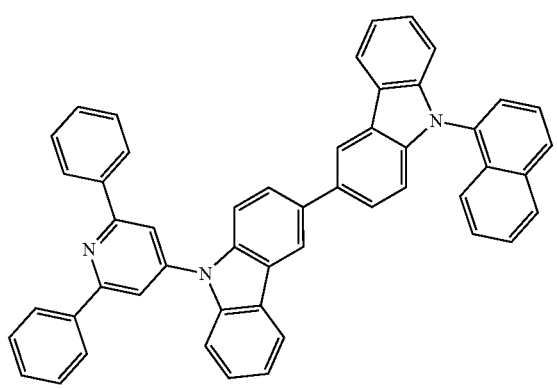
[B-4]
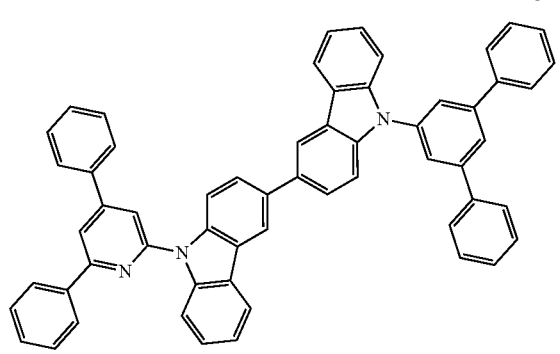
[B-8]
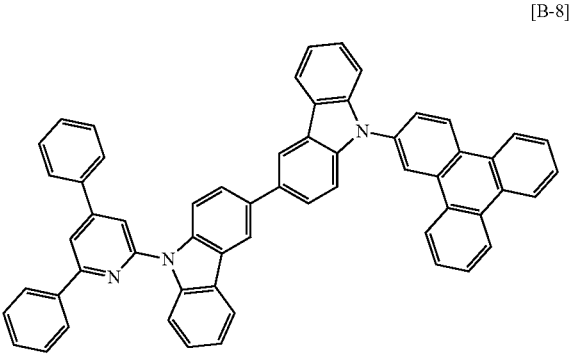
[B-5]
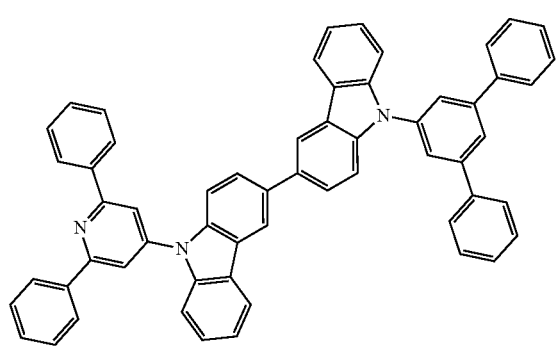
[B-9]
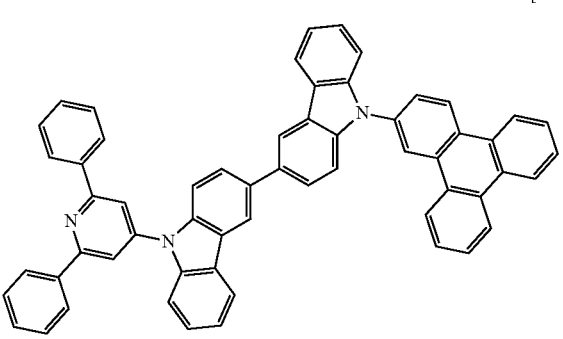
[B-6]
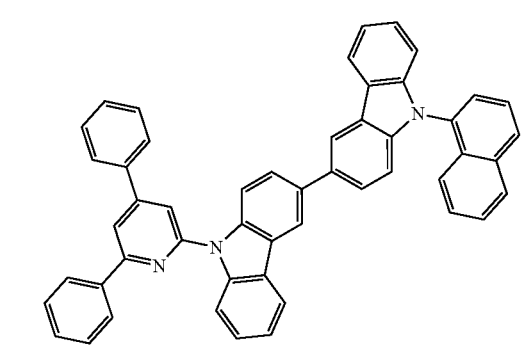
[B-10]
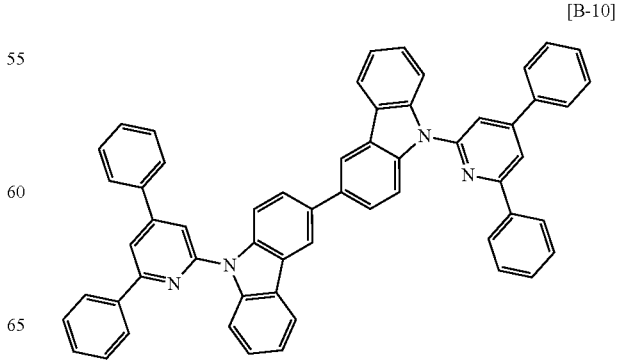

[B-11]
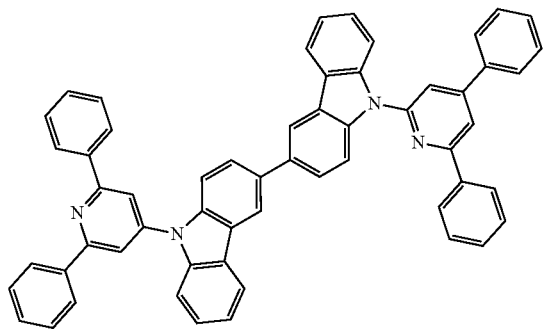
[B-15]
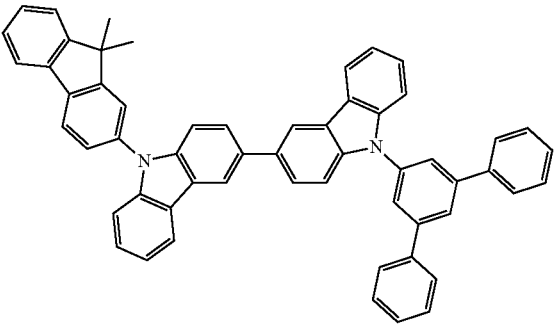
[B-12]
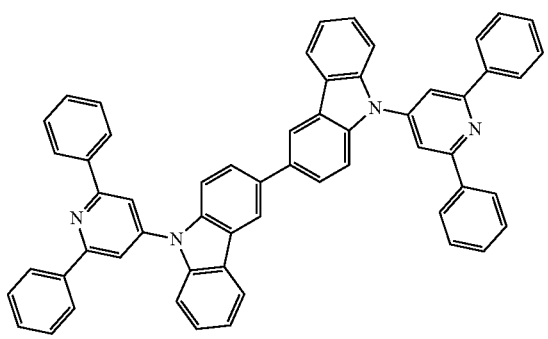
[B-16]
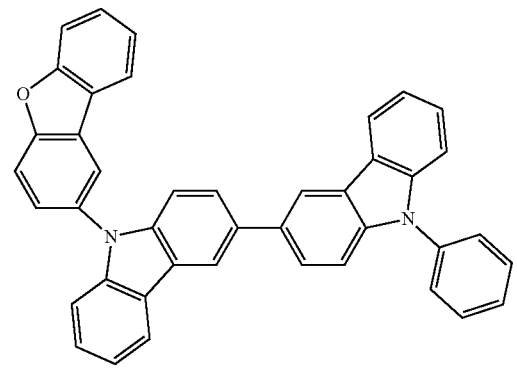
[B-13]
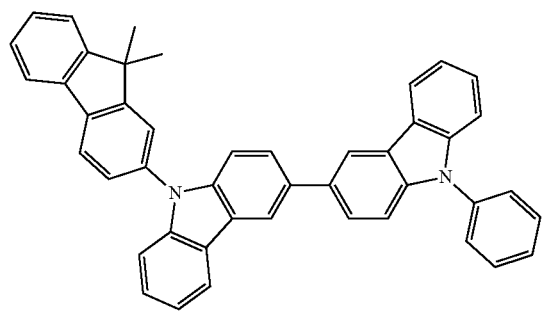
[B-17]
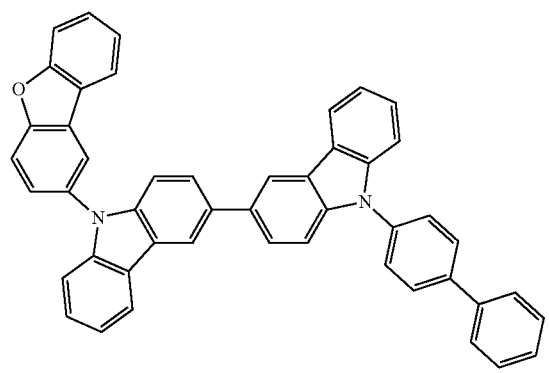
[B-14]
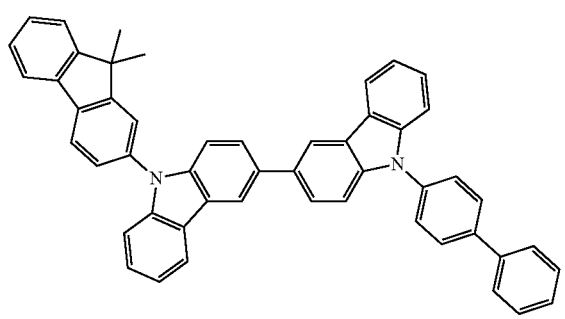
[B-18]
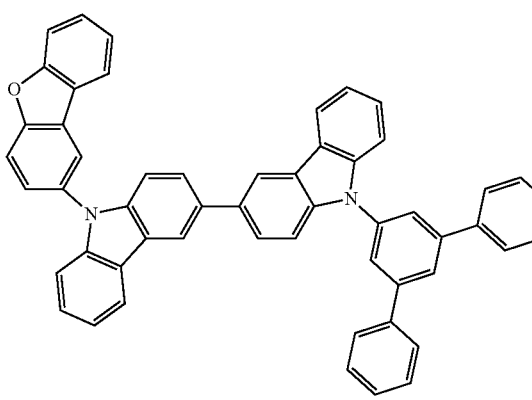

[B-19]
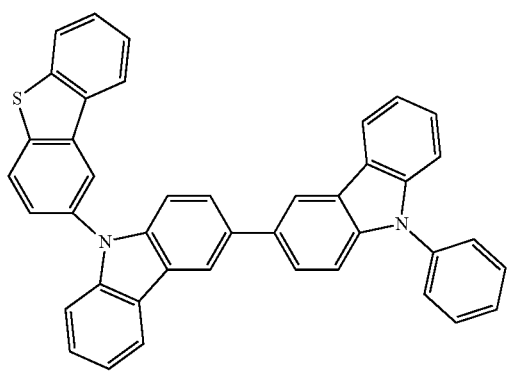
[B-22]
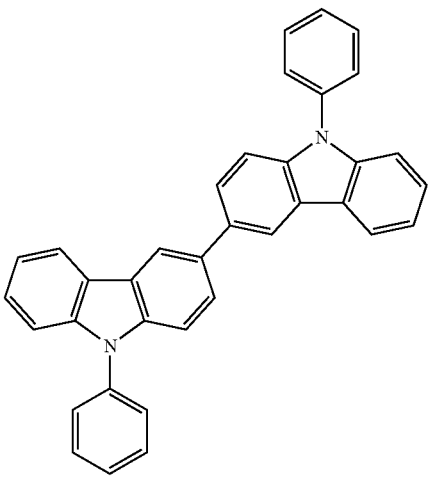
[B-20]
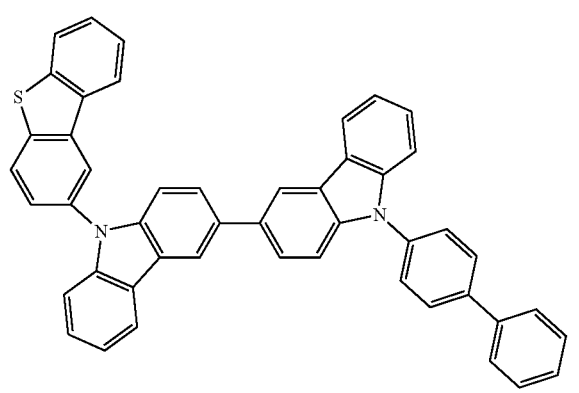
[B-23]
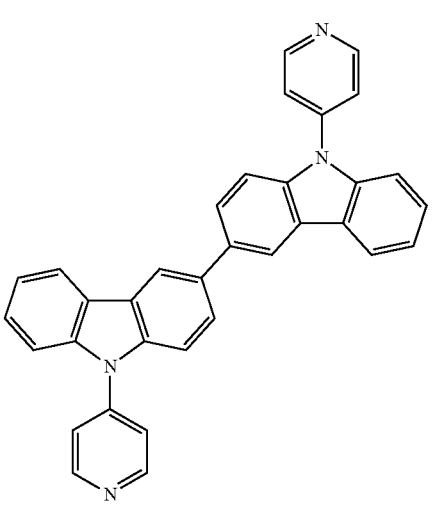
[B-21]
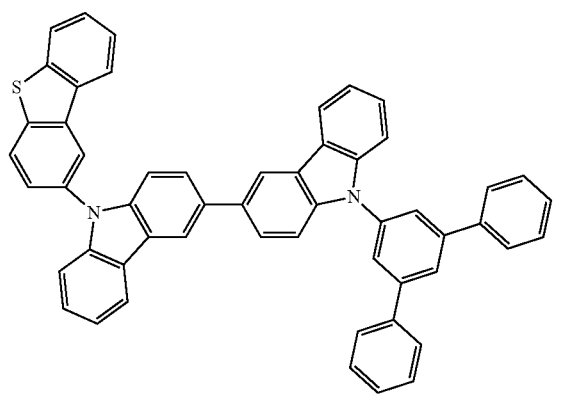
[B-24]
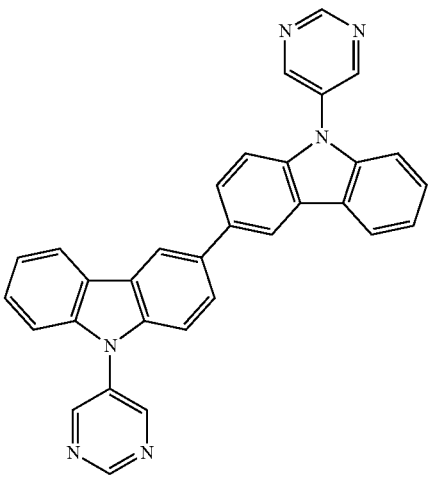

[B-25]
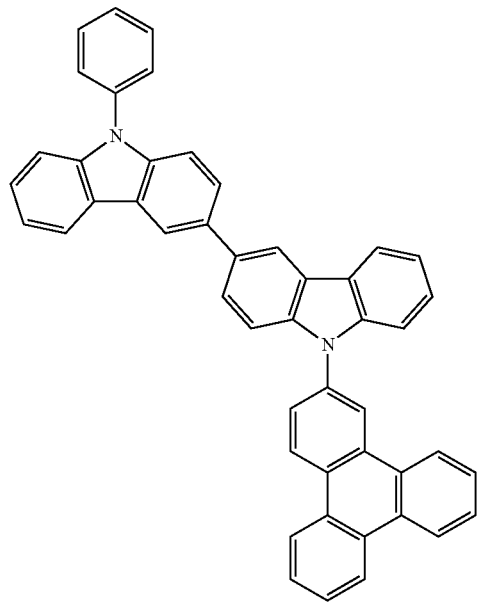
[B-27]
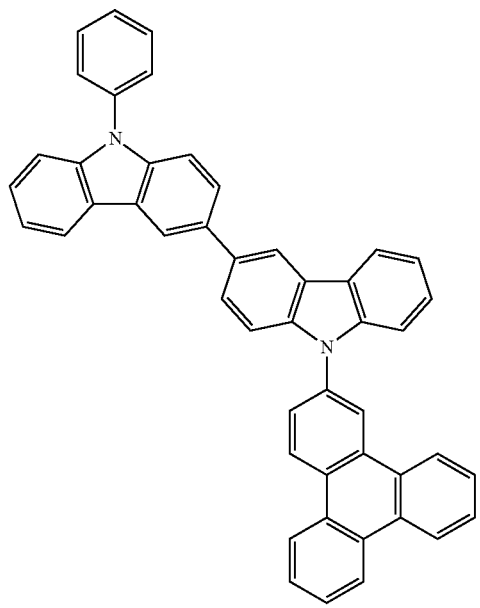
[B-26]
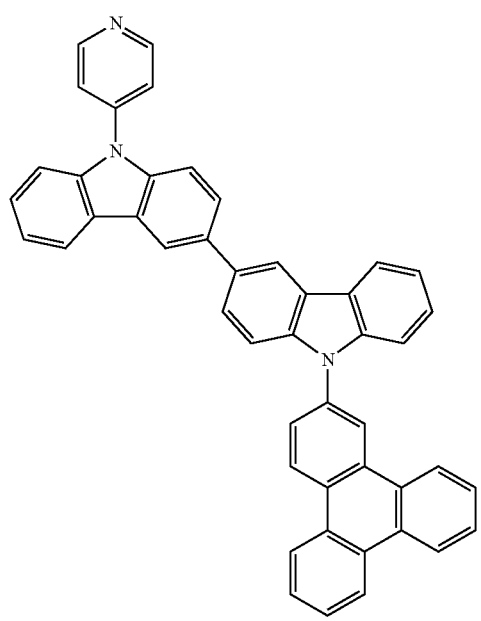
[B-28]
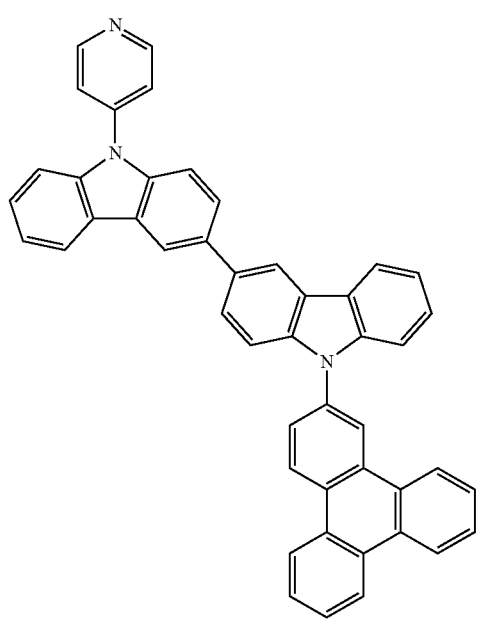

[B-29]
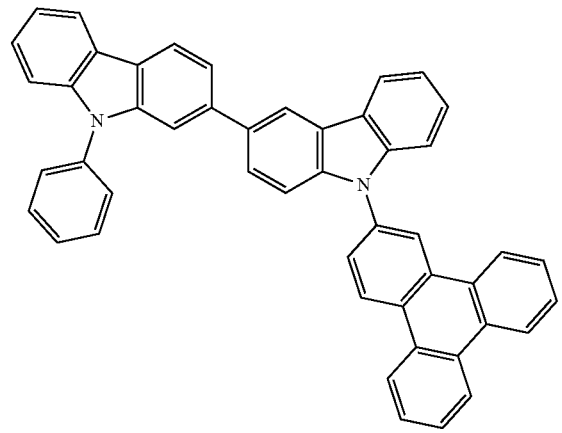
[B-30]
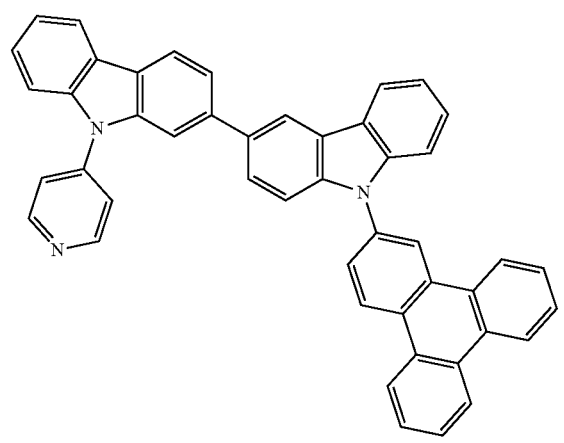
[B-31]
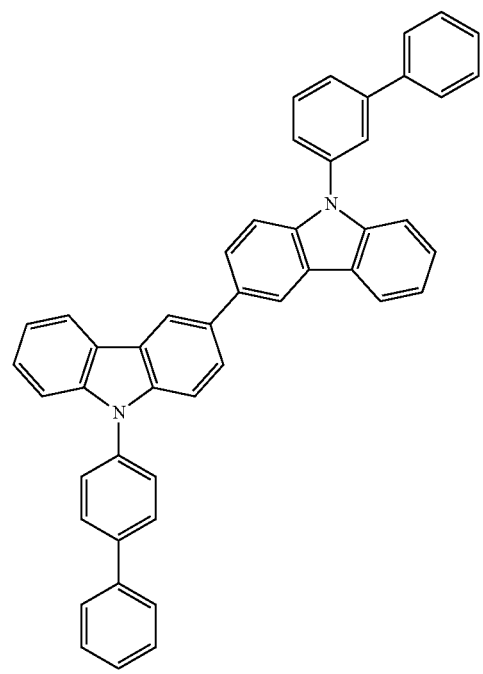
[B-32]
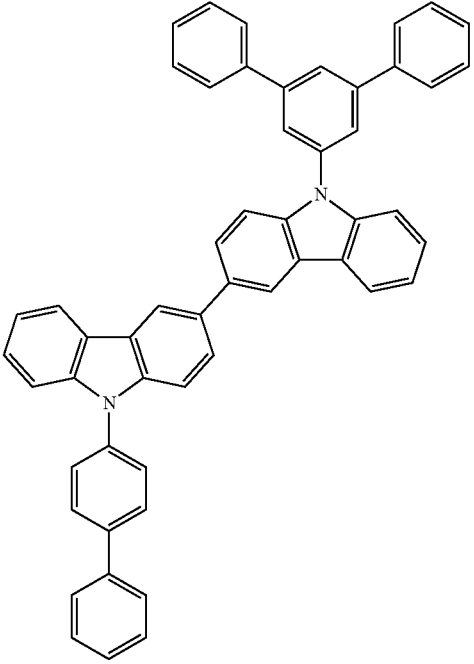
[B-33]
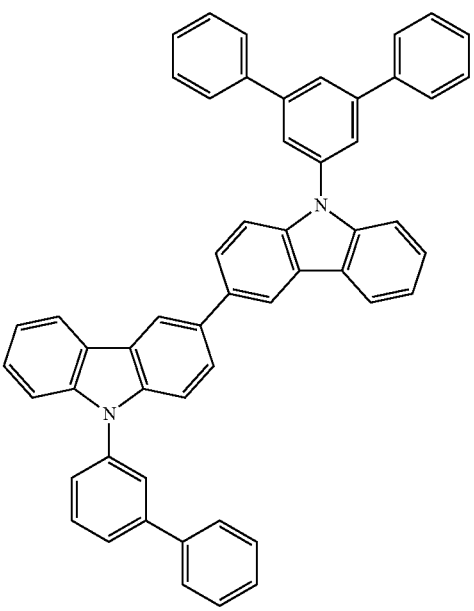

[B-34]
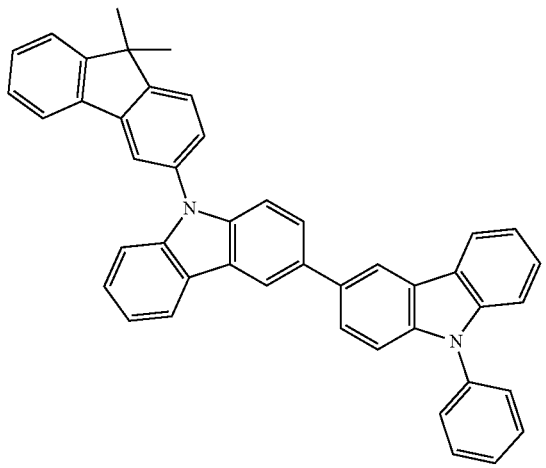
[B-37]
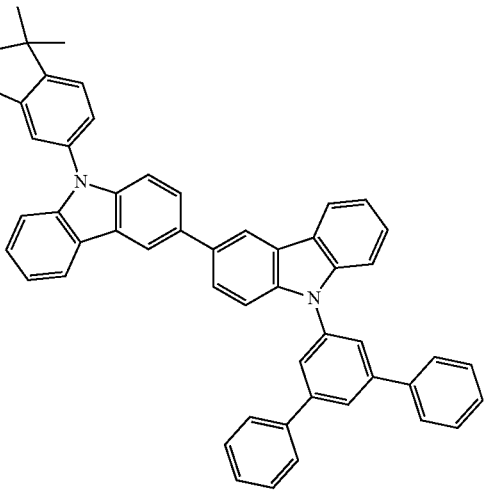
[B-35]
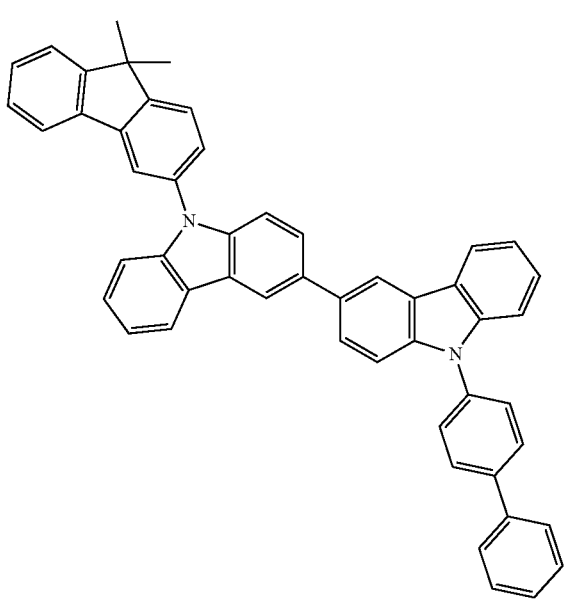
[B-38]
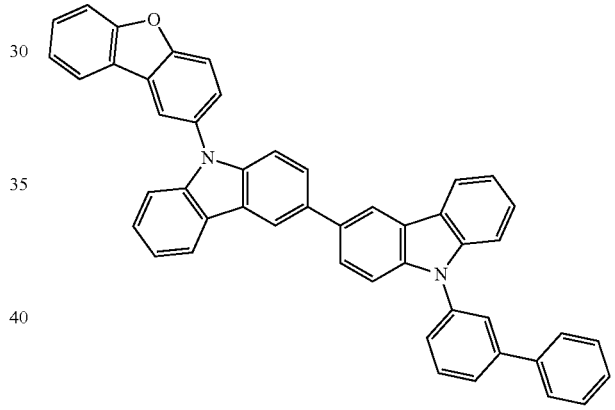
[B-36]
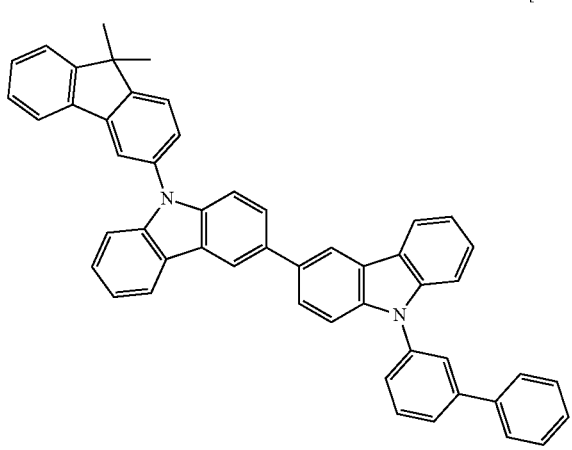
[B-39]
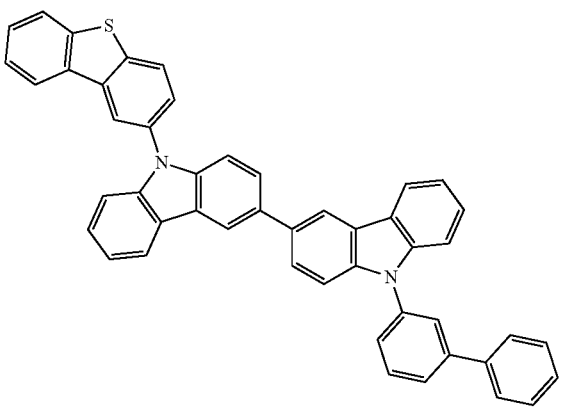

[B-40]
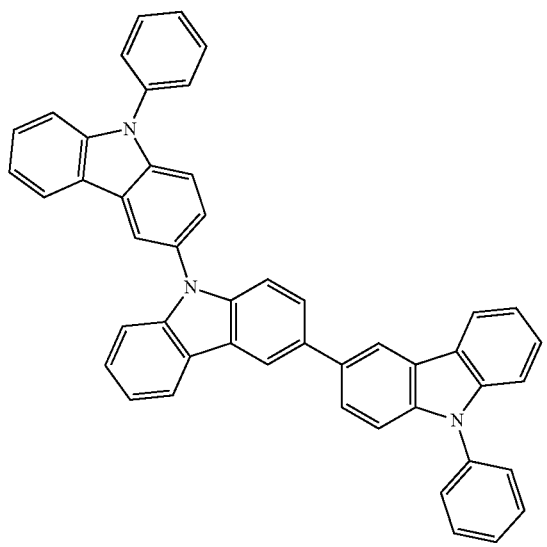
[B-41]
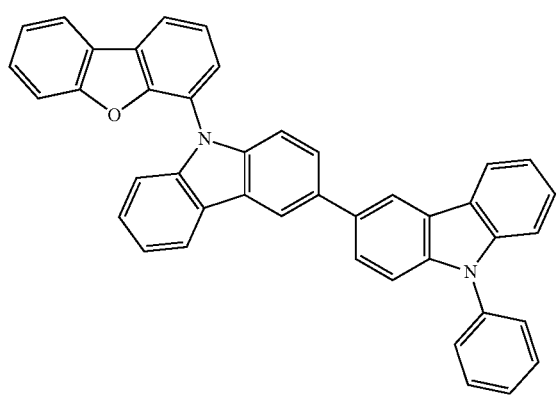
[B-42]
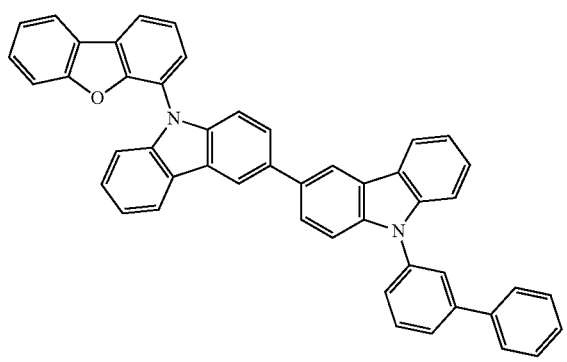
[B-43]
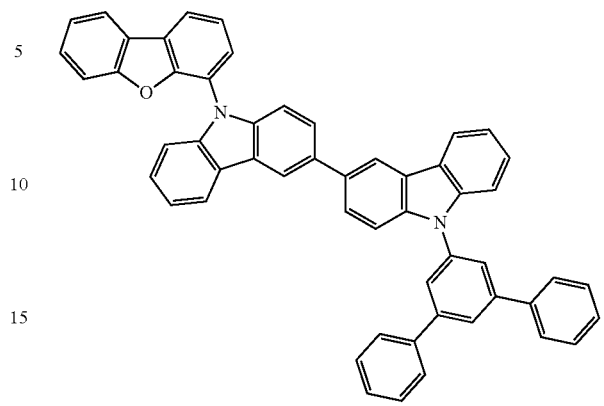
[B-44]
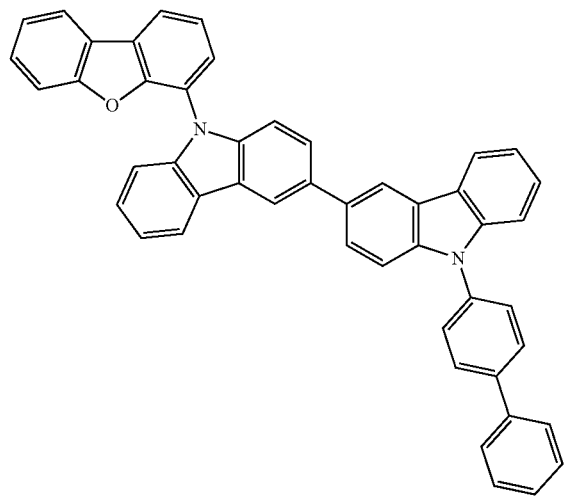
[B-45]
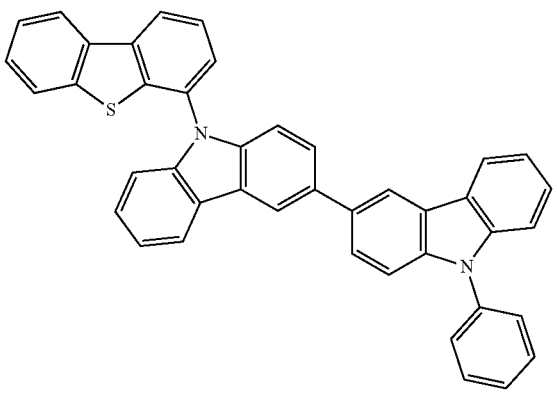

[B-46]
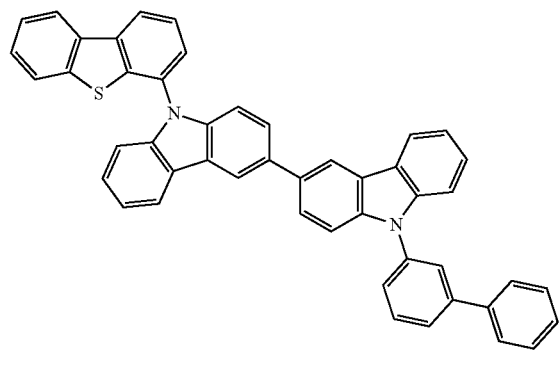
[B-47]
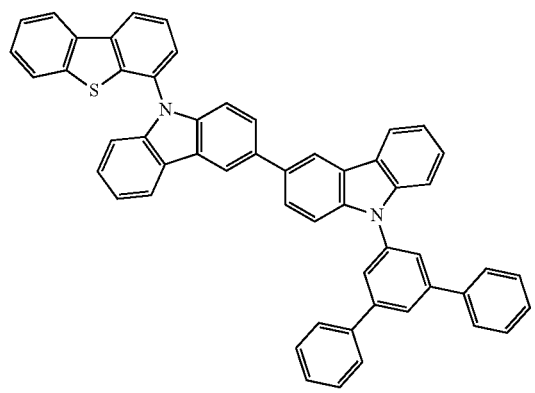
[B-48]
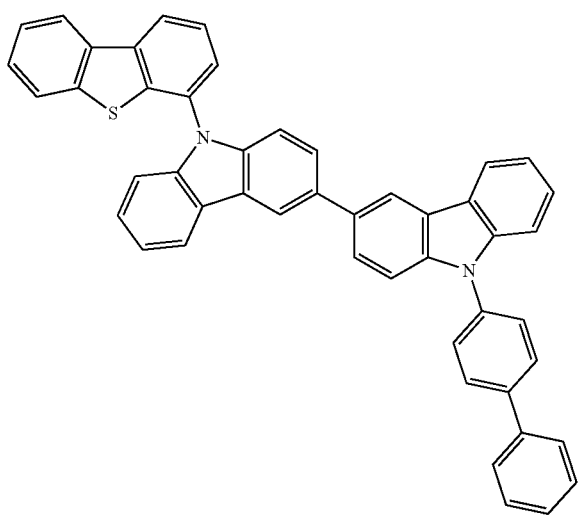
[B-49]
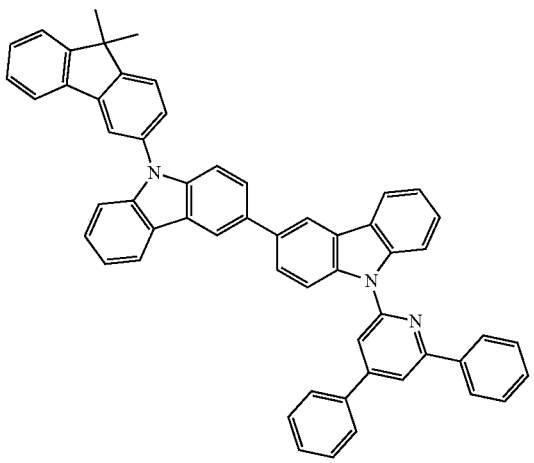
[B-50]
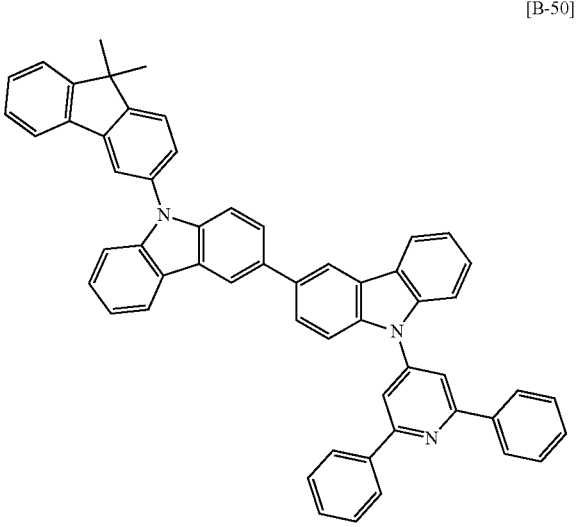
[B-51]
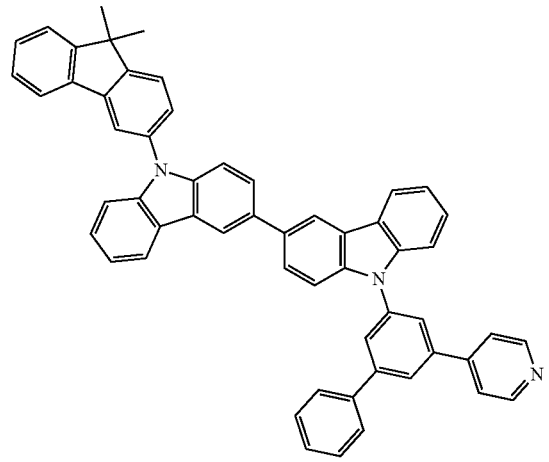

[B-52]
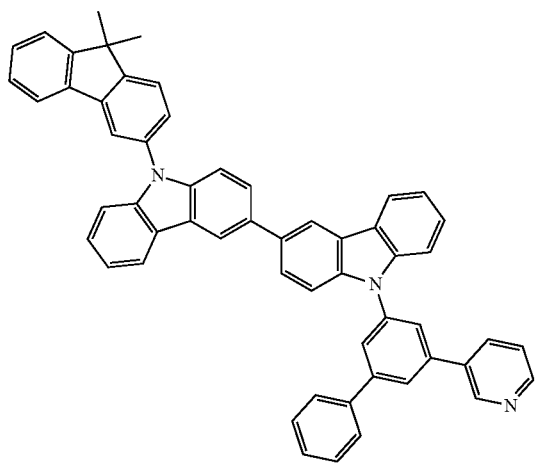
[B-55]
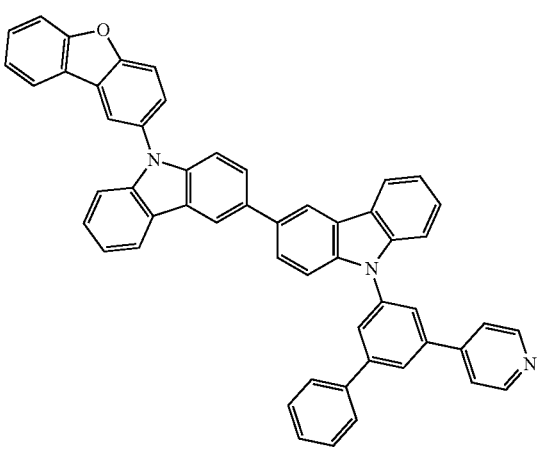
[B-53]
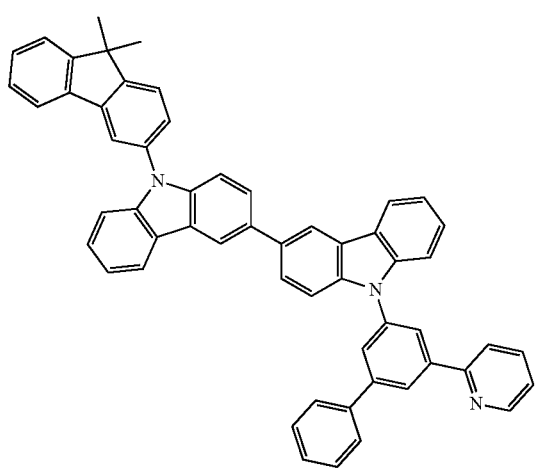
[B-56]
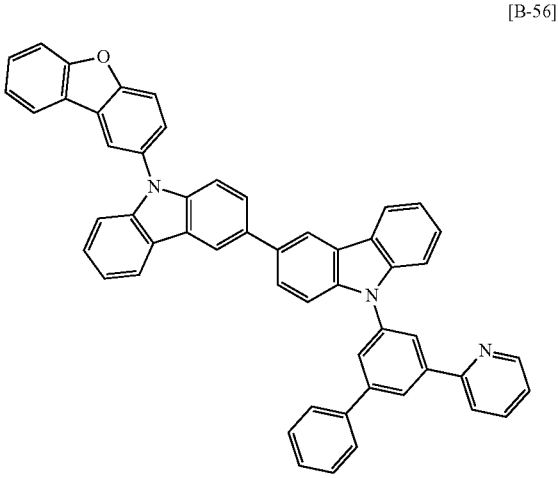
[B-54]
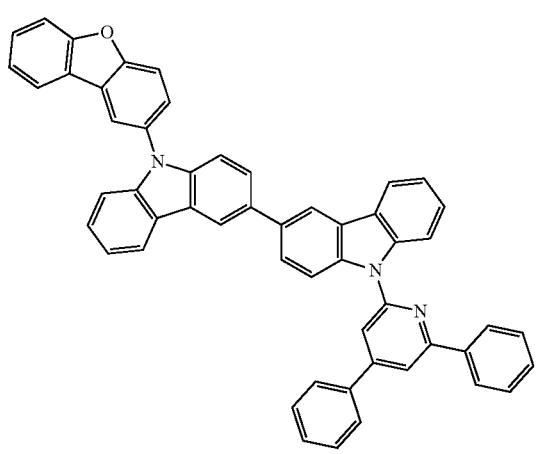
[B-57]
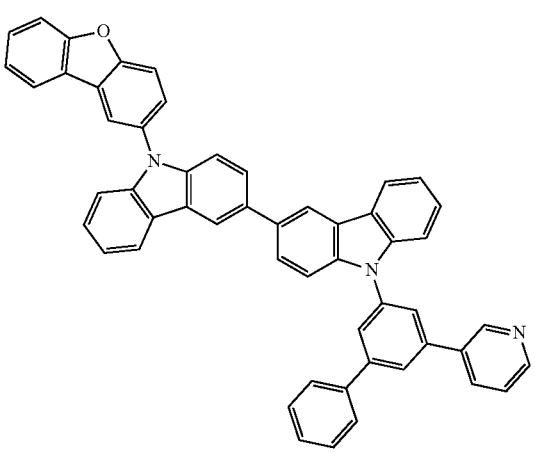

[B-58]
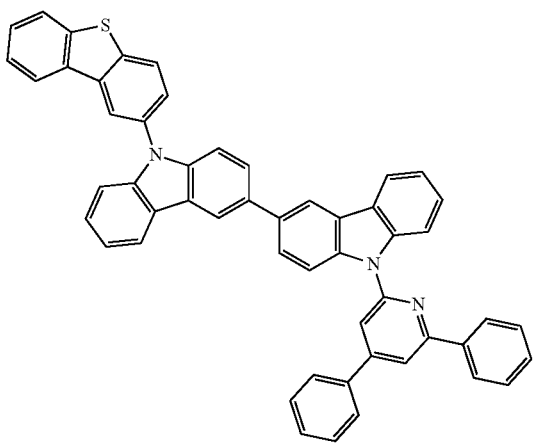
[B-61]
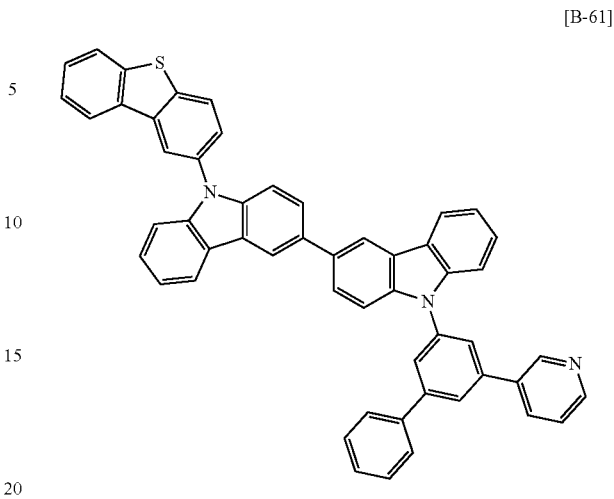
[B-59]
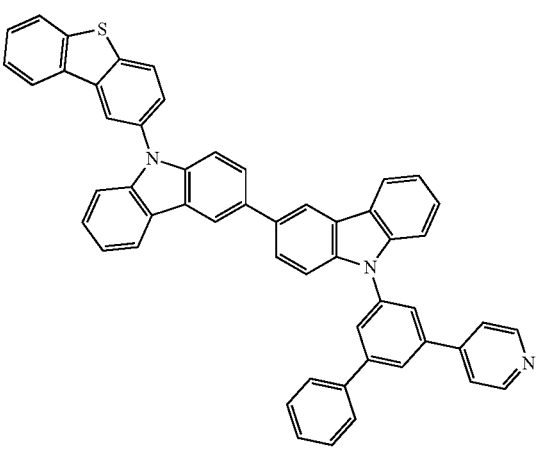
[B-62]
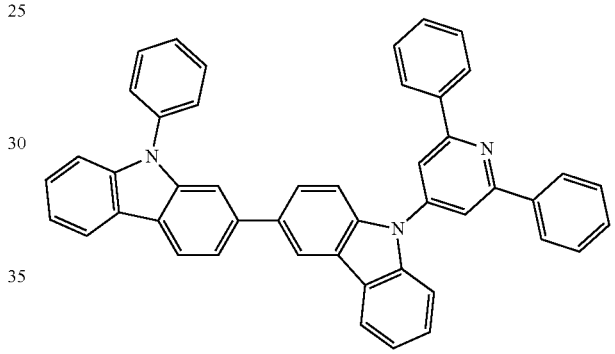
[B-63]
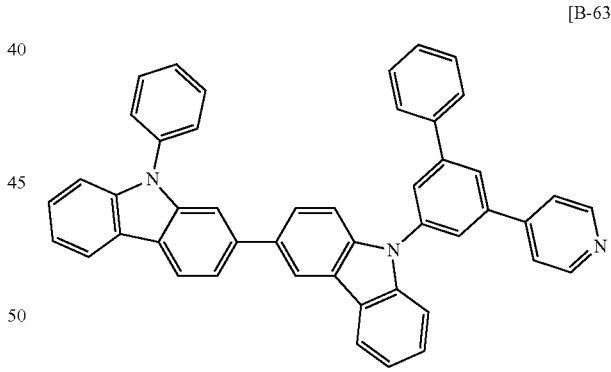
[B-60]
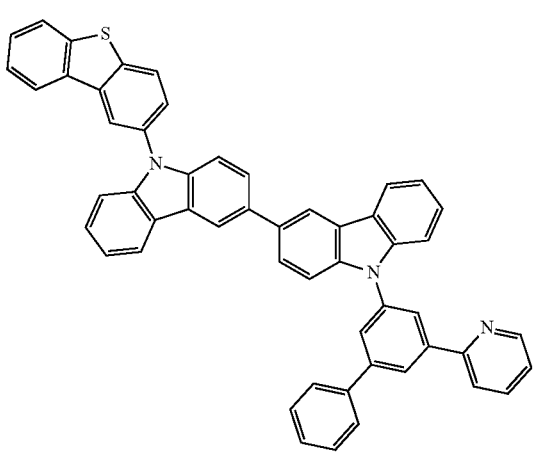
[B-64]
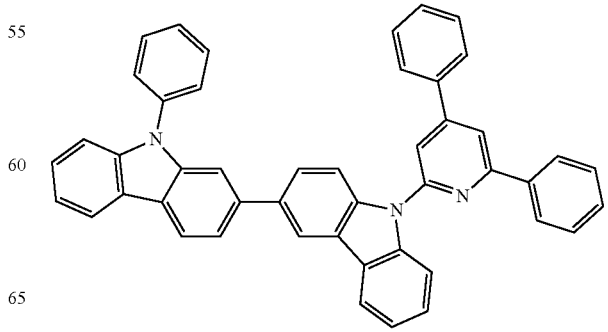

[B-65]
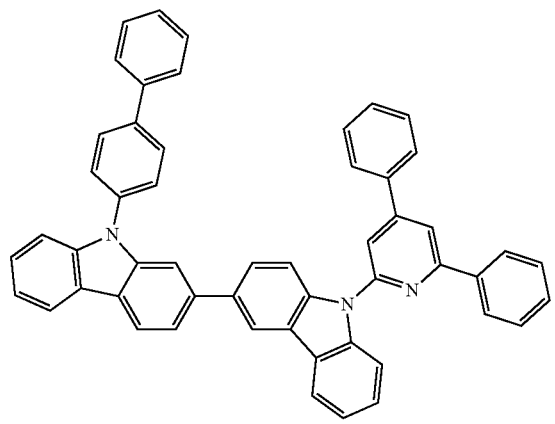
[B-66]
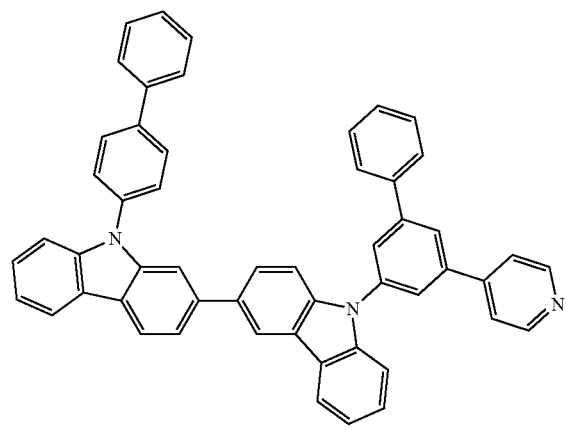
[B-67]
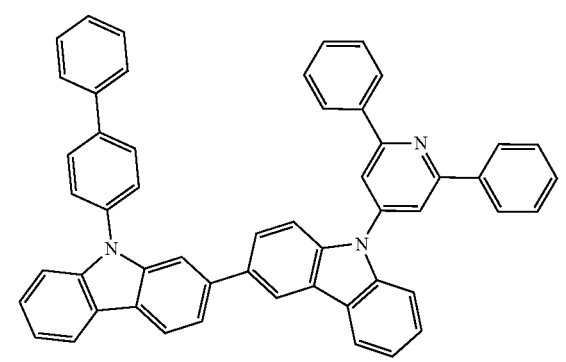
[B-68]
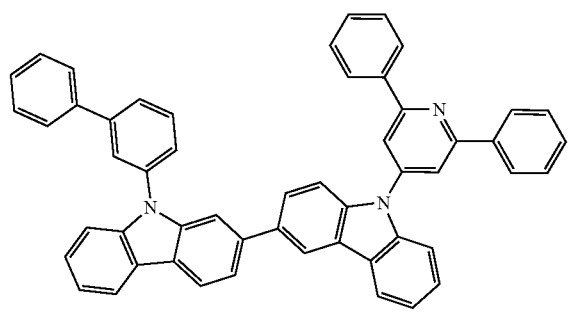
[B-69]
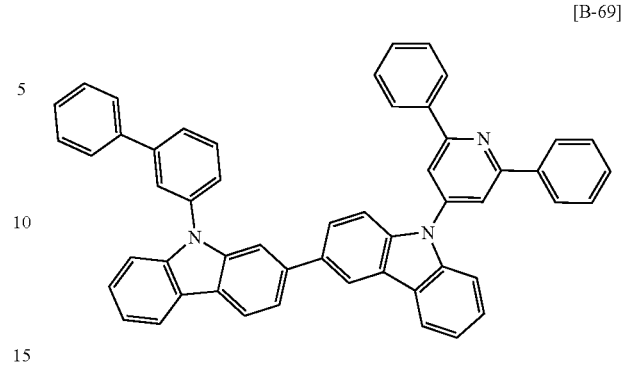
[B-70]
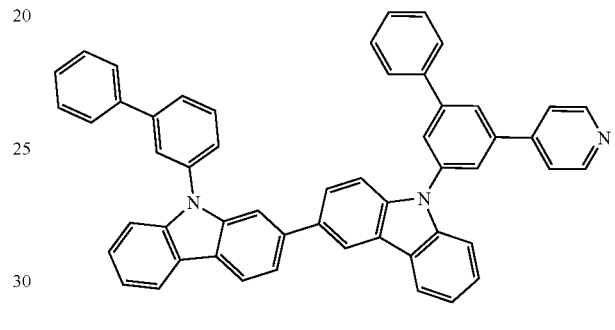
[B-71]
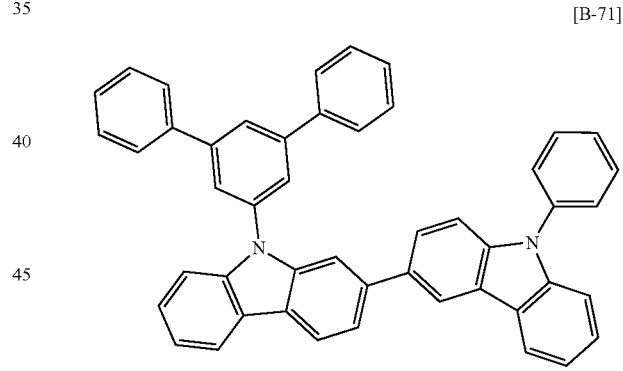
[B-72]
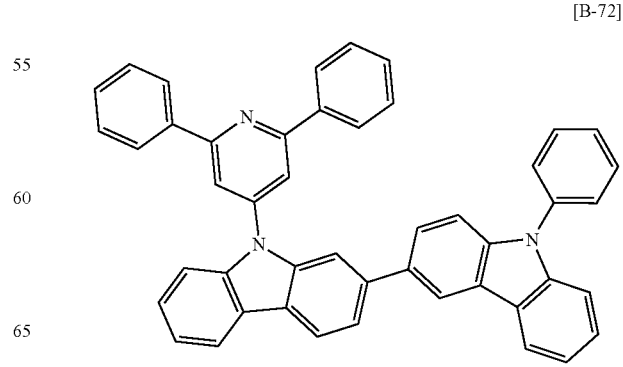

[B-73]
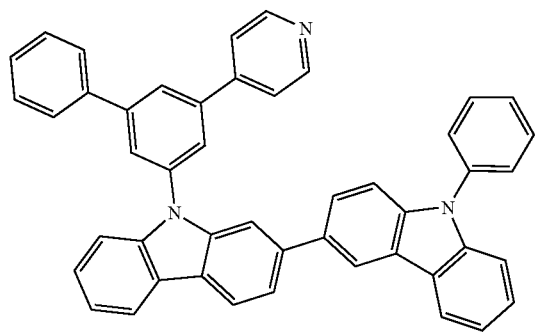
[B-74]
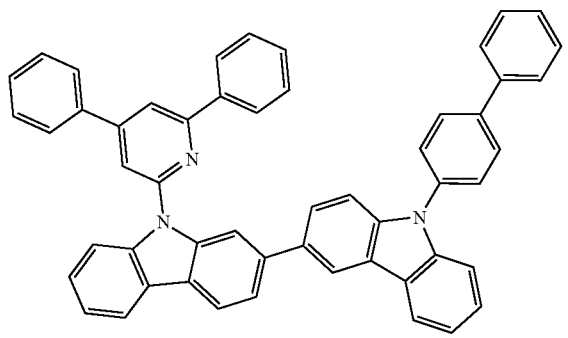
[B-75]
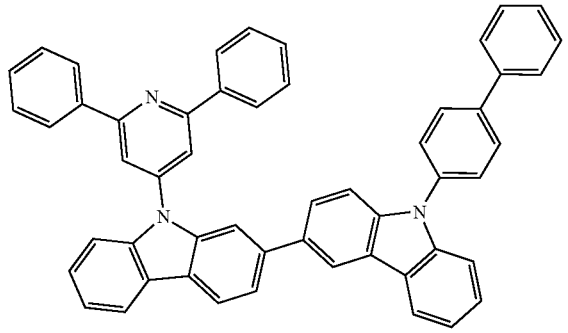
[B-76]
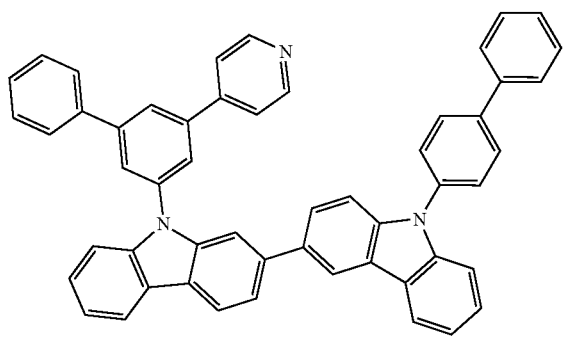
[B-77]
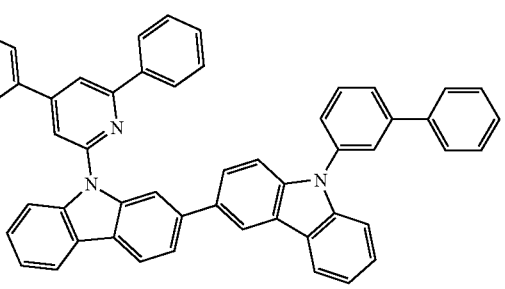
[B-78]
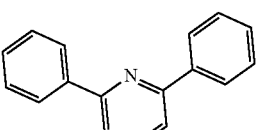
[B-79]
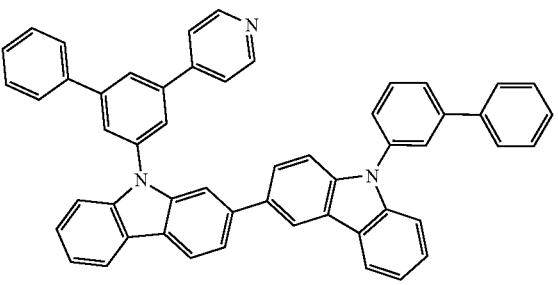
[B-80]
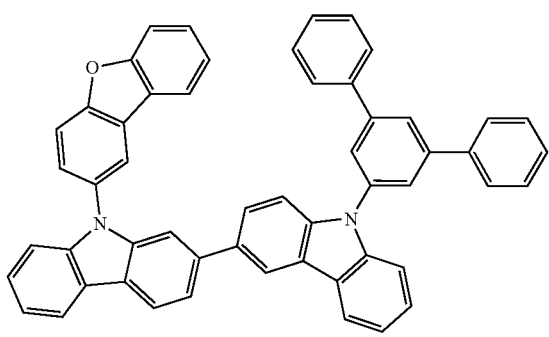
[B-81]
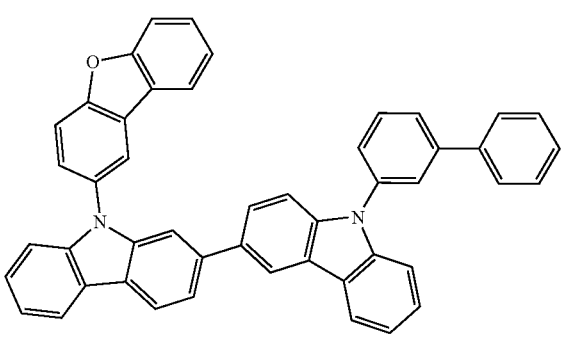

[B-82]
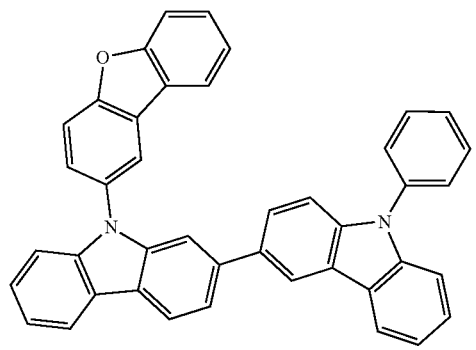
[B-86]
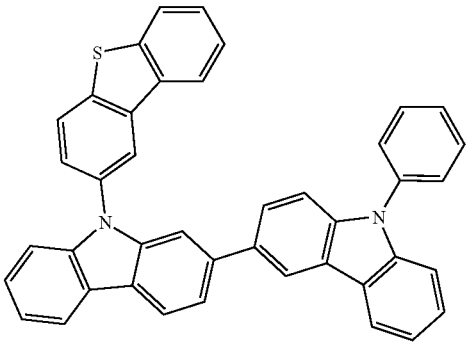
[B-83]
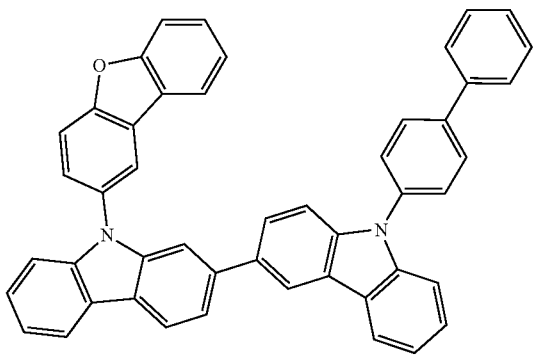
[B-87]
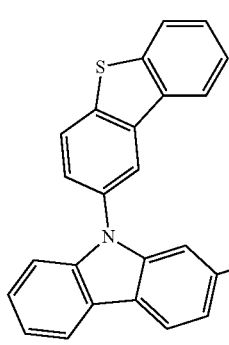
[B-84]
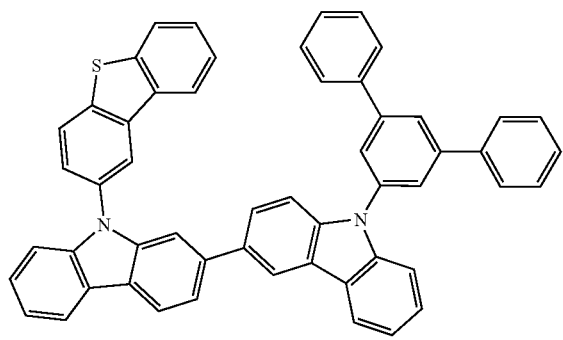
[B-88]
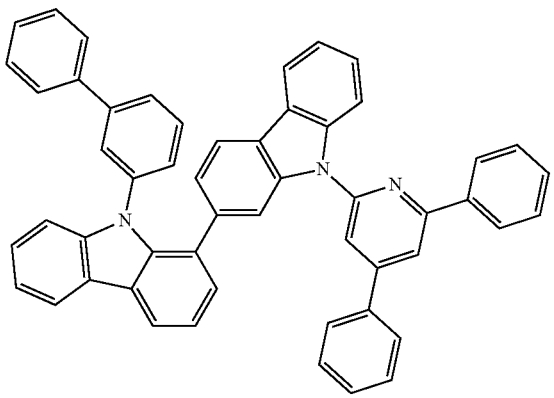
[B-85]
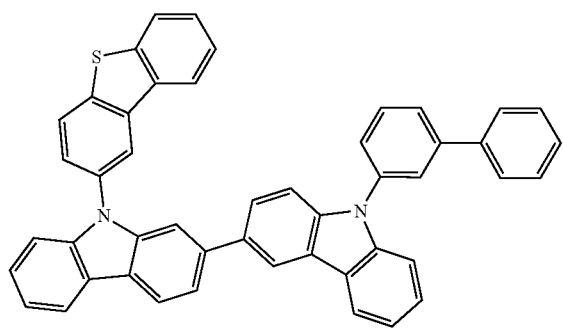
[B-89]
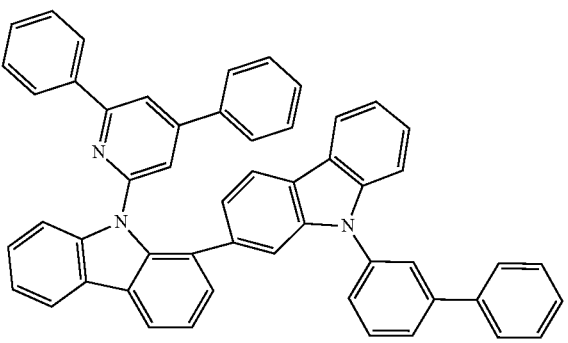

-continued
[B-90]
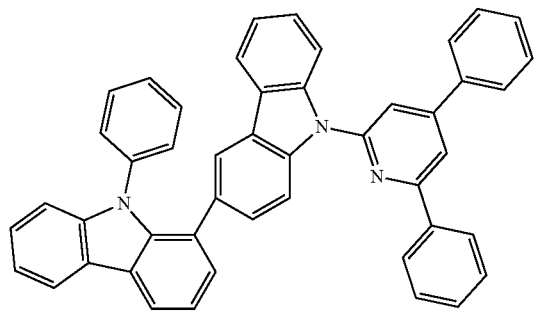
[B-94]
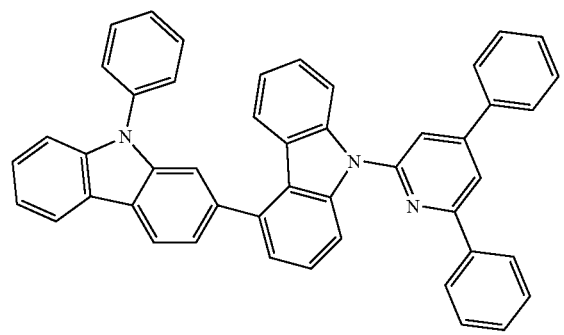
[B-91]
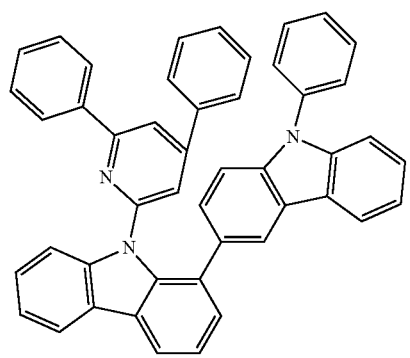
[B-95]
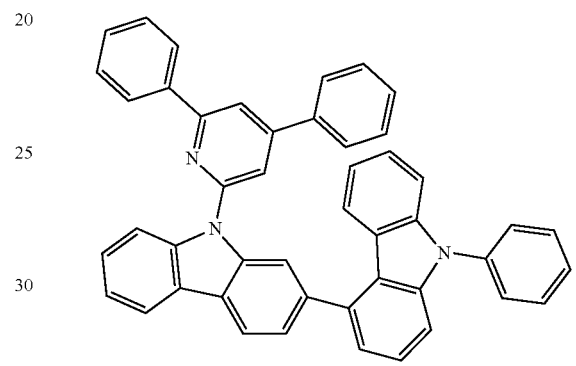
[B-92]
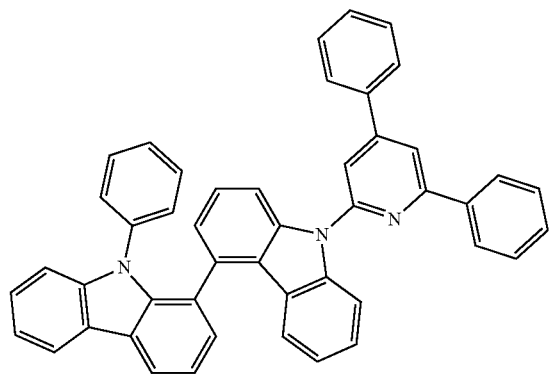
[B-96]
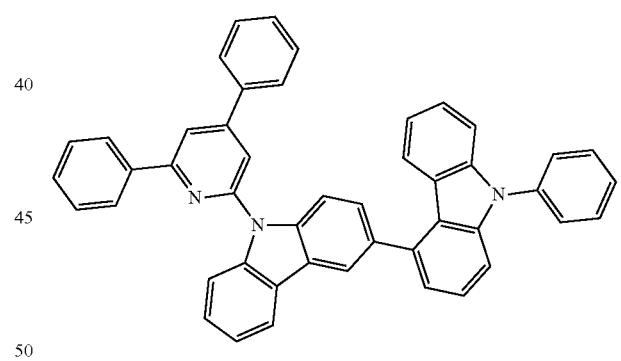
[B-93]
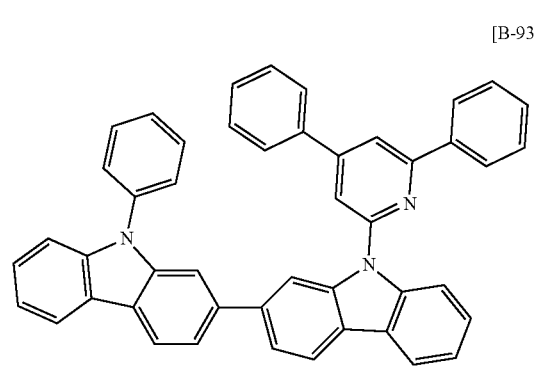
[B-97]
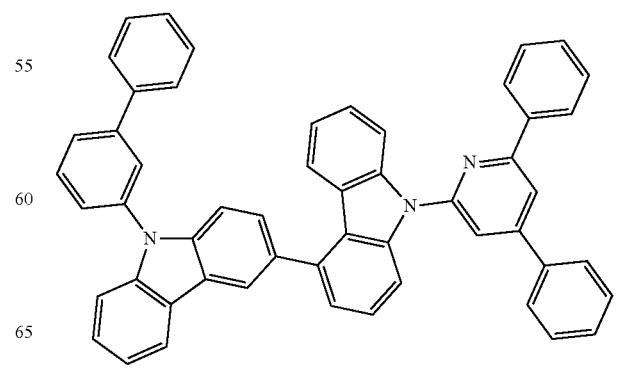

[B-98]
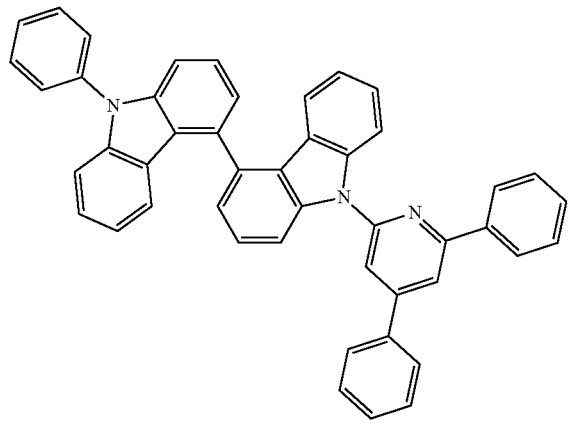
[B-100]
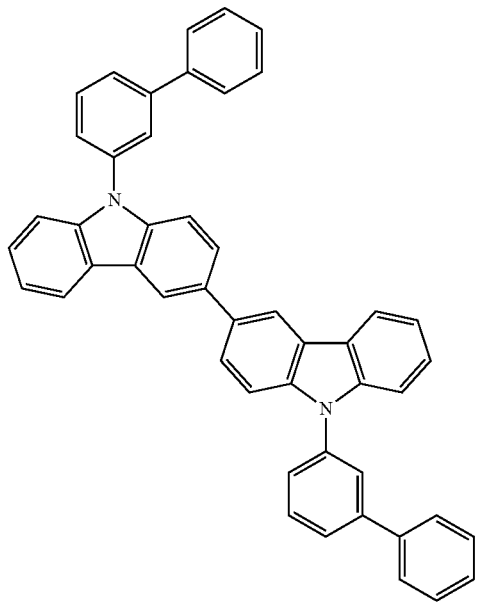
[B-101]
[B-99]
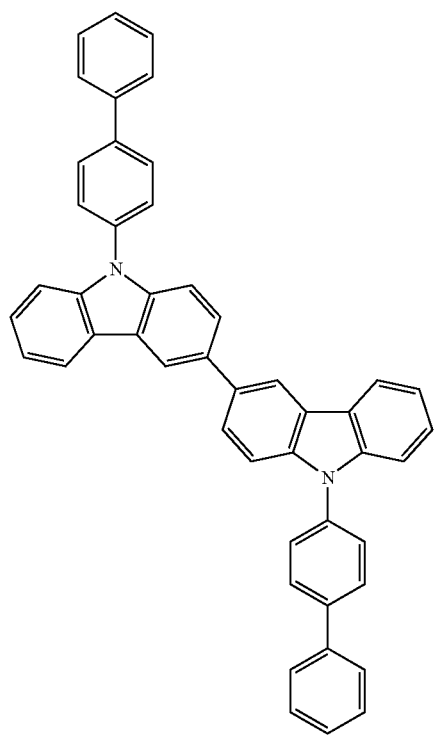
[B-102]
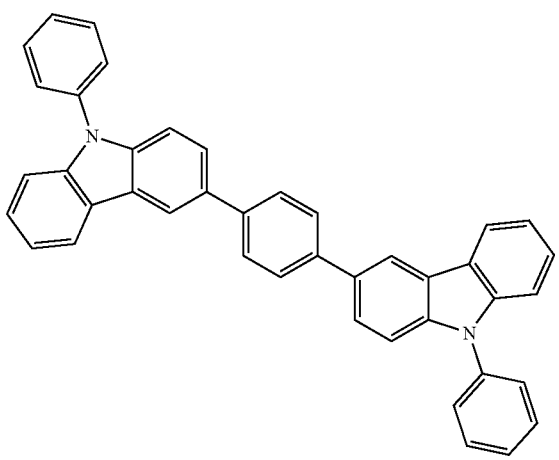

[B-103]
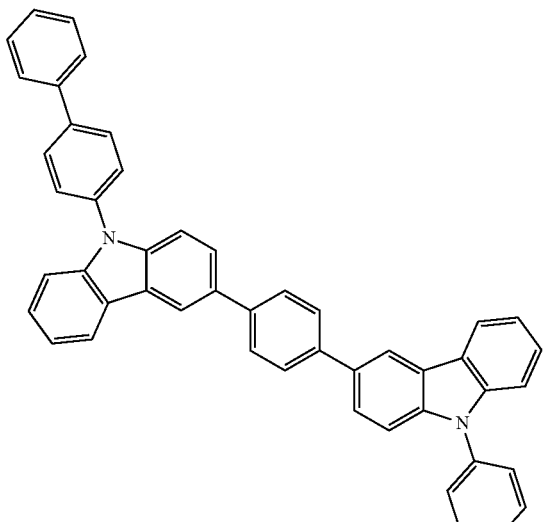
[B-104]
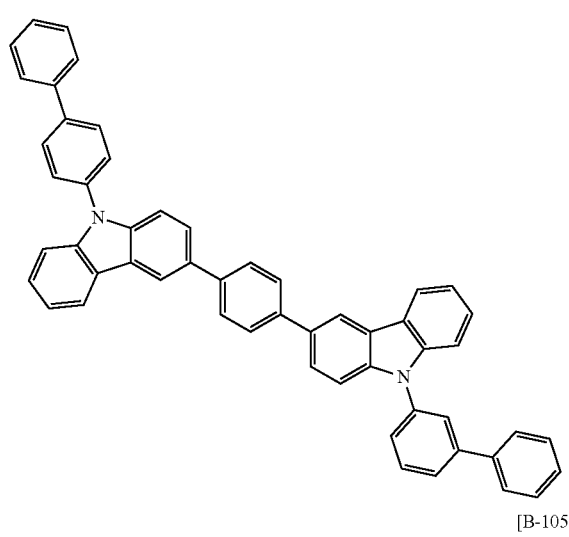
[B-105]
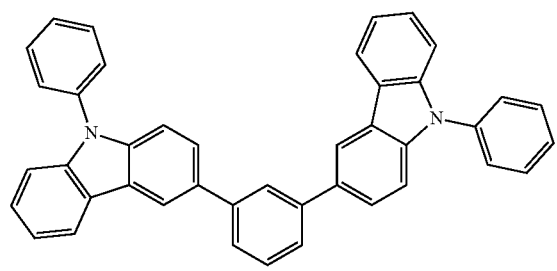
[B-106]
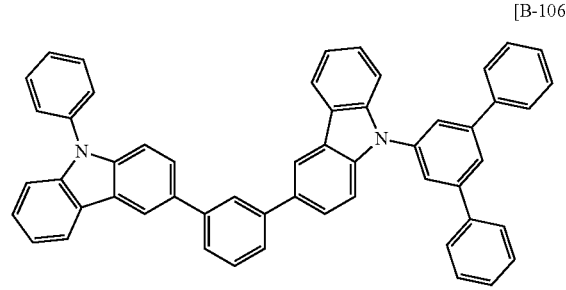
[B-107]
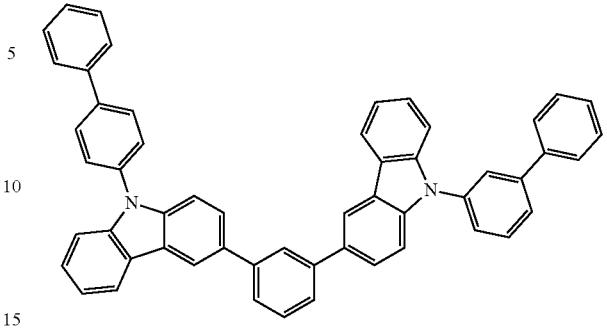
[B-108]
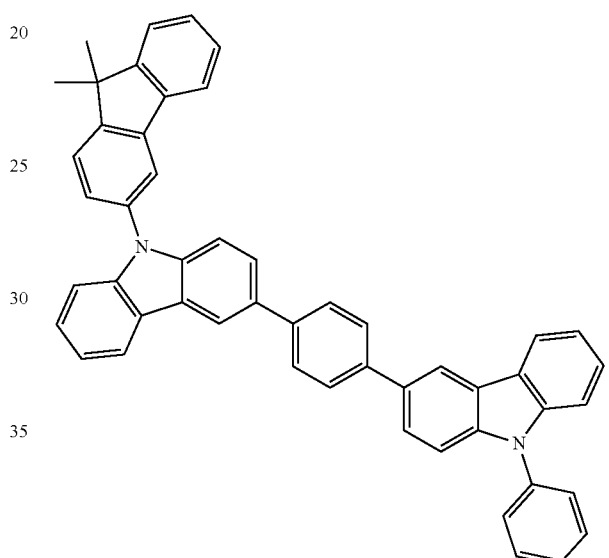
[B-109]
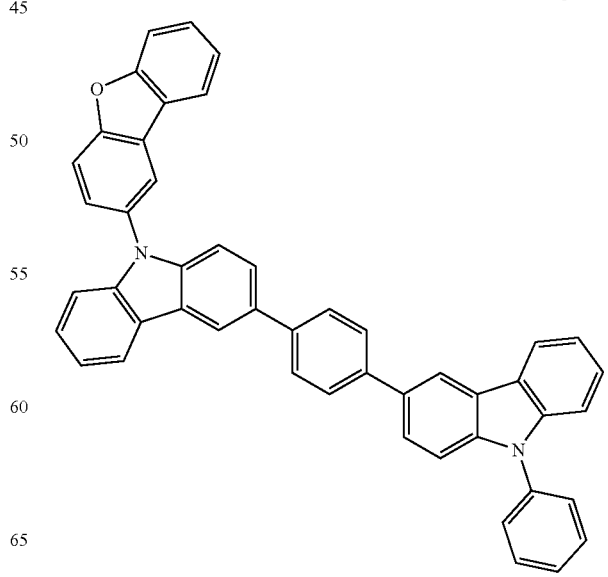

[B-110]
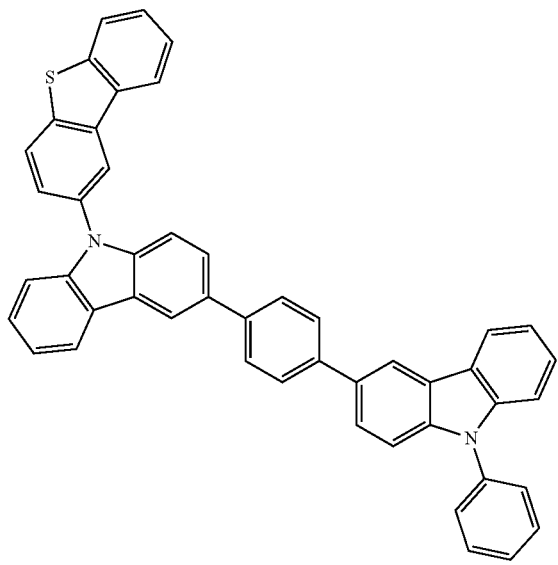
[B-111]
[B-112]
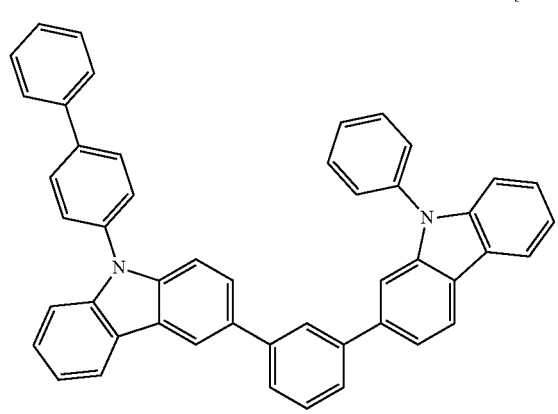
[B-113]
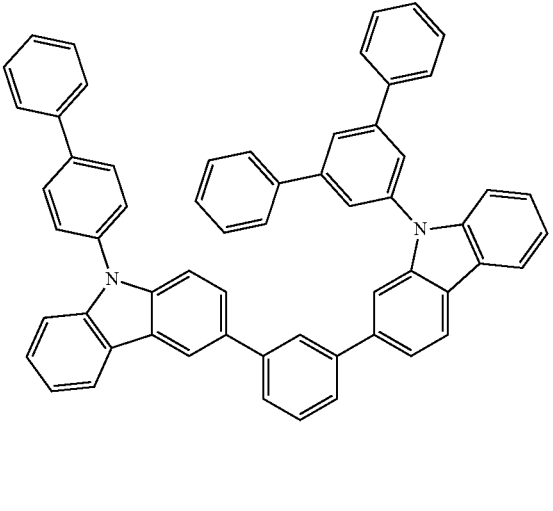
[B-114]
[B-115]
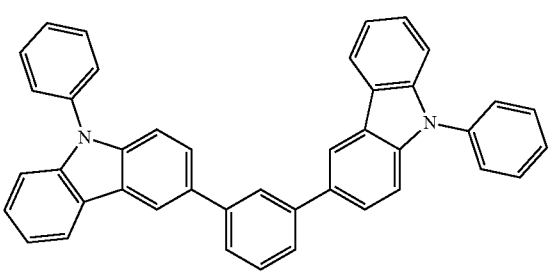
[B-116]
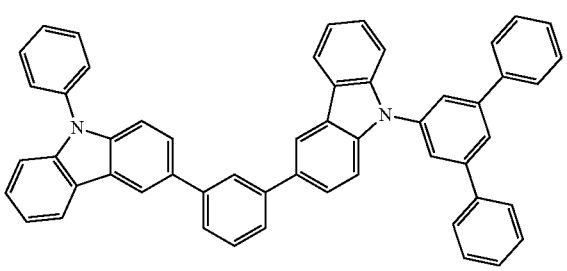

[B-117]
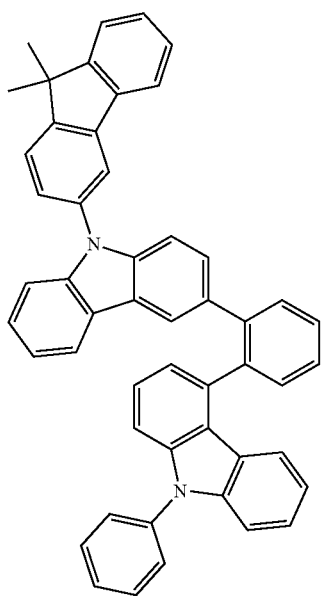
[B-118]
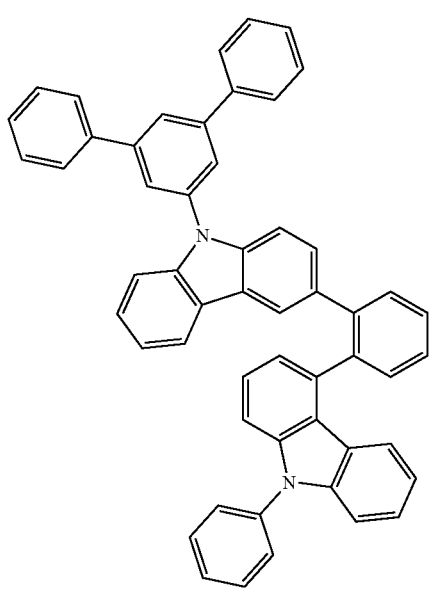
[B-119]
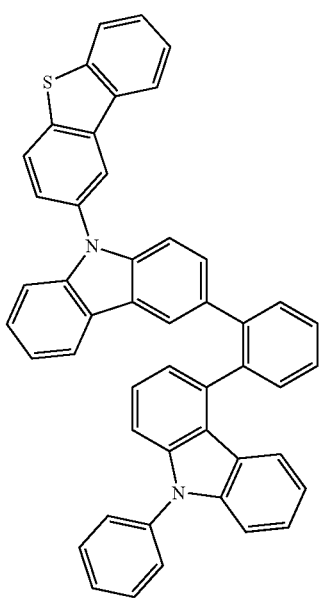
[B-120]
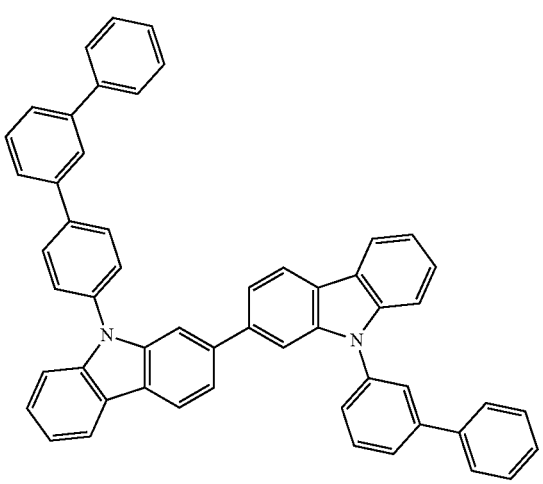
[B-121]
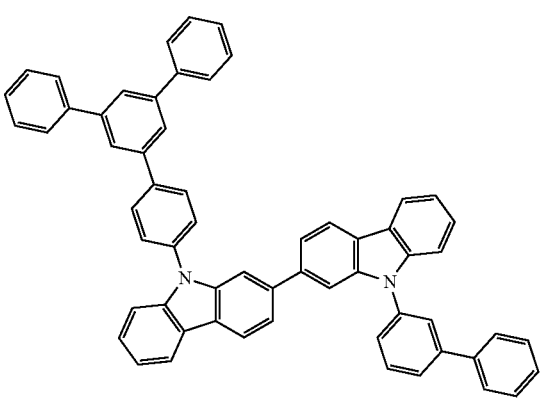

[B-122]
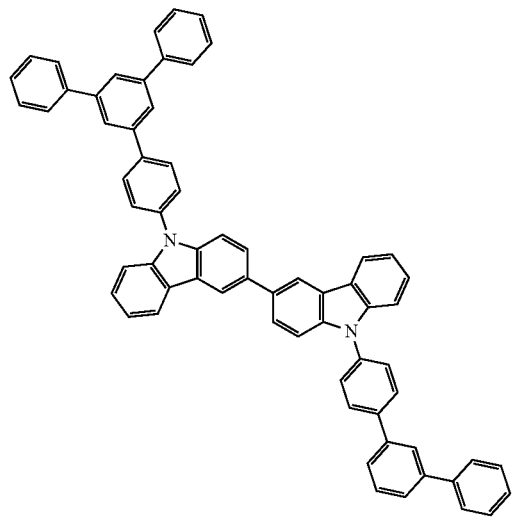
[B-124]
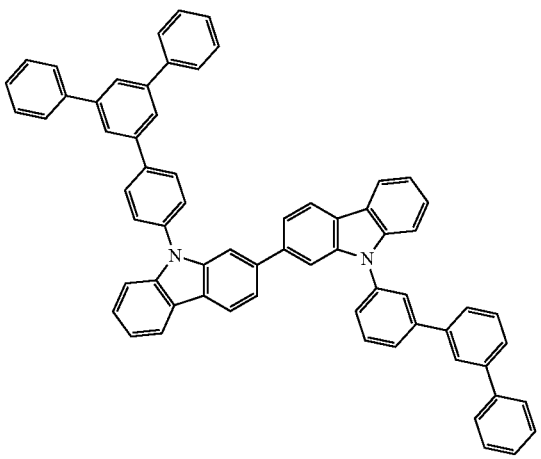
[B-123]
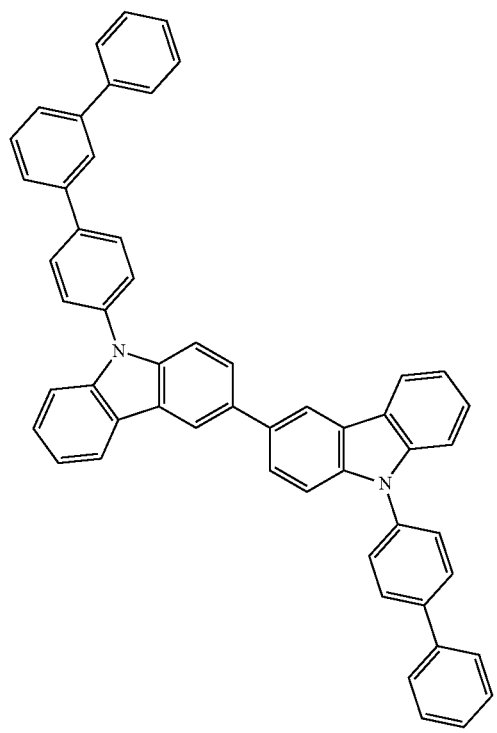
[B-125]
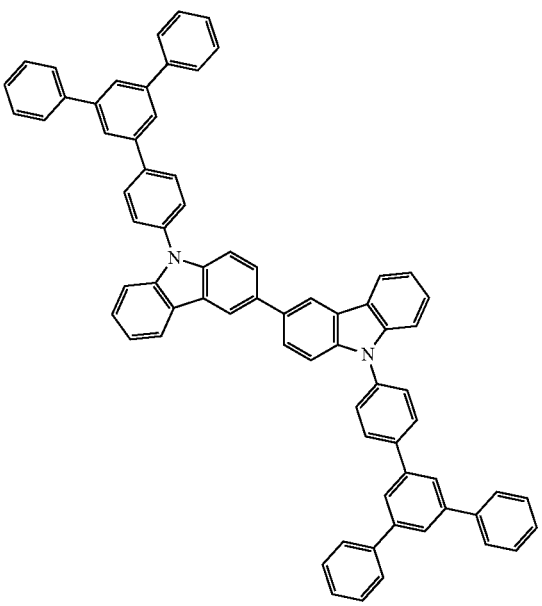

[B-126]
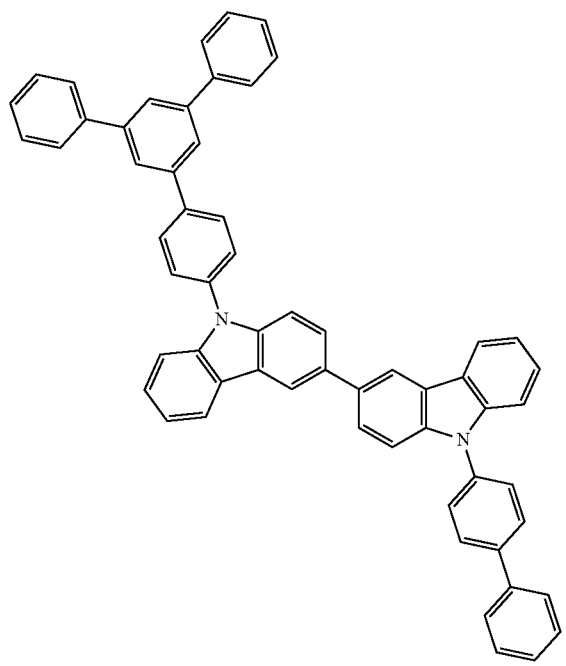
[B-127]
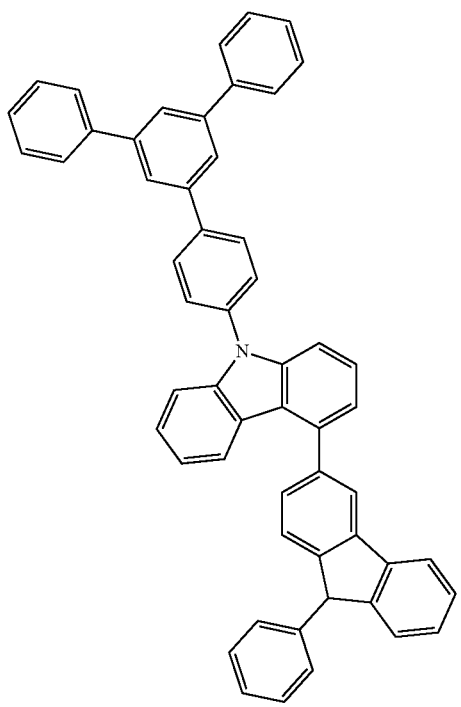
[B-128]
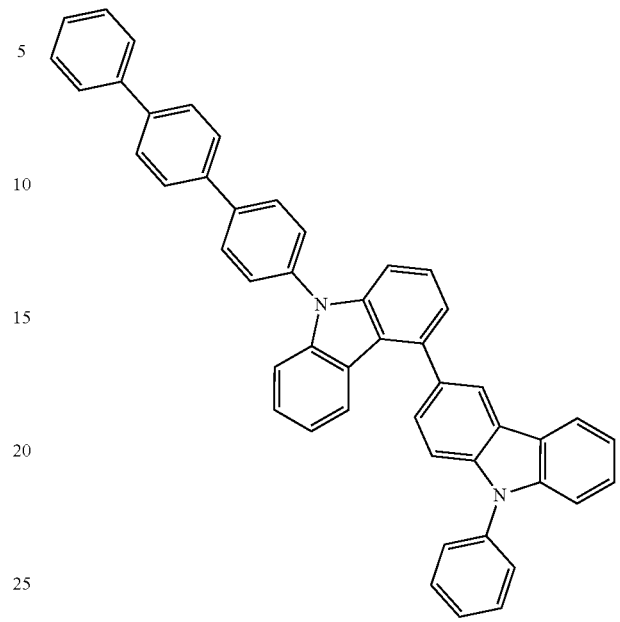
[B-129]
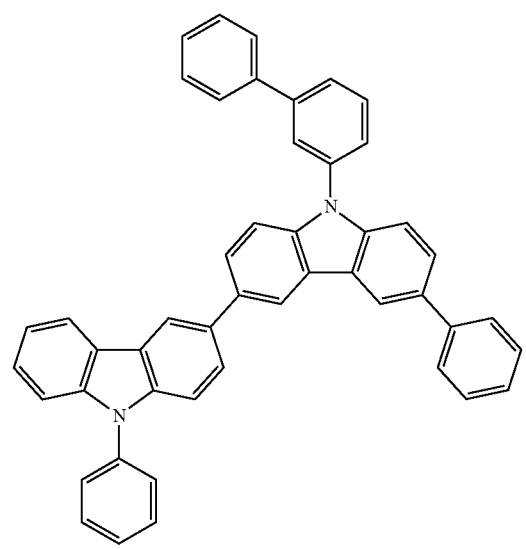

[B-130]
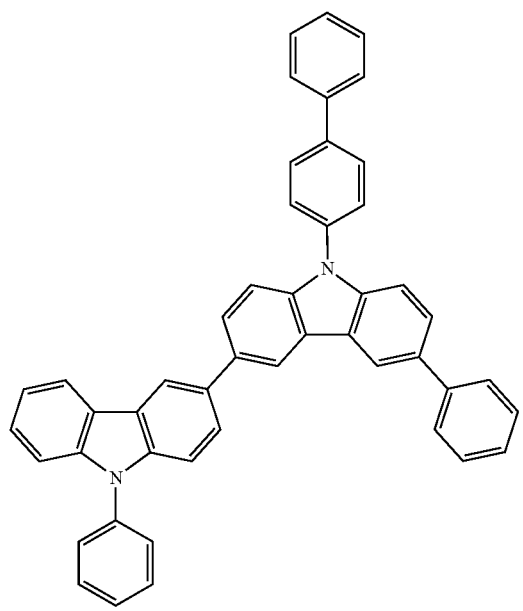
[B-131]
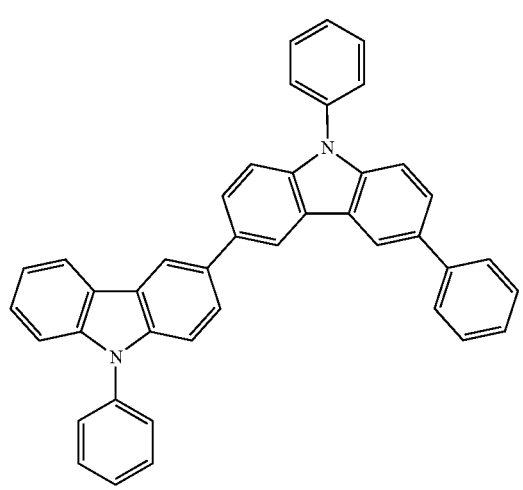
[B-132]
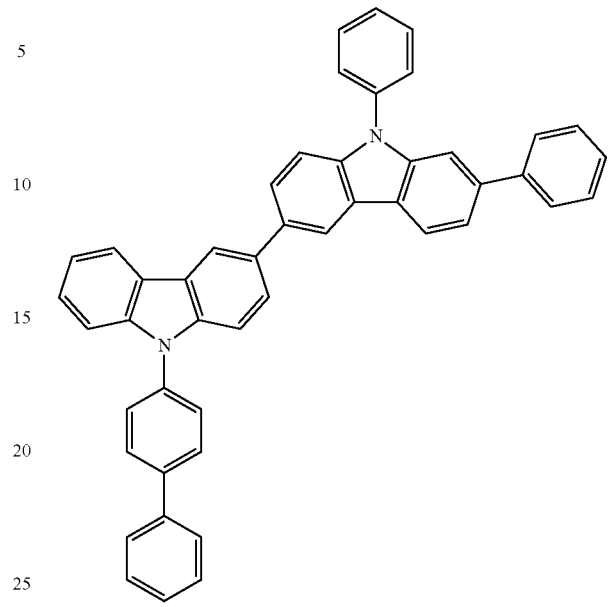
[B-133]
[B-134]
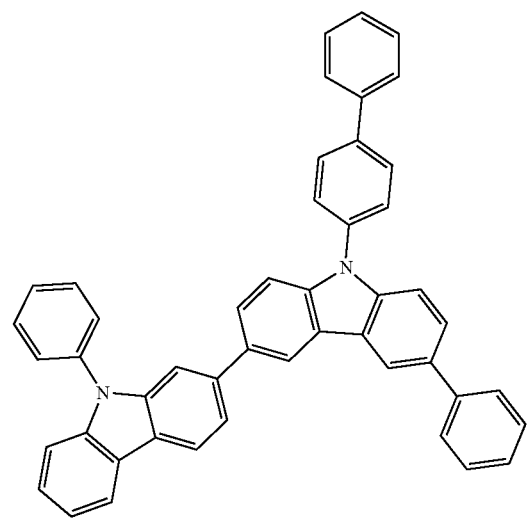

[B-135]
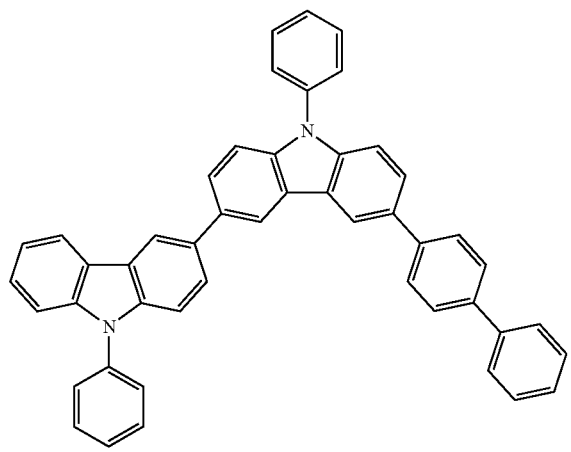
[B-137]
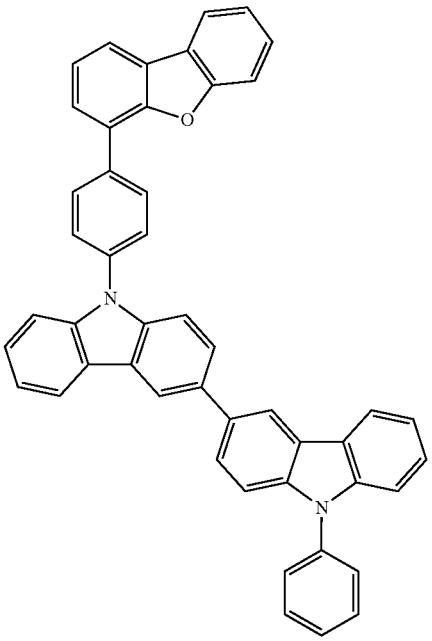
[B-138]
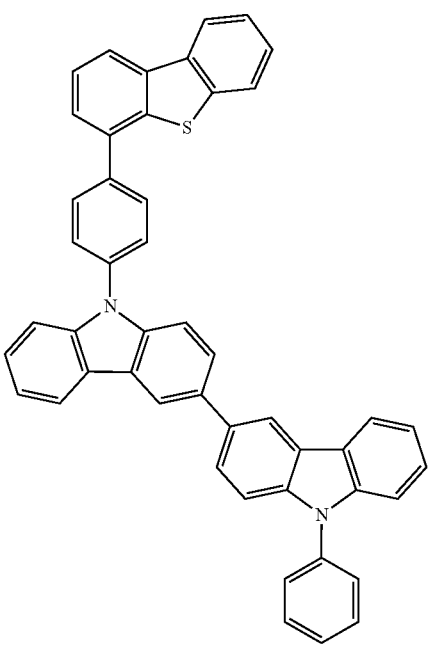
[B-136]
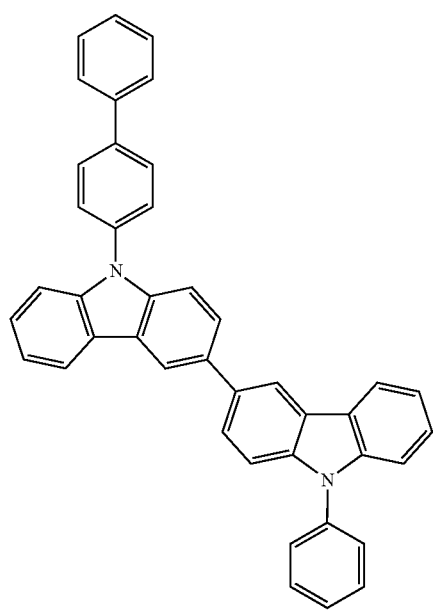
[C-1]
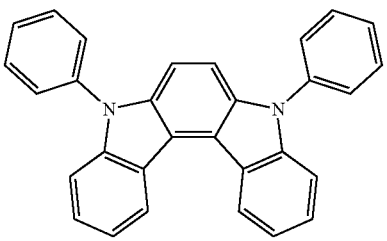

[C-2]
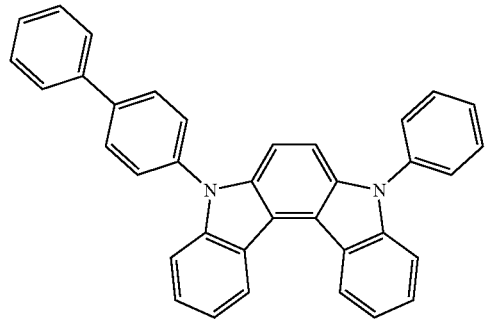
[C-3]
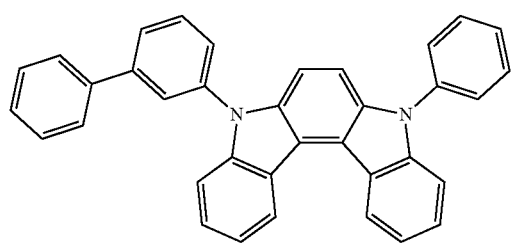
[C-4]
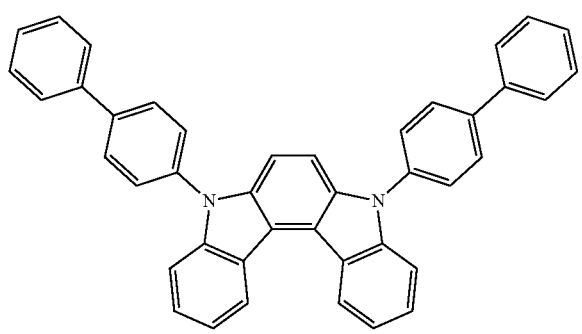
[C-7]
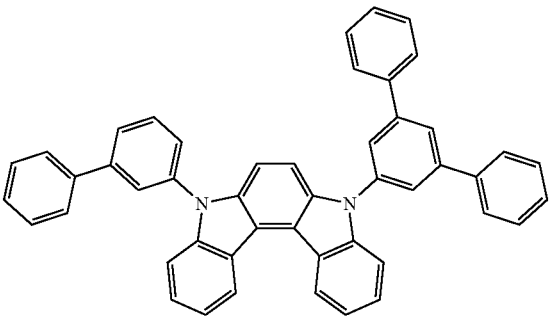
[C-8]
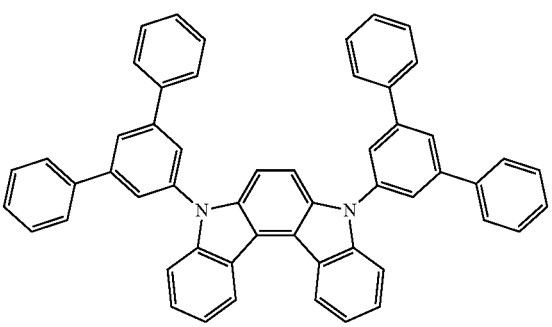
[C-5]
[C-6]
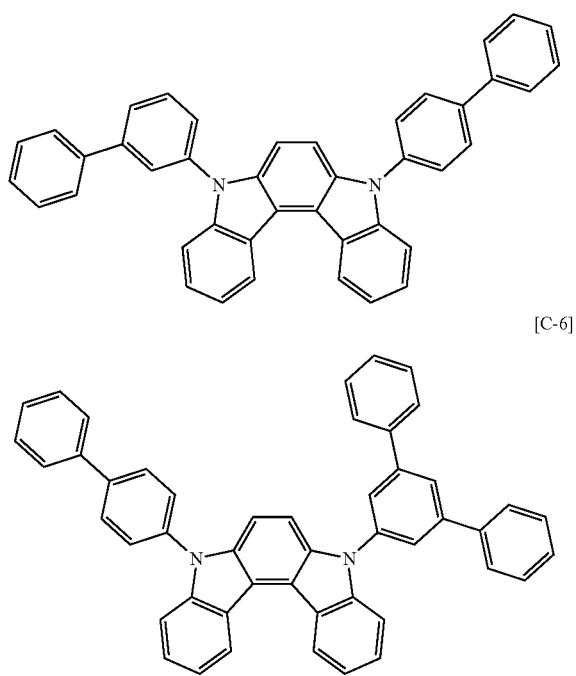
[C-9]
[C-10]
[C-11]
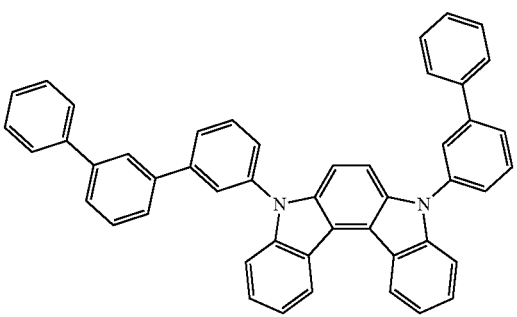

[C-12]
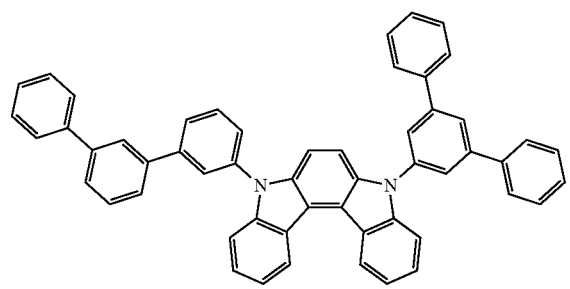
[C-13]
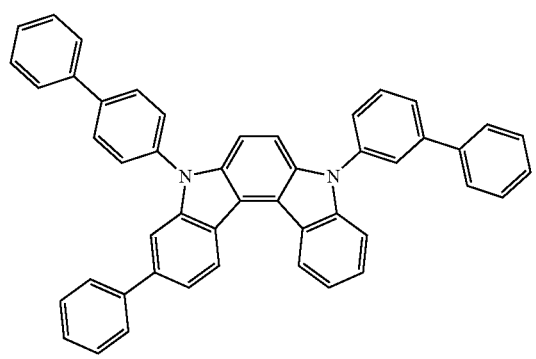
[C-14]
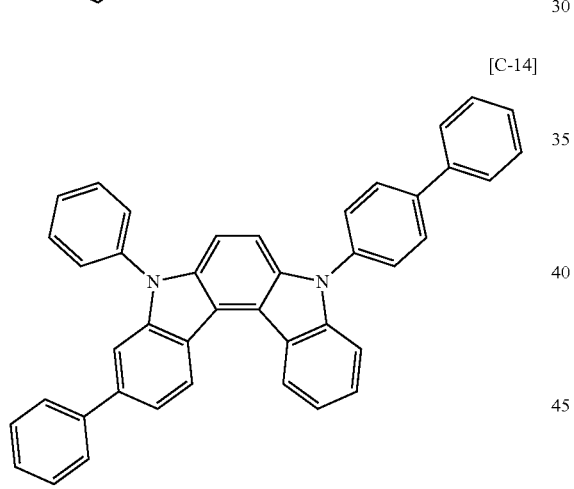
[C-15]
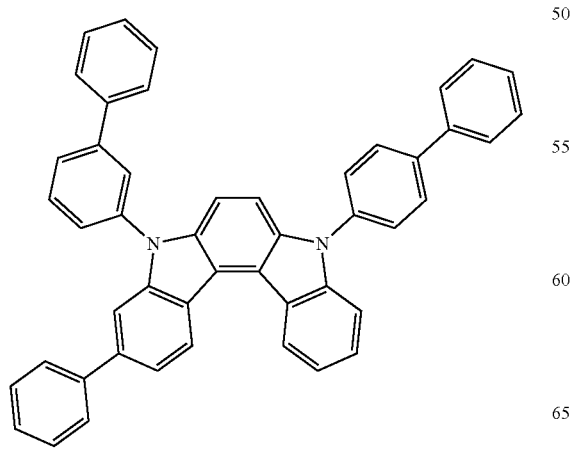
[C-16]
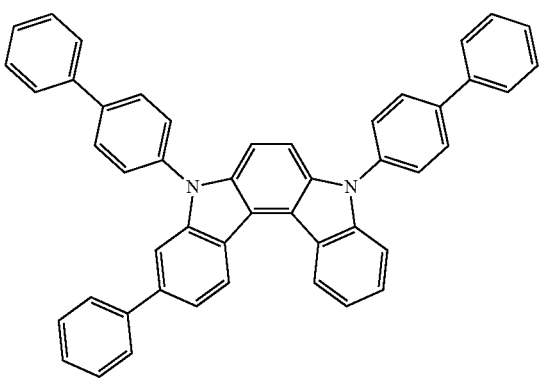
[C-17]
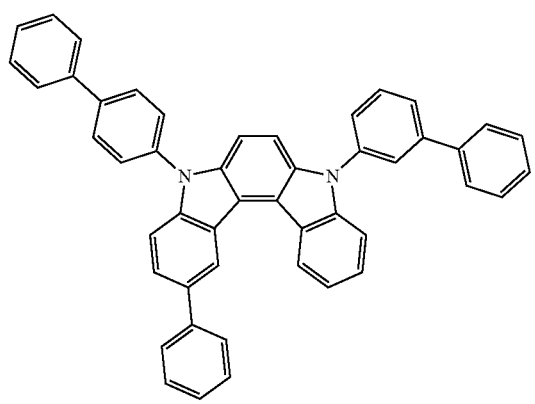
[C-18]
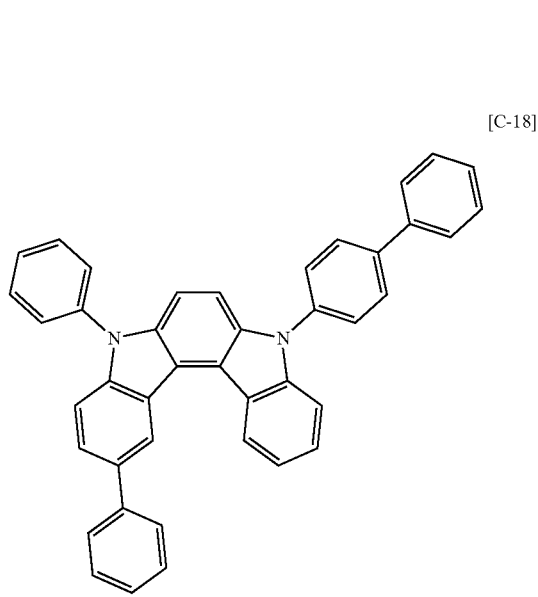

[C-19]
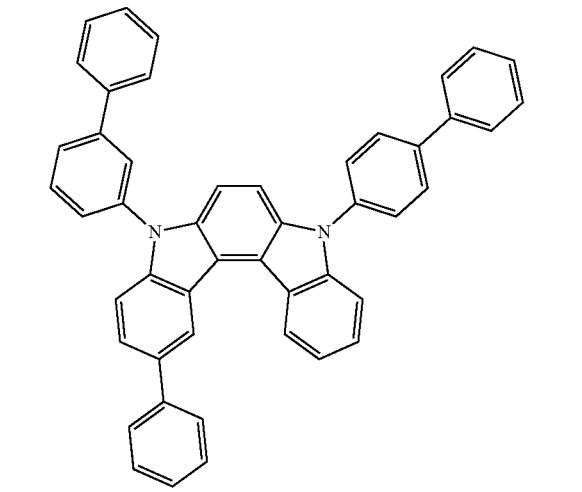
[C-20]
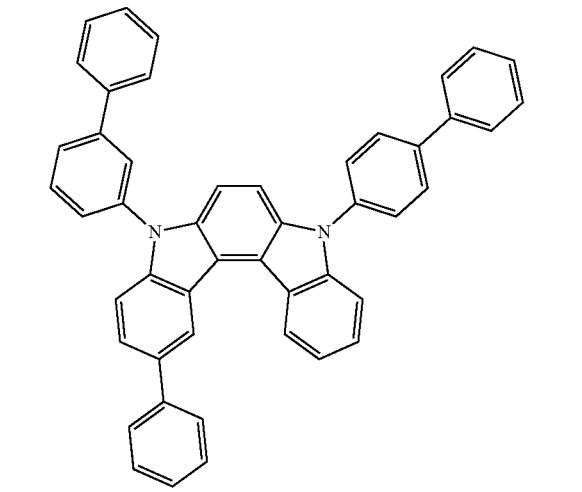
[C-21]
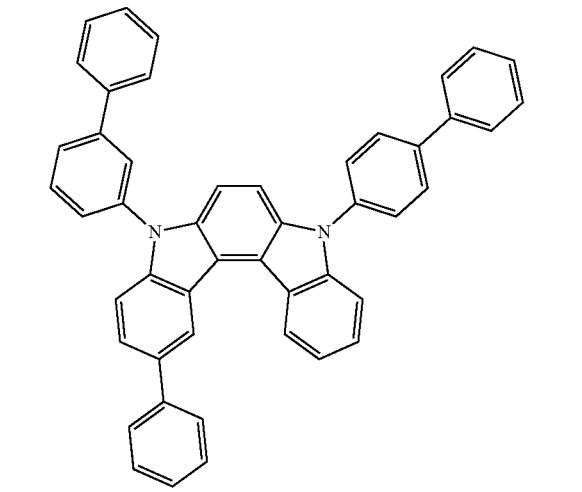
[C-22]
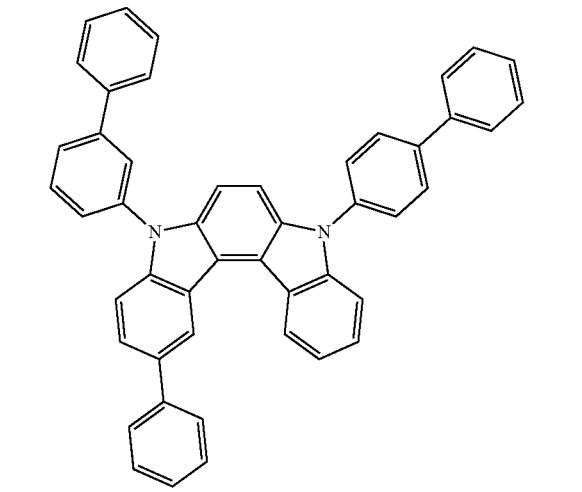
[C-23]
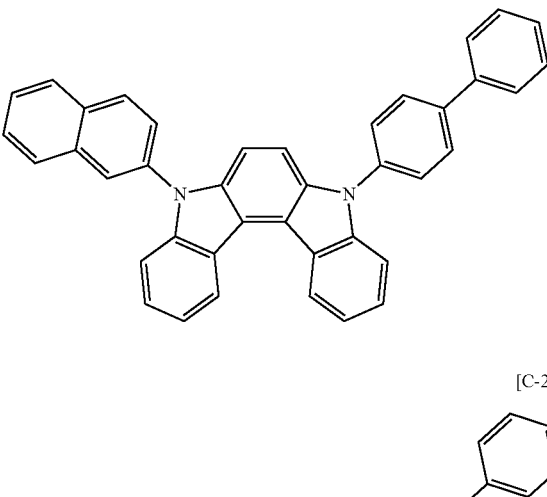
[C-24]
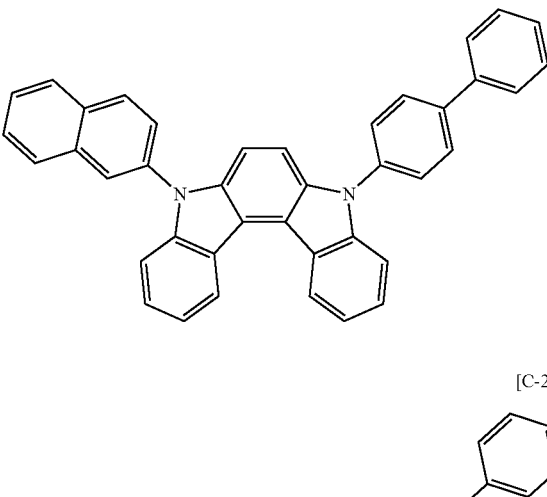
[C-25]
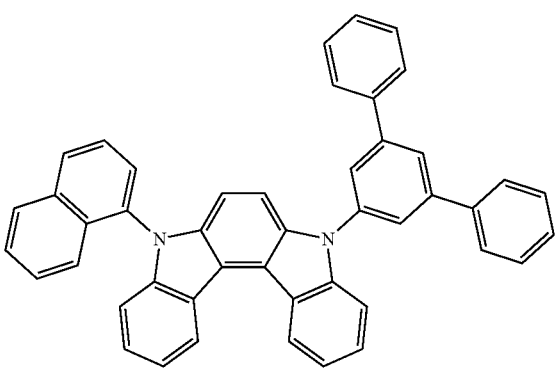
[C-26]
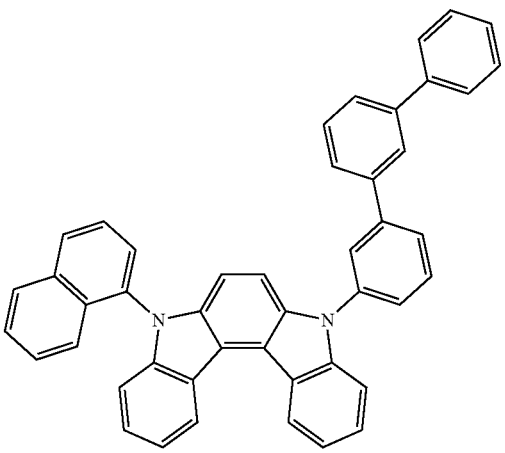

[C-27]
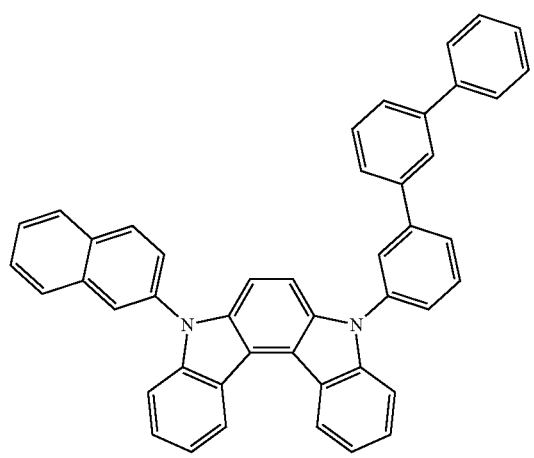
[C-28]
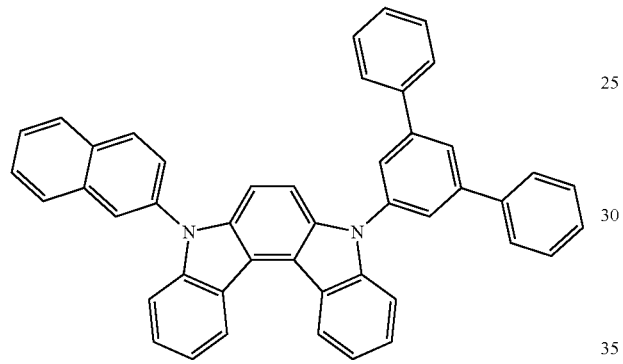
[C-29]
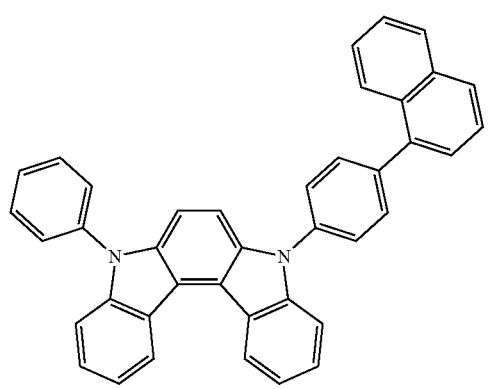
[C-30]
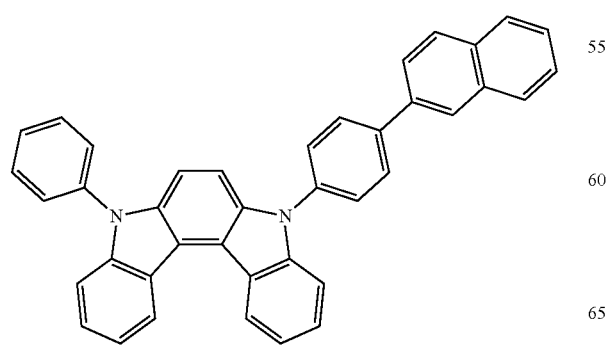
[C-31]
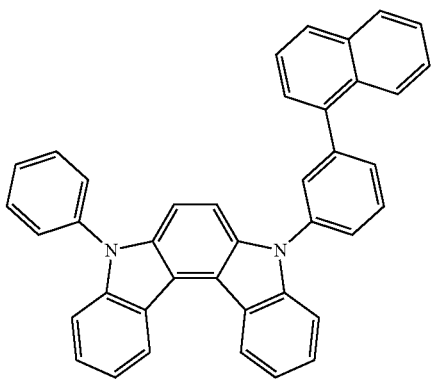
[C-32]
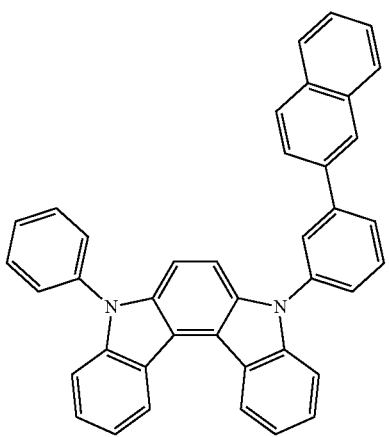
[C-33]
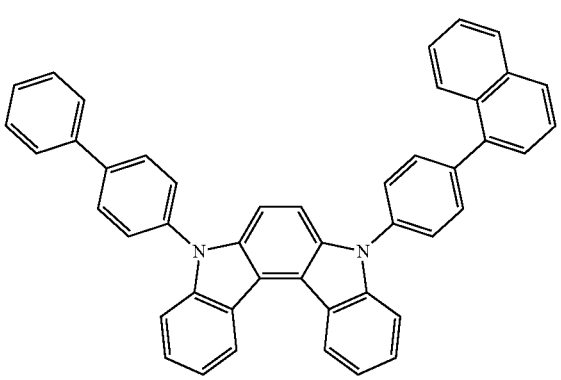
[C-34]
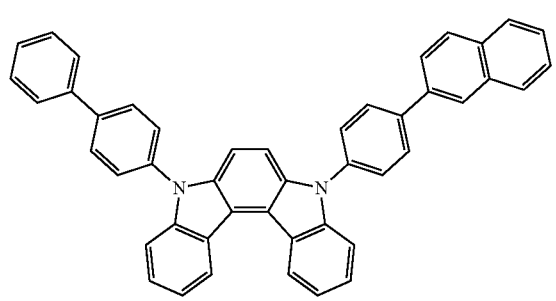

[C-35]
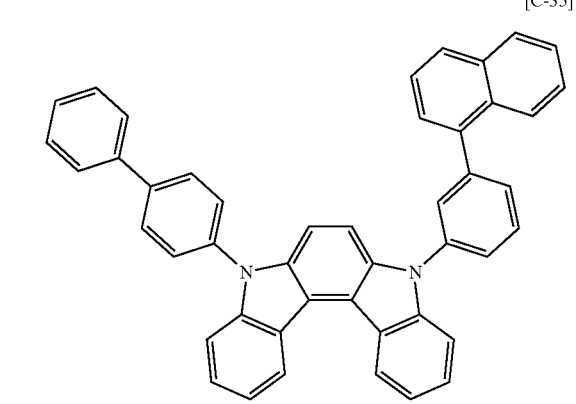
[C-36]
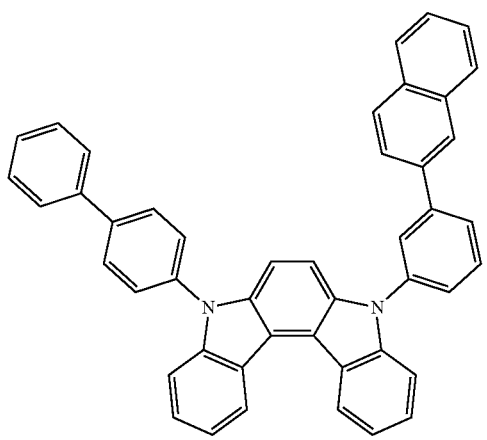
[C-37]
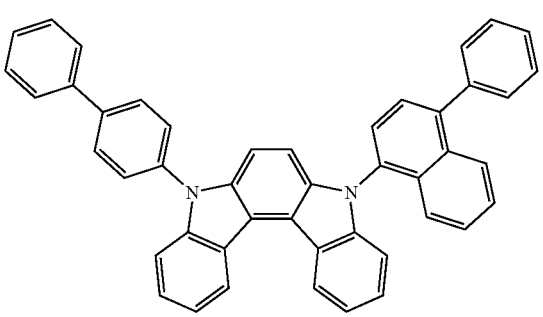
[C-38]
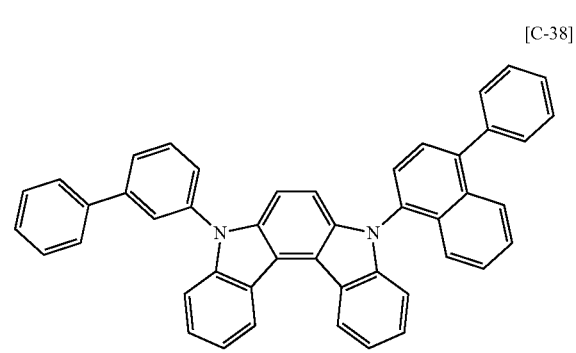
[C-39]
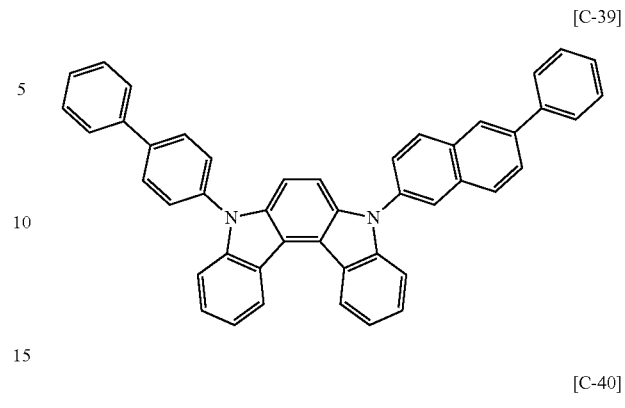
[C-40]
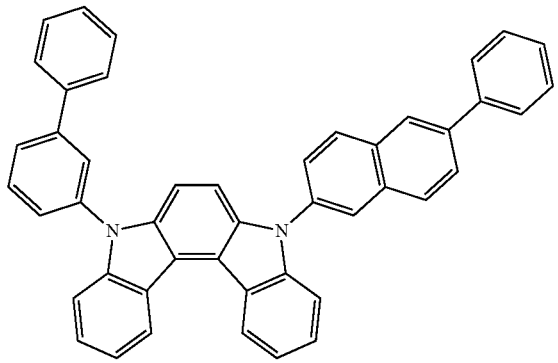
[C-41]
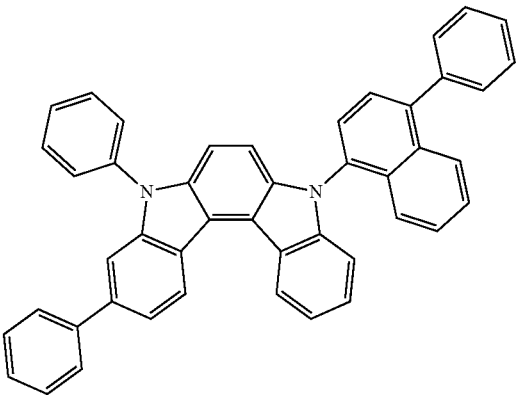
[C-42]
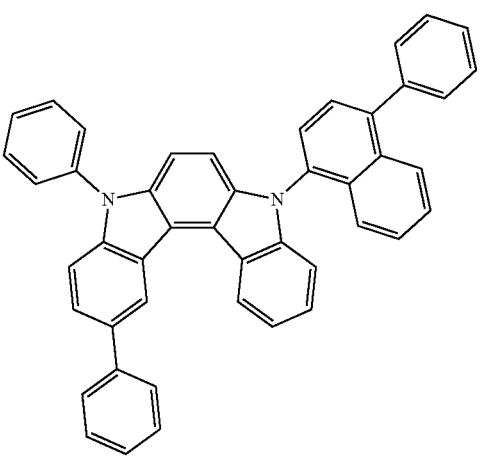

[C-43]
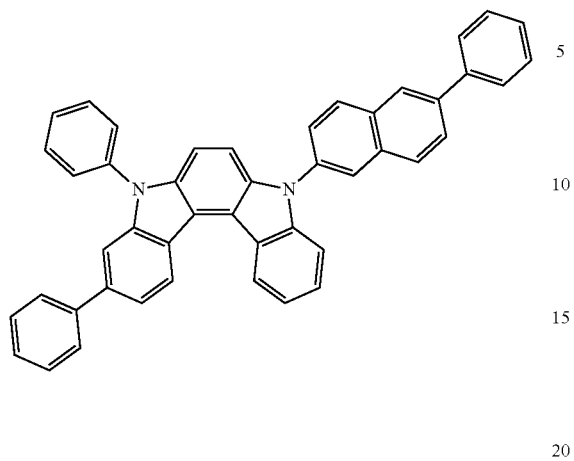
[C-44]
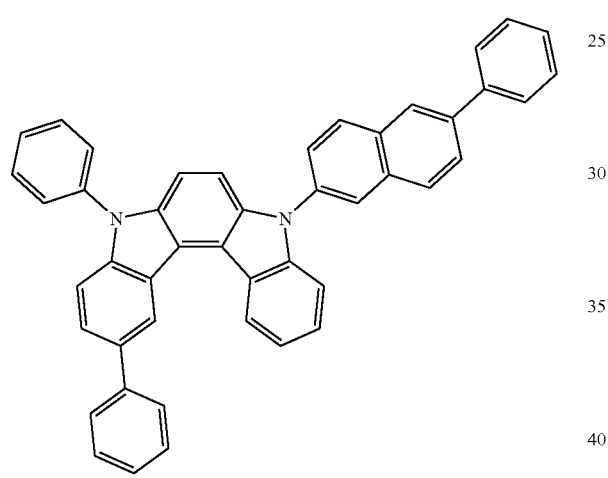
[C-45]
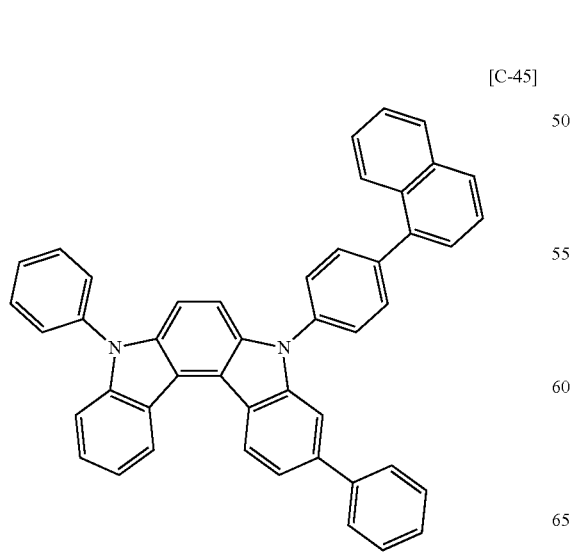
[C-46]
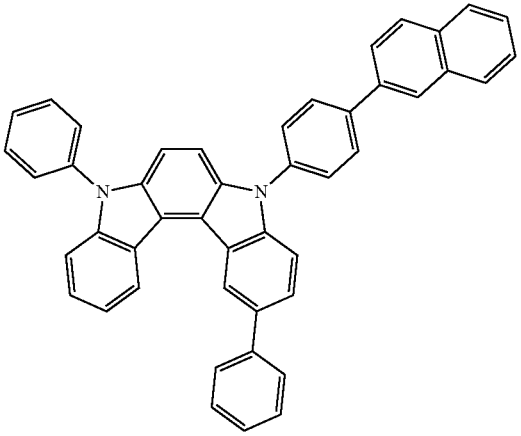
[C-47]
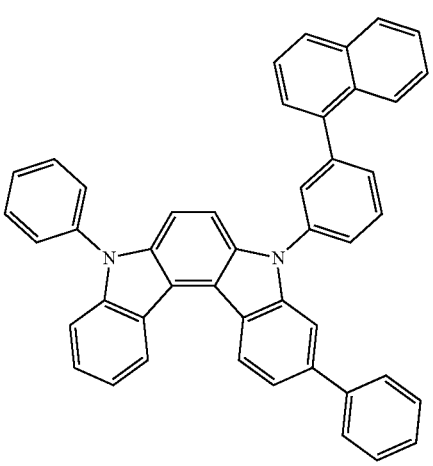
[C-48]
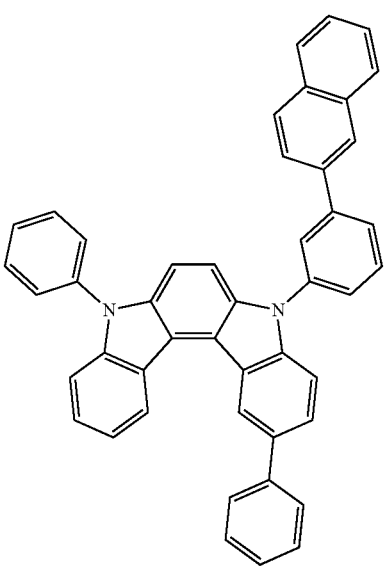

[C-49]
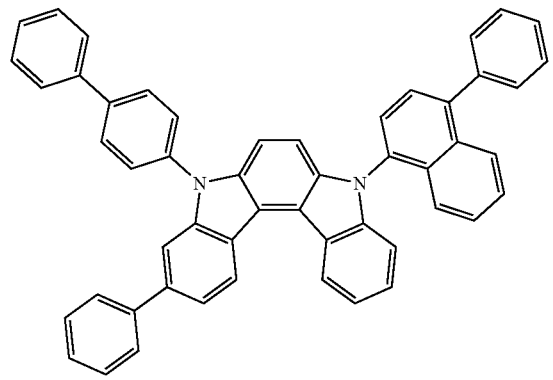
[C-50]
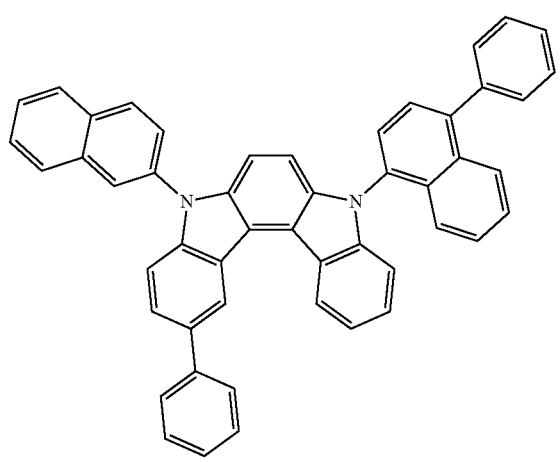
[C-51]
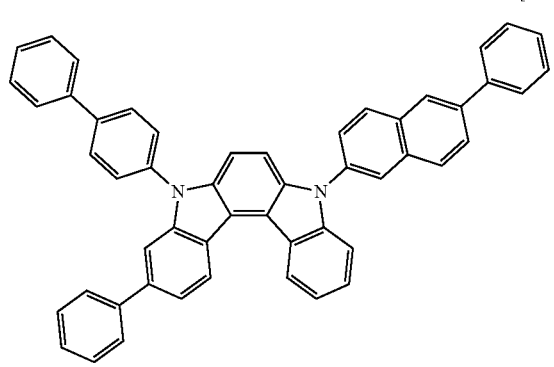
[C-52]
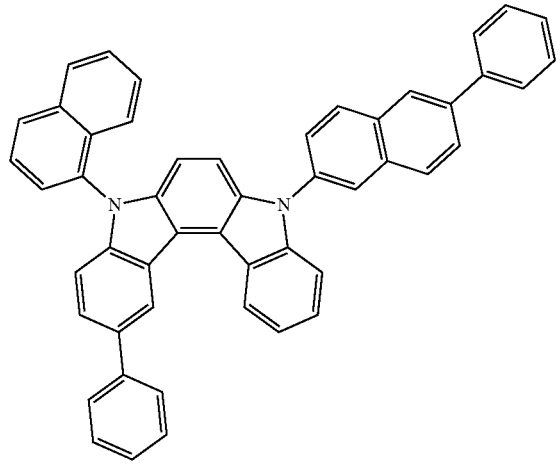
[C-53]
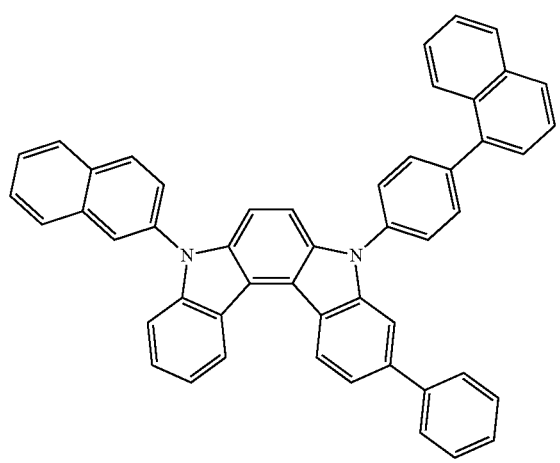
[C-54]
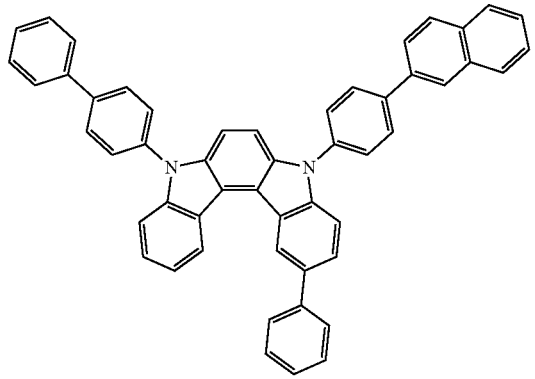

[C-55]

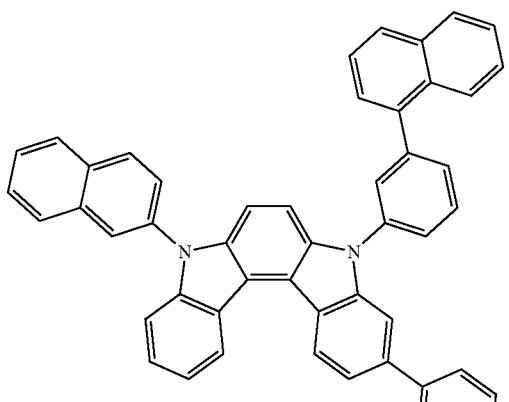

[C-56]

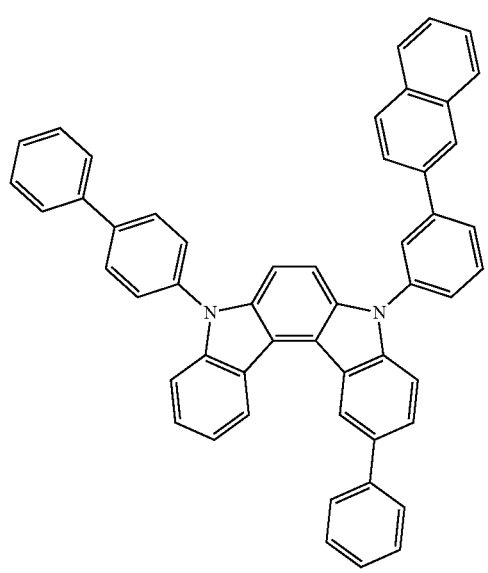

The first compound and the second compound may be, e.g., included in a weight ratio of about 1:99 to about 99:1. Within the range, a desirable weight ratio may be adjusted using an electron transport capability of the first compound and a hole transport capability of the second compound to realize bipolar characteristics and thus to improve efficiency and a life-span. Within the range, they may be, e.g., included in a weight ratio of about 10:90 to about 90:10, about 20:80 to about 80:20, about 20:80 to about 70:30, about 20:80 to about 60:40, or about 20:80 to about 50:50. In an implementation, they may be, e.g., included in a weight ratio of about 20:80 to about 40:60, about 30:70, about 40:60, or about 50:50, or about 30:70.

In an implementation, the first compound may be represented by Chemical Formula 1-1a-IV, Chemical Formula 1-2b-IV, Chemical Formula 1-3c-III, Chemical Formula 1-4c-I, Chemical Formula 1-4c-III, Chemical Formula 1-4c-IV, Chemical Formula 1-4d-II, or Chemical Formula 1-4d-IV and the second compound may be represented by Chemical Formula 2-8.

In an implementation, the first compound may be represented by Chemical Formula 1-1a-IV and the second compound may be represented by Chemical Formula 3A, Chemical Formula 3C, or Chemical Formula 3D.

At least one compound may be included in addition to the aforementioned first compound and second compound.

The aforementioned compound for the organic optoelectronic device or composition for the organic optoelectronic device may further include a dopant.

The dopant may be, e.g., a phosphorescent dopant. In an implementation, the dopant may be, e.g., a red, green, or blue phosphorescent dopant, and may be, e.g., a red or green phosphorescent dopant.

The dopant is a material mixed with the aforementioned compound or composition for the organic optoelectronic device in a small amount to cause light emission and generally a material such as a metal complex that emits light by multiple excitations into a triplet or more. The dopant may be, e.g., an inorganic, organic, or organic/inorganic compound, and one or more types thereof may be used.

Examples of the dopant may be a phosphorescent dopant and examples of the phosphorescent dopant may include an organometal compound including Ir, Pt, Os, Ti, Zr, Hf, Eu, Tb, Tm, Fe, Co, Ni, Ru, Rh, Pd, or a combination thereof. The phosphorescent dopant may be, e.g., a compound represented by Chemical Formula Z.

$$L^cMX^c$$ [Chemical Formula Z]

In Chemical Formula Z, M may be, e.g., a metal, and $L^c$ and $X^c$ may each independently be, e.g., a ligand to form a complex compound with M.

The M may be, e.g., Ir, Pt, Os, Ti, Zr, Hf, Eu, Tb, Tm, Fe, Co, Ni, Ru, Rh, Pd, or a combination thereof and $L^c$ and $X^c$ may be, e.g., a bidendate ligand.

The aforementioned compound or composition for the organic optoelectronic device may be formed by a dry film formation method such as chemical vapor deposition (CVD).

Hereinafter, an organic optoelectronic device including the aforementioned compound or the aforementioned composition is described.

The organic optoelectronic device may be a suitable device to convert electrical energy into photoenergy and vice versa, and may be, e.g., an organic photoelectric device, an organic light emitting diode, an organic solar cell, or an organic photo conductor drum.

Herein, an organic light emitting diode as one example of an organic optoelectronic device is described referring to drawings.

Figure 2:
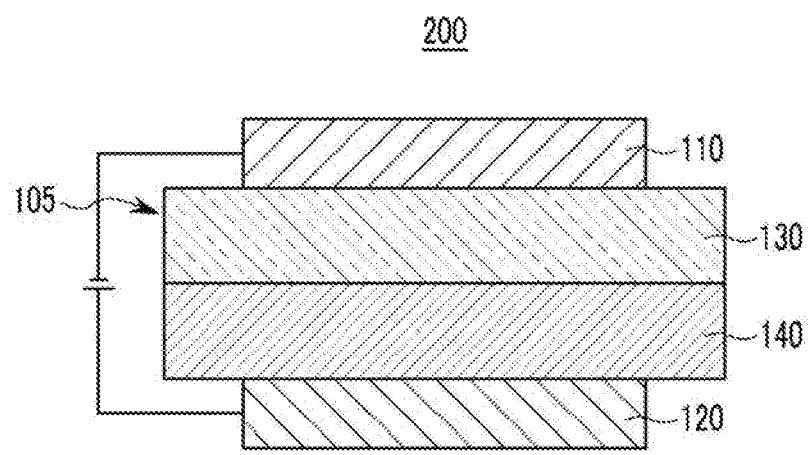

FIGS. 1 and 2 are cross-sectional views showing organic light emitting diodes according to embodiments.

Referring to FIG. 1, an organic light emitting diode 100 according to an embodiment may include an anode 120 and a cathode 110 facing each other and an organic layer 105 between the anode 120 and the cathode 110.

The anode 120 may be made of a conductor having a large work function to facilitate hole injection, and may be, e.g., a metal, a metal oxide and/or a conductive polymer. The anode 120 may be, e.g., a metal such as nickel, platinum, vanadium, chromium, copper, zinc, gold, and the like or an alloy thereof, a metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline.

The cathode 110 may be made of a conductor having a small work function to facilitate electron injection, and may be, e.g., a metal, a metal oxide and/or a conductive polymer. The cathode 110 may be, e.g., a metal such as magnesium, calcium, sodium, potassium, titanium, indium, yttrium, lithium, gadolinium, aluminum silver, tin, lead, cesium, barium, and the like or an alloy thereof, a multi-layer structure material such as LiF/Al, LiO$_2$/Al, LiF/Ca, LiF/Al and BaF$_2$/Ca.

The organic layer 105 may include the aforementioned compound or composition for the organic optoelectronic device.

The organic layer 105 may include a light emitting layer 130 and the light emitting layer 130 may include the aforementioned compound or composition for the organic optoelectronic device.

The composition for an organic optoelectronic device further including a dopant may be, e.g., a green light emitting composition.

The light emitting layer 130 may include, e.g., the first compound and the second compound as a phosphorescent host.

The organic layer may further include an auxiliary layer in addition to the light emitting layer.

The auxiliary layer may be, e.g., a hole auxiliary layer 140.

Referring to FIG. 2, an organic light emitting diode 200 may further include the hole auxiliary layer 140 in addition to the light emitting layer 130. The hole auxiliary layer 140 may further increase hole injection and/or hole mobility and blocks electrons between the anode 120 and the light emitting layer 130.

The hole auxiliary layer 140 may include, e.g., a compound of Group D.

In an implementation, the hole auxiliary layer 140 may include, e.g., a hole transport layer between the anode 120 and the light emitting layer 130 and a hole transport auxiliary layer between the light emitting layer 130 and the hole transport layer and a compound of Group D may be included in the hole transport auxiliary layer.

[Group D]

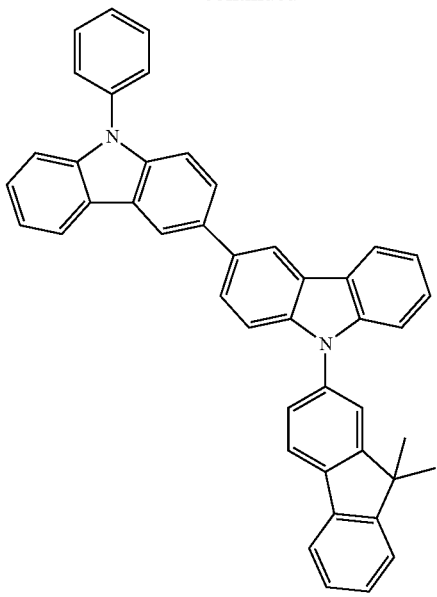

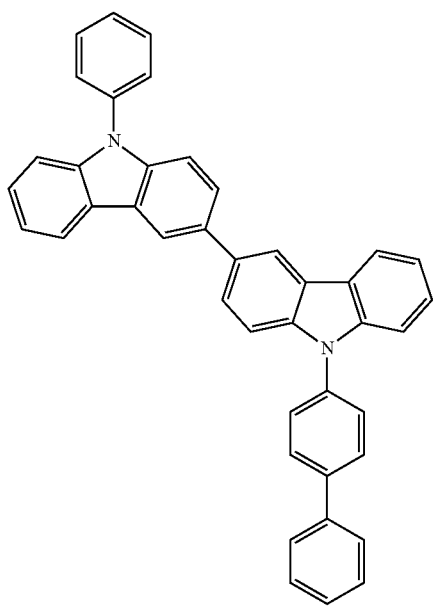

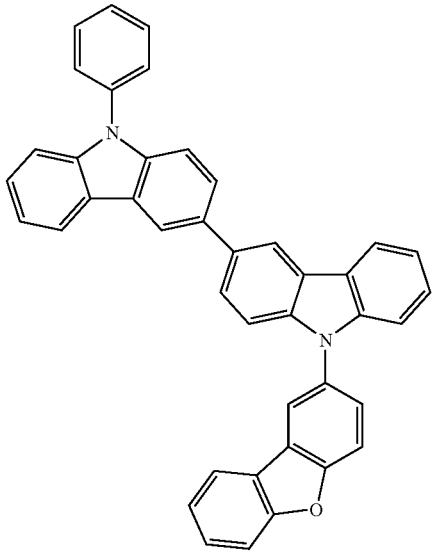

215
-continued
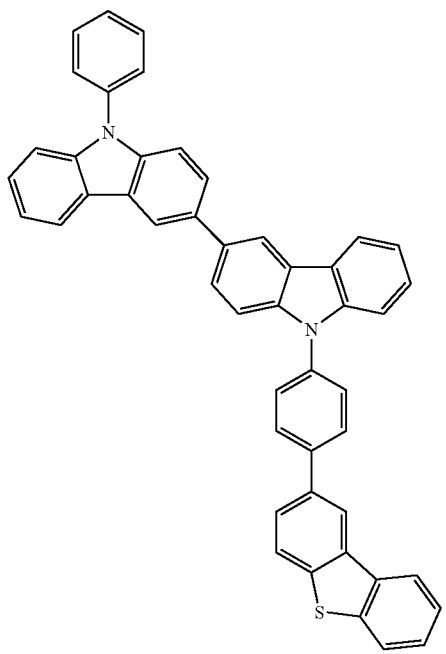
216
-continued
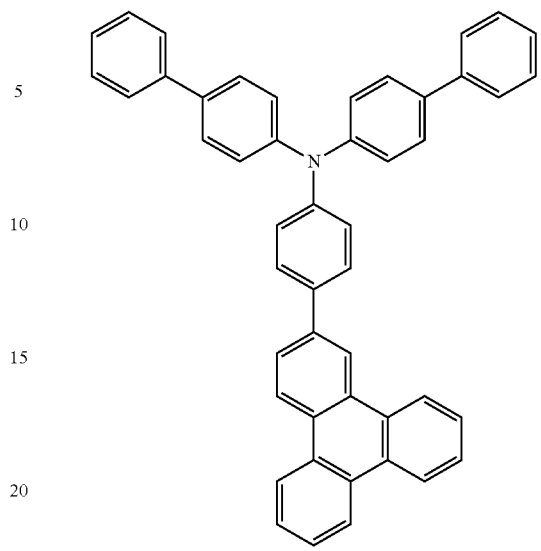
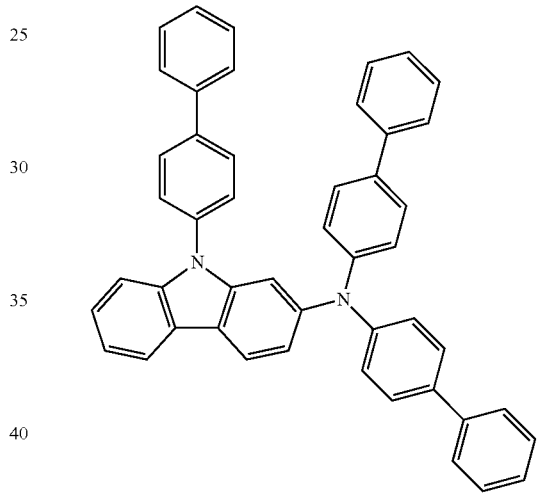
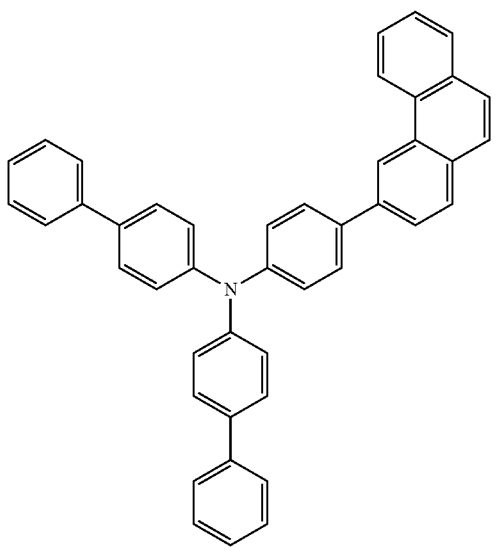
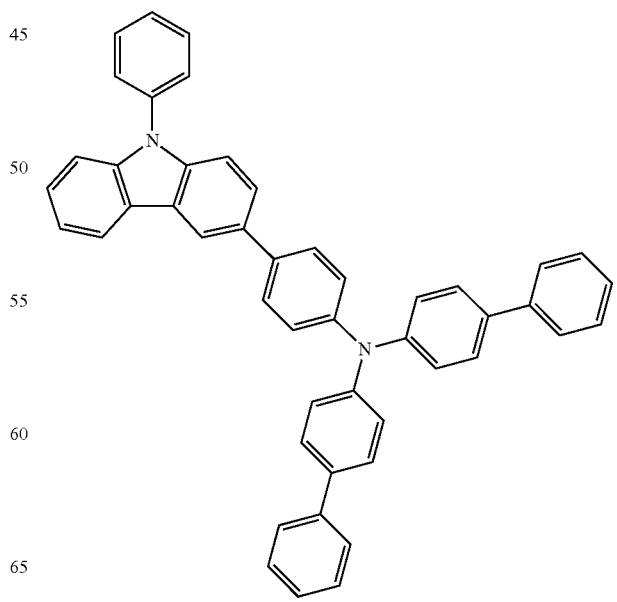

217
-continued
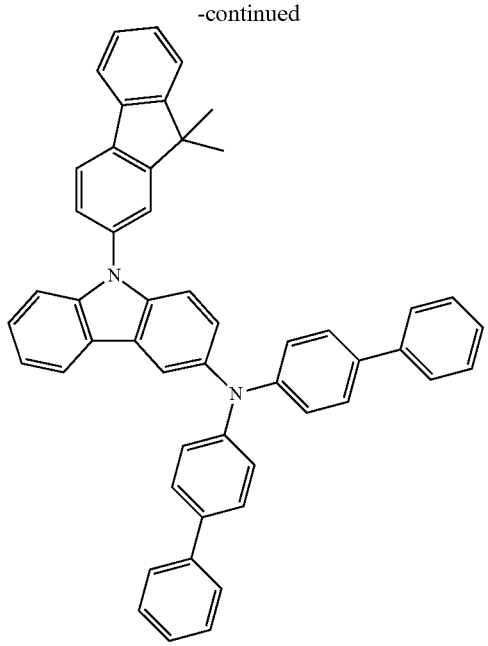
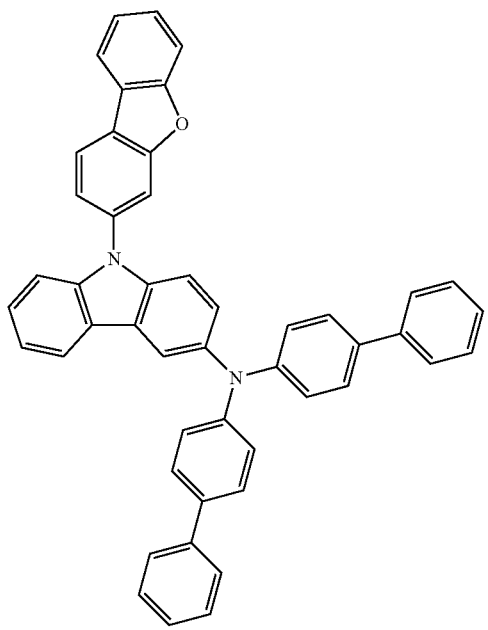
218
-continued
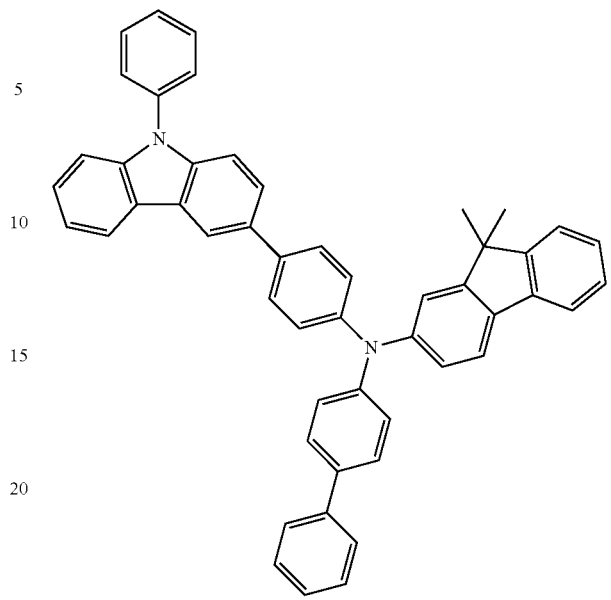
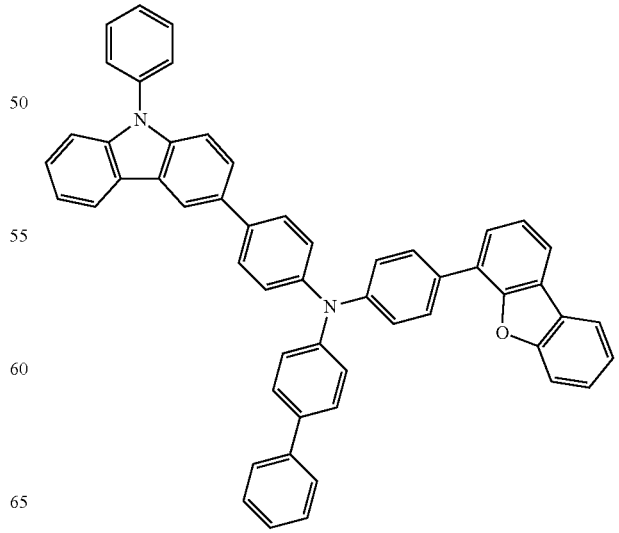

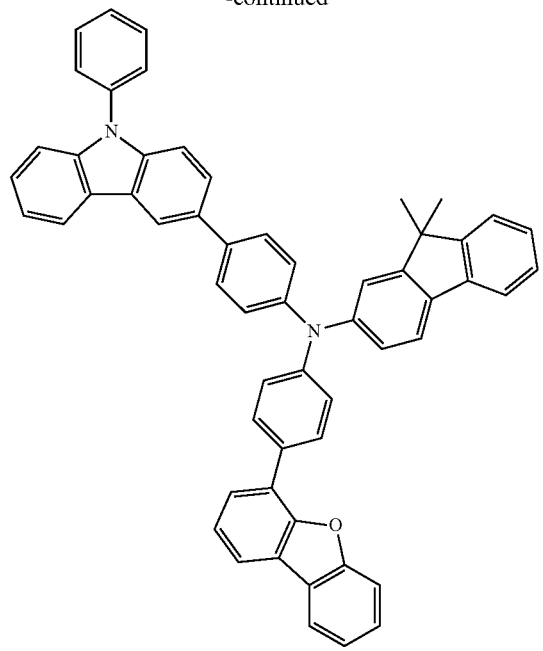
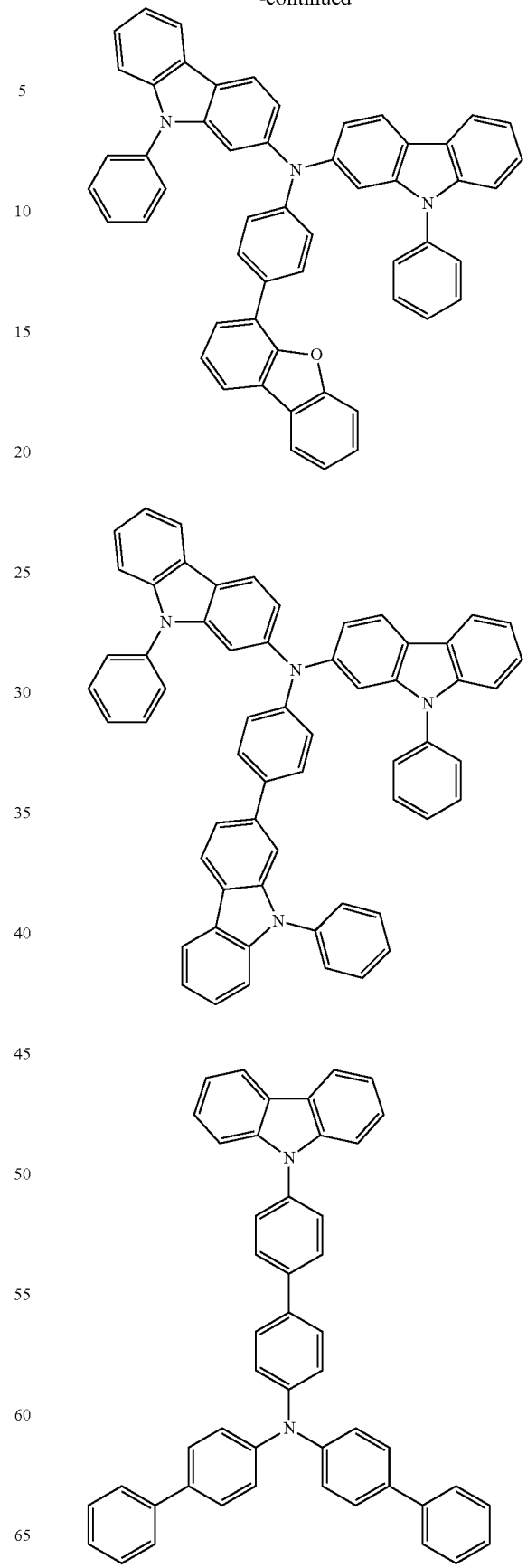

221
-continued
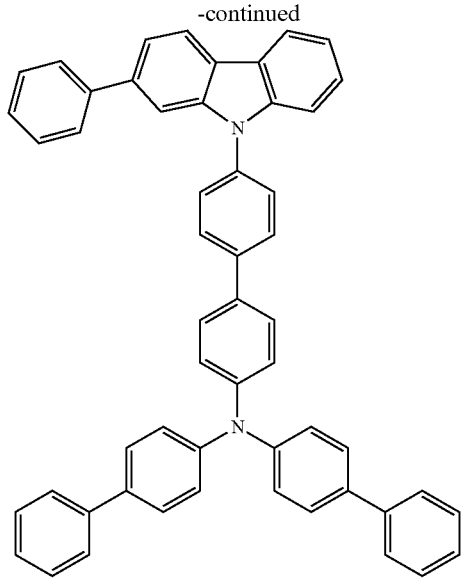
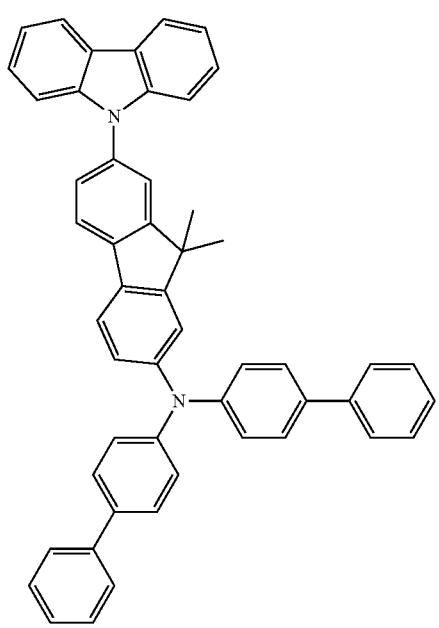
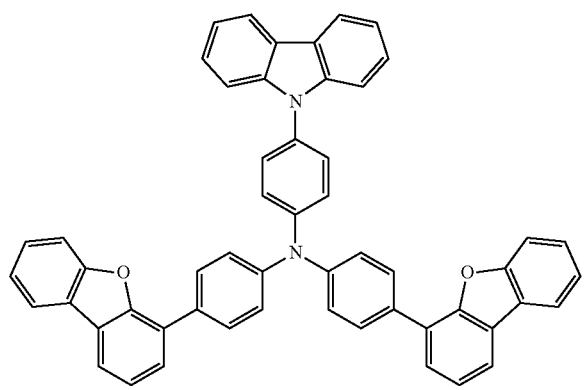
222
-continued
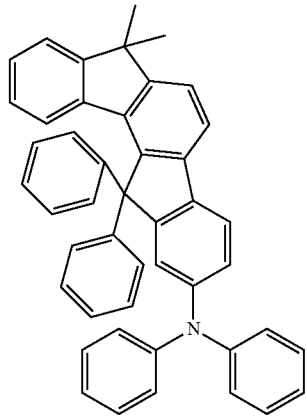
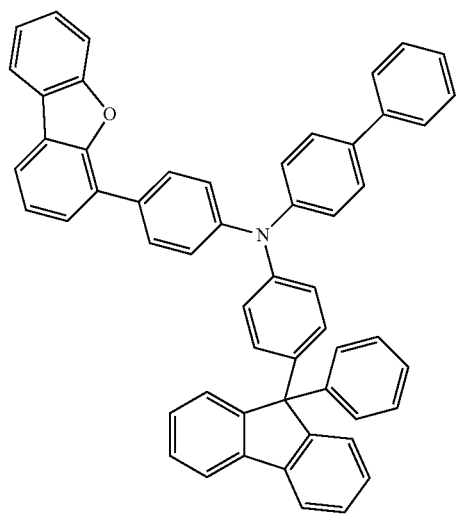
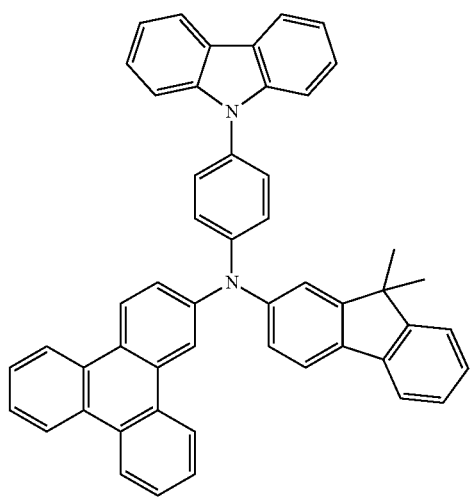

223
-continued
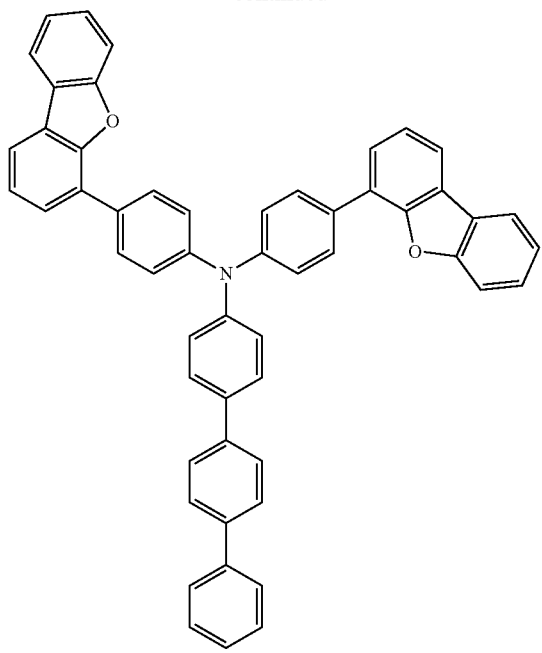
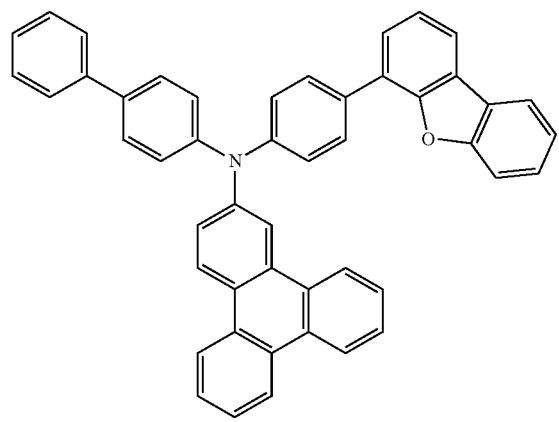
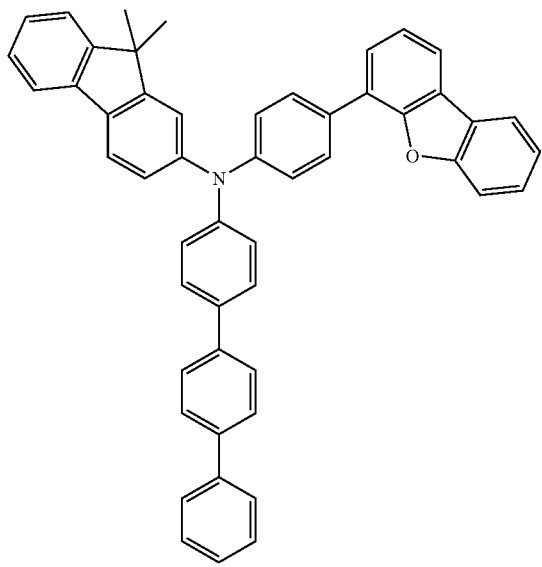
224
-continued
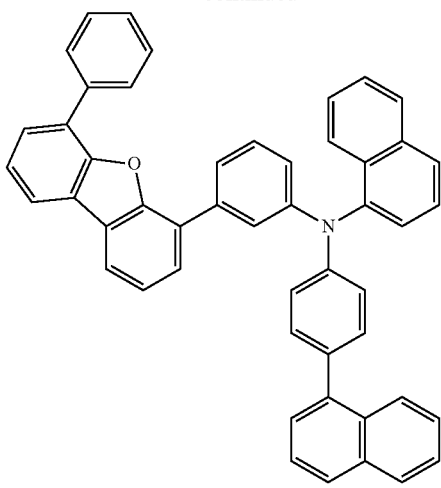
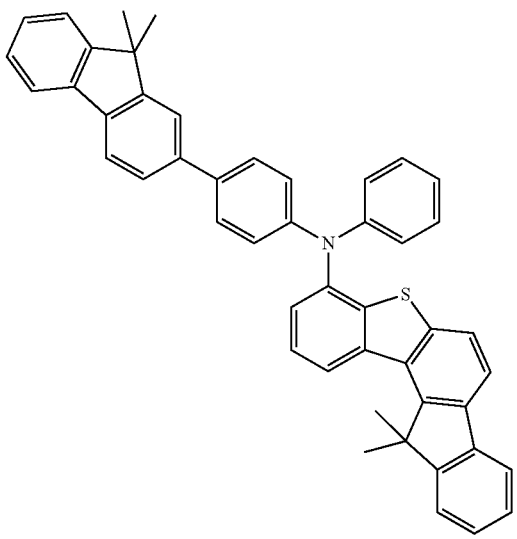
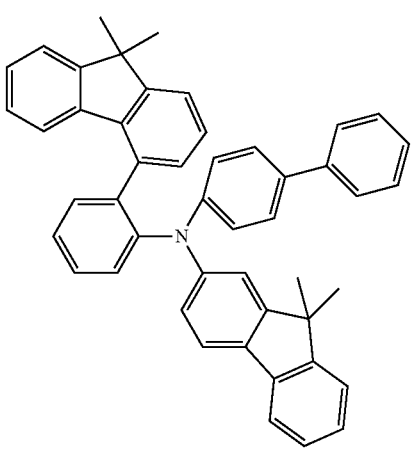

225
-continued
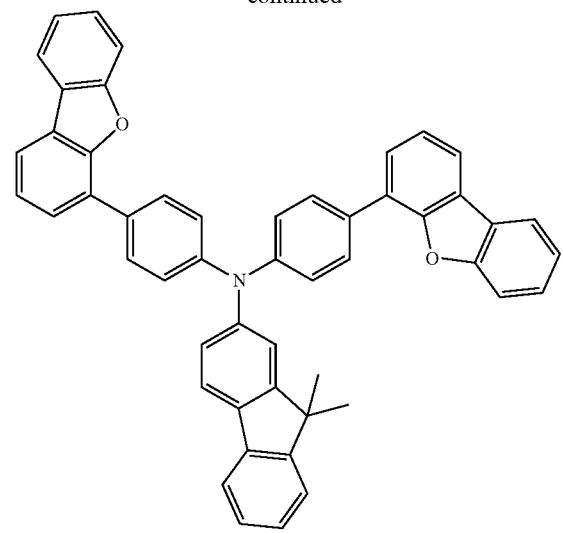
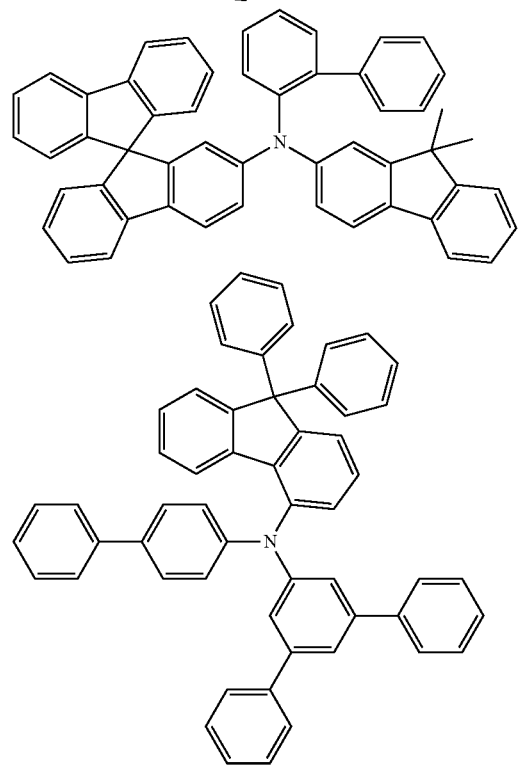
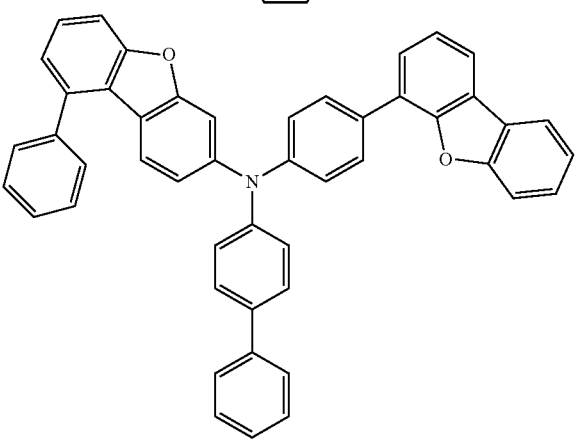
226
-continued
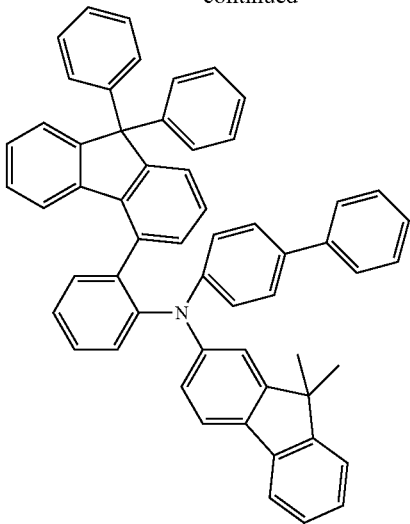
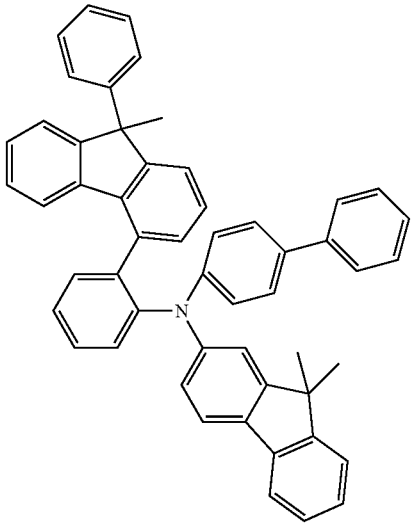
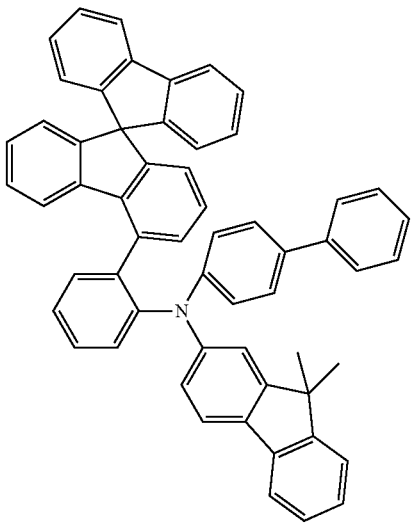

227
-continued
228
-continued
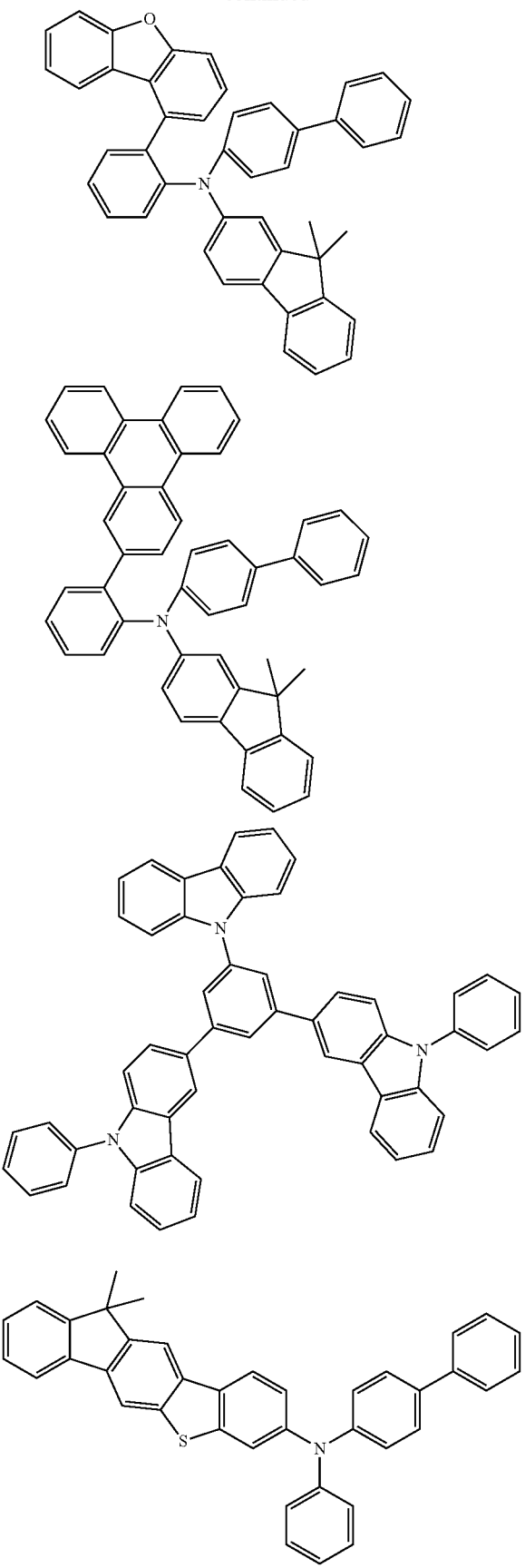
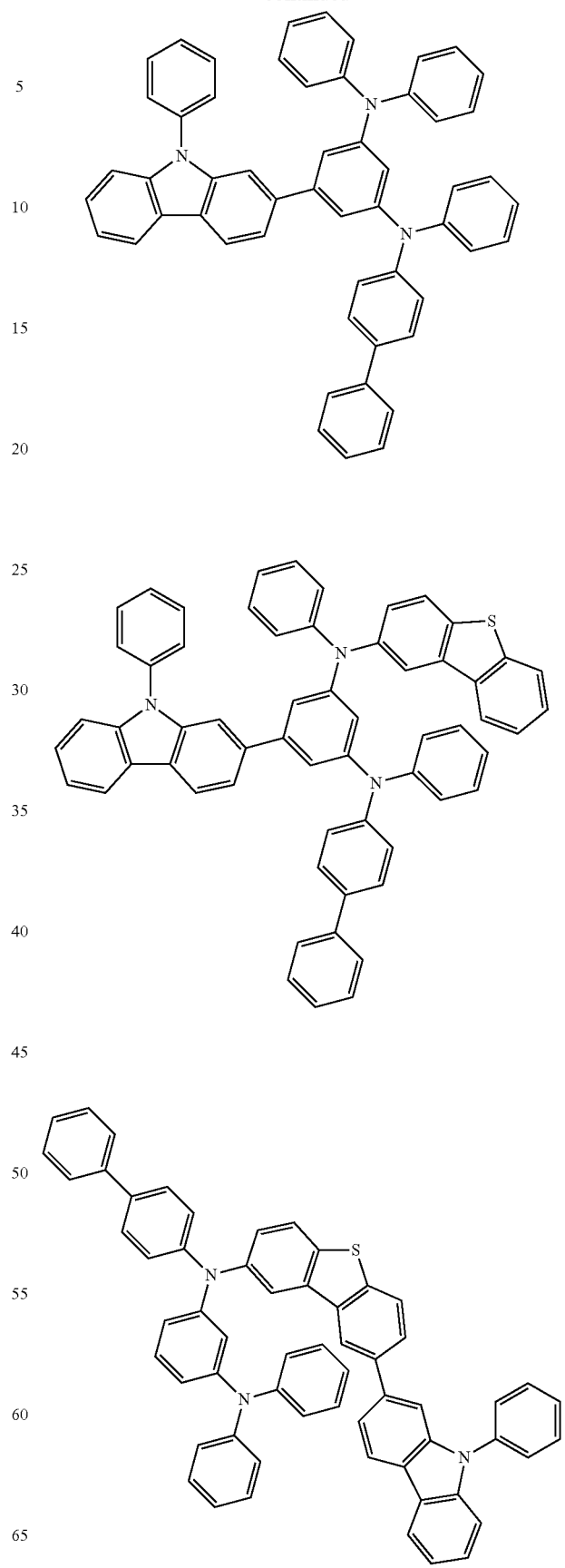

229
-continued
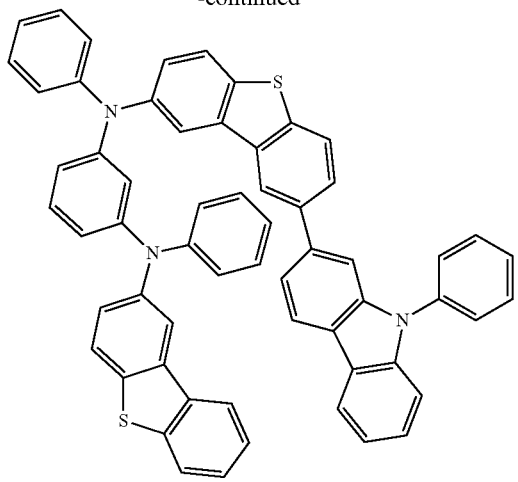
230
-continued
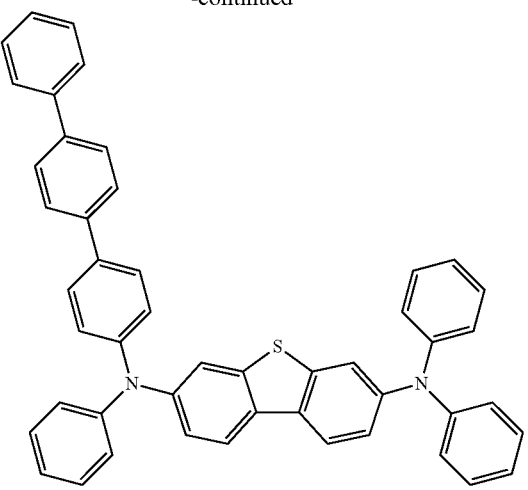
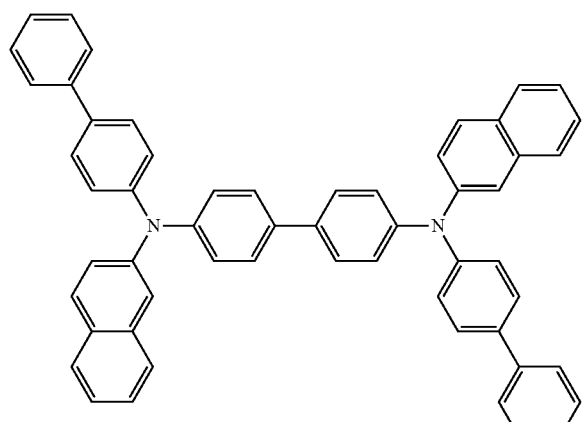
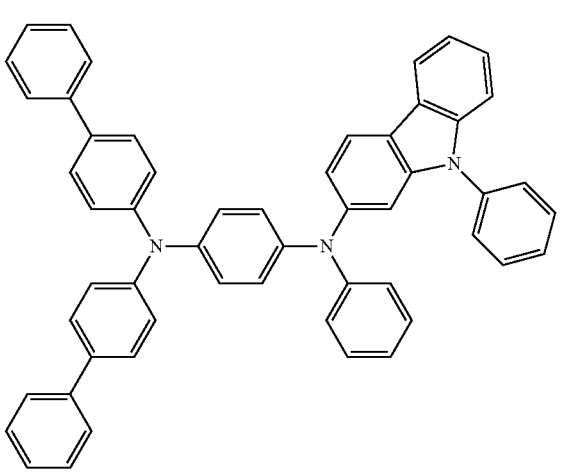
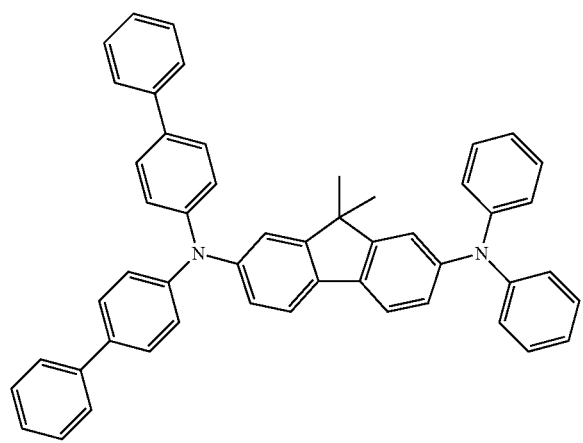
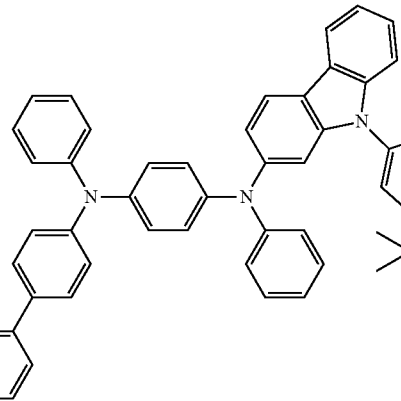

231
-continued
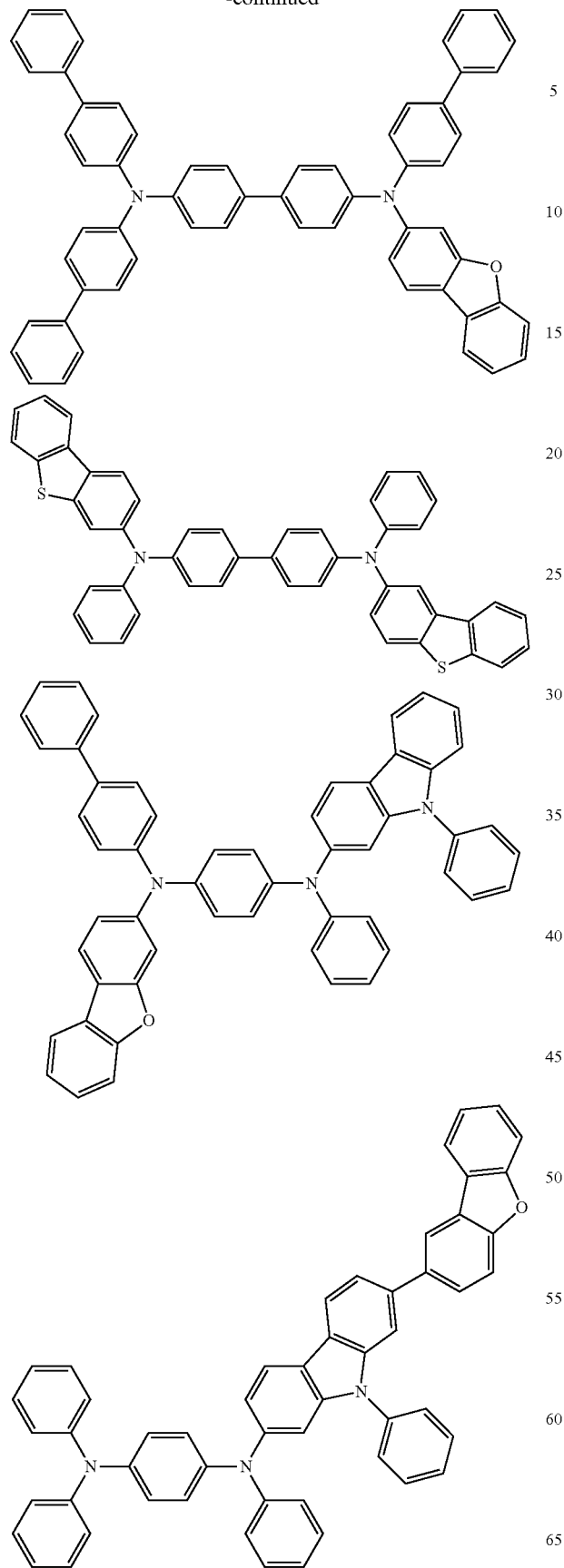
232
-continued
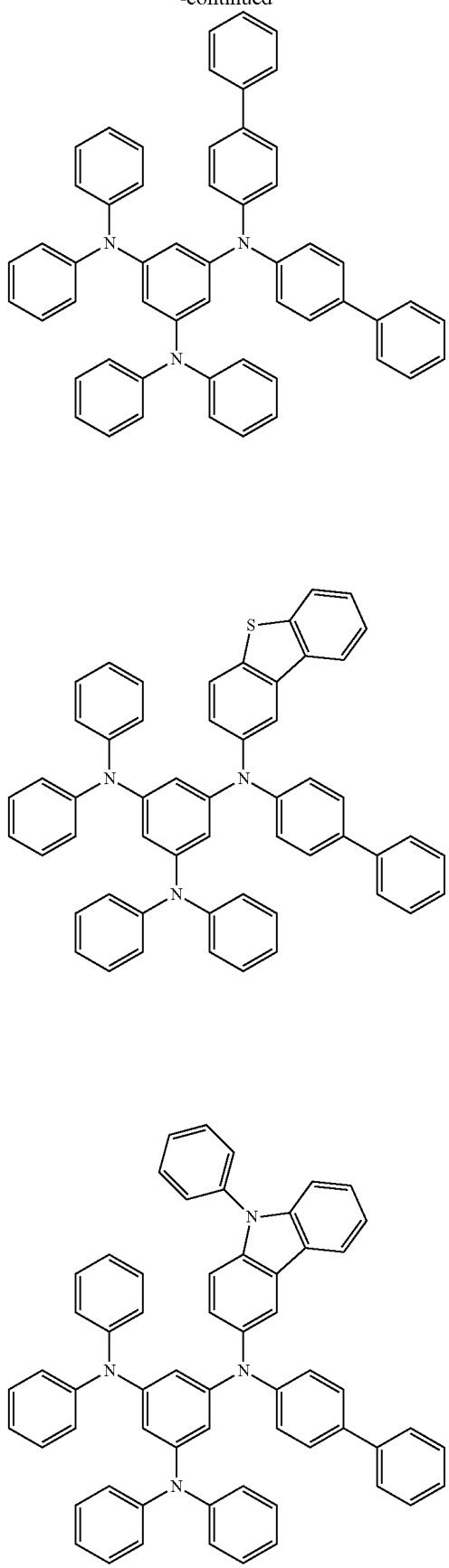

233
-continued
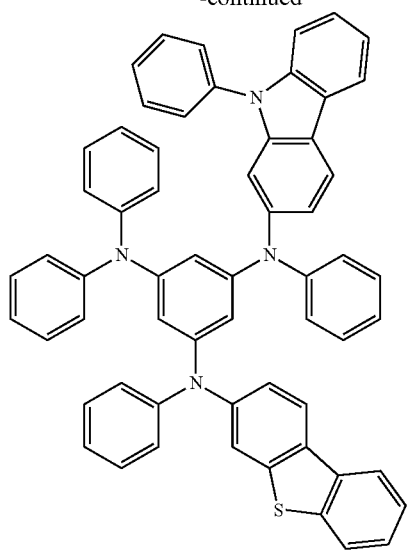
234
-continued
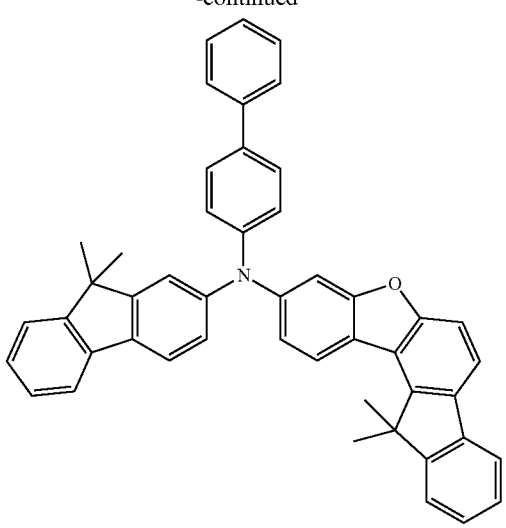
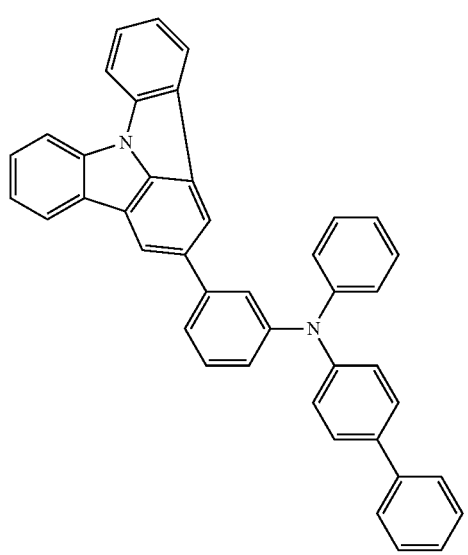
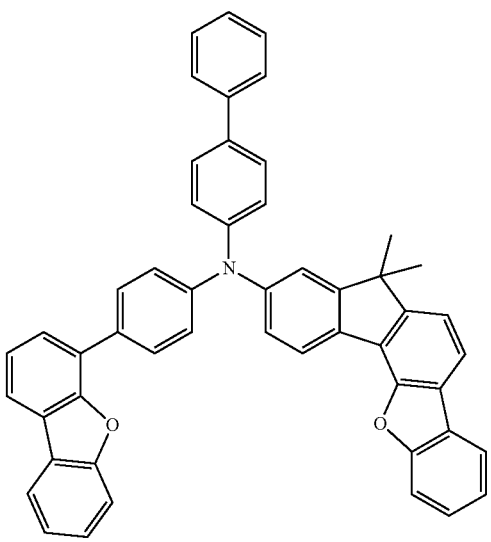
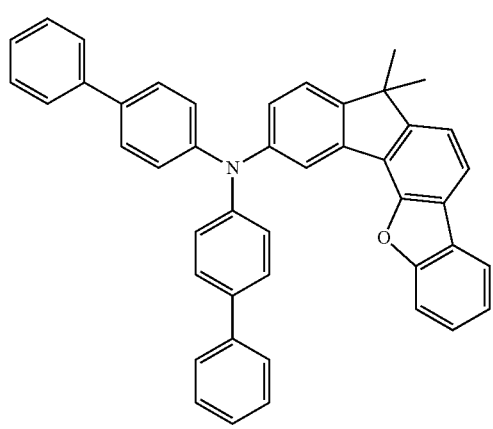
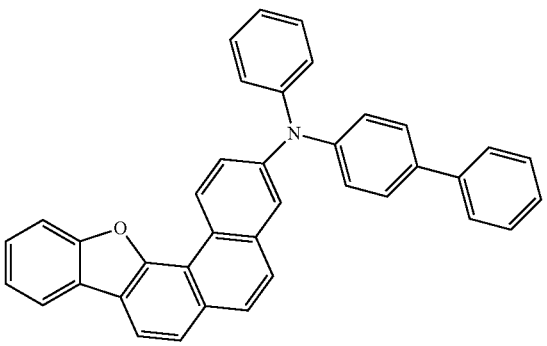

235
-continued
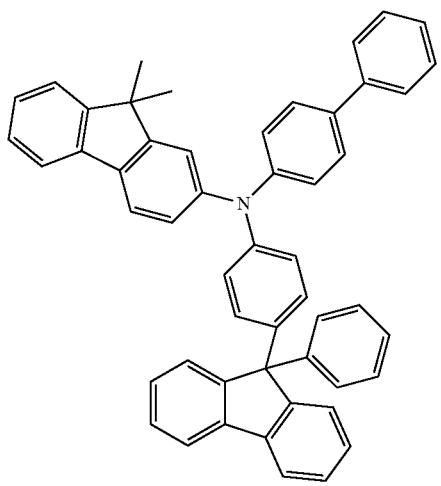
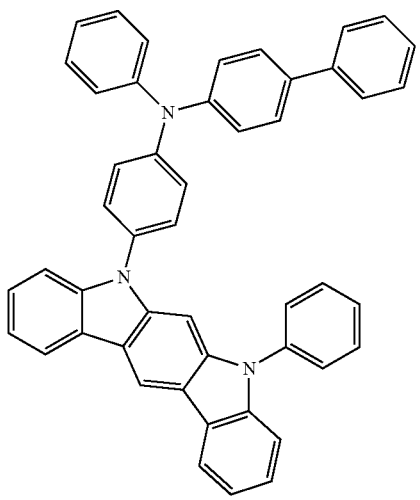
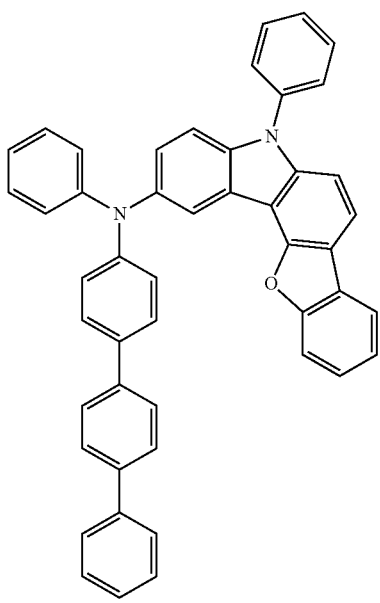
236
-continued
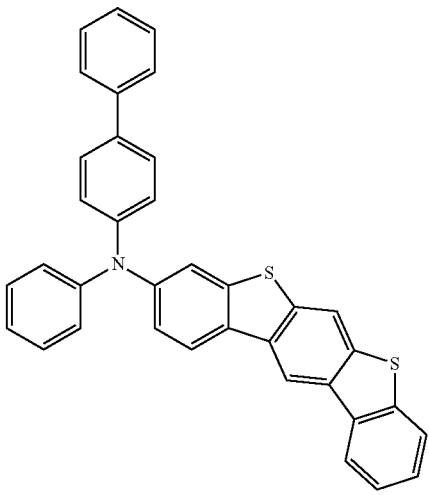
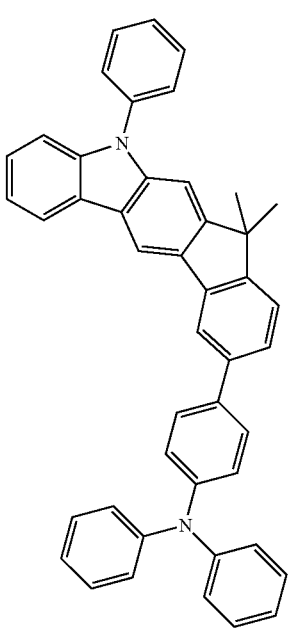
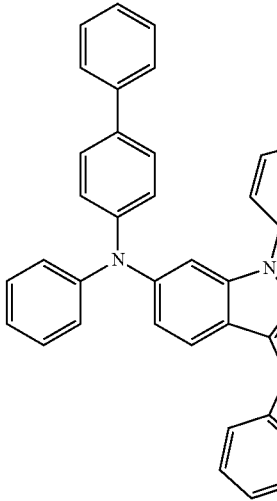

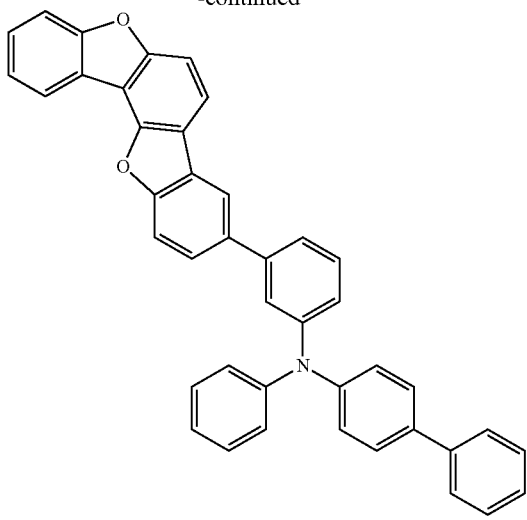

In an implementation, in addition to the aforementioned compounds, compounds described in U.S. Pat. No. 5,061,569 A, JP 1993-009471 A, WO 1995-009147 A1, JP 1995-126615 A, JP 1998-095973 A, and compounds having a similar structure thereto may be used as the hole transport auxiliary layer.

In an implementation, the organic light emitting diode may further include an electron transport layer, an electron injection layer, and a hole injection layer as the organic layer 105 in FIG. 1 or 2.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in Examples and Synthesis Examples were purchased from Sigma-Aldrich Co. Ltd., TCI Inc., Tokyo Chemical Industry, or P&H Tech insofar as there is no particular comment, or were synthesized by suitable methods.

(Preparation of Compound for Organic Optoelectronic Device)

The compounds were synthesized through the following steps.

(Preparation of Compound 1)

Synthesis Example 1: Synthesis of Intermediate I-1

[Reaction Scheme 1]

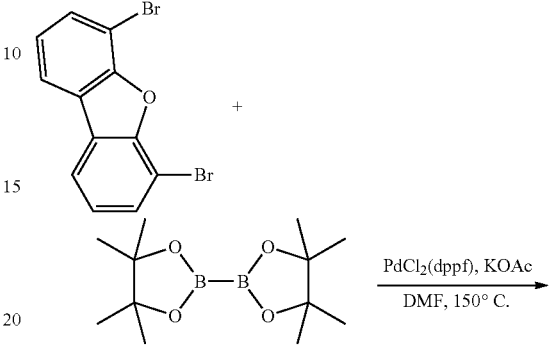

4,6-dibromodibenzofuran (50 g, 153 mmol) purchased from Tokyo Chemical Industry Co., Ltd. (http://www.tci-chemicals.com/) was dissolved in 1.5 L of dimethylformamide (DMF) under a nitrogen atmosphere, and bis(pinacolato)diboron (85.5 g, 337 mmol), (1,1'-bis(diphenylphosphine)ferrocene)dichloropalladium (II) (2.50 g, 3.06 mmol), and potassium acetate (75.1 g, 765 mmol) were added thereto and then, heated and refluxed at 150° C. for 5 hours. When a reaction was complete, water was added to the reaction solution, and the mixture was filtered and then dried in a vacuum oven. This obtained residue was separated and purified through flash column chromatography to obtain Intermediate I-1 (56.6 g, 88%).

HRMS (70 eV, EI+): m/z calcd for $C_{24}H_{30}B_2O_5$: 420.2279, found: 420.

Elemental Analysis: C, 69%; H, 7%

Synthesis Example 2: Synthesis of Intermediate I-2

[Reaction Scheme 2]

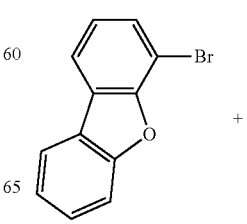

-continued

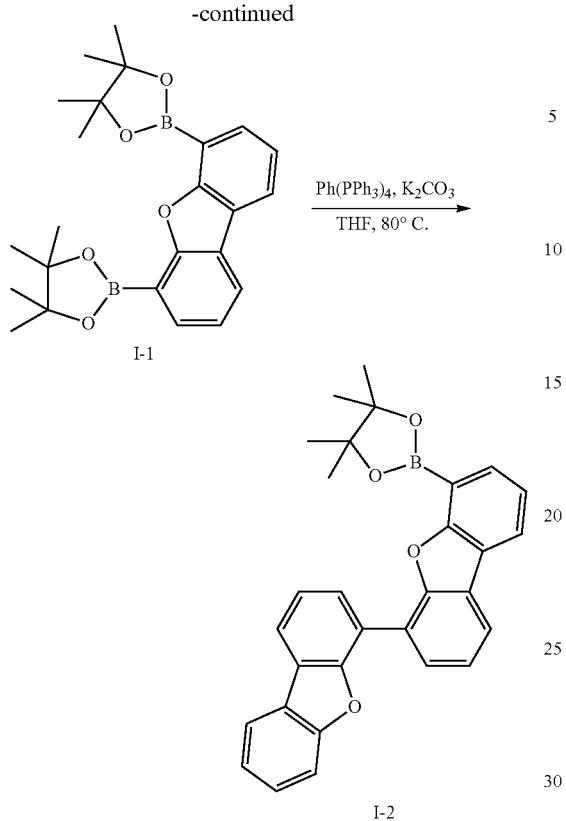

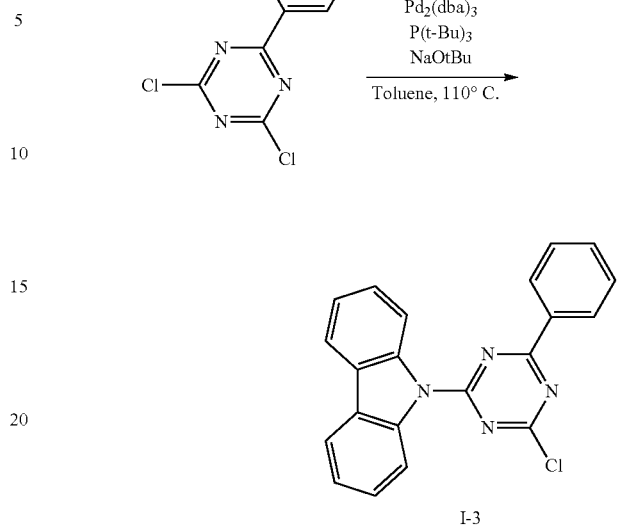

4-bromodibenzofuran (50 g, 202 mmol) purchased from Tokyo Chemical Industry Co., Ltd. (http://www.tcichemicals.com/) was dissolved in 0.8 L of tetrahydrofuran (THF) under a nitrogen atmosphere, and Intermediate I-1 (102 g, 243 mmol) and tetrakis(triphenylphosphine) palladium (2.33 g, 2.02 mmol) were added thereto and then, stirred therewith. Potassium carbonate saturated in water (69.8 g, 505 mmol) was added thereto and then heated and refluxed at 80° C. for 8 hours. When a reaction was complete, water was added to the reaction solution, and then the mixture was extracted with dichloromethane (DCM), treated with magnesium sulfate anhydrous to remove moisture, and then filtered and concentrated under a reduced pressure. This obtained residue was separated and purified through flash column chromatography to obtain Intermediate I-2 (67.9 g, 73%).

HRMS (70 eV, EI+): m/z calcd for $C_{30}H_{25}BO_4$: 460.1846, found: 460.

Elemental Analysis: C, 78%; H, 5%

Synthesis Example 3: Synthesis of Intermediate I-3

[Reaction Scheme 3]

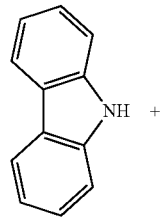

9H-carbazole (50 g, 299 mmol) purchased from Tokyo Chemical Industry Co., Ltd. (http://www.tcichemicals.com/) was dissolved in 0.1 L of toluene under a nitrogen atmosphere, and 2,4-dichloro-6-phenyl-1,3,5-triazine (101 g, 449 mmol), tris(diphenylideneacetone) dipalladium (0) (2.74 g, 2.99 mmol), tris(tertbutyl)phosphine (2.42 g, 12.0 mmol), and sodium tert-butoxide (34.5 g, 359 mmol) were sequentially added thereto and then, heated and refluxed at 110° C. for 12 hours. When a reaction was complete, water was added to the reaction solution, and the mixture was extracted with dichloromethane (DCM), treated with magnesium sulfate anhydrous to remove moisture, and then filtered and concentrated under a reduced pressure. This obtained residue was separated and purified through flash column chromatography to obtain Intermediate I-3 (74.7 g, 70%).

HRMS (70 eV, EI+): m/z calcd for $C_{21}H_{13}ClN_4$: 356.0829, found: 356.

Elemental Analysis: C, 71%; H, 4%

Synthesis Example 4: Synthesis of Compound 1

[Reaction Scheme 4]

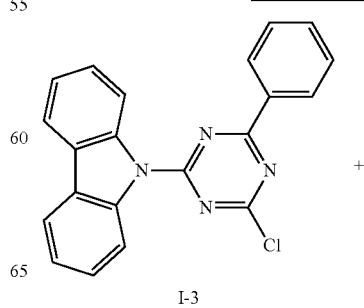

241
-continued
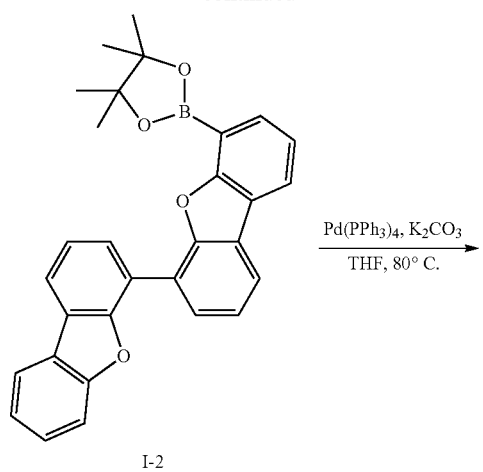
I-2
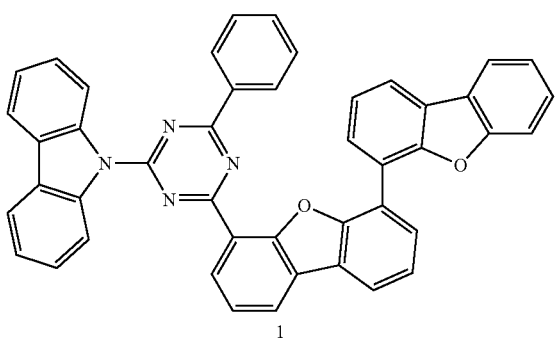
1
Intermediate I-3 (10 g, 28.0 mmol) and Intermediate I-2 (12.9 g, 28.0 mmol) were used to obtain Compound 1 (17.6 g, 96%) according to the same method as Synthesis Example 2.
HRMS (70 eV, EI+): m/z calcd for $C_{45}H_{26}N_4O_2$: 654.2056, found: 654.
Elemental Analysis: C, 83%; H, 4%
Synthesis Example 5: Synthesis of Intermediate I-4
[Reaction Scheme 5]
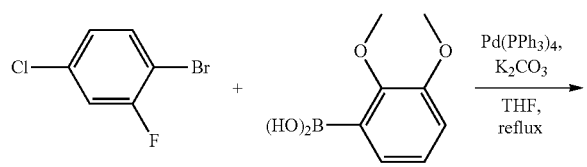 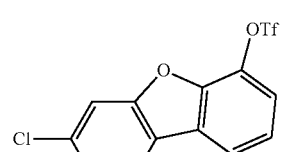
I-4-1
242
-continued
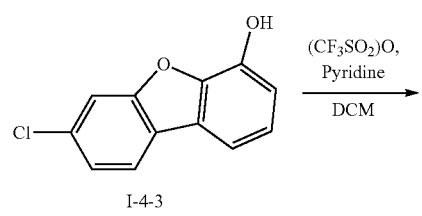
I-4-1
I-4-2
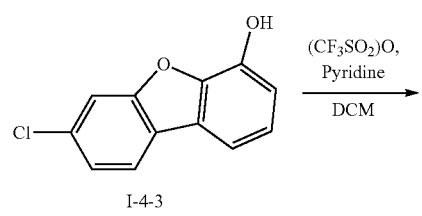
I-4-2
I-4-3
I-4-3
I-4-4
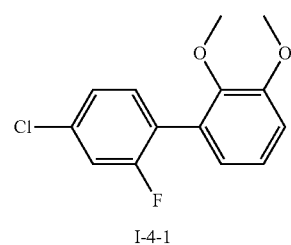 + 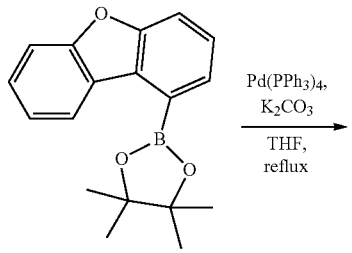
I-4-4

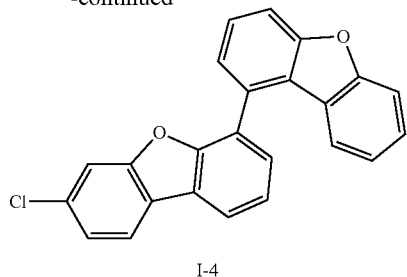

I-4

1st Step: Synthesis of Intermediate I-4-1

1-bromo-4-chloro-2-fluorobenzene (60 g, 289 mmol) purchased from Tokyo Chemical Industry Co., Ltd. (http://www.tcichemicals.com/) was dissolved in 0.5 L of tetrahydrofuran (THF) under a nitrogen atmosphere, and 2,3-dimethoxyphenylboronic acid (57.8 g, 317 mmol) and tetrakis(triphenylphosphine) palladium (3.34 g, 2.89 mmol) were added thereto and then, stirred therewith. Potassium carbonate saturated in water (99.7 g, 722 mmol) was added thereto and then, heated and refluxed for 21 hours. When a reaction was complete, water was added to the reaction solution and then, the mixture was extracted with dichloromethane (DCM), treated with magnesium sulfate anhydrous to remove moisture, and then filtered and concentrated under a reduced pressure. This obtained residue was separated and purified through flash column chromatography to obtain Intermediate I-4 (67.5 g, 88%).

HRMS (70 eV, EI+): m/z calcd for $C_{14}H_{12}ClFO_2$: 266.0510, found: 266.

Elemental Analysis: C, 63%; H, 5%

2nd Step: Synthesis of Intermediate I-4-2

Intermediate I-4-1 (67.5 g, 253 mmol) was dissolved in 0.8 L of a 1.0 M boron tribromide solution under a nitrogen atmosphere and then stirred for 5 hours. When a reaction was complete, the reaction solution was cooled down to 0° C., and 0.8 L of a saturated sodium thiosulfate aqueous solution was slowly added thereto in a dropwise fashion for 30 minutes. Subsequently, water was added thereto, and the mixture was extracted with dichloromethane (DCM), treated with magnesium sulfate anhydrous to remove moisture, and then filtered and concentrated under a reduced pressure. This obtained residue was separated and purified through flash column chromatography to obtain Intermediate I-4-2 (60.0 g, 99%).

HRMS (70 eV, EI+): m/z calcd for $C_{12}H_{18}ClFO_2$: 238.0197, found: 238.

Elemental Analysis: C, 60%; H, 3%

3rd Step: Synthesis of Intermediate I-4-3

Intermediate I-4-2 (60.0 g, 253 mmol) was dissolved in 0.3 L of N-methyl-2-pyrrolidone (NMP) under a nitrogen atmosphere, and potassium carbonate (70.0 g, 506 mmol) were added thereto and then, heated and stirred therewith for 14 hours. When a reaction was complete, the solvent was distilled and removed, water was added to the reaction solution, and the mixture was extracted with dichloromethane (DCM), treated with magnesium sulfate anhydrous to remove moisture, and then filtered and concentrated under a reduced pressure.

This obtained residue was separated and purified through flash column chromatography to obtain Intermediate I-4-3 (40.4 g, 73%).

HRMS (70 eV, EI+): m/z calcd for $C_{12}H_7ClO_2$: 218.0135, found: 218.

Elemental Analysis: C, 66%; H, 3%

4th Step: Synthesis of Intermediate I-4-4

Intermediate I-4-3 (35 g, 160 mmol) was dissolved in 0.3 L of dichloromethane (DCM) under a nitrogen atmosphere and then cooled down to 0° C. Pyridine (15.2 g, 192 mmol), and trifluoromethanesulfonic anhydride (54.2 g, 192 mmol) were added thereto and then stirred therewith at room temperature. After 14 hours, the reaction solution was cooled down to 0° C., water was slowly added thereto for 30 minutes, and the mixture was extracted with dichloromethane (DCM), treated with magnesium sulfate anhydrous to remove moisture, and then filtered and concentrated under a reduced pressure. This obtained residue was separated and purified through flash column chromatography to obtain Intermediate I-4-4 (55.0 g, 98%).

HRMS (70 eV, EI+): m/z calcd for $C_{13}H_6ClF_3O_4S$: 349.9627, found: 350.

Elemental Analysis: C, 45%; H, 2%

5th Step: Synthesis of Intermediate I-4

Intermediate I-4-4 (50 g, 143 mmol) and dibenzofuran-1-ylboronic acid (46.3 g, 157 mmol) purchased from Tokyo Chemical Industry Co., Ltd. were used to obtain Intermediate I-4 (11.7 g, 95%) according to the same method as the 1st step of Synthesis Example 5.

HRMS (70 eV, EI+): m/z calcd for $C_{24}H_{13}ClO_2$: 368.0604, found: 368.

Elemental Analysis: C, 78%; H, 4%

Synthesis Example 6: Synthesis of Intermediate I-5

[Reaction Scheme 6]

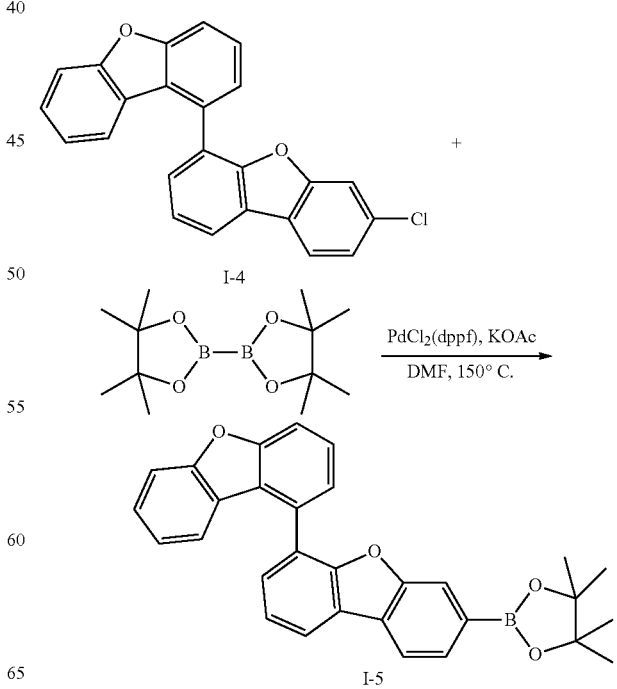

Intermediate I-4 (30 g, 81.3 mmol) was used to obtain Intermediate I-5 (27.0 g, 72%) according to the same method as Synthesis Example 1.

HRMS (70 eV, EI+): m/z calcd for $C_{30}H_{25}BO_4$: 460.1846, found: 460.

Elemental Analysis: C, 78%; H, 5%

Synthesis Example 7: Synthesis of Compound 17

[Reaction Scheme 7]

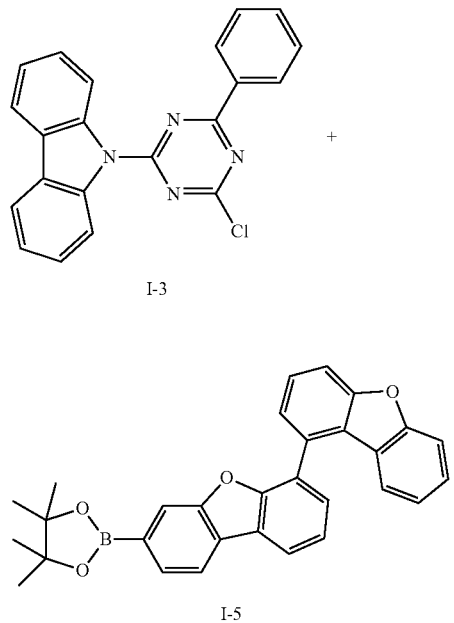

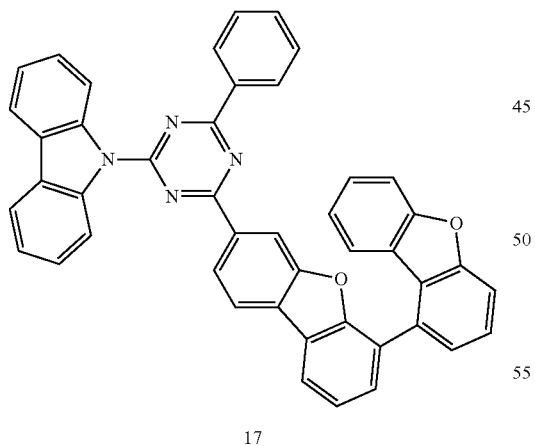

17

Intermediate I-3 (10 g, 28.0 mmol) and Intermediate I-5 (12.9 g, 28.0 mmol) were used to obtain Compound 17 (16.5 g, 90%) according to the same method as Synthesis Example 2.

HRMS (70 eV, EI+): m/z calcd for $C_{45}H_{26}N_4O_2$: 654.2056, found: 654.

Elemental Analysis: C, 83%; H, 4%

Synthesis Example 8: Synthesis of Intermediate I-7

[Reaction Scheme 8]

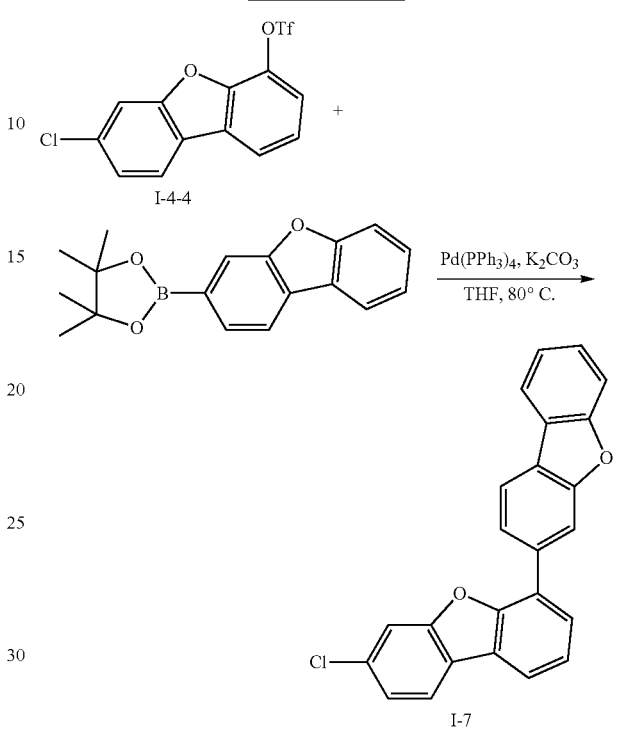

Intermediate I-4-4 (30 g, 85.5 mmol) and 2-(dibenzofuran-3-yl)-4,4,5,5-tetramethyl-1,3,2-dioxaborolane (27.7 g, 94.1 mmol) purchased from Ukseung Chemical Co., Ltd. (http://www.ukseung.co.kr/) were used to obtain Compound I-7 (27.1 g, 86%) according to the same method as Synthesis Example 2.

HRMS (70 eV, EI+): m/z calcd for $C_{24}H_{13}ClO_2$: 368.0604, found: 368.

Elemental Analysis: C, 78%; H, 4%

Synthesis Example 9: Synthesis of Intermediate I-8

[Reaction Scheme 9]

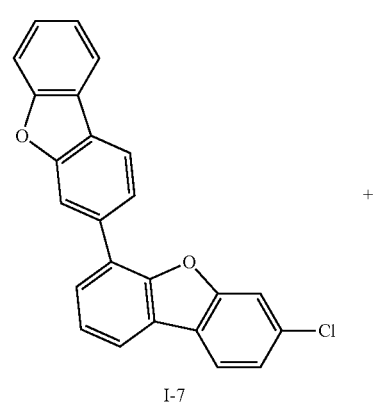

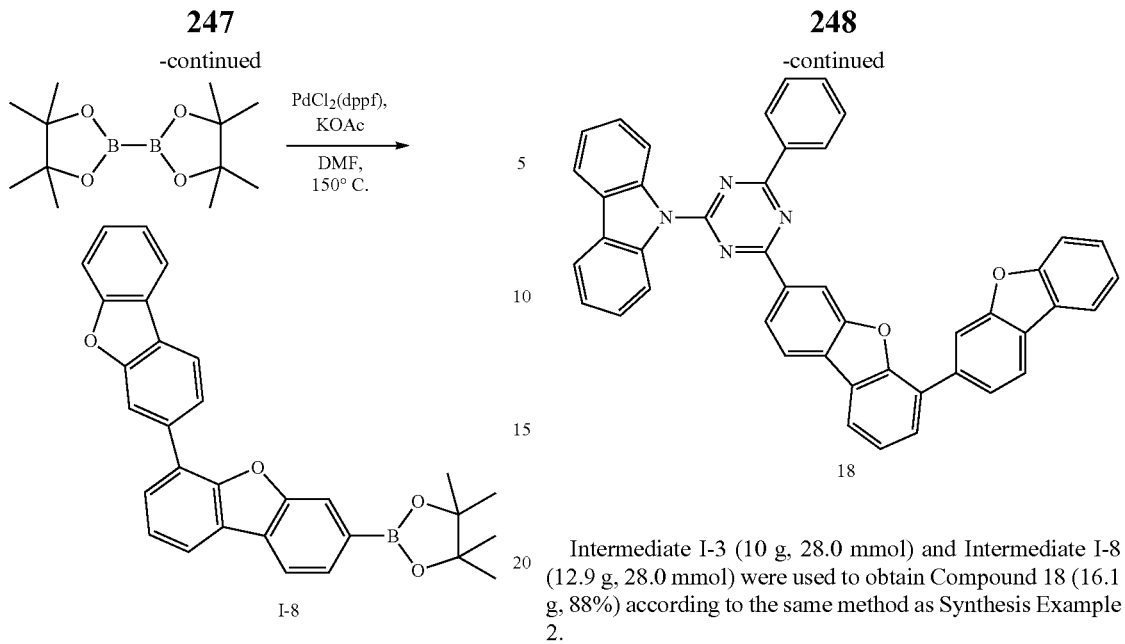

Intermediate I-7 (26 g, 70.5 mmol) was used to obtain Intermediate I-8 (22.7 g, 70%) according to the same method as Synthesis Example 1.

HRMS (70 eV, EI+): m/z calcd for $C_{30}H_{25}BO_4$: 460.1846, found: 460.

Elemental Analysis: C, 78%; H, 5%

Synthesis Example 10: Synthesis of Compound 18

[Reaction Scheme 10]

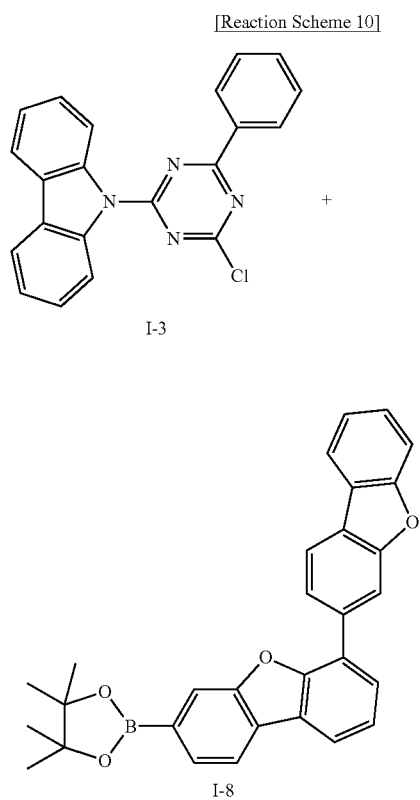

Intermediate I-3 (10 g, 28.0 mmol) and Intermediate I-8 (12.9 g, 28.0 mmol) were used to obtain Compound 18 (16.1 g, 88%) according to the same method as Synthesis Example 2.

HRMS (70 eV, EI+): m/z calcd for $C_{45}H_{26}N_4O_2$: 654.2056, found: 654.

Elemental Analysis: C, 83%; H, 4%

Synthesis Example 11: Synthesis of Intermediate I-9

[Reaction Scheme 11]

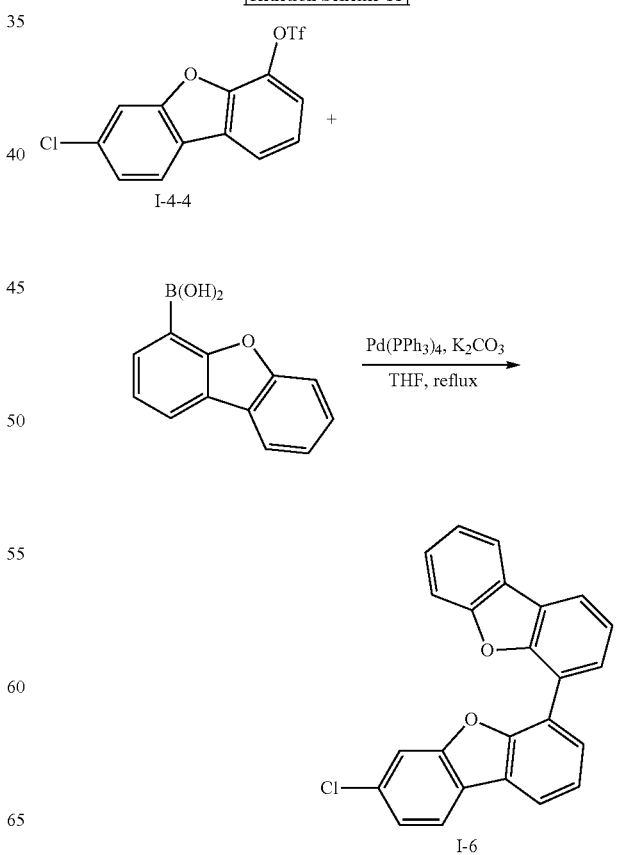

Synthesis Example 12: Synthesis of Compound 20

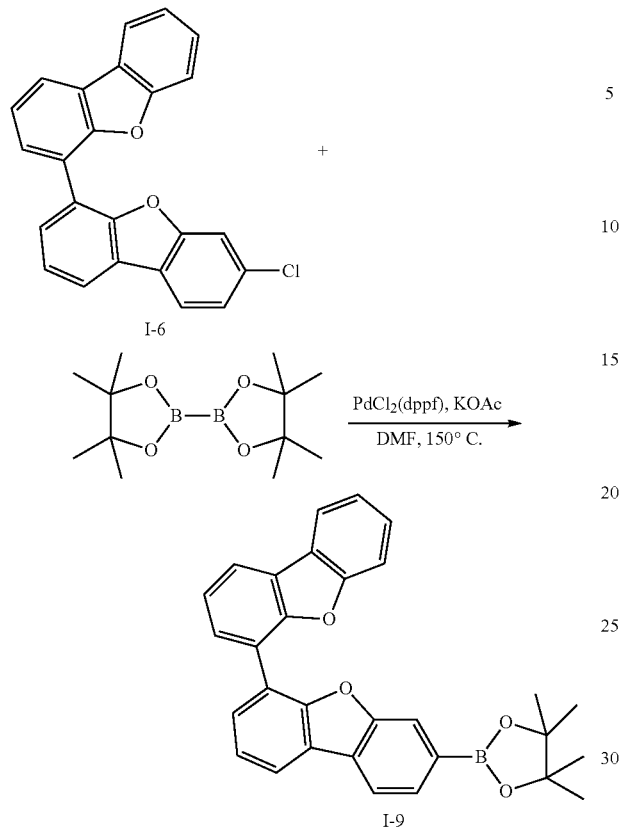

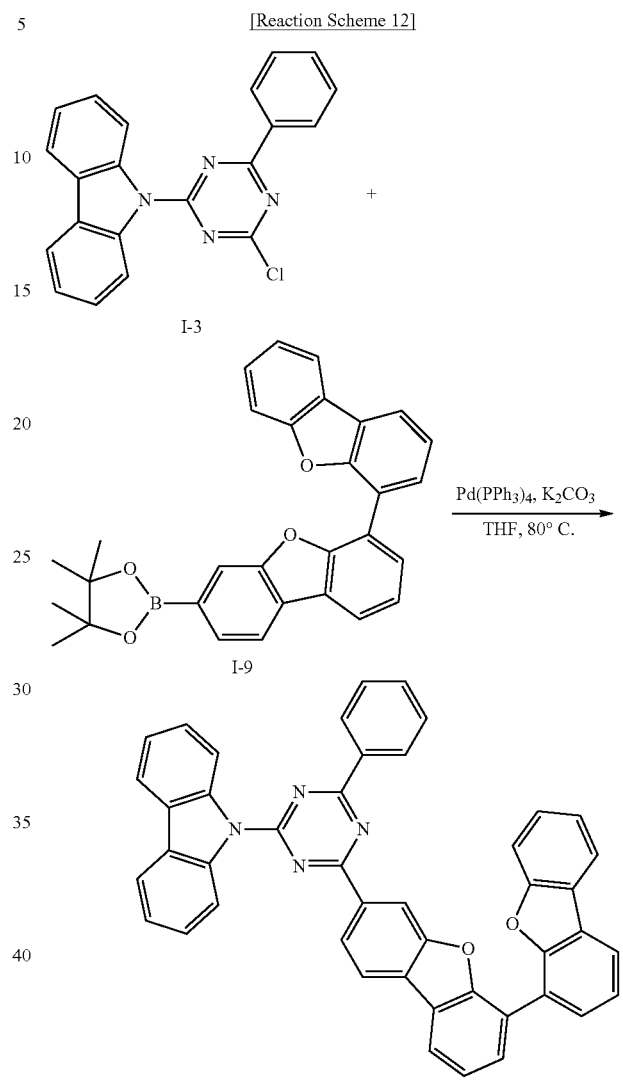

1st Step: Synthesis of Intermediate I-6

Intermediate I-4-4 (50 g, 143 mmol) and dibenzofuran-4-ylboronic acid (57.8 g, 157 mmol) purchased from Tokyo Chemical Industry Co., Ltd. (http://www.tcichemicals.com/) were used to obtain Intermediate I-6 (46.9 g, 89%) according to the same method as the 1st step of Synthesis Example 1.

HRMS (70 eV, EI+): m/z calcd for $C_{24}H_{13}ClO_2$: 368.0604, found: 368.

Elemental Analysis: C, 78%; H, 4%

2nd Step: Synthesis of Intermediate I-9

Intermediate I-6 (55 g, 149 mmol) was dissolved in 0.5 L of dimethylformamide (DMF) under a nitrogen atmosphere, and bis(pinacolato) diboron (45.4 g, 179 mmol), (1,1'-bis(diphenylphosphine)ferrocene)dichloropalladium (II) (1.22 g, 1.49 mmol), and potassium acetate (43.9 g, 447 mmol) were added thereto and then, heated and refluxed at 150° C. for 5 hours. When a reaction was complete, water was added to the reaction solution, and then the mixture was filtered and concentrated and dried in a vacuum oven. This obtained residue was separated and purified through flash column chromatography to obtain Intermediate I-9 (48.0 g, 70%).

HRMS (70 eV, EI+): m/z calcd for $C_{30}H_{25}BO_4$: 460.1846, found: 460.

Elemental Analysis: C, 78%; H, 5%

Intermediate I-3 (10 g, 28.0 mmol) and Intermediate I-9 (12.9 g, 28.0 mmol) were used to obtain Compound 20 (17.4 g, 95%) according to the same method as Synthesis Example 2.

HRMS (70 eV, EI+): m/z calcd for $C_{45}H_{26}N_4O_2$: 654.2056, found: 654.

Elemental Analysis: C, 83%; H, 4%

Synthesis Example 13: Synthesis of Intermediate I-10

[Reaction Scheme 13]

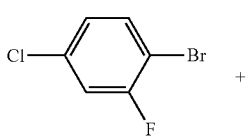

+

-continued

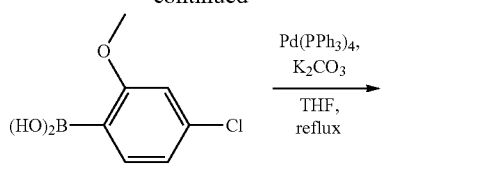

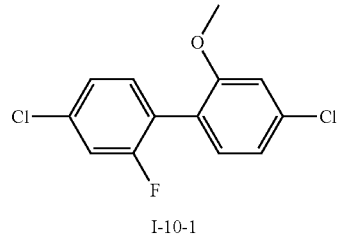
I-10-1

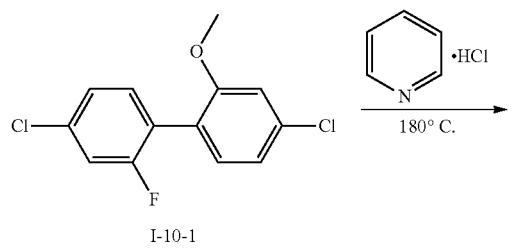

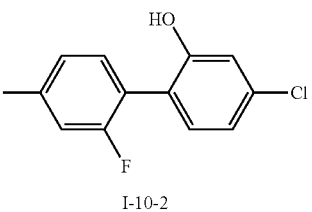
I-10-2

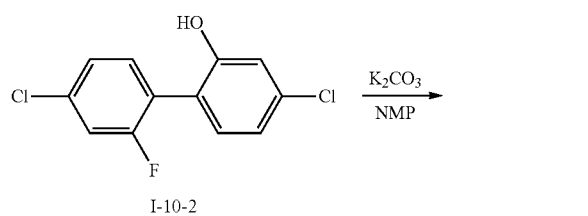
I-10-3

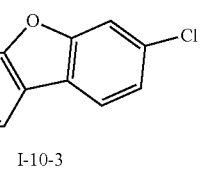
I-10-3

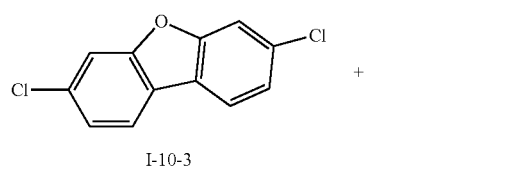

-continued

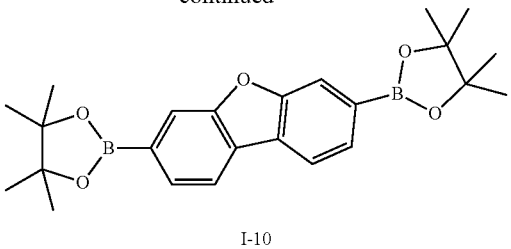
I-10

1st Step: Synthesis of Intermediate I-10-1

1-bromo-4-chloro-2-fluorobenzene (100 g, 482 mmol) purchased from Tokyo Chemical Industry Co., Ltd. (http://www.tcichemicals.com/) and 4-chloro-2-methoxyphenylboronic acid (98.8 g, 530 mmol) were used to obtain Intermediate I-10-1 (122 g, 93%) according to the same method as the 1st step of Synthesis Example 5.

HRMS (70 eV, EI+): m/z calcd for C13H9Cl2FO: 270.0014, found: 270.

Elemental Analysis: C, 58%; H, 3%

2nd Step: Synthesis of Intermediate I-10-2

Intermediate I-10-1 (120 g, 443 mmol) and pyridine hydrochloride (469 g, 4061 mmol) were put under a nitrogen atmosphere and then heated and refluxed at 180° C. for 12 hours. When a reaction was complete, water was added to the reaction solution, and then the mixture was extracted with ethyl acetate (EA), treated with magnesium sulfate anhydrous to remove moisture, and then filtered and concentrated under a reduced pressure. This obtained residue was separated and purified through flash column chromatography to obtain Intermediate I-10-2 (88.8 g, 78%).

HRMS (70 eV, EI+): m/z calcd for $C_{12}H_8ClFO$: 255.9858, found: 256.

Elemental Analysis: C, 56%; H, 3%

3rd Step: Synthesis of Intermediate I-10-3

Intermediate I-10-2 (87 g, 338 mmol) was dissolved in 0.3 L of N-methyl-2-pyrrolidone (NMP) under a nitrogen atmosphere, and potassium carbonate (70.0 g, 506 mmol) was added thereto and heated and refluxed therewith for 14 hours. When a reaction was complete, the solvent was distilled and removed, water was added to the reaction solution, and then the mixture was extracted with dichloromethane (DCM), treated with magnesium sulfate anhydrous to remove moisture, and then filtered and concentrated under a reduced pressure. This obtained residue was separated and purified through flash column chromatography to obtain Intermediate I-10-3 (73.0 g, 91%).

HRMS (70 eV, EI+): m/z calcd for $C_{12}H_6Cl_2O$: 235.9796, found: 236.

Elemental Analysis: C, 61%; H, 3%

4th Step: Synthesis of Intermediate I-10

Intermediate I-10-3 (71 g, 299 mmol) was dissolved in 0.5 L of dimethylformamide (DMF) under a nitrogen atmosphere, and bis(pinacolato)diboron (45.4 g, 179 mmol), (1,1'-bis(diphenylphosphine)ferrocene)dichloropalladium (II) (1.22 g, 1.49 mmol), and potassium acetate (43.9 g, 447 mmol) were added thereto and then, heated and refluxed at 150° C. for 15 hours. When a reaction was complete, water was added to the reaction solution, and then the mixture was filtered and dried in a vacuum oven. This obtained residue was separated and purified through flash column chromatography to obtain Intermediate I-10 (64.2 g, 51%).

HRMS (70 eV, EI+): m/z calcd for $C_{24}H_{30}B_2O_5$: 420.2279, found: 420.

Elemental Analysis: C, 69%; H, 7%

Synthesis Example 14: Synthesis of Intermediate I-11

[Reaction Scheme 14]

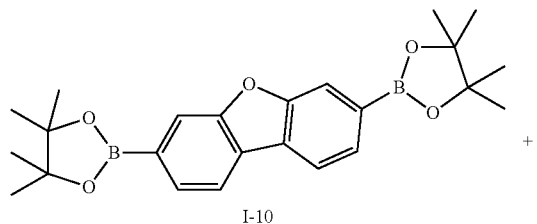

I-10

+

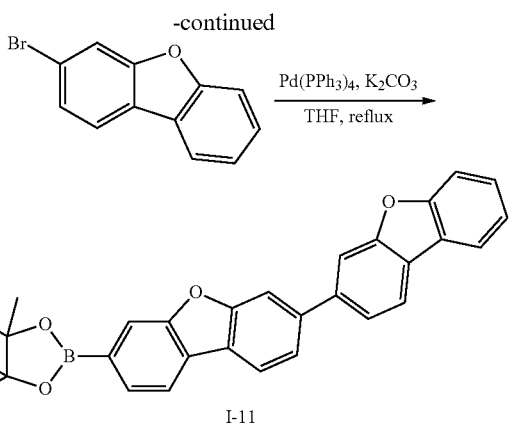

I-11

Intermediate I-10 (30 g, 71.4 mmol) and 3-bromodibenzofuran (15.9 g, 64.3 mmol) purchased from Ukseung Chemical Co., Ltd. (http://www.ukseung.co.kr/) were used to obtain Intermediate I-11 (15.1 g, 51%) according to the same method as Synthesis Example 2.

HRMS (70 eV, EI+): m/z calcd for $C_{30}H_{25}BO_4$: 460.1846, found: 460.

Elemental Analysis: C, 78%; H, 5%

Synthesis Example 15: Synthesis of Compound 22

[Reaction Scheme 15]

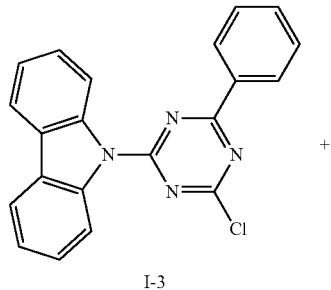

I-3

+

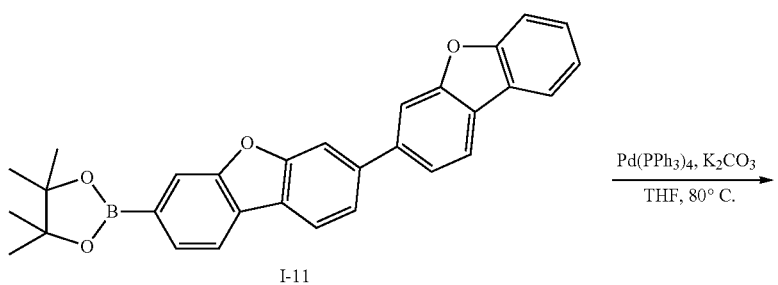

I-11

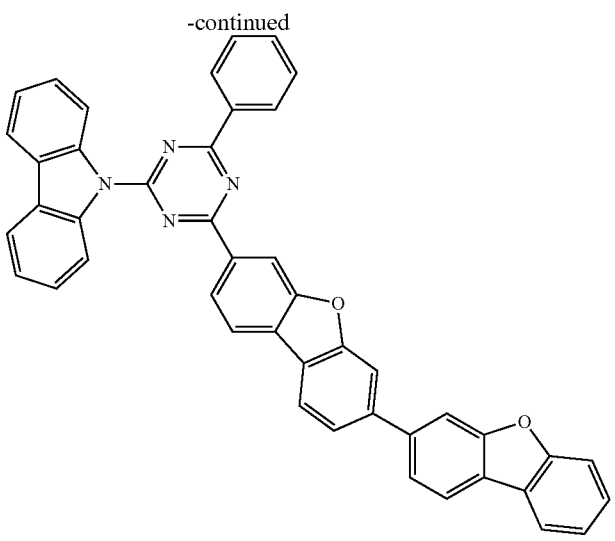

22

Intermediate I-3 (10 g, 28.0 mmol) and Intermediate I-11 (12.9 g, 28.0 mmol) were used to obtain Compound 22 (13.4 g, 73%) according to the same method as Synthesis Example 2.

HRMS (70 eV, EI+): m/z calcd for $C_{45}H_{26}N_4O_2$: 654.2056, found: 654.

Elemental Analysis: C, 83%; H, 4%

Synthesis Example 16: Synthesis of Intermediate I-12

[Reaction Scheme 16]

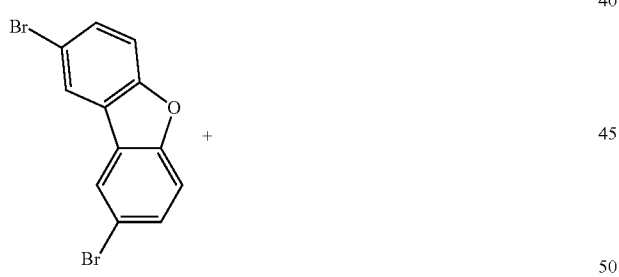

+

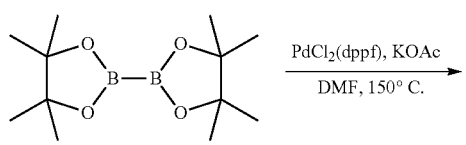

$\xrightarrow{\text{PdCl}_2\text{(dppf), KOAc}}_{\text{DMF, 150° C.}}$

-continued

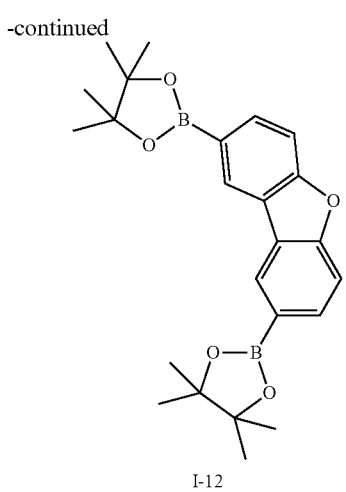

I-12

2,8-dibromodibenzofuran (50 g, 153 mmol) purchased from Tokyo Chemical Industry Co., Ltd. (http://www.tci-chemicals.com/) was used to obtain Intermediate I-12 (37.4 g, 58%) according to the same method as Synthesis Example 1.

HRMS (70 eV, EI+): m/z calcd for $C_{24}H_{30}B_2O_5$: 420.2279, found: 420.

Elemental Analysis: C, 69%; H, 7%

Synthesis Example 17: Synthesis of Intermediate I-13

Synthesis Example 18: Synthesis of Compound 41

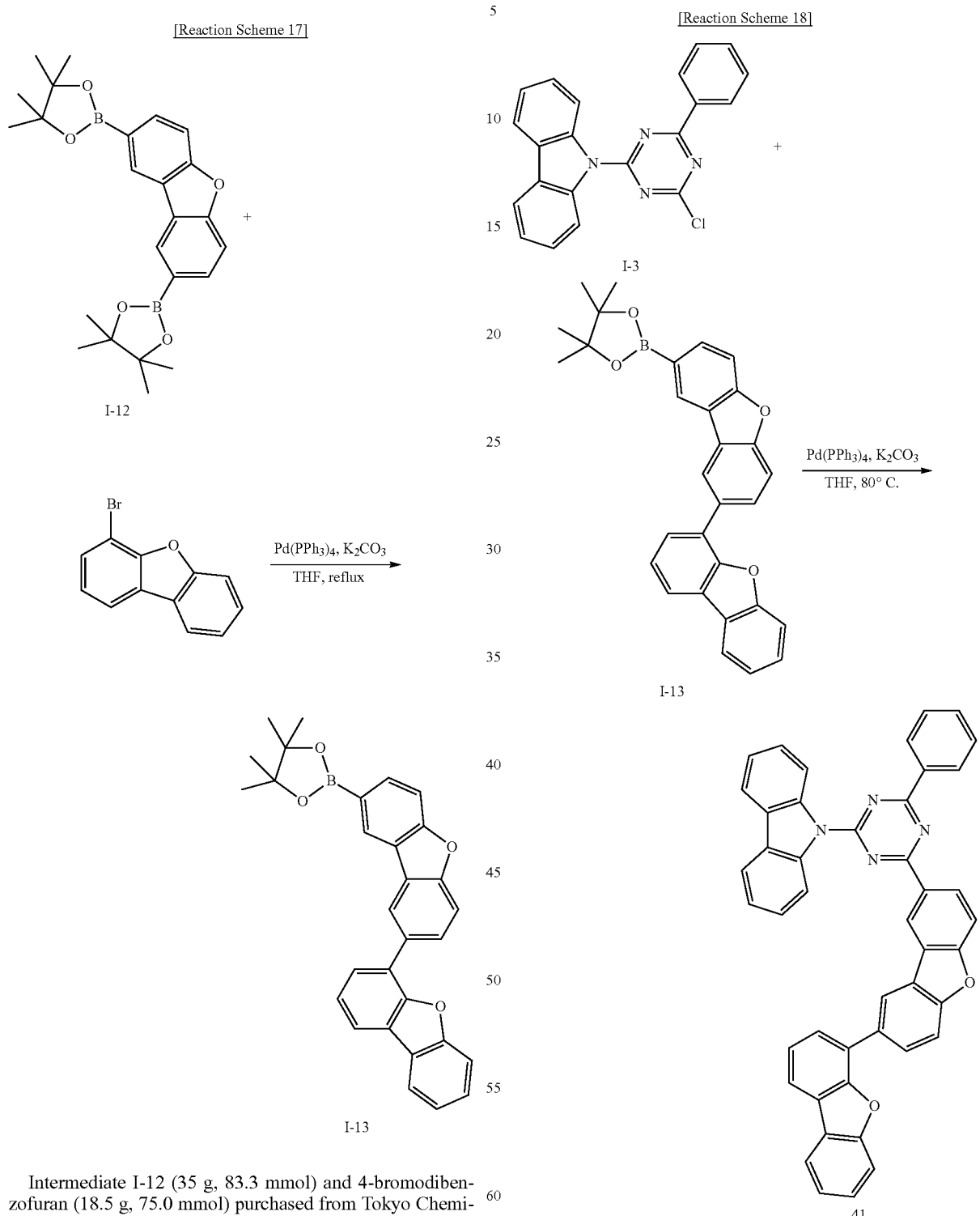

Intermediate I-12 (35 g, 83.3 mmol) and 4-bromodibenzofuran (18.5 g, 75.0 mmol) purchased from Tokyo Chemical Industry Co., Ltd. (http://www.tcichemicals.com/) were used to obtain Intermediate I-13 (22.6 g, 59%). according to the same method as Synthesis Example 2

HRMS (70 eV, EI+): m/z calcd for $C_{30}H_{25}BO_4$: 460.1846, found: 460.

Elemental Analysis: C, 78%; H, 5%

Intermediate I-3 (10 g, 28.0 mmol) and Intermediate I-13 (12.9 g, 28.0 mmol) were used to obtain Compound 41 (14.7 g, 80%) according to the same method as Synthesis Example 2.

HRMS (70 eV, EI+): m/z calcd for $C_{45}H_{26}N_4O_2$: 654.2056, found: 654.

Elemental Analysis: C, 83%; H, 4%

Synthesis Example 19: Synthesis of Intermediate I-14

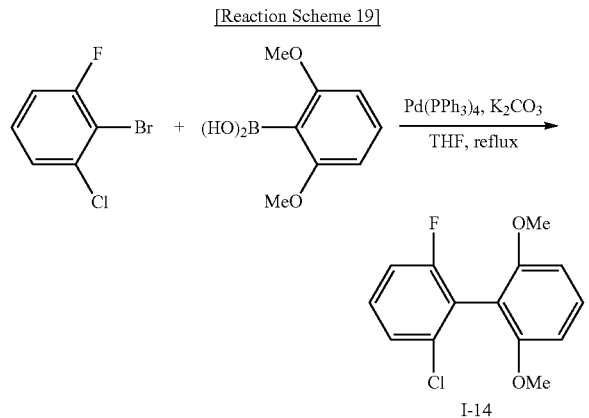

2-bromo-1-chloro-3-fluorobenzene (100 g, 477 mmol) purchased from Alfa Chemistry (https://www.alfa-chemistry.com/) and 2,6-dimethoxyphenylboronic acid (95.6 g, 525 mmol) purchased from Sigma Aldrich Co., Ltd. (http://www.sigmaaldrich.com/) were used to obtain Intermediate I-14 (89.1 g, 70%) according to the same method as Synthesis Example 2.

HRMS (70 eV, EI+): m/z calcd for $C_{14}H_{12}ClFO_2$: 266.0510, found: 266.

Elemental Analysis: C, 63%; H, 5%

Synthesis Example 20: Synthesis of Intermediate I-15

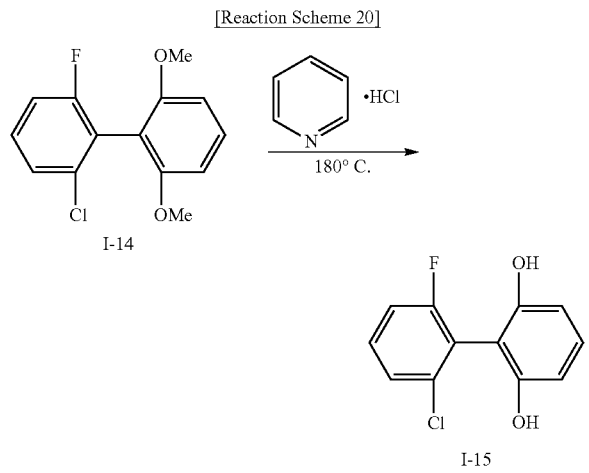

Intermediate I-14 (80 g, 300 mmol) and pyridine hydrochloride (347 g, 3,000 mmol) were put under a nitrogen atmosphere and then heated and refluxed at 180° C. for 12 hours. When a reaction was complete, water was added to the reaction solution, and then the mixture was extracted with ethyl acetate (EA), treated with magnesium sulfate anhydrous to remove moisture, and then filtered and concentrated under a reduced pressure. This obtained residue was separated and purified through flash column chromatography to obtain Intermediate I-15 (53.7 g, 75%).

HRMS (70 eV, EI+): m/z calcd for $C_{12}H_8ClFO_2$: 238.0197, found: 238.

Elemental Analysis: C, 60%; H, 3%

Synthesis Example 21: Synthesis of Intermediate I-16

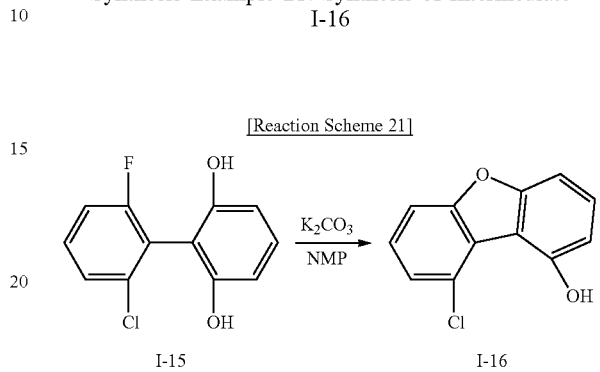

Intermediate I-15 (50.0 g, 210 mmol) was dissolved in 0.3 L of N-methyl-2-pyrrolidone (NMP) under a nitrogen atmosphere, and potassium carbonate (58.0 g, 420 mmol) was added thereto and then, heated and refluxed for 14 hours. When a reaction was complete, the solvent was distilled and removed, water was added to the reaction solution, and then the mixture was extracted with dichloromethane (DCM), treated with magnesium sulfate anhydrous to remove moisture, and then, filtered and concentrated under a reduced pressure. This obtained residue was separated and purified through flash column chromatography to obtain Intermediate I-16 (32.1 g, 70%).

HRMS (70 eV, EI+): m/z calcd for $C_{12}H_7ClO_2$: 218.0135, found: 218.

Elemental Analysis: C, 66%; H, 3%

Synthesis Example 22: Synthesis of Intermediate I-17

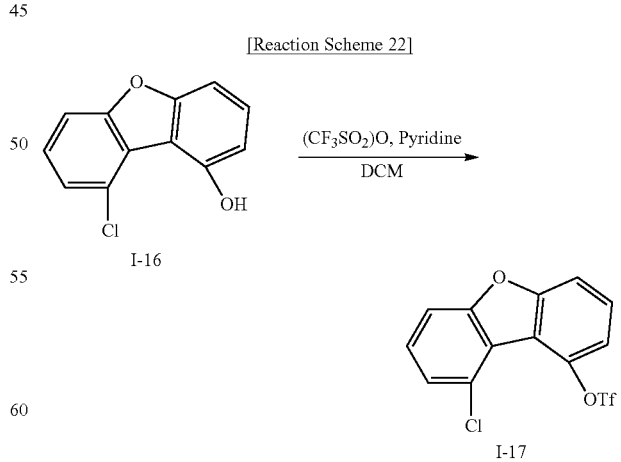

Intermediate I-16 (30 g, 137 mmol) was dissolved in 0.3 L of dichloromethane (DCM) under a nitrogen atmosphere and then, cooled down to 0° C. Pyridine (15.2 g, 192 mmol), and trifluoromethanesulfonic anhydride (46.4 g, 164 mmol)

were added thereto and then, stirred therewith at room temperature. After 14 hours, the reaction solution was cooled down to 0° C., water was slowly added thereto for 30 minutes, and the mixture was extracted with dichloromethane (DCM), treated with magnesium sulfate anhydrous to remove moisture, and then filtered and concentrated under reduced pressure. This obtained residue was separated and purified through flash column chromatography to obtain Intermediate I-17 (47.1 g, 98%).

HRMS (70 eV, EI+): m/z calcd for $C_{13}H_6ClF_3O_4S$: 349.9627, found: 350.

Elemental Analysis: C, 45%; H, 2%

Synthesis Example 23: Synthesis of Intermediate I-18

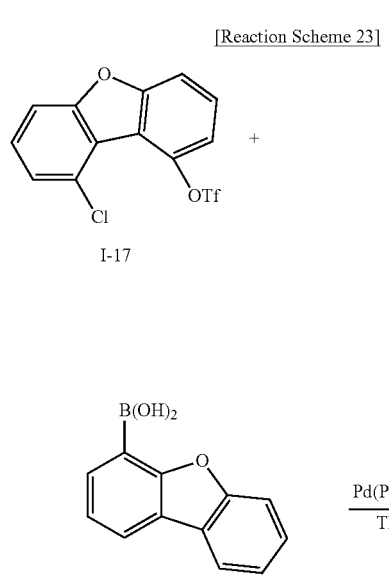

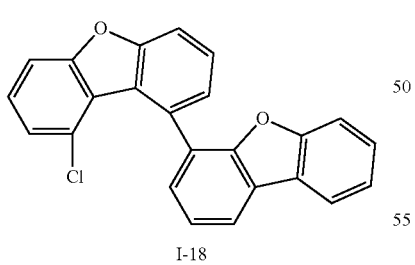

Intermediate I-17 (45 g, 128 mmol) and dibenzofuran-4-ylboronic acid (29.9 g, 141 mmol) purchased from Tokyo Chemical Industry Co., Ltd. (http://www.tcichemicals.com/) were used to obtain Intermediate I-18 (38.2 g, 81%) according to the same method as Synthesis Example 2.

HRMS (70 eV, EI+): m/z calcd for $C_{24}H_{13}ClO_2$: 368.0604, found: 368.

Elemental Analysis: C, 78%; H, 4%

Synthesis Example 24: Synthesis of Intermediate I-19

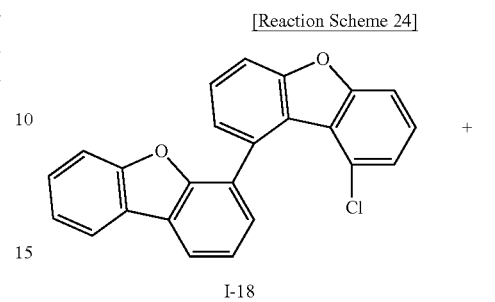

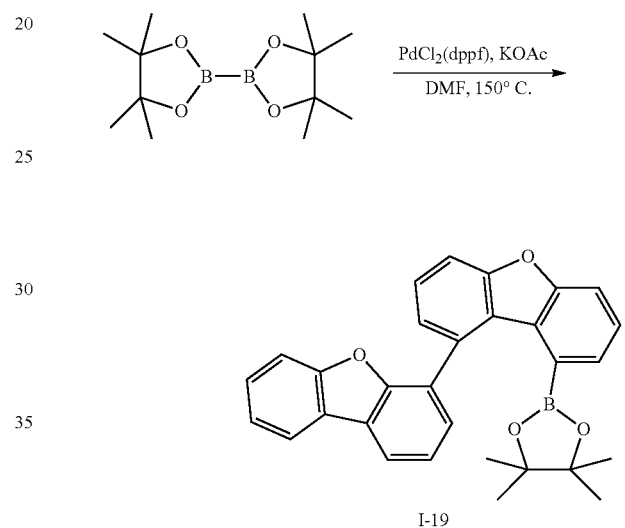

Intermediate I-18 (35 g, 94.9 mmol) were used to obtain Intermediate 19 (24.0 g, 55% according to the same method as Synthesis Example 1.

HRMS (70 eV, EI+): m/z calcd for $C_{30}H_{25}BO_4$: 460.1846, found: 460.

Elemental Analysis: C, 78%; H, 5%

Synthesis Example 25: Synthesis of Compound 57

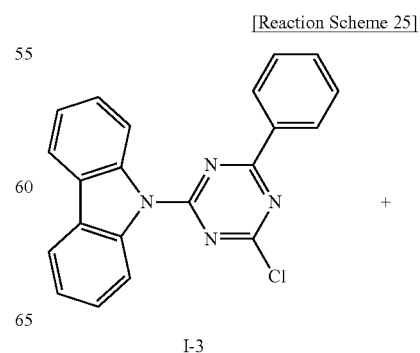

-continued

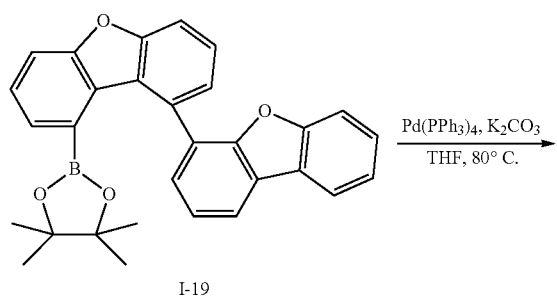

I-19

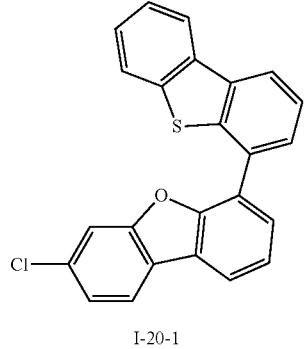

I-20-1

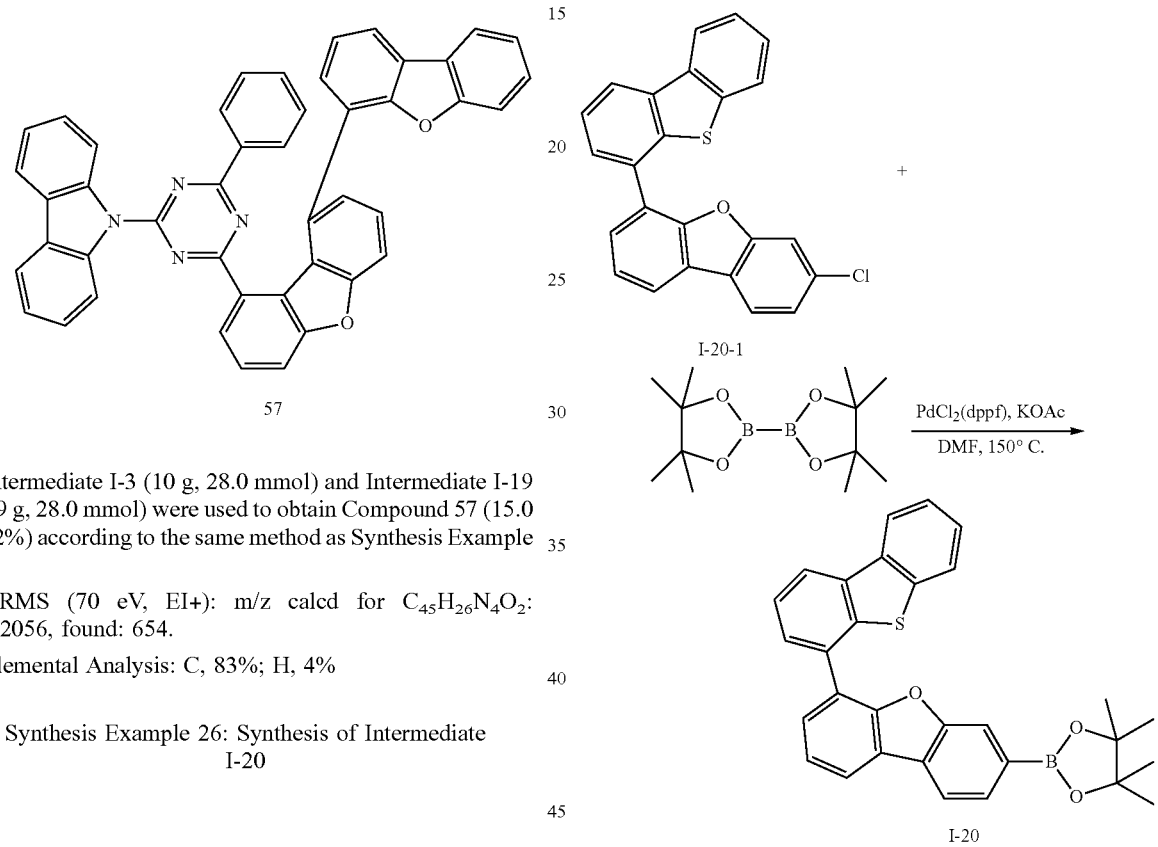

57

Intermediate I-3 (10 g, 28.0 mmol) and Intermediate I-19 (12.9 g, 28.0 mmol) were used to obtain Compound 57 (15.0 g, 82%) according to the same method as Synthesis Example 2.

HRMS (70 eV, EI+): m/z calcd for $C_{45}H_{26}N_4O_2$: 654.2056, found: 654.

Elemental Analysis: C, 83%; H, 4%

Synthesis Example 26: Synthesis of Intermediate I-20

[Reaction Scheme 26]

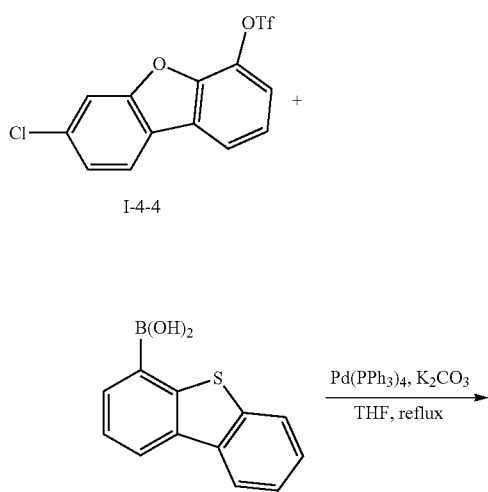

1st Step: Synthesis of Intermediate I-20-1

Intermediate I-4-4 (50 g, 143 mmol) and dibenzothiophen-4-ylboronic acid (35.9 g, 157 mmol) purchased from Tokyo Chemical Industry Co., Ltd. (http://www.tcichemicals.com/) were used to obtain Intermediate I-20-1 (48.4 g, 88%) according to the same method as the 1st step of Synthesis Example 5.

HRMS (70 eV, EI+): m/z calcd for $C_{24}H_{13}ClOS$: 384.0376, found: 384.

Elemental Analysis: C, 75%; H, 3%

2nd Step: Synthesis of Intermediate I-20

Intermediate I-20-1 (47 g, 122 mmol) were used to obtain Intermediate I-20 (40.1 g, 69%) according to the same method as Synthesis Example 1.

HRMS (70 eV, EI+): m/z calcd for $C_{30}H_{25}BO_3S$: 476.1617, found: 476.

Elemental Analysis: C, 76%; H, 5%

Synthesis Example 27: Synthesis of Compound 68

[Reaction Scheme 27]

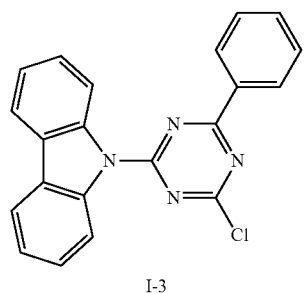

I-3

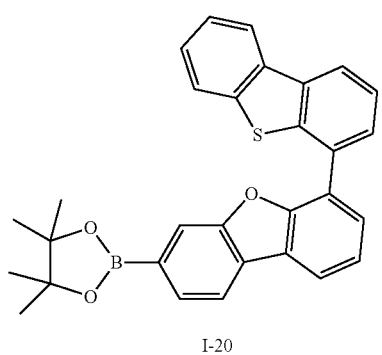

I-20

Pd(PPh₃)₄, K₂CO₃
THF, 80° C.

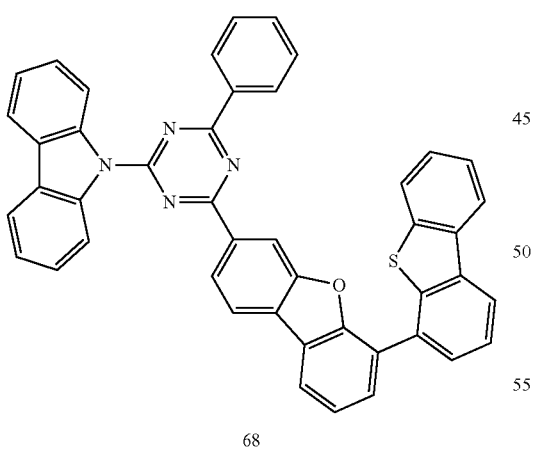

68

Intermediate I-3 (10 g, 28.0 mmol) and Intermediate I-20 (13.3 g, 28.0 mmol) were used to obtain Compound 68 (17.7 g, 94%) according to the same method as Synthesis Example 2.

HRMS (70 eV, EI+): m/z calcd for $C_{45}H_{26}N_4OS$: 670.1827, found: 670.

Elemental Analysis: C, 81%; H, 4%

Synthesis Example 28: Synthesis of Intermediate I-21

[Reaction Scheme 28]

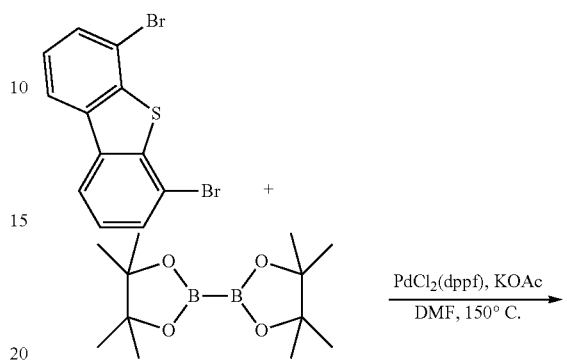

PdCl₂(dppf), KOAc
DMF, 150° C.

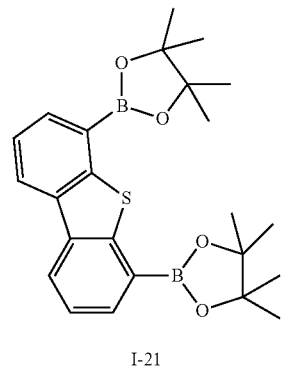

I-21

4,6-dibromodibenzothiophene (50 g, 146 mmol) purchased from Tokyo Chemical Industry Co., Ltd. (http://www.tcichemicals.com/) were used to obtain Intermediate I-21 (33.2 g, 52%) according to the same method as Synthesis Example 1.

HRMS (70 eV, EI+): m/z calcd for $C_{24}H_{30}B_2O_4S$: 436.2051, found: 436.

Elemental Analysis: C, 66%; H, 7%

Synthesis Example 29: Synthesis of Intermediate I-22

[Reaction Scheme 29]

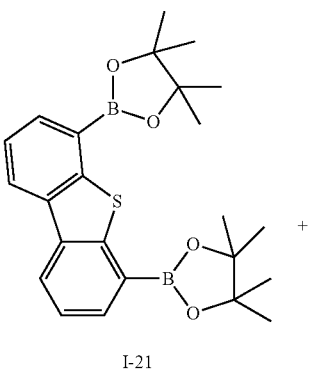

I-21

+

-continued

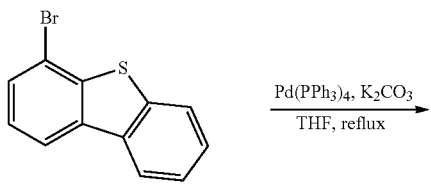

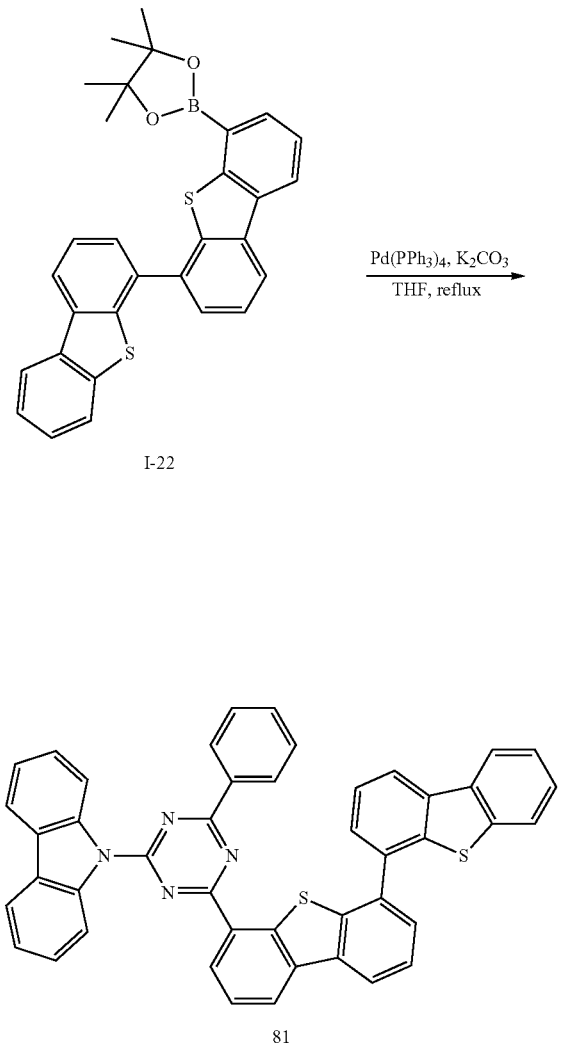

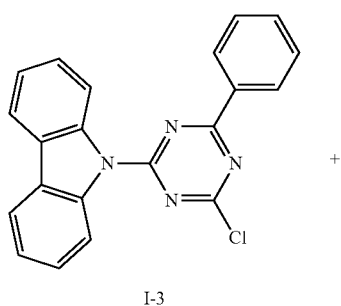

I-22

Intermediate I-21 (30 g, 68.8 mmol) and 4-bromodibenzothiophene (16.3 g, 61.9 mmol) purchased from Tokyo Chemical Industry Co., Ltd. (http://www.tcichemicals.com/) were used to obtain Intermediate I-22 (16.8 g, 55%) according to the same method as Synthesis Example 2.

HRMS (70 eV, EI+): m/z calcd for $C_{30}H_{25}BO_2S_2$: 492.1389, found: 492.

Elemental Analysis: C, 73%; H, 5%

Synthesis Example 30: Synthesis of Compound 81

[Reaction Scheme 30]

Intermediate I-3 (10 g, 28.0 mmol) and Intermediate I-22 (13.8 g, 28.0 mmol) were used to obtain Compound 81 (17.1 g, 89%) according to the same method as Synthesis Example 2.

HRMS (70 eV, EI+): m/z calcd for $C_{45}H_{26}N_4S_2$: 686.1599, found: 686.

Elemental Analysis: C, 79%; H, 4%

Synthesis Example 31: Intermediate I-23

[Reaction Scheme 31]

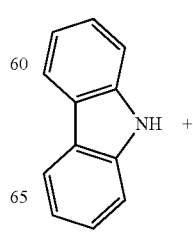

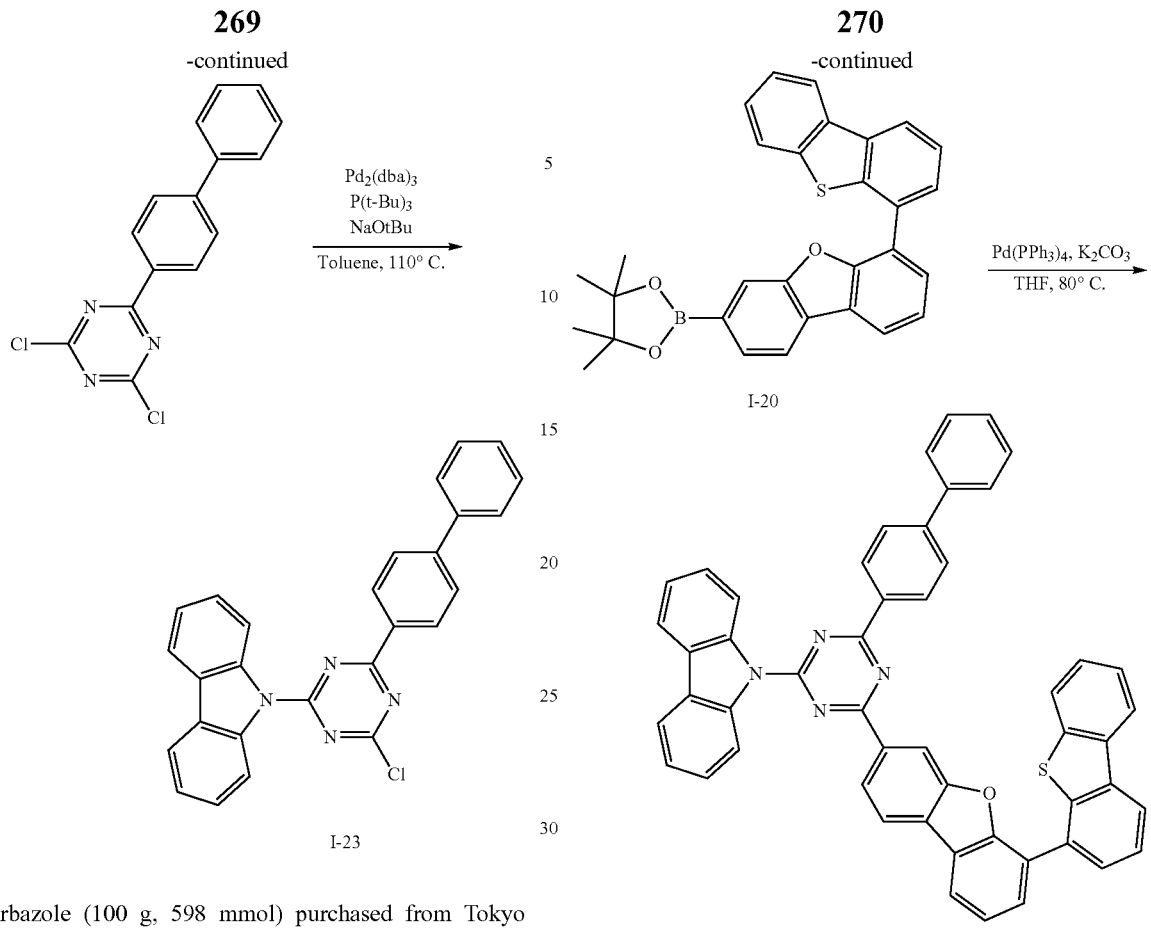

Carbazole (100 g, 598 mmol) purchased from Tokyo Chemical Industry Co., Ltd. (http://www.tcichemicals.com/) and 2-(biphenyl-4-yl)-4,6-dichloro-1,3,5-triazine (217 g, 718 mmol) purchased from Sigma Aldrich Co., Ltd. were used to obtain Intermediate I-23 (181 g, 70%) according to the same method as Synthesis Example 3.

HRMS (70 eV, EI+): m/z calcd for $C_{27}H_{17}ClN_4$: 432.1142, found: 432.

Elemental Analysis: C, 75%; H, 4%

Synthesis Example 32: Synthesis of Compound 104

[Reaction Scheme 32]

[Reaction Scheme 32]

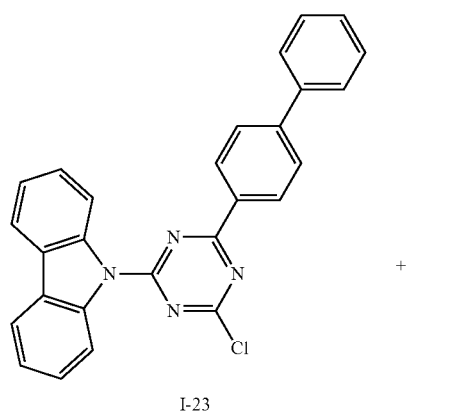

Intermediate I-23 (10 g, 23.1 mmol) and Intermediate I-20 (11.0 g, 23.1 mmol) were used to obtain Compound 104 (16.6 g, 96%) according to the same method as Synthesis Example 2.

HRMS (70 eV, EI+): m/z calcd for $C_{51}H_{30}N_4OS$: 746.2140, found: 746.

Elemental Analysis: C, 82%; H, 4%

Synthesis Example 33: Synthesis of Intermediate I-24

[Reaction Scheme 33]

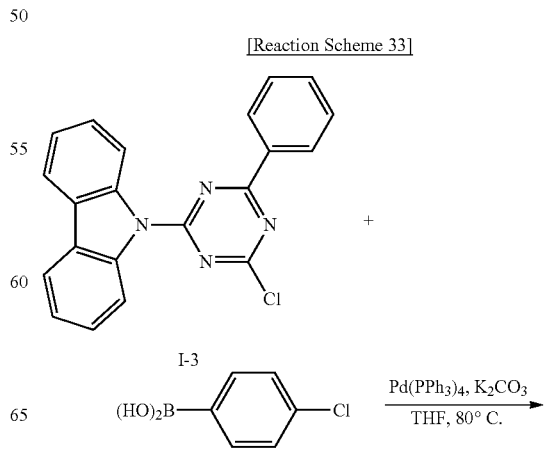

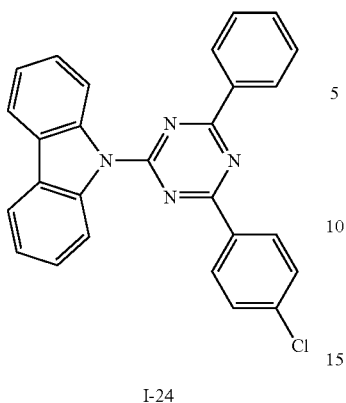

I-24

Intermediate I-3 (50 g, 140 mmol) and 4-chlorophenylboronic acid (24.1 g, 154 mmol) purchased from Tokyo Chemical Industry Co., Ltd. (http://www.tcichemicals.com/) were used to obtain Intermediate I-24 (56.4 g, 93%) according to the same method as Synthesis Example 2.

HRMS (70 eV, EI+): m/z calcd for $C_{27}H_{17}ClN_4$: 432.1142, found: 432.

Elemental Analysis: C, 75%; H, 4%

Synthesis Example 34: Synthesis of Compound 137

[Reaction Scheme 34]

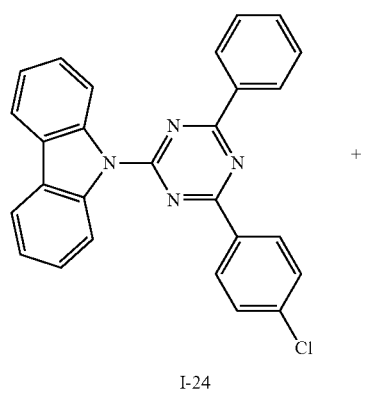

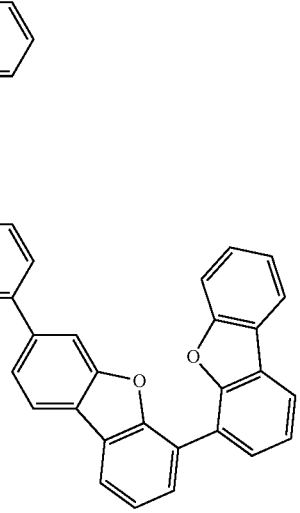

137

Intermediate I-24 (10 g, 23.1 mmol) was dissolved in 0.1 L of dioxane under a nitrogen atmosphere, and Intermediate I-9 (10.6 g, 23.1 mmol), tris(diphenylideneacetone) dipalladium (0) (0.21 g, 0.23 mmol), tris(tert butyl)phosphine (0.19 g, 0.92 mmol), and cesium carbonate (9.03 g, 27.7 mmol) were sequentially added thereto and then heated and refluxed at 100° C. for 20 hours. When a reaction was complete, water was added to the reaction solution, and then the mixture was extracted with dichloromethane (DCM), treated with magnesium sulfate anhydrous to remove moisture, and then filtered and concentrated under a reduced pressure. This obtained residue was separated and purified through flash column chromatography to obtain Compound 137 (8.44 g, 50%).

HRMS (70 eV, EI+): m/z calcd for $C_{51}H_{30}N_4O_2$: 730.2369, found: 730.

Elemental Analysis: C, 84%; H, 4%

Synthesis Example 35: Synthesis of Intermediate I-25

[Reaction Scheme 35]

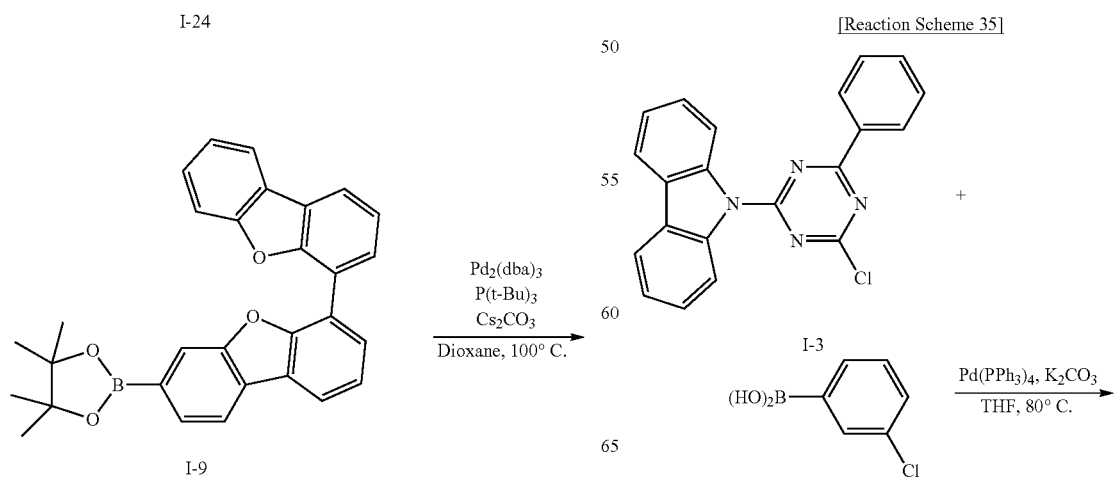

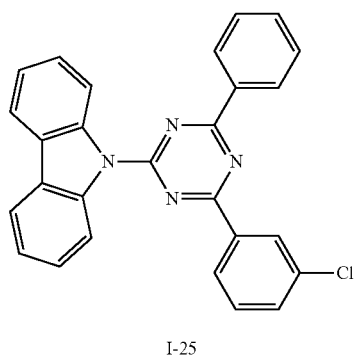

I-25

Intermediate I-3 (50 g, 140 mmol) and 3-chlorophenylboronic acid (24.1 g, 154 mmol) purchased from Tokyo Chemical Industry Co., Ltd. (http://www.tcichemicals.com/) were used to obtain Intermediate I-25 (57.6 g, 95%) according to the same method as Synthesis Example 2.

HRMS (70 eV, EI+): m/z calcd for $C_{27}H_{17}ClN_4$: 432.1142, found: 432.

Elemental Analysis: C, 75%; H, 4%

Synthesis Example 36: Synthesis of Intermediate I-26

[Reaction Scheme 36]

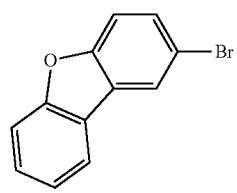

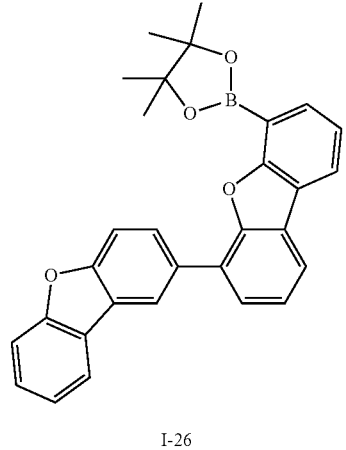

I-26

2-bromodibenzofuran (50 g, 202 mmol) purchased from Tokyo Chemical Industry Co., Ltd. (http://www.tcichemicals.com/) and Intermediate I-1 (24.1 g, 93.5 mmol) were used to obtain Synthesis Example 2 to obtain Intermediate I-26 (56.7 g, 61%) according to the same method as Synthesis Example 2.

HRMS (70 eV, EI+): m/z calcd for $C_{30}H_{25}BO_4$: 460.1846, found: 460.

Elemental Analysis: C, 78%; H, 5%

Synthesis Example 37: Synthesis of Compound 173

[Reaction Scheme 37]

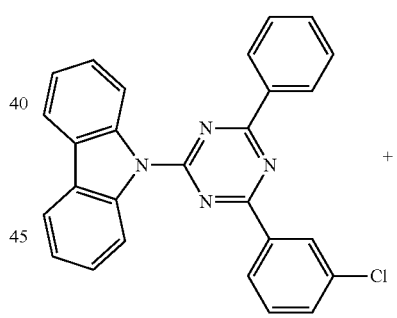

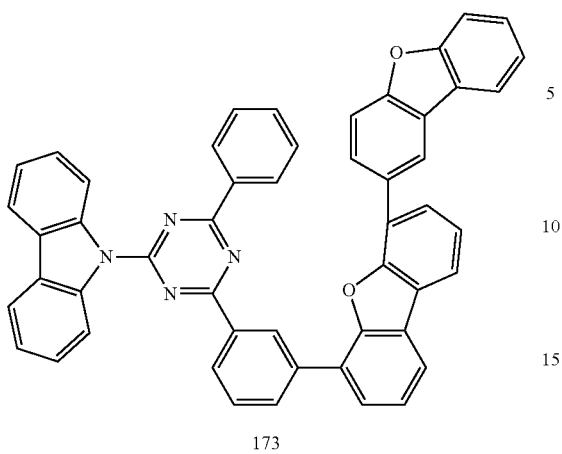

173

Intermediate I-25 (10 g, 13.7 mmol) and Intermediate I-26 (6.30 g, 13.7 mmol) were used to obtain Compound 173 (9.01 g, 90%) according to the same method as Synthesis Example 35.

HRMS (70 eV, EI+): m/z calcd for $C_{51}H_{30}N_4O_2$: 730.2369, found: 730.

Elemental Analysis: C, 84%; H, 4%

Synthesis Example 38: Synthesis of Compound Host 1

Host 1

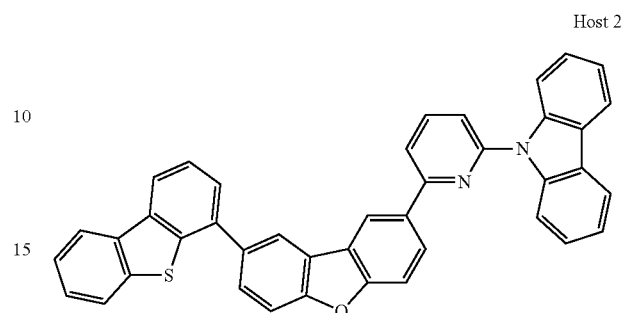

Compound Host 1 was synthesized by referring to the synthesis method of WIPO Publication No. WO 2013-035275.

HRMS (70 eV, EI+): m/z calcd for $C_{45}H_{27}N_5O$: 653.22, found: 653.

Elemental Analysis: C, 83%; H, 4%

Synthesis Example 39: Synthesis of Compound Host 2

Host 2

Compound Host 2 was synthesized by referring to the synthesis method of WIPO Publication No. WO 2013-035275.

HRMS (70 eV, EI+): m/z calcd for $C_{41}H_{24}N_2OS$: 592.1609, found: 592.

Elemental Analysis: C, 83%; H, 4%

Synthesis Example 40: Synthesis of Compound Host 3

Host 3

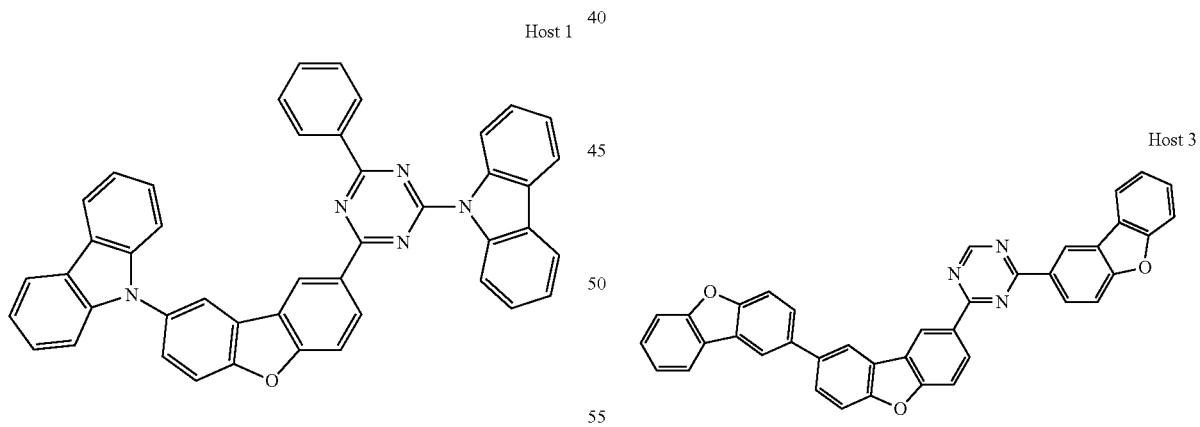

Compound Host 3 was synthesized by referring to the synthesis method of U.S. Pat. No. 9,978,952.

HRMS (70 eV, EI+): m/z calcd for $C_{39}H_{21}N_3O_3$: 579.1583, found: 579.

Elemental Analysis: C, 81%; H, 4%

Synthesis Example 41: Synthesis of Compound Host 4

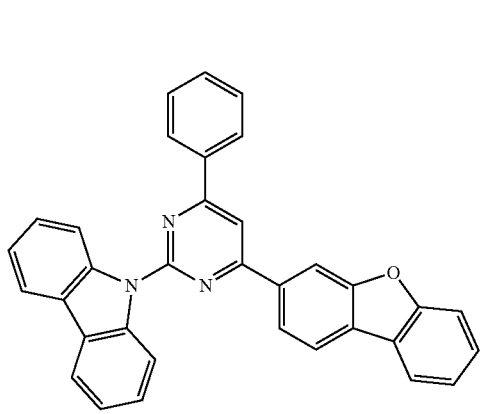

Host 4

Compound Host 4 was synthesized by referring to the synthesis method of WIPO Publication No. WO 2013-077362.

HRMS (70 eV, EI+): m/z calcd for $C_{34}H_{21}N_3O$: 487.1685, found: 487.

Elemental Analysis: C, 84%; H, 4%

Synthesis Example 42: Synthesis of Compound Host 5

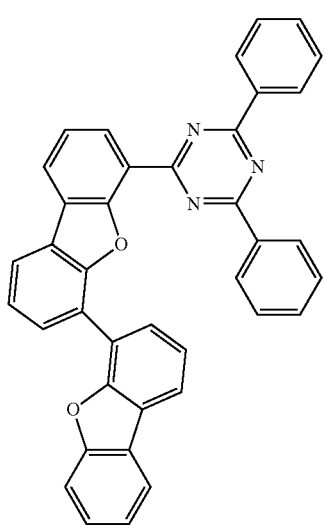

Host 5

Compound Host 5 was synthesized by referring to the synthesis method of Korean Patent Publication No. KR 10-1788094.

HRMS (70 eV, EI+): m/z calcd for $C_{39}H_{23}N_3O_2$: 565.1790, found: 565.

Elemental Analysis: C, 83%; H, 4%

Synthesis Example 43: Synthesis of Compound Host 6

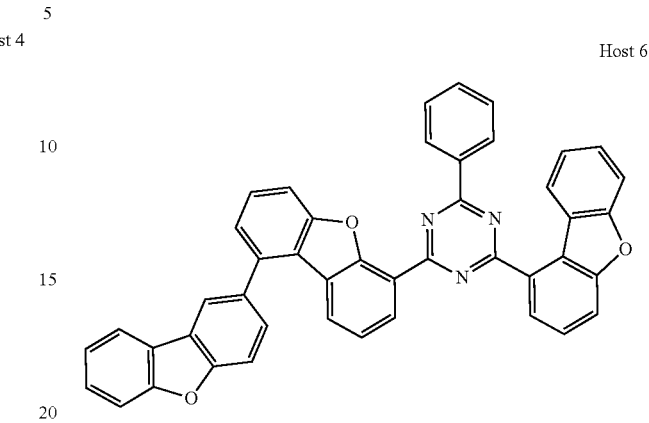

Host 6

Compound Host 6 was synthesized by referring to the synthesis method of Korean Patent Publication No. KR 10-2018-0061076.

HRMS (70 eV, EI+): m/z calcd for $C_{45}H_{25}N_3O_3$: 656.1896, found: 656.

Elemental Analysis: C, 82%; H, 4%

Synthesis Example 44: Synthesis of Compound Host 7

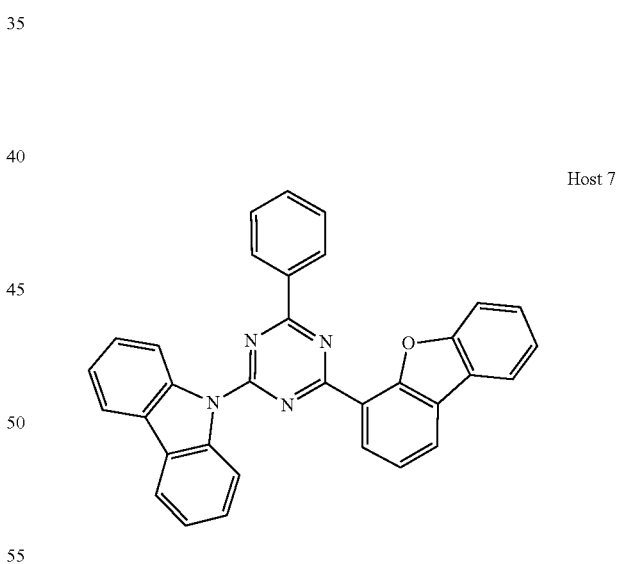

Host 7

Compound Host 7 was synthesized by referring to the synthesis method of Korean Patent Publication No. KR 10-2015-0070860.

HRMS (70 eV, EI+): m/z calcd for $C_{33}H_{20}N_4O$: 488.1637, found: 488.

Elemental Analysis: C, 81%; H, 4%

Synthesis Example 45: Synthesis of Compound Host 8

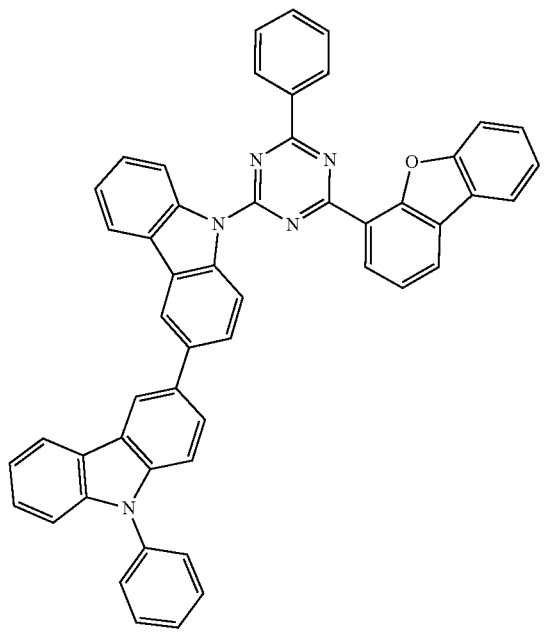

Host 8

Compound Host 8 was synthesized by referring to the synthesis method of Korean Patent Publication No. KR 10-2015-0042335.

HRMS (70 eV, EI+): m/z calcd for $C_{51}H_{31}N_5O$: 729.2529, found: 729.

Elemental Analysis: C, 84%; H, 4%

Synthesis Example 46: Synthesis of Compound E-1

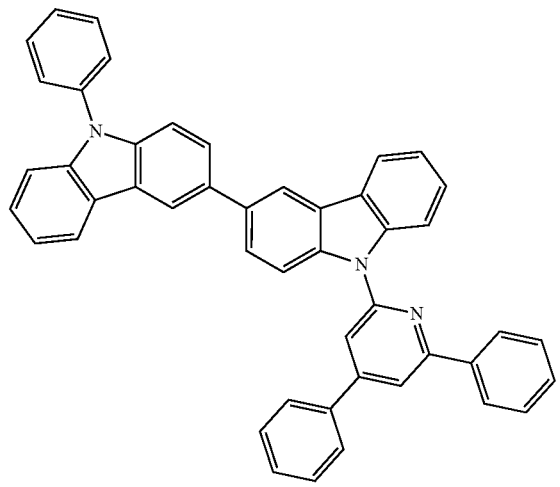

E-1

Compound E-1 was synthesized by referring to the synthesis method of Korean Patent Publication No. KR 10-2015-0117173.

HRMS (70 eV, EI+): m/z calcd for $C_{47}H_{31}N_3$: 637.2518, found: 637.

Elemental Analysis: C, 89%; H, 5%

Synthesis Example 47: Synthesis of Compound E-23

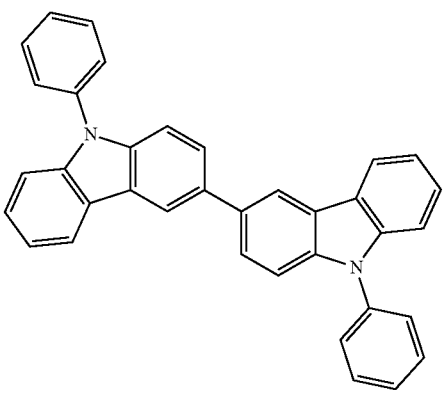

E-23

Compound E-23 was synthesized by referring to the synthesis method of Korean Patent Publication No. KR 10-2015-0117173.

HRMS (70 eV, EI+): m/z calcd for $C_{36}H_{24}N_2$: 484.1939, found: 484.

Elemental Analysis: C, 89%; H, 5%

Synthesis Example 48: Synthesis of Compound E-31

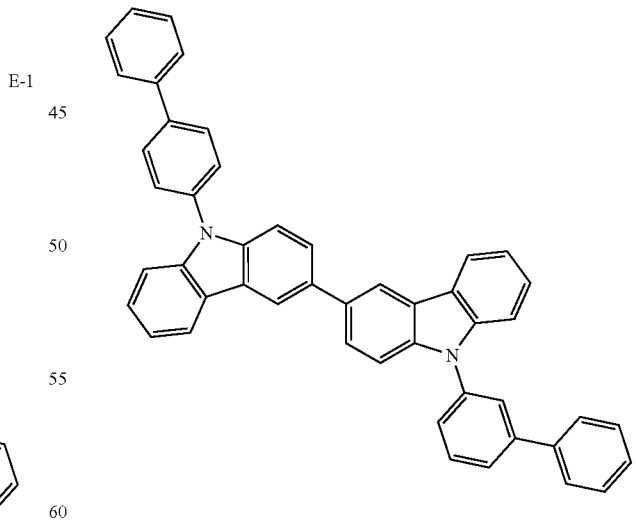

E-31

Compound E-31 was synthesized by referring to the synthesis method of Korean Patent Publication No. KR 10-2015-0117173.

HRMS (70 eV, EI+): m/z calcd for $C_{48}H_{32}N_2$: 636.2565, found: 636.

Elemental Analysis: C, 91%; H, 5%

Synthesis Example 49: Synthesis of Compound F-1

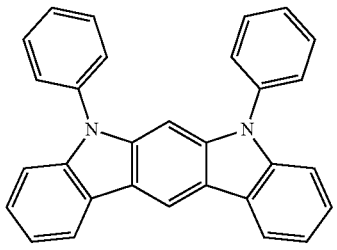
F-1

Compound F-1 was synthesized by referring to the synthesis method of Korean Patent Publication No. KR 10-2015-0117173.

HRMS (70 eV, EI+): m/z calcd for $C_{30}H_{20}N_2$: 408.1626, found: 408.

Elemental Analysis: C, 88%; H, 5%

Synthesis Example 50: Synthesis of Compound F-43

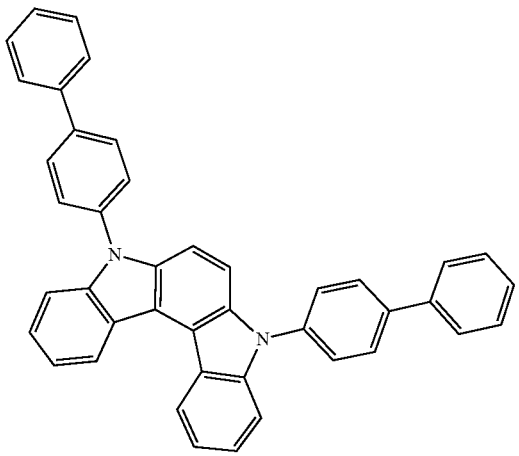
F-43

Compound F-43 was synthesized by referring to the synthesis method of Korean Patent Publication No. KR 10-2017-0026359.

HRMS (70 eV, EI+): m/z calcd for $C_{42}H_{28}N_2$: 560.2252, found: 560.

Elemental Analysis: C, 90%; H, 5%

Synthesis Example 51: Synthesis of Compound F-58

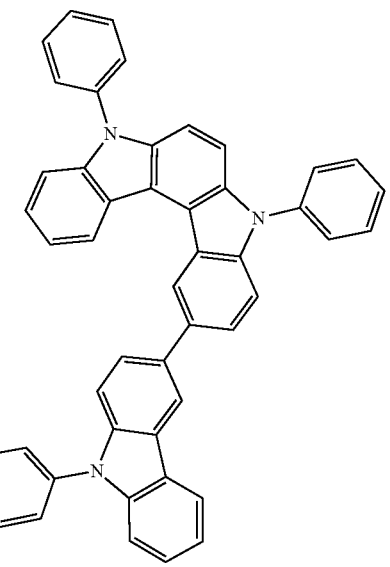
F-58

Compound F-58 was synthesized by referring to the synthesis method of Korean Patent Publication No. KR 10-2017-0120413.

HRMS (70 eV, EI+): m/z calcd for $C_{48}H_{31}N_3$: 649.2518, found: 649.

Elemental Analysis: C, 89%; H, 5%

Synthesis Example 52: Synthesis of Compound F-88

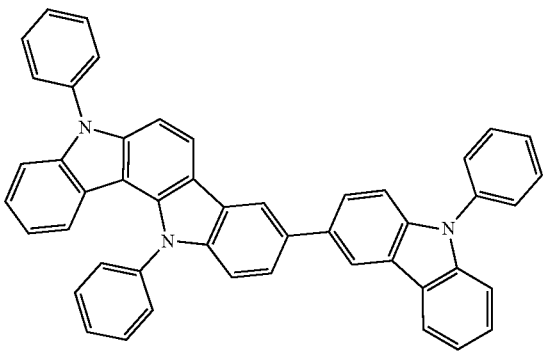
F-88

Compound F-88 was synthesized by referring to the synthesis method of Korean Patent Publication No. KR 10-2017-0120413.

HRMS (70 eV, EI+): m/z calcd for $C_{48}H_{31}N_3$: 649.2518, found: 649.

Elemental Analysis: C, 89%; H, 5%

(Manufacture of Organic Light Emitting Diode)

Example 1

A glass substrate coated with ITO (indium tin oxide) as a 1,500 Å-thick thin film was washed with distilled water.

After washing with the distilled water, the glass substrate was ultrasonic wave-washed with isopropyl alcohol, acetone, or methanol, and dried and then moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å-thick on the injection layer, and Compound C was deposited to be 1,020 Å-thick to form a hole transport layer. On the hole transport layer, Compound 1 and Compound E-31 were simultaneously used as hosts, and 10 wt % of tris(2-phenylpyridine) iridium (III) [Ir(ppy)$_3$] as a dopant was doped with vacuum deposition to form a 400 Å-thick light emitting layer. Herein, Compound 1 and Compound E-31 were used in a weight ratio of 3:7. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1,200 Å thick on the electron transport layer, manufacturing an organic light emitting diode.

The organic light emitting diode had a five-layered organic thin layer structure as follows:

A structure of ITO/Compound A (700 Å)/Compound B (50 Å)/Compound C (1,020 Å)/EML[Compound 1:Compound E-31:Ir(ppy)$_3$=X:X:10%] (400 Å)/Compound D:Liq (300 Å)/Liq (15 Å)/Al (1,200 Å). (X=weight ratio)

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

Example 2 to Example 30

Organic light emitting diodes were respectively manufactured according to the same method as Example 1 except for using the compositions in Table 1.

Comparative Examples 1 to 18

Organic light emitting diodes were respectively manufactured except for using the compositions in Table 1 according to the same method as Example 1.

Evaluation

Driving voltage, luminous efficiency, and life-span characteristics of the organic light emitting diodes according to Examples 1 to 30 and Comparative Examples 1 to 18 were evaluated.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Power efficiency (cd/A) at the same current density (10 mA/cm$^2$) were calculated by using the luminance, current density, and voltages (V) from the items (1) and (2).

(4) Measurement of Life-Span

The results were obtained by measuring a time when current efficiency (cd/A) was decreased down to 97%, while luminance (cd/m$^2$) was maintained to be 6,000 cd/m$^2$

TABLE 1

| Nos. | Host (weight ratio: 3:7) First host | Second host | Driving voltage (V) | Color (EL color) | Efficiency (cd/A) | Life-span T97(h) |
|---|---|---|---|---|---|---|
| Example 1 | Compound 1 | Compound E-31 | 4.05 | Green | 68.0 | 1,300 |
| Example 2 | Compound 17 | Compound E-31 | 4.28 | Green | 67.0 | 1,150 |
| Example 3 | Compound 18 | Compound E-31 | 4.17 | Green | 68.3 | 1,250 |
| Example 4 | Compound 57 | Compound E-31 | 4.20 | Green | 68.5 | 1,180 |
| Example 5 | Compound 20 | Compound E-31 | 4.00 | Green | 69.1 | 1,350 |
| Example 6 | Compound 22 | Compound E-31 | 4.13 | Green | 62.1 | 1,010 |
| Example 7 | Compound 41 | Compound E-31 | 4.22 | Green | 69.5 | 1,170 |
| Example 8 | Compound 68 | Compound E-31 | 4.15 | Green | 68.1 | 1,180 |
| Example 9 | Compound 81 | Compound E-31 | 4.33 | Green | 68.5 | 1,030 |
| Example 10 | Compound 104 | Compound E-31 | 4.08 | Green | 65.2 | 1,100 |
| Example 11 | Compound 137 | Compound E-31 | 4.31 | Green | 65.5 | 1,370 |
| Example 12 | Compound 173 | Compound E-31 | 4.22 | Green | 66.2 | 1,210 |
| Example 13 | Compound 1 | Compound E-1 | 4.25 | Green | 62.0 | 1,010 |
| Example 14 | Compound 1 | Compound E-23 | 4.28 | Green | 65.1 | 1,230 |
| Example 15 | Compound 1 | Compound F-1 | 4.18 | Green | 67.8 | 1,100 |
| Example 16 | Compound 1 | Compound F-43 | 4.11 | Green | 65.9 | 1,200 |
| Example 17 | Compound 1 | Compound F-58 | 4.21 | Green | 66.9 | 1,160 |
| Example 18 | Compound 1 | Compound F-88 | 4.09 | Green | 66.1 | 1,180 |
| Example 19 | Compound 1 | | 4.31 | Green | 50.0 | 800 |
| Example 20 | Compound 17 | | 4.42 | Green | 49.8 | 750 |
| Example 21 | Compound 18 | | 4.28 | Green | 52.3 | 810 |
| Example 22 | Compound 57 | | 4.25 | Green | 51.0 | 830 |
| Example 23 | Compound 20 | | 4.20 | Green | 55.0 | 920 |
| Example 24 | Compound 22 | | 4.30 | Green | 48.5 | 780 |
| Example 25 | Compound 41 | | 4.22 | Green | 57.2 | 800 |
| Example 26 | Compound 68 | | 4.25 | Green | 56.3 | 750 |
| Example 27 | Compound 81 | | 4.33 | Green | 55.0 | 700 |
| Example 28 | Compound 104 | | 4.19 | Green | 54.3 | 820 |
| Example 29 | Compound 137 | | 4.35 | Green | 55.0 | 850 |
| Example 30 | Compound 173 | | 4.30 | Green | 53.1 | 790 |
| Comparative Example 1 | CBP | | 5.5 | Green | 19.3 | 0.5 |
| Comparative Example 2 | Compound E-31 | | 5.3 | Green | 2.8 | 10 |
| Comparative Example 3 | Host 1 | Compound E-31 | 4.40 | Green | 62.5 | 530 |

TABLE 1-continued

| Nos. | Host (weight ratio: 3:7) First host | Second host | Driving voltage (V) | Color (EL color) | Efficiency (cd/A) | Life-span T97(h) |
|---|---|---|---|---|---|---|
| Comparative Example 4 | Host 2 | Compound E-31 | 4.91 | Green | 31.5 | 10 |
| Comparative Example 5 | Host 3 | Compound E-31 | 4.33 | Green | 40.1 | 30 |
| Comparative Example 6 | Host 4 | Compound E-31 | 4.30 | Green | 65.2 | 320 |
| Comparative Example 7 | Host 5 | Compound E-31 | 4.82 | Green | 35.2 | 480 |
| Comparative Example 8 | Host 6 | Compound E-31 | 4.33 | Green | 40.1 | 500 |
| Comparative Example 9 | Host 7 | Compound E-31 | 4.30 | Green | 65.2 | 610 |
| Comparative Example 10 | Host 8 | Compound E-31 | 4.91 | Green | 52.1 | 650 |
| Comparative Example 11 | Host 1 | | 4.32 | Green | 66.8 | 520 |
| Comparative Example 12 | Host 2 | | 5.22 | Green | 32.1 | 10 |
| Comparative Example 13 | Host 3 | | 4.81 | Green | 48.9 | 20 |
| Comparative Example 14 | Host 4 | | 4.58 | Green | 58.9 | 120 |
| Comparative Example 15 | Host 5 | | 4.7 | Green | 42.5 | 250 |
| Comparative Example 16 | Host 6 | | 4.50 | Green | 45.8 | 350 |
| Comparative Example 17 | Host 7 | | 4.32 | Green | 60.1 | 530 |
| Comparative Example 18 | Host 8 | | 4.88 | Green | 52.2 | 300 |

Referring to Table 1, the organic light emitting diodes according to Examples 1 to 30 exhibited substantially improved driving voltage, and in particular, significantly improved luminous efficiency and life-span characteristics, compared with the organic light emitting diodes according to Comparative Examples 1 to 18.

One or more embodiments may provide a compound for an organic optoelectronic device capable of realizing an organic optoelectronic device having high efficiency and a long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by Chemical Formula 1:

[Chemical Formula 1]

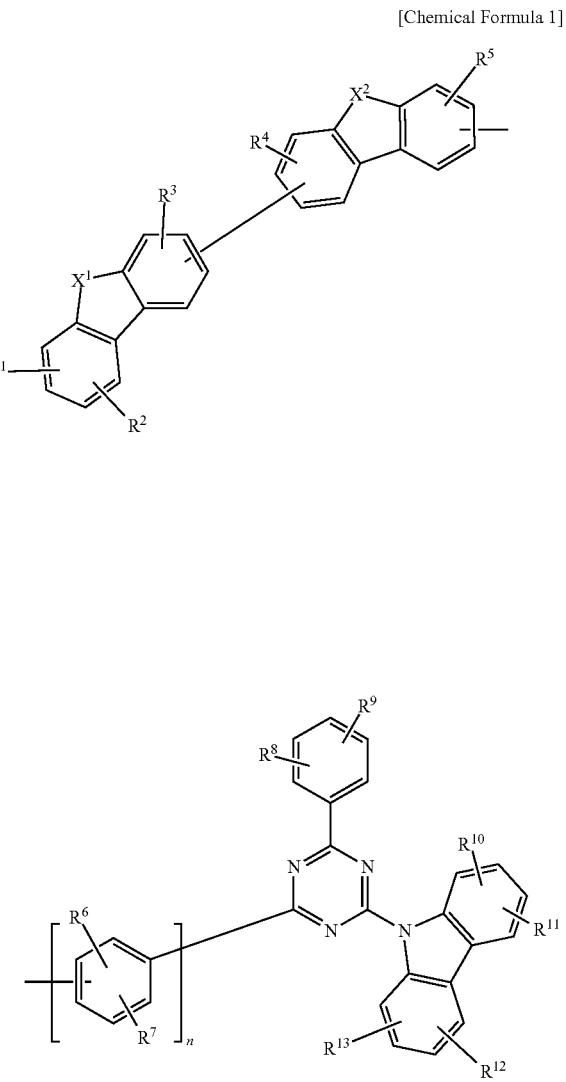

wherein, in Chemical Formula 1, $X^1$ and $X^2$ are independently O or S, $R^1$ to $R^{13}$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof, $R^{10}$ to $R^{13}$ are separate or adjacent groups are linked to each other to provide a substituted or unsubstituted aliphatic, aromatic, or heteroaromatic monocyclic ring or a substituted or unsubstituted aliphatic, aromatic, or heteroaromatic polycyclic ring, and n is 0 or 1.

2. The compound as claimed in claim 1, wherein the compound represented by Chemical Formula 1 is represented by one of Chemical Formula 1-1 to Chemical Formula 1-4:

[Chemical Formula 1-1]
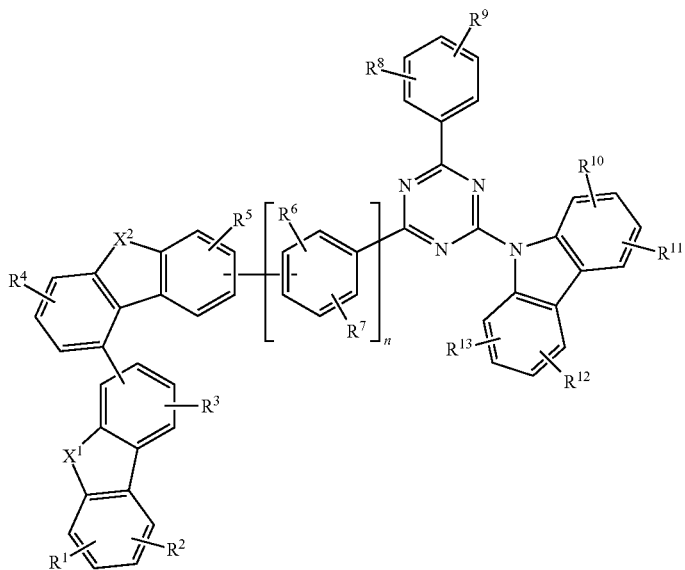
[Chemical Formula 1-2]
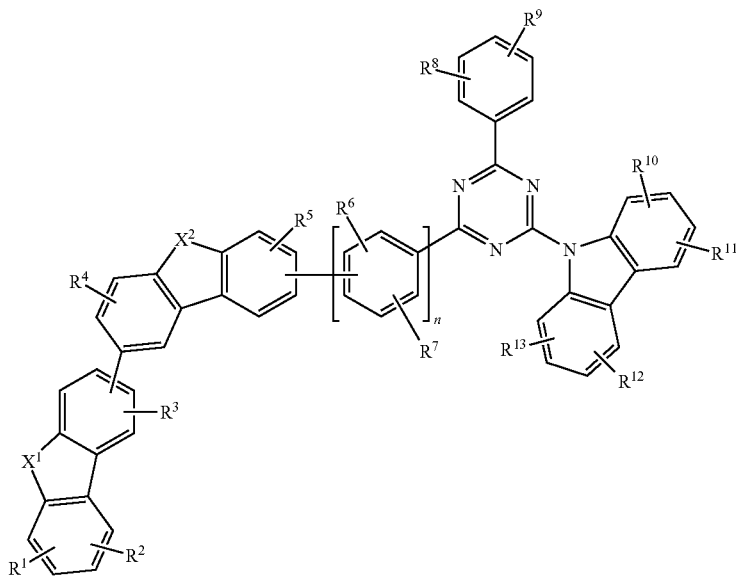
[Chemical Formula 1-3]
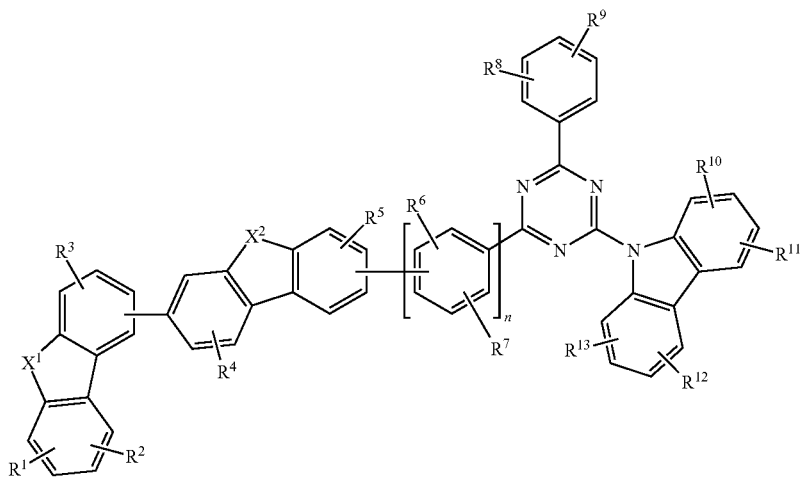

[Chemical Formula 1-4]

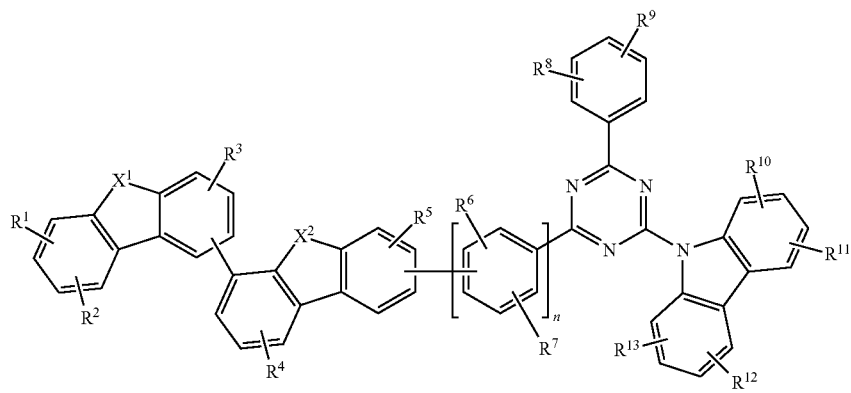

wherein, in Chemical Formula 1-1 to Chemical Formula 1-4, $X^1$ and $X^2$ are independently O or S, $R^1$ to $R^{13}$ are independently hydrogen, deuterium, a cyano group, a halogen, a substituted or unsubstituted C1 to C10 alkyl group, a substituted or unsubstituted C6 to C12 aryl group, a substituted or unsubstituted C2 to C20 heterocyclic group, or a combination thereof, $R^{10}$ to $R^{13}$ are separate or adjacent groups are linked to each other to provide a substituted or unsubstituted aliphatic, aromatic, or heteroaromatic monocyclic ring or a substituted or unsubstituted aliphatic, aromatic, or heteroaromatic polycyclic ring, and n is 0 or 1.

3. The compound as claimed in claim 2, wherein:

the compound represented by Chemical Formula 1 is represented by Chemical Formula 1-1, and Chemical Formula 1-1 is represented by one of Chemical Formula 1-1a to Chemical Formula 1-1d:

[Chemical Formula 1-1a]

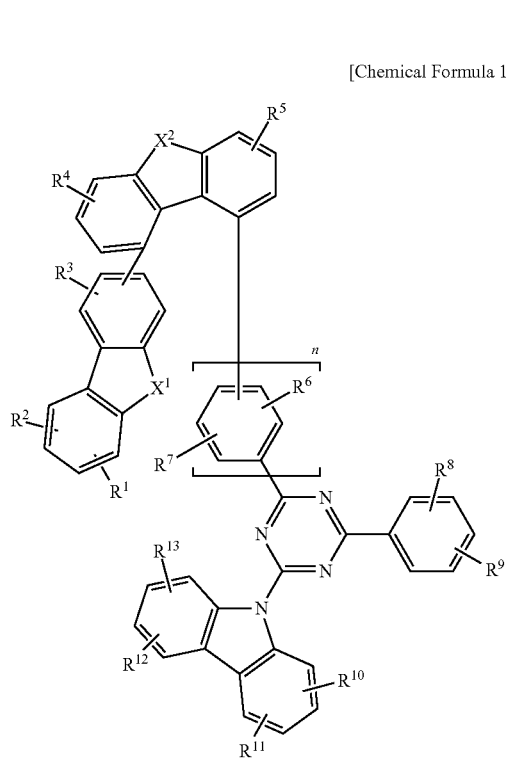

[Chemical Formula 1-1b]

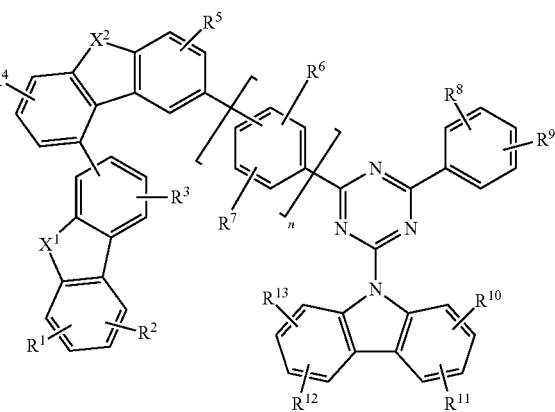

[Chemical Formula 1-1c]

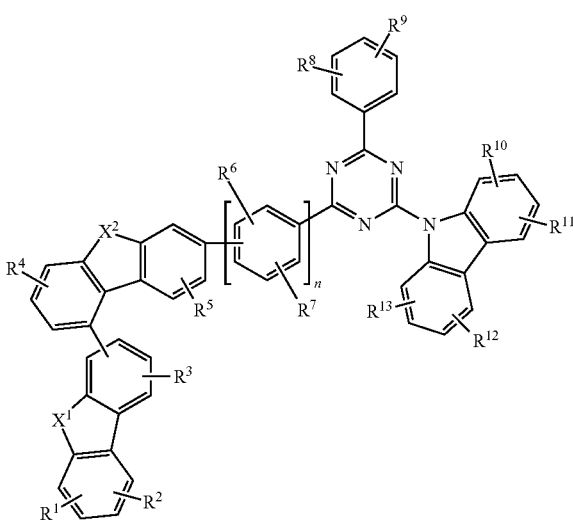

-continued

[Chemical Formula 1-1d]

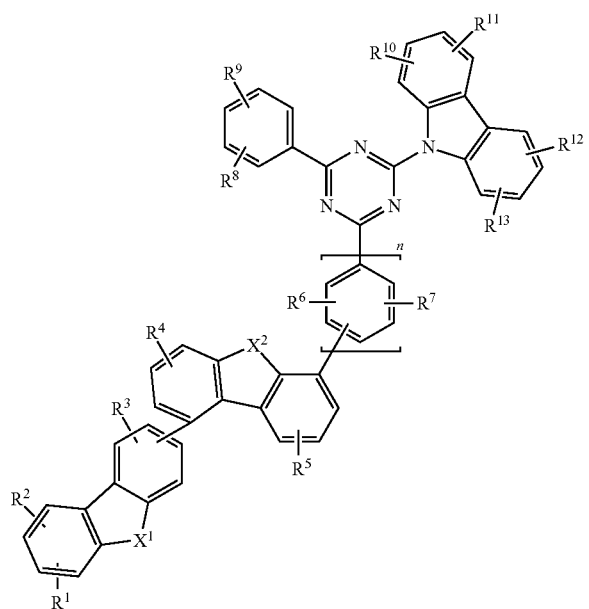

wherein, in Chemical Formula 1-1a to Chemical Formula 1-1d, $X^1$ and $X^2$ are independently O or S, $R^1$ to $R^{13}$ are independently hydrogen, deuterium, a cyano group, a halogen, a substituted or unsubstituted C1 to C10 alkyl group, a C6 to C12 aryl group, a C2 to C20 heterocyclic group, or a combination thereof, $R^{10}$ to $R^{13}$ are separate or adjacent groups are linked to each other to provide a substituted or unsubstituted aliphatic, aromatic, or heteroaromatic monocyclic ring or a substituted or unsubstituted aliphatic, aromatic, or heteroaromatic polycyclic ring, and n is 0 or 1.

4. The compound as claimed in claim 2, wherein:

the compound represented by Chemical Formula 1 is represented by Chemical Formula 1-2, and Chemical Formula 1-2 is represented by one of Chemical Formula 1-2a to Chemical Formula 1-2d:

[Chemical Formula 1-2a]

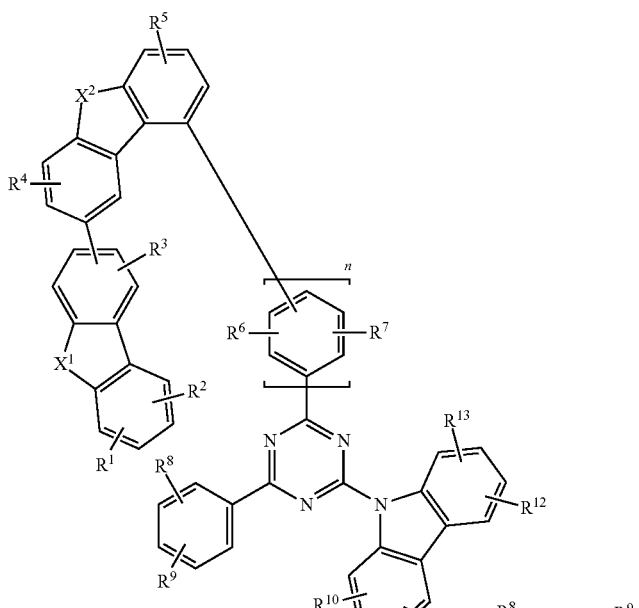

[Chemical Formula 1-2b]

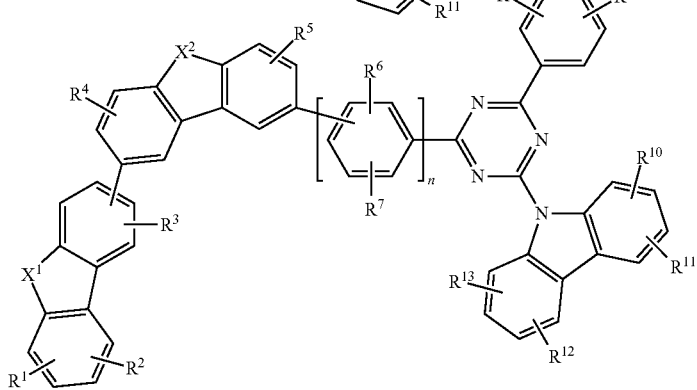

[Chemical Formula 1-2c]

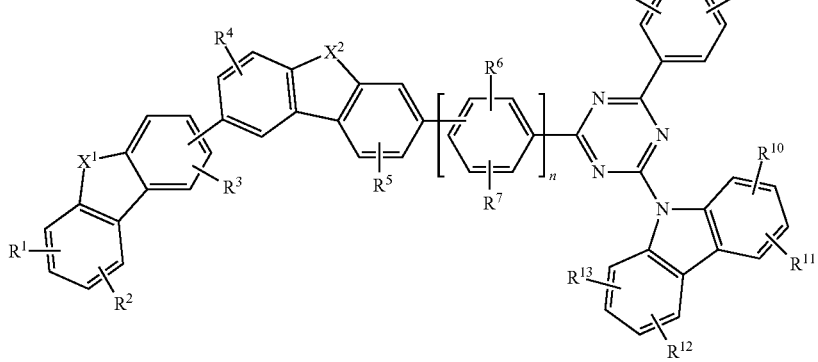

[Chemical Formula 1-2d]

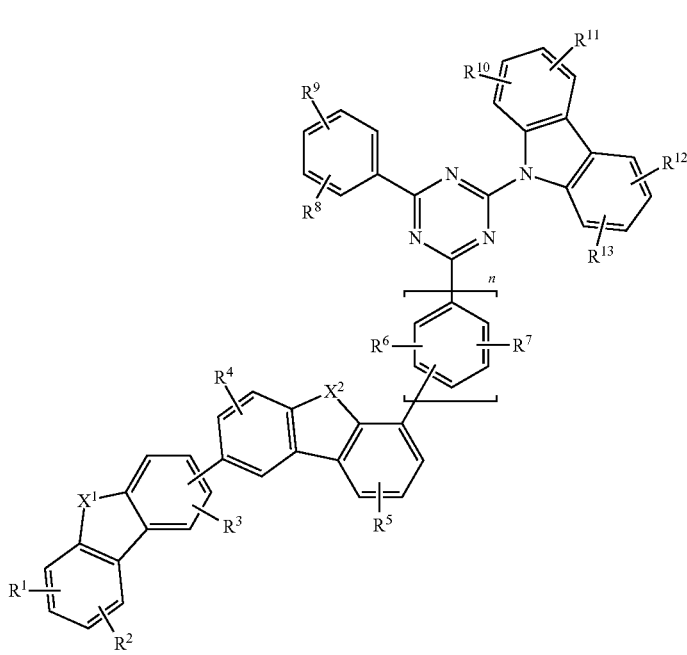

wherein, in Chemical Formula 1-2a to Chemical Formula 1-2d, $X^1$ and $X^2$ are independently O or S, $R^1$ to $R^{13}$ are independently hydrogen, deuterium, a cyano group, a halogen, a substituted or unsubstituted C1 to C10 alkyl group, a C6 to C12 aryl group, a C2 to C20 heterocyclic group, or a combination thereof, $R^{10}$ to $R^{13}$ are separate or adjacent groups are linked to each other to provide a substituted or unsubstituted aliphatic, aromatic, or heteroaromatic monocyclic ring or a substituted or unsubstituted aliphatic, aromatic, or heteroaromatic polycyclic ring, and n is 0 or 1.

5. The compound as claimed in claim 2, wherein:
the compound represented by Chemical Formula 1 is represented by Chemical Formula 1-3, and
Chemical Formula 1-3 is represented by one of Chemical Formula 1-3a to Chemical Formula 1-3d:

[Chemical Formula 1-3a]
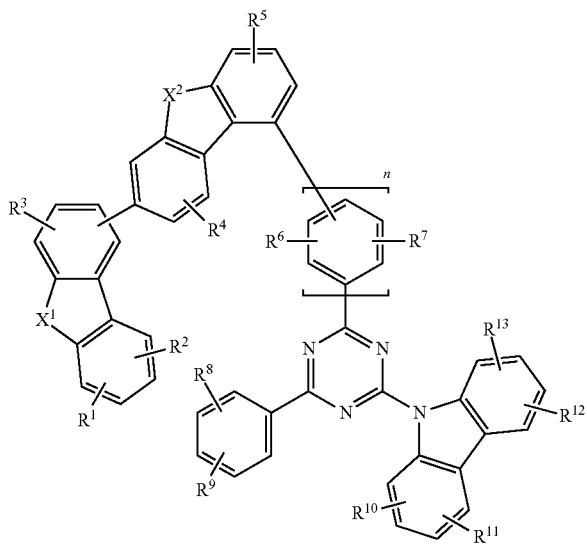
[Chemical Formula 1-3b]
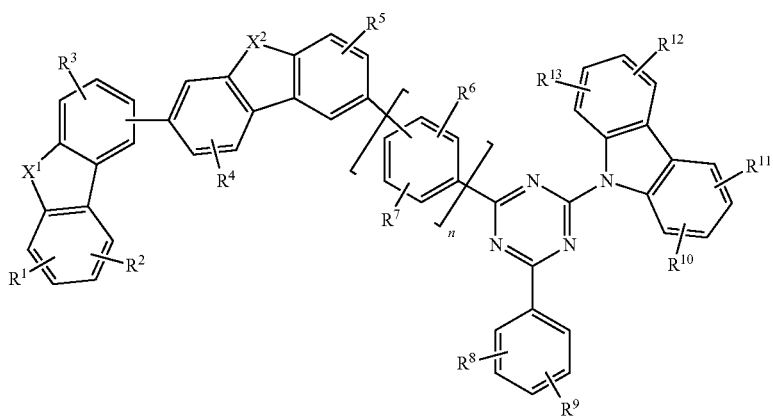
[Chemical Formula 1-3c]
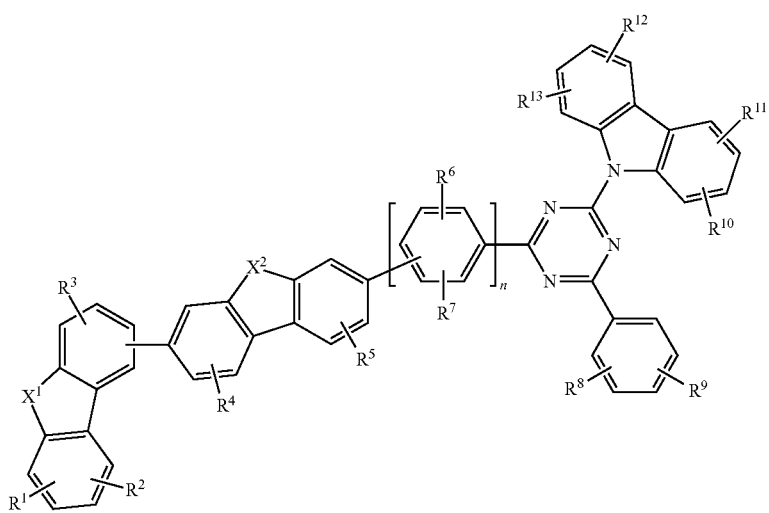

-continued

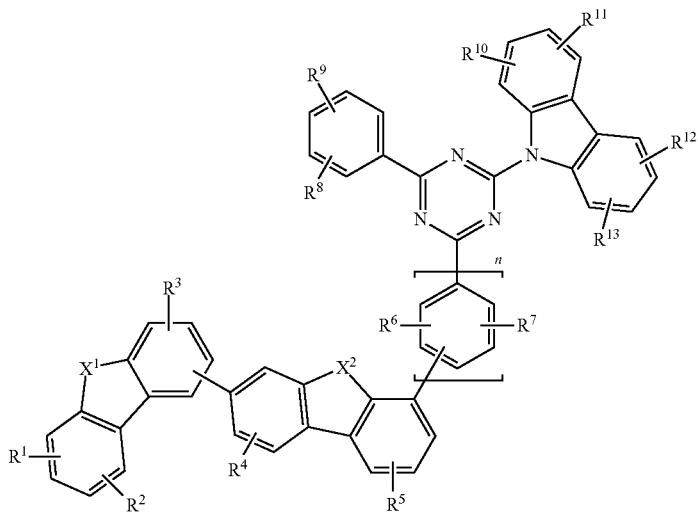

wherein, in Chemical Formula 1-3a to Chemical Formula 1-3d, $X^1$ and $X^2$ are independently O or S, $R^1$ to $R^{13}$ are independently hydrogen, deuterium, a cyano group, a halogen, a substituted or unsubstituted C1 to C10 alkyl group, a C6 to C12 aryl group, a C2 to C20 heterocyclic group, or a combination thereof, $R^{10}$ to $R^{13}$ are separate or adjacent groups are linked to each other to provide a substituted or unsubstituted aliphatic, aromatic, or heteroaromatic monocyclic ring or a substituted or unsubstituted aliphatic, aromatic, or heteroaromatic polycyclic ring, and n is 0 or 1.

6. The compound as claimed in claim 2, wherein:
the compound represented by Chemical Formula 1 is represented by Chemical Formula 1-4, and
Chemical Formula 1-4 is represented by one of Chemical Formula 1-4a to Chemical Formula 1-4d:

[Chemical Formula 1-4a]

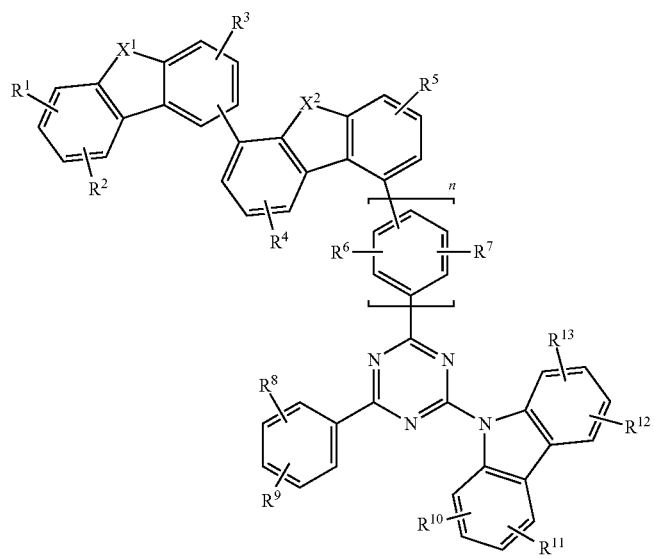

[Chemical Formula 1-4b]

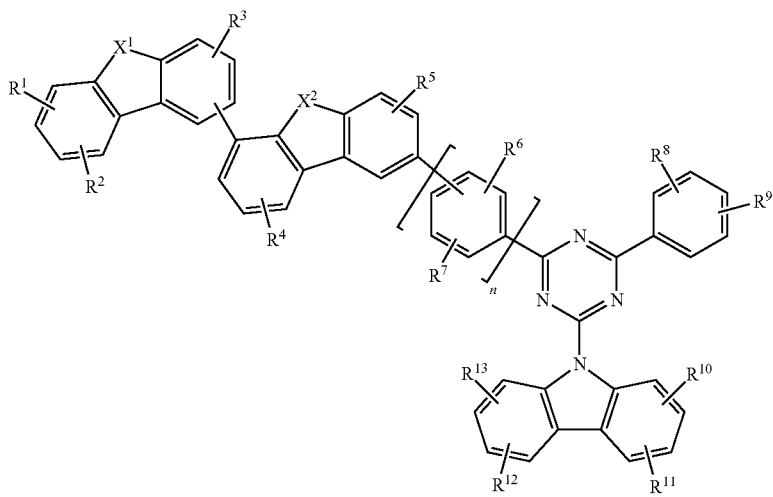

[Chemical Formula 1-4c]

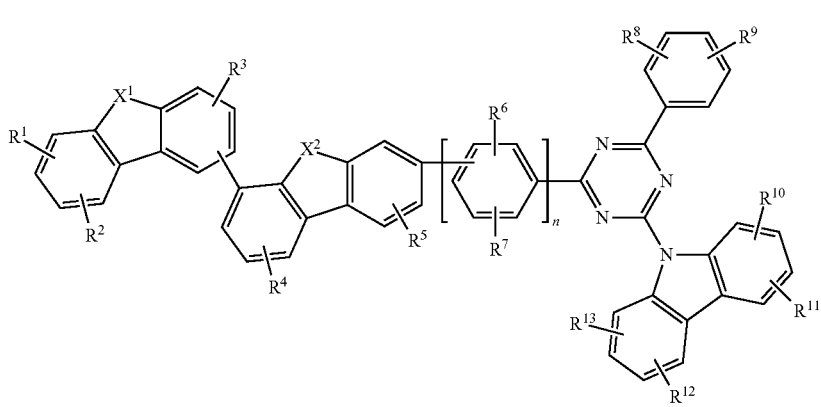

[Chemical Formula 1-4d]

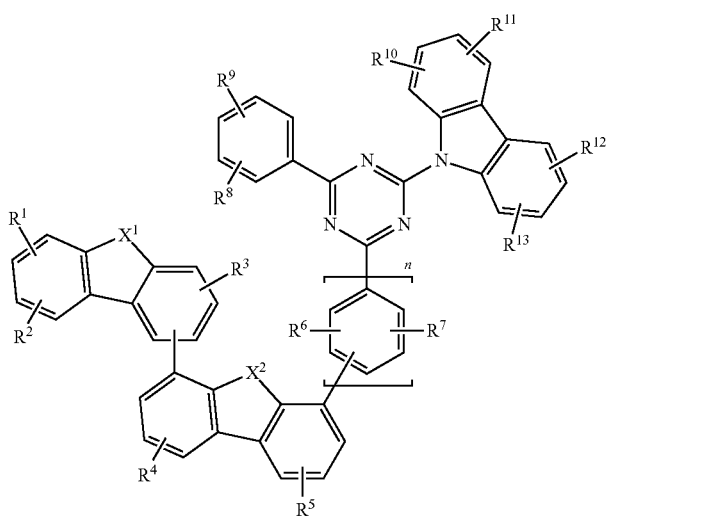

wherein, in Chemical Formula 1-4a to Chemical Formula 1-4d, $X^1$ and $X^2$ are independently O or S, $R^1$ to $R^{13}$ are independently hydrogen, deuterium, a cyano group, a halogen, a substituted or unsubstituted C1 to C10 alkyl group, a C6 to C12 aryl group, a C2 to C20 heterocyclic group, or a combination thereof, $R^{10}$ to $R^{13}$ are separate or adjacent groups are linked to each other to provide a substituted or unsubstituted aliphatic, aromatic, or heteroaromatic monocyclic ring or a substituted or unsubstituted aliphatic, aromatic, or heteroaromatic polycyclic ring, and n is 0 or 1.

7. The compound as claimed in claim 1, wherein the compound represented by Chemical Formula 1 is represented by one of Chemical Formula 1A to Chemical Formula 1G:

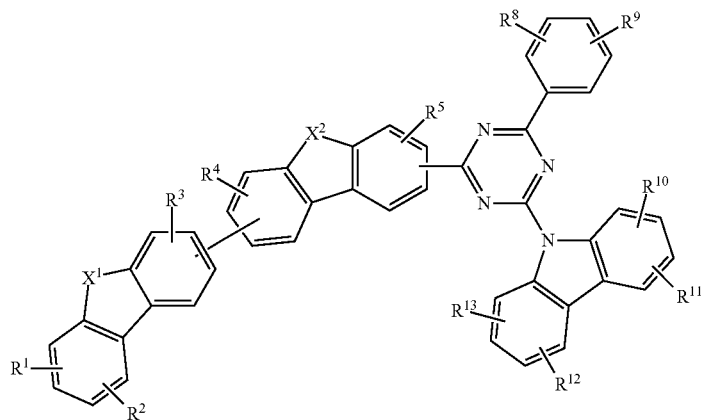
[Chemical Formula 1A]
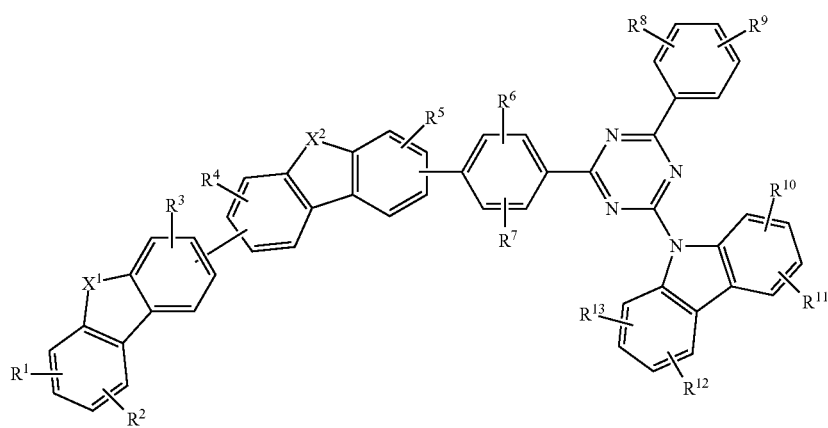
[Chemical Formula 1B]
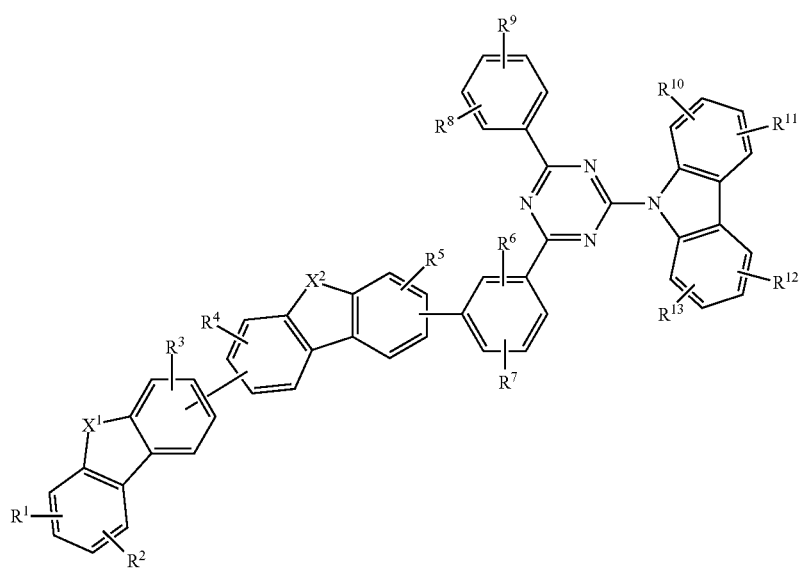
[Chemical Formula 1C]

-continued
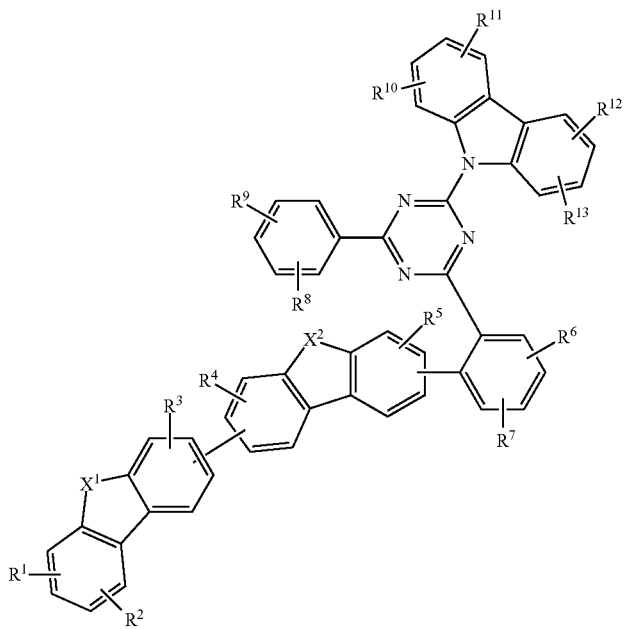
[Chemical Formula 1D]
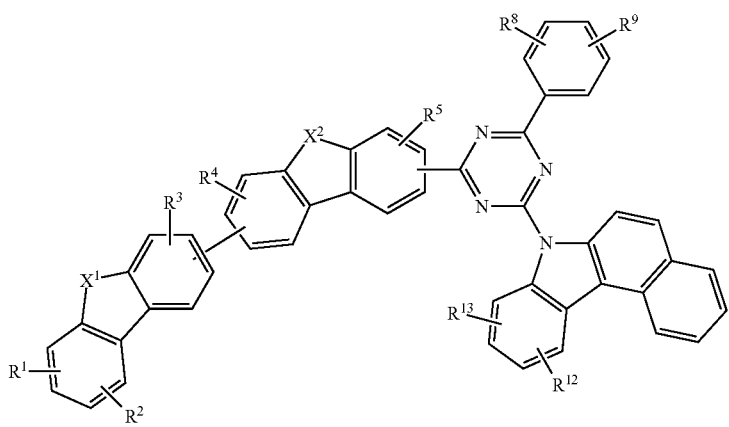
[Chemical Formula 1E]
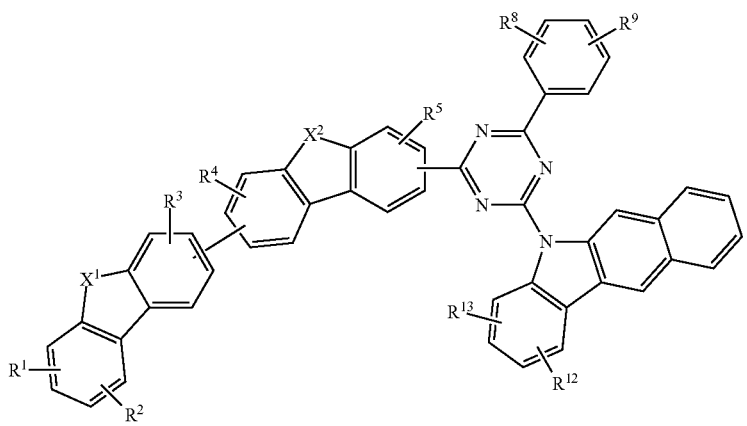
[Chemical Formula 1F]

-continued

[Chemical Formula 1G]

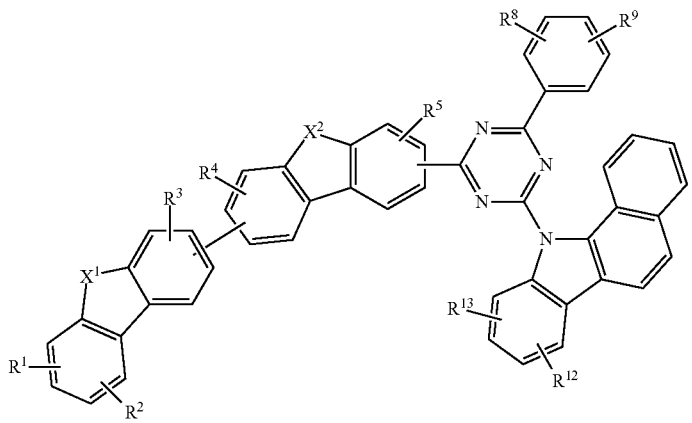

wherein, in Chemical Formula 1A to Chemical Formula 1G, $X^1$ and $X^2$ are independently O or S, and $R^1$ to $R^{13}$ are independently hydrogen, deuterium, a cyano group, a halogen, a substituted or unsubstituted C1 to C10 alkyl group, a C6 to C12 aryl group, a C2 to C20 heterocyclic group, or a combination thereof.

8. The compound as claimed in claim 1, wherein the compound represented by Chemical Formula 1 is represented by Chemical Formula 1-1a-IV, Chemical Formula 1-2b-IV, Chemical Formula 1-3c-III, Chemical Formula 1-4c-I, Chemical Formula 1-4c-III, Chemical Formula 1-4c-IV, Chemical Formula 1-4d-II, or Chemical Formula 1-4d-IV:

[Chemical Formula 1-1a-IV]

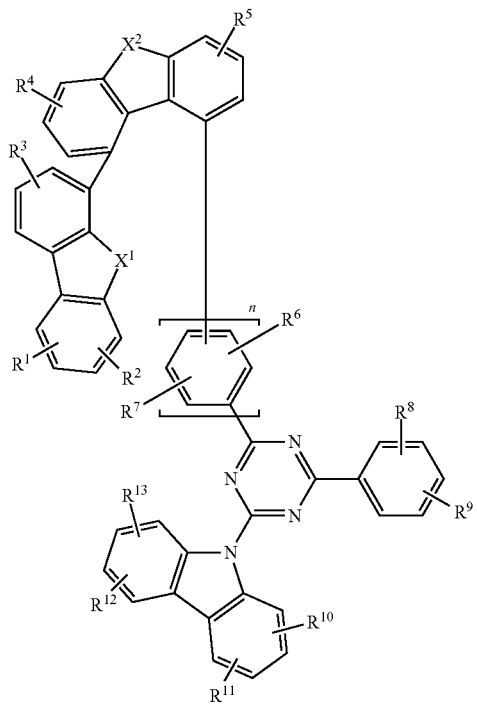

[Chemical Formula 1-2b-IV]
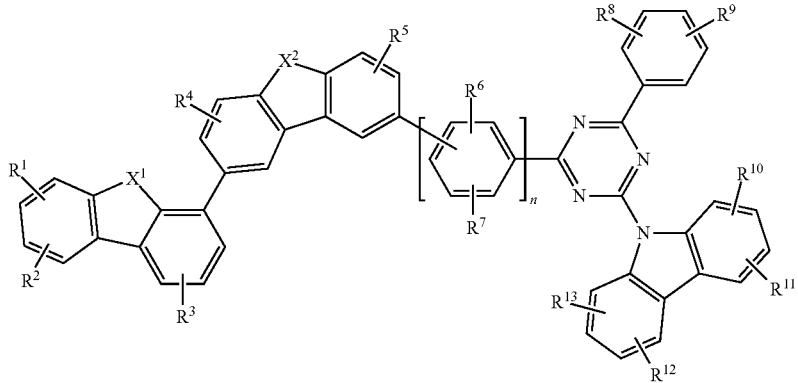
[Chemical Formula 1-3c-III]
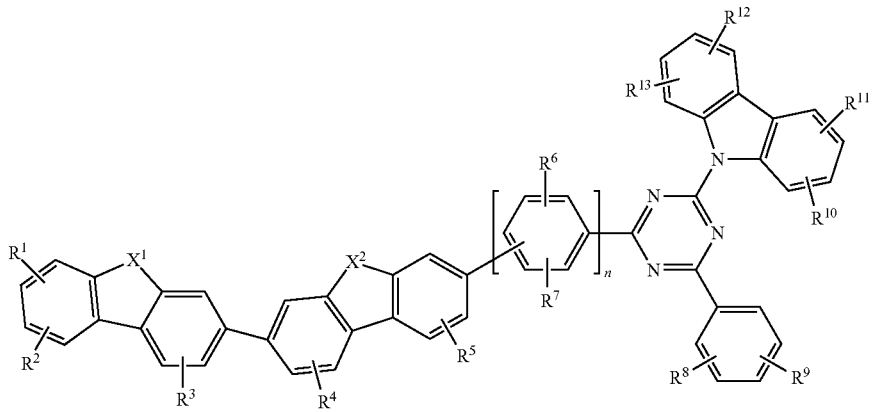
[Chemical Formula 1-4c-I]
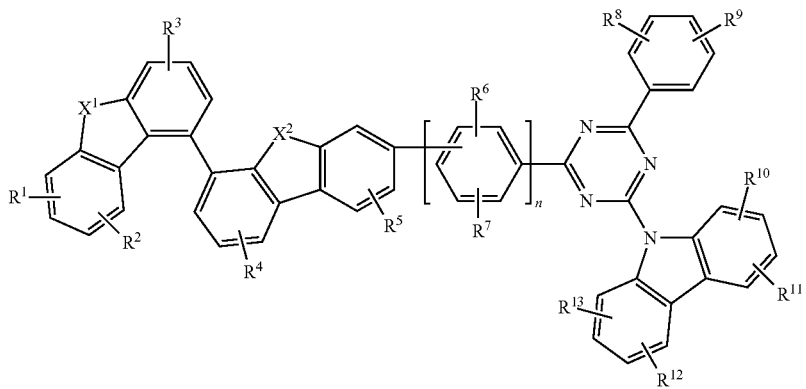

-continued

[Chemical Formula 1-4c-III]

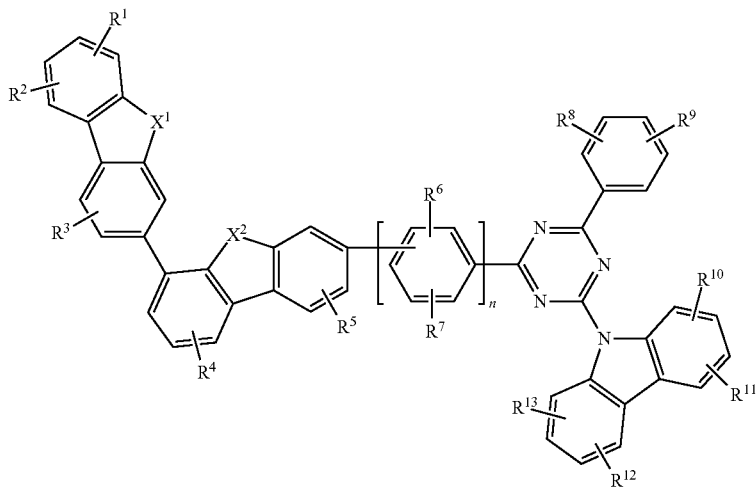

[Chemical Formula 1-4c-IV]

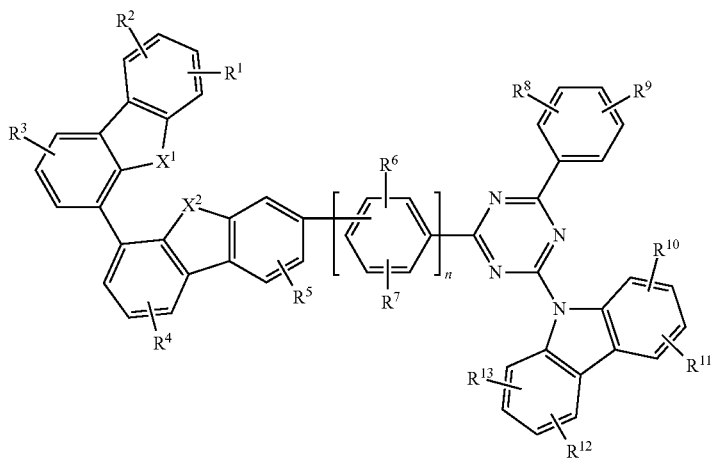

[Chemical Formula 1-4d-II]

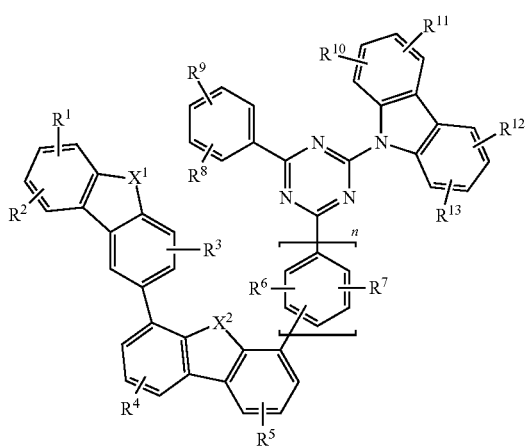

[Chemical Formula 1-4d-IV]

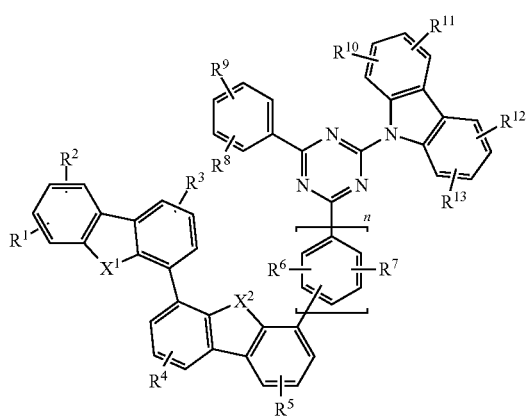

wherein, in Chemical Formula 1-1a-IV, Chemical Formula 1-2b-IV, Chemical Formula 1-3c-III, Chemical Formula 1-4c-I, Chemical Formula 1-4c-III, Chemical Formula 1-4c-IV, Chemical Formula 1-4d-II, and Chemical Formula 1-4d-IV, $X^1$ and $X^2$ are independently O or S, $R^1$ to $R^{13}$ are independently hydrogen, deuterium, a cyano group, a halogen, a substituted or unsubstituted C1 to C10 alkyl group, a C6 to C12 aryl group, a C2 to C20 heterocyclic group, or a combination thereof, $R^{10}$ to $R^{13}$ are separate or adjacent groups are linked to each other to provide a substituted or unsubstituted aliphatic, aromatic, or heteroaromatic monocyclic ring or a substituted or unsubstituted aliphatic, aromatic, or heteroaromatic polycyclic ring, and n is 0 or 1.

9. The compound as claimed in claim 1, wherein the compound represented by Chemical Formula 1 is a compound of Group 1:
[Group 1]
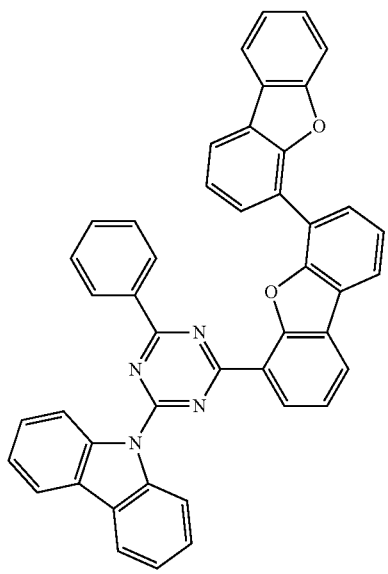
1
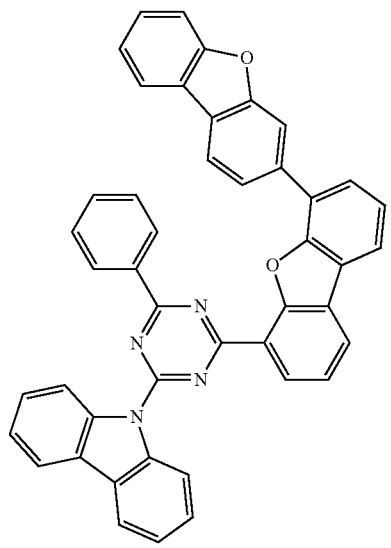
2
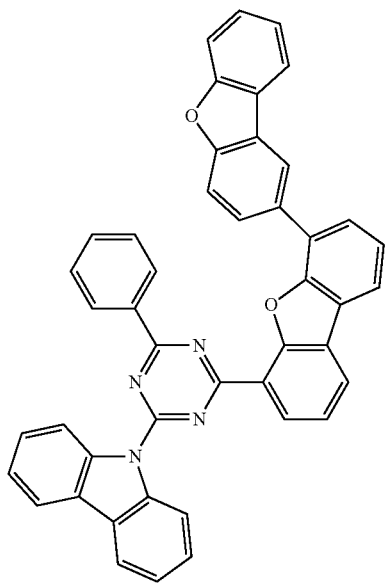
3
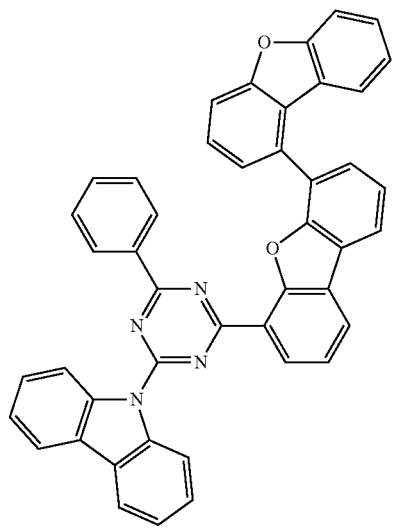
4

5
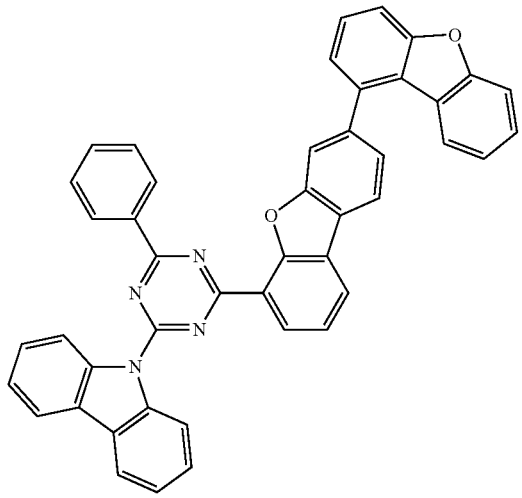
6
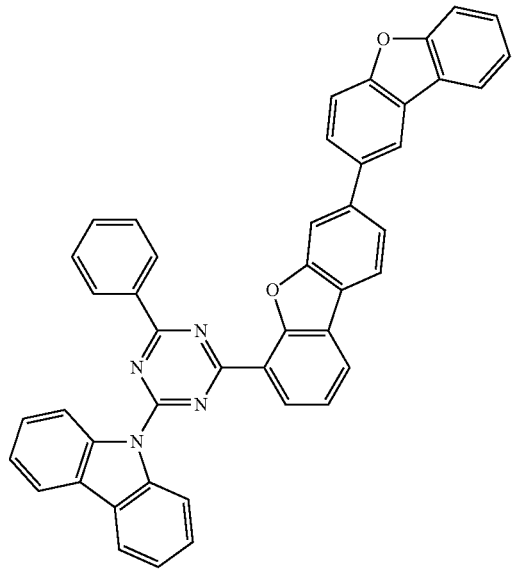
7
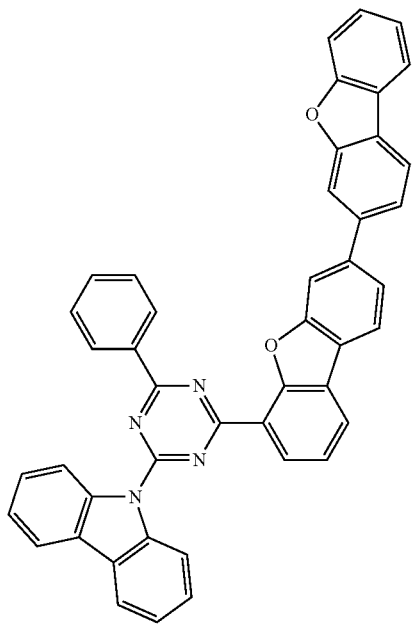
8
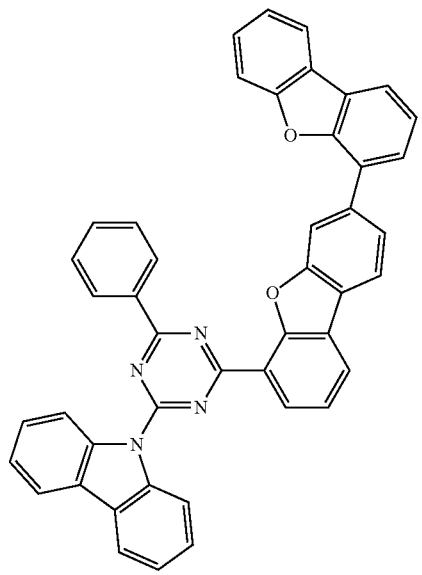

9
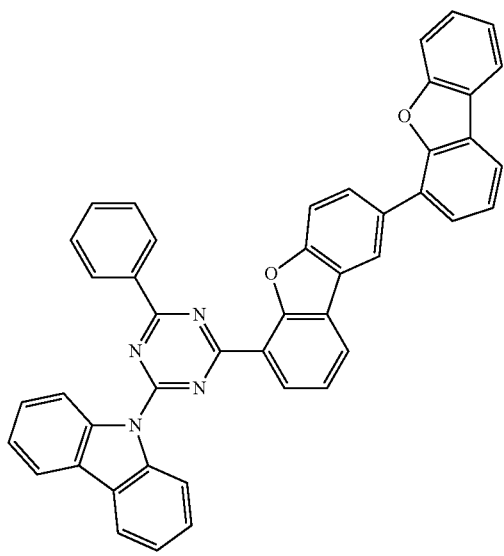
10
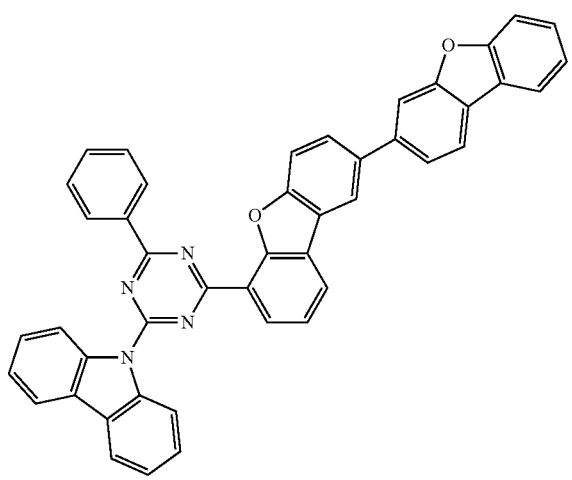
11
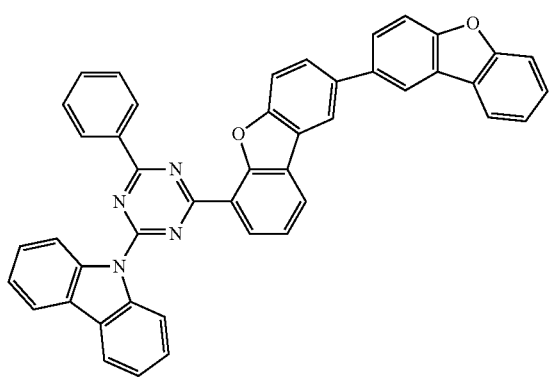
12
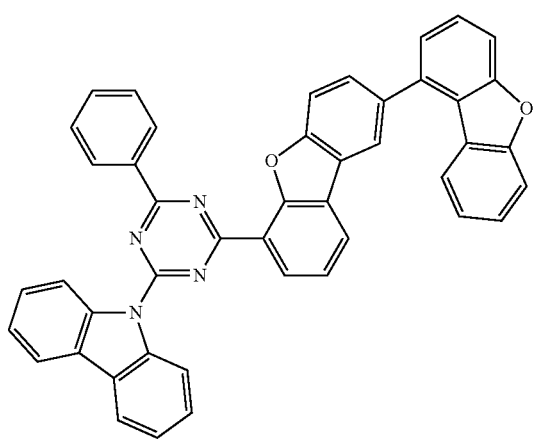
13
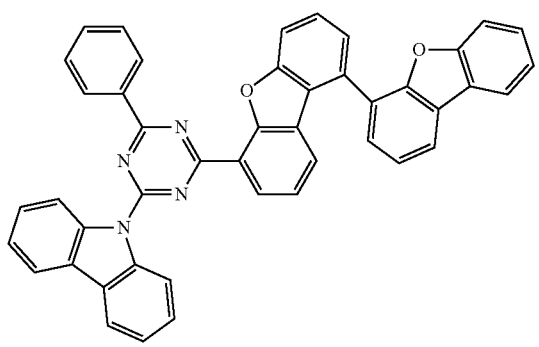
14
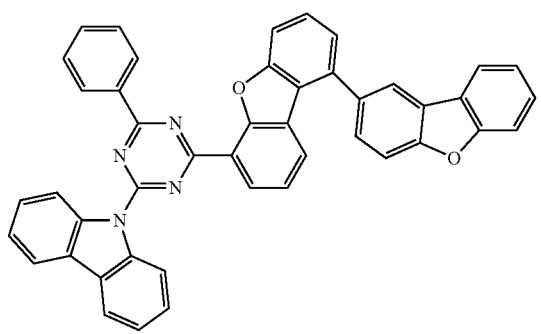

-continued
15
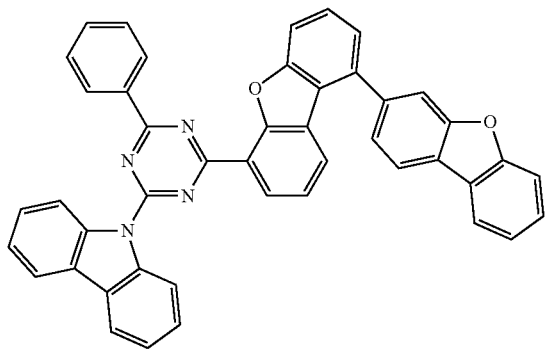
16
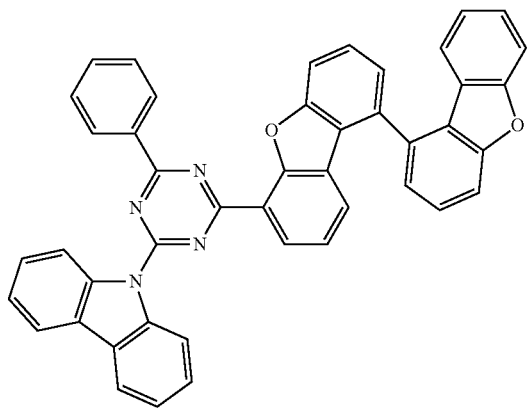
17
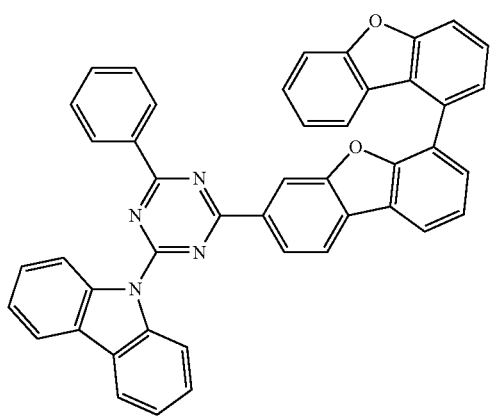
18
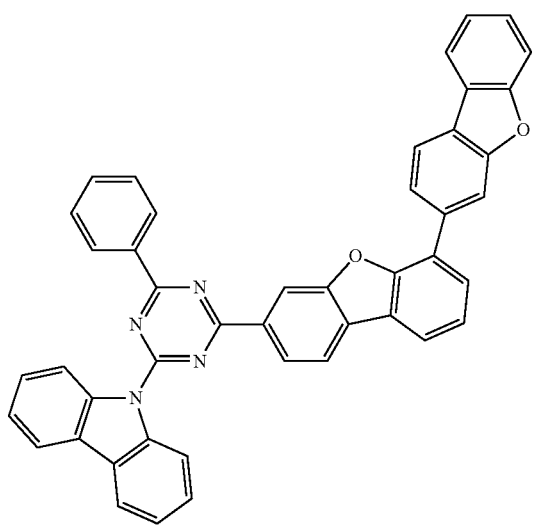
19
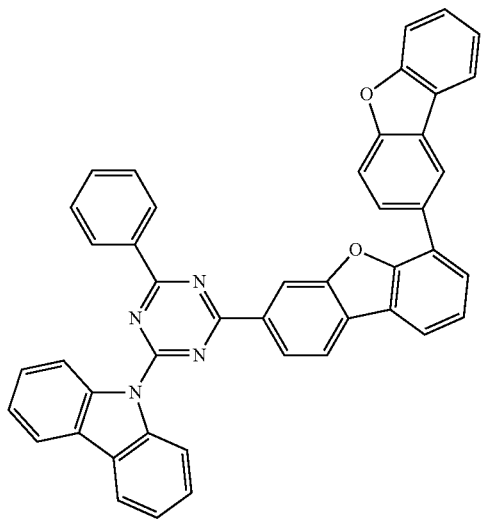
20
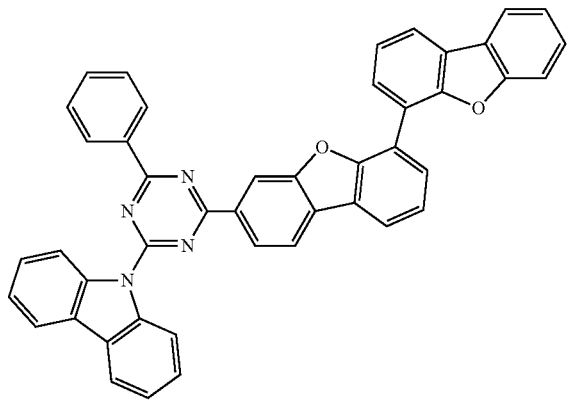

-continued
21
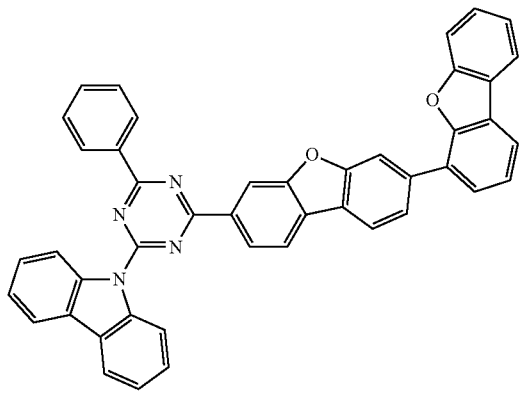
22
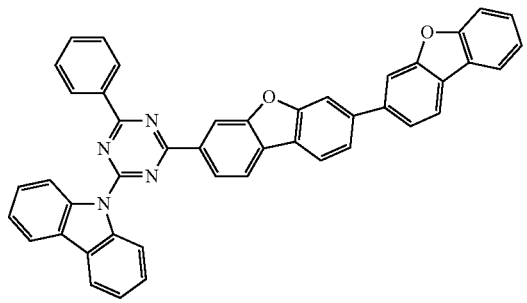
23
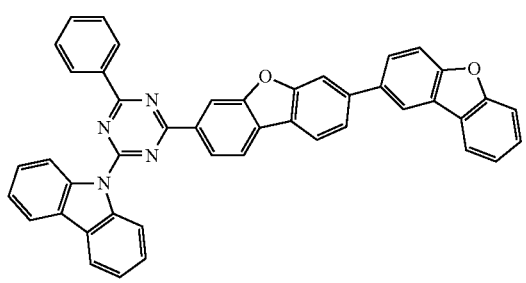
24
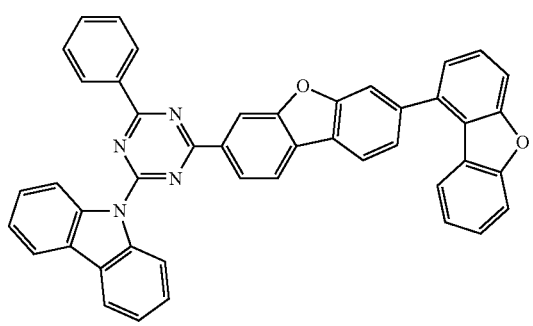
25
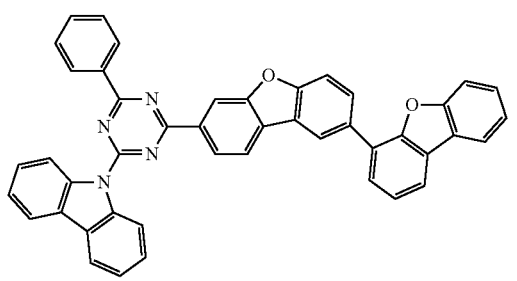
26
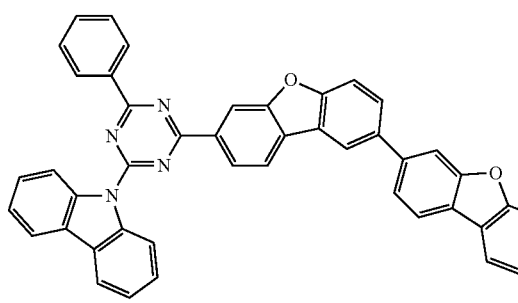
27
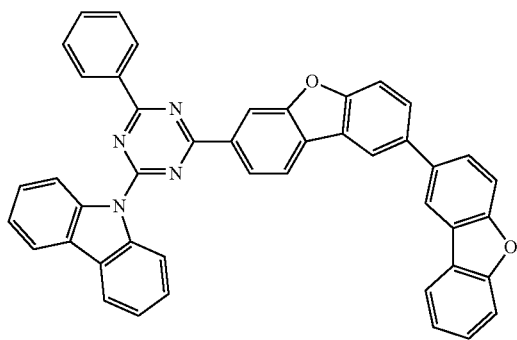
28
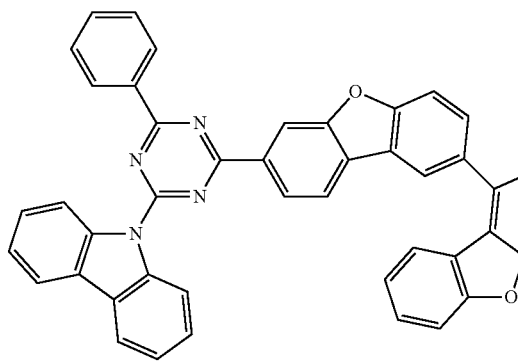

321      322
-continued
29
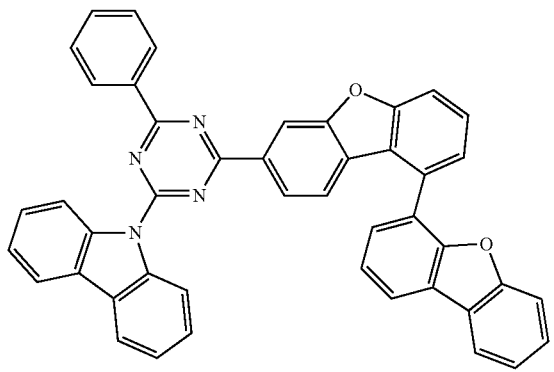
30
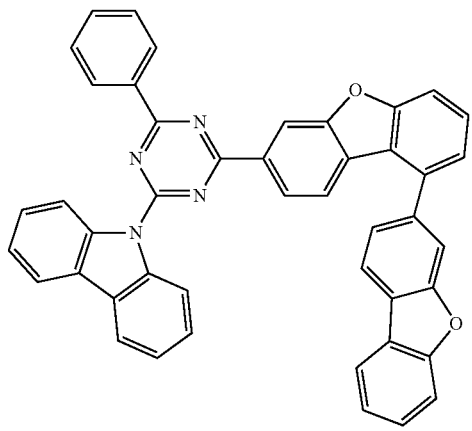
31
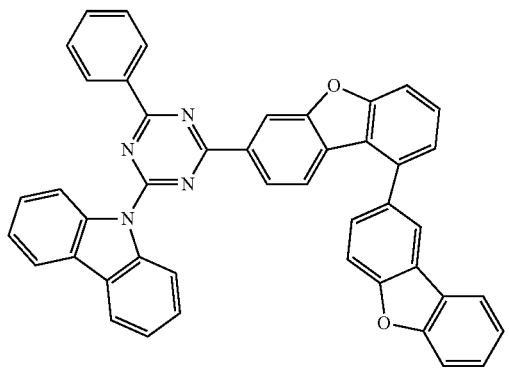
32
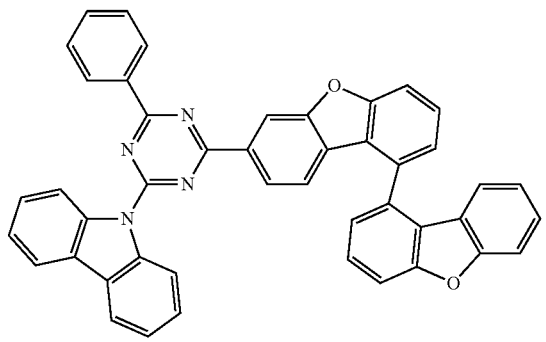
33
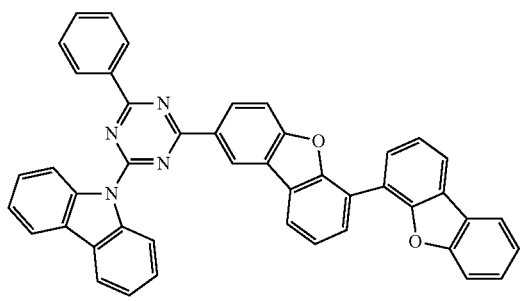
34
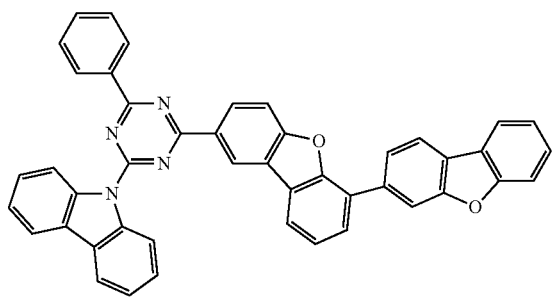
35
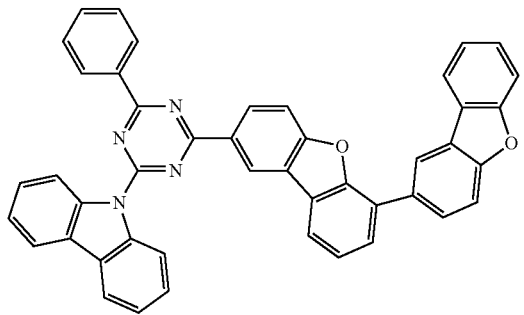
36
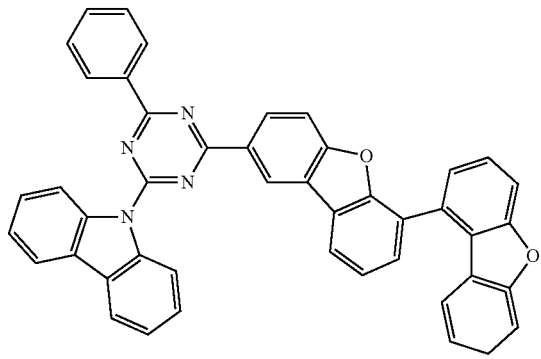

-continued
37
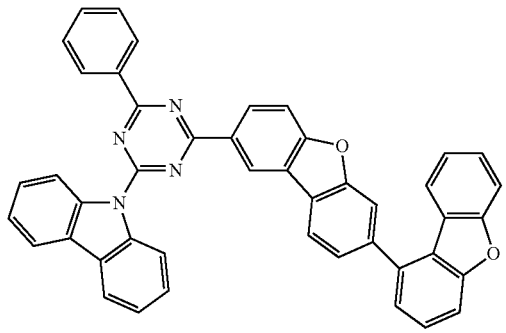
38
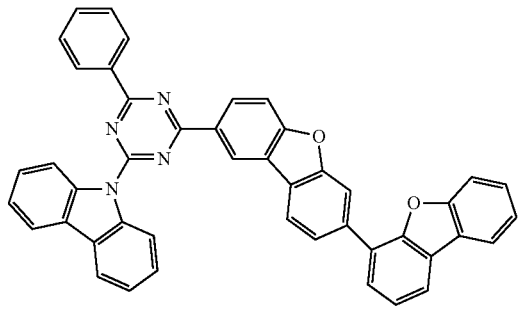
39
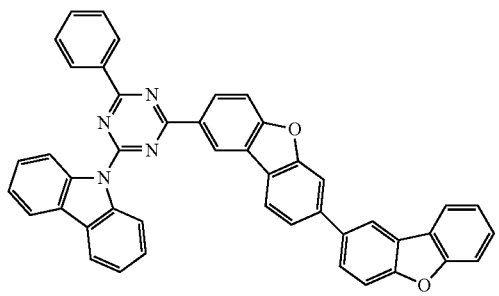
40
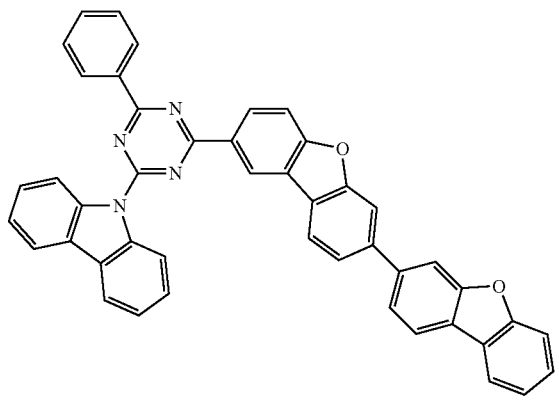
41
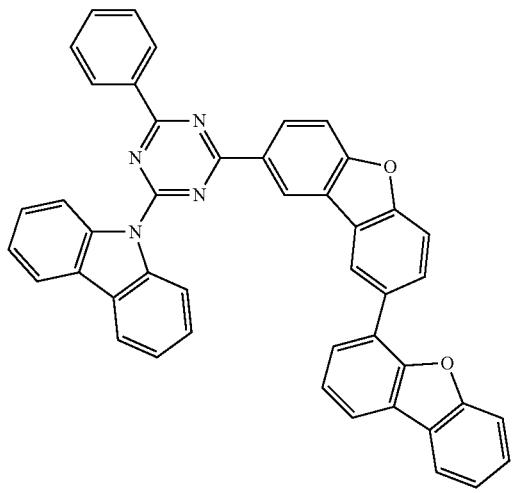
42
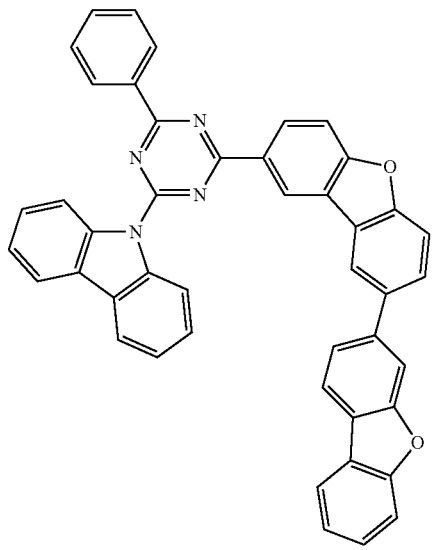

43
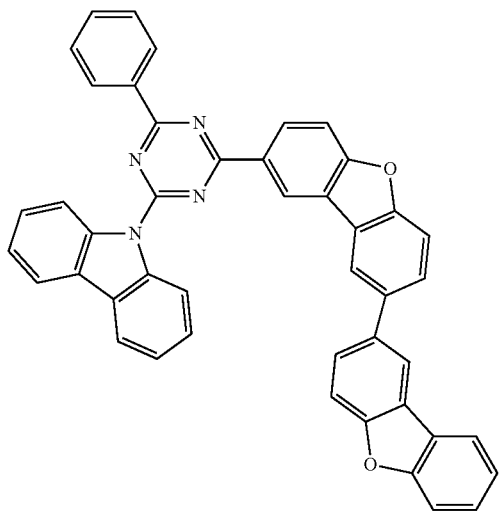
44
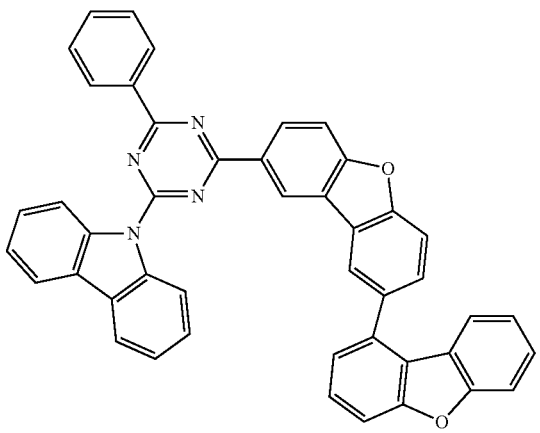
45
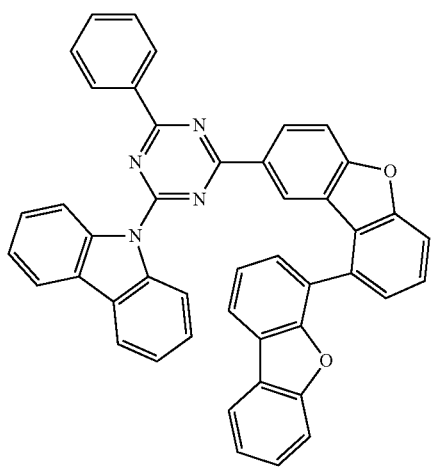
46
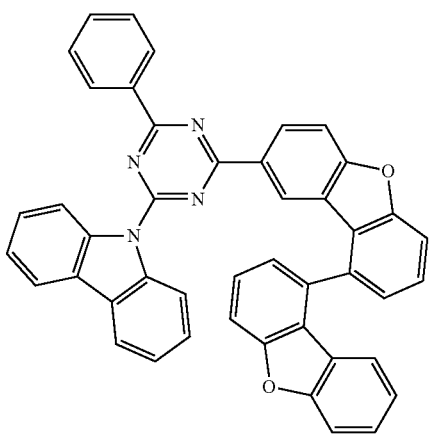
47
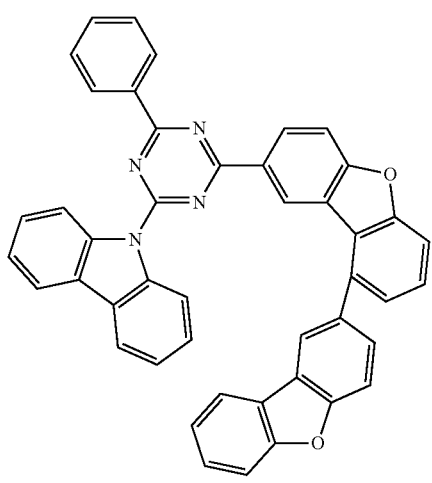
48
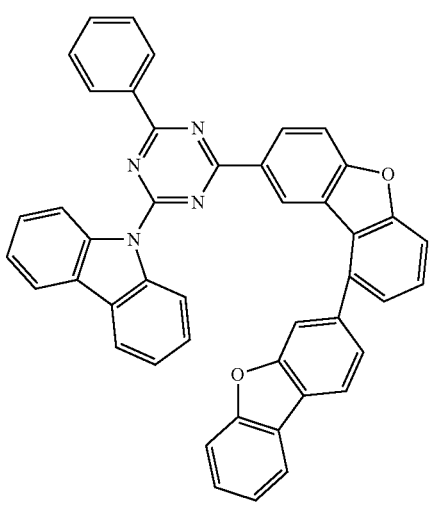

49
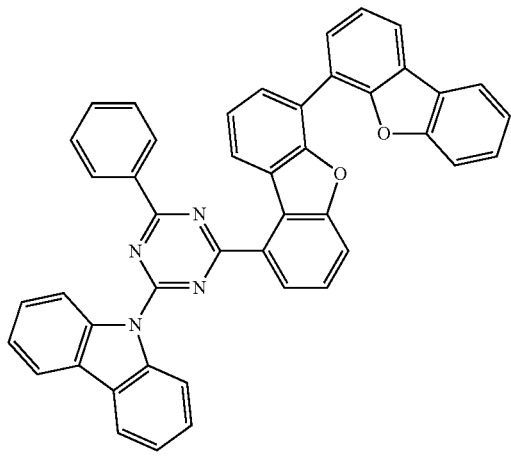
50
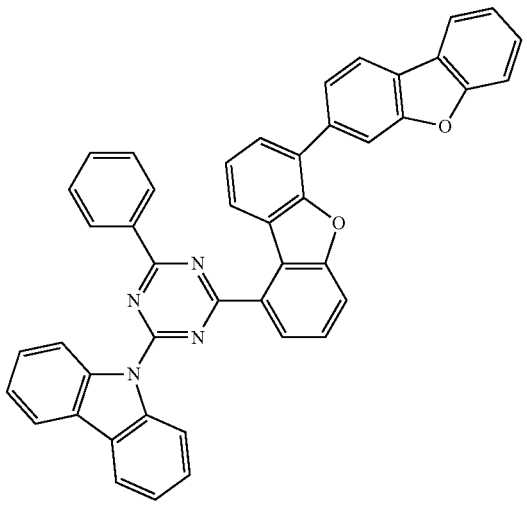
51
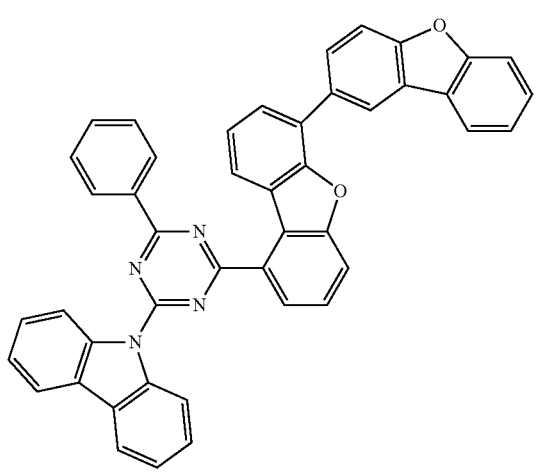
52
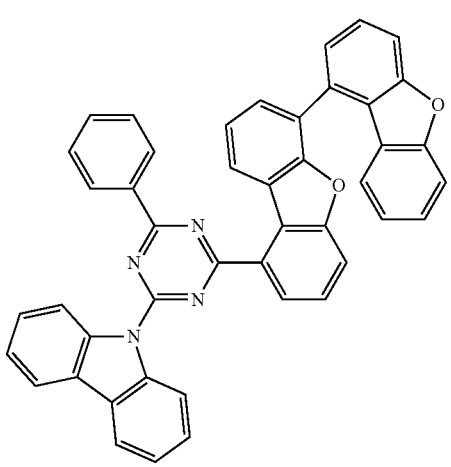
53
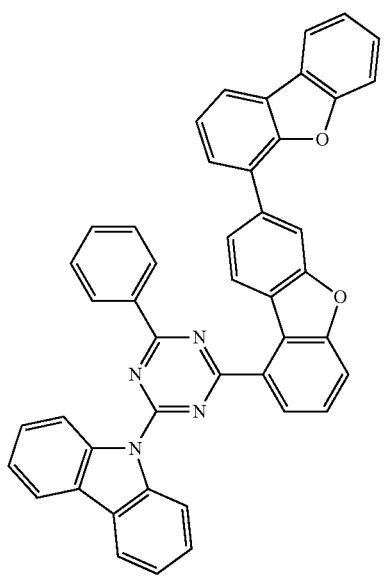
54
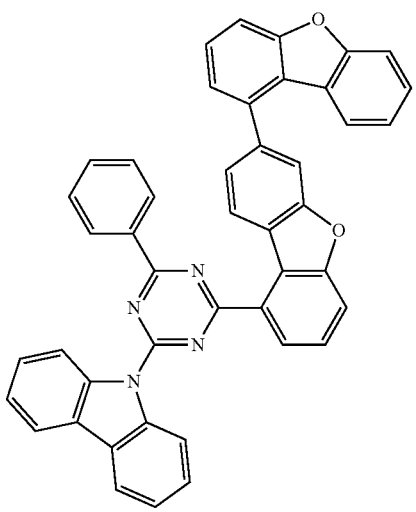

329
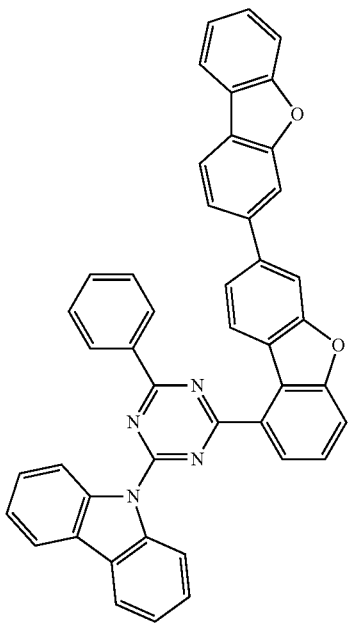
55
330
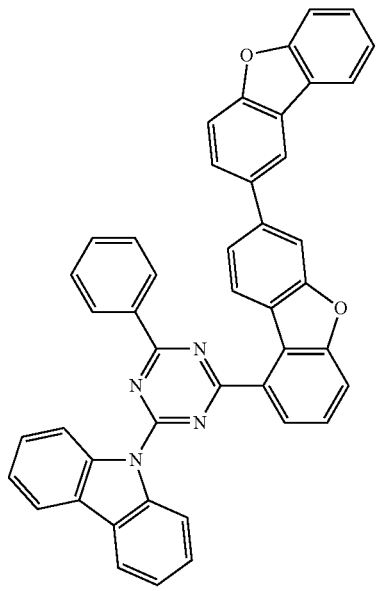
56
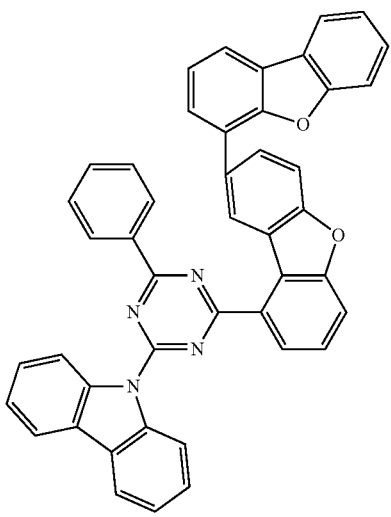
57
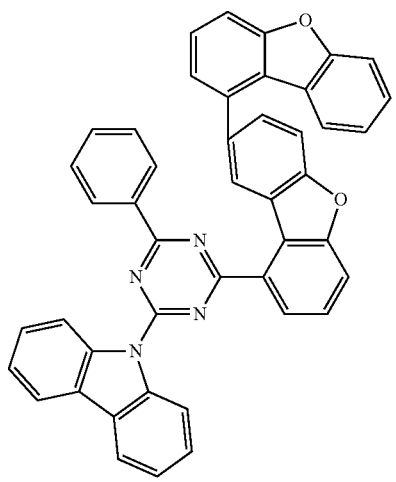
58

331
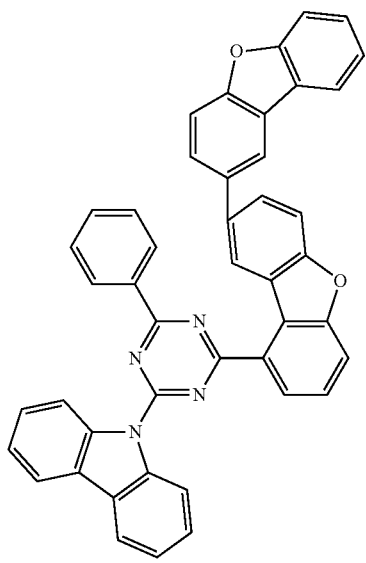
332
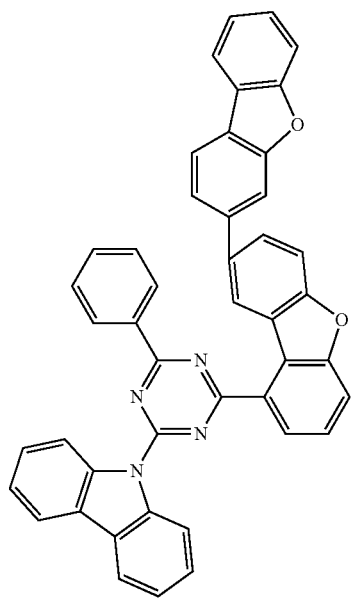
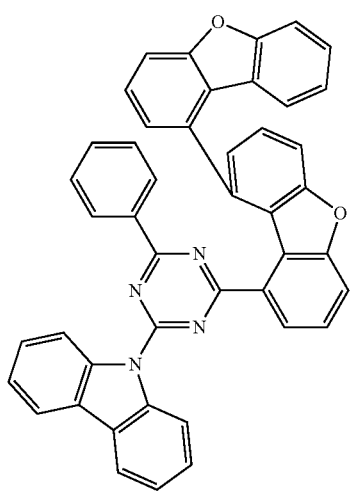
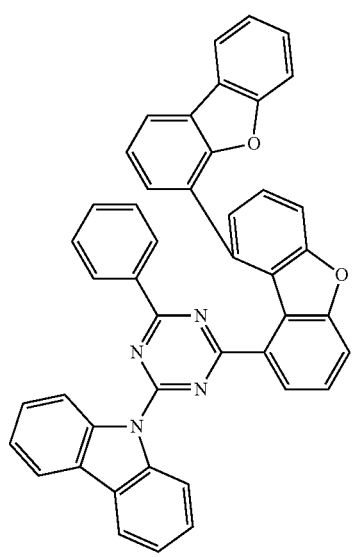

63
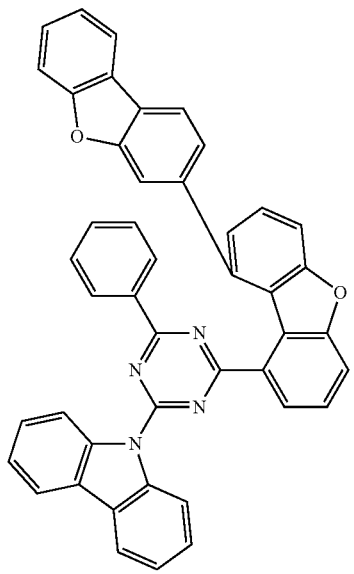
64
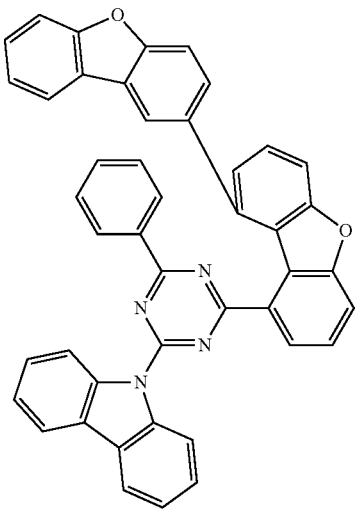
65
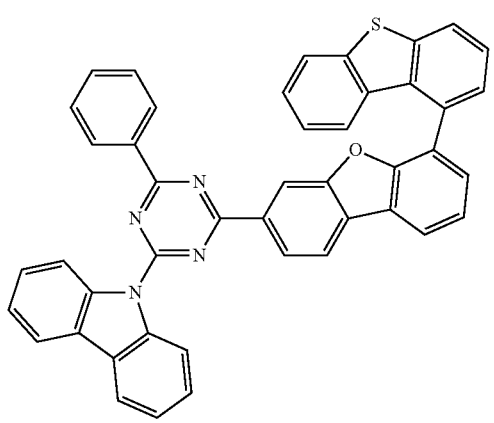
66
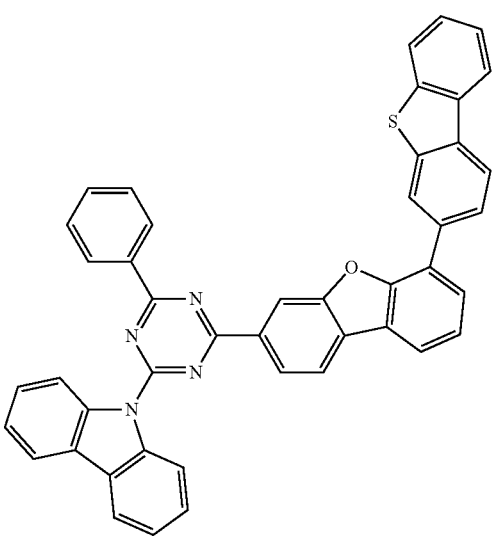
67
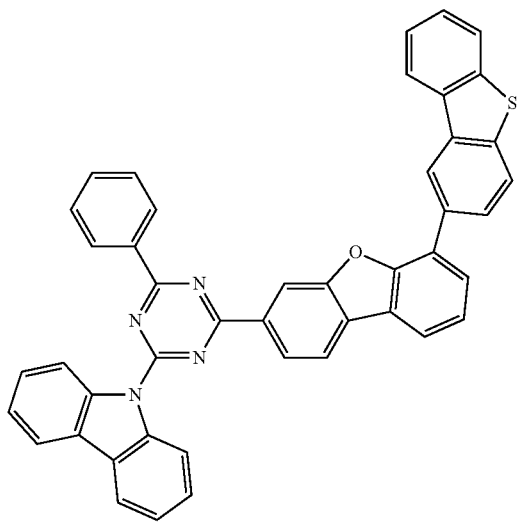
68
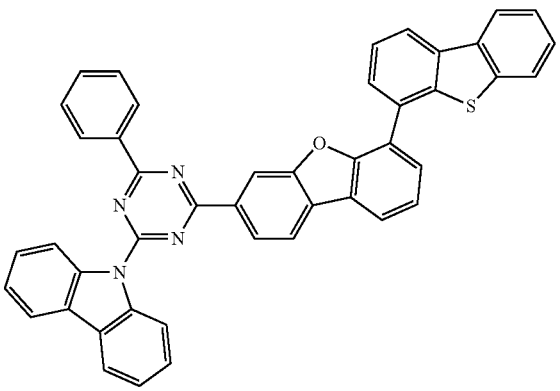

-continued
69
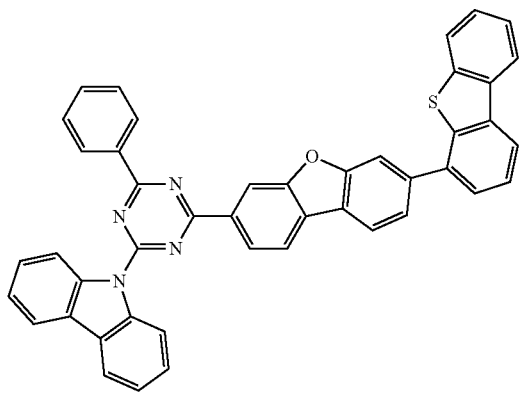
70
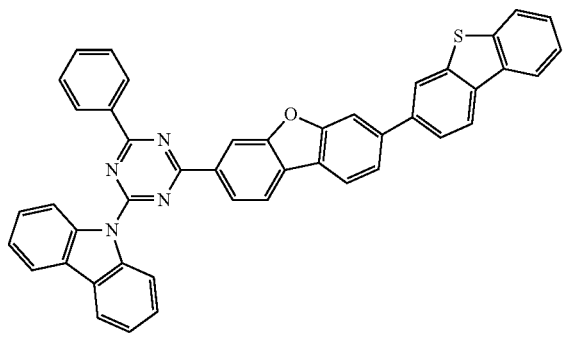
71
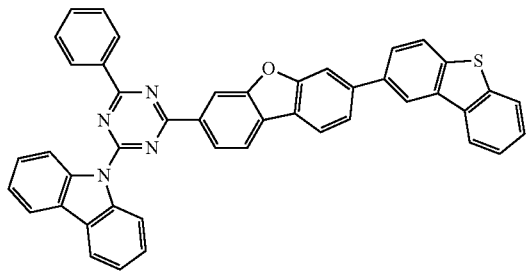
72
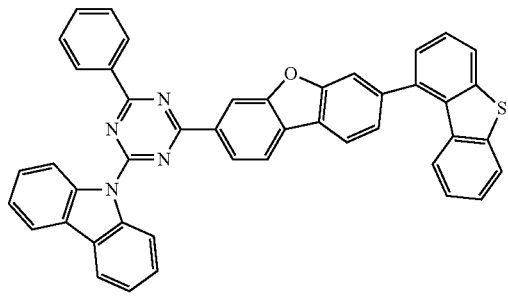
73
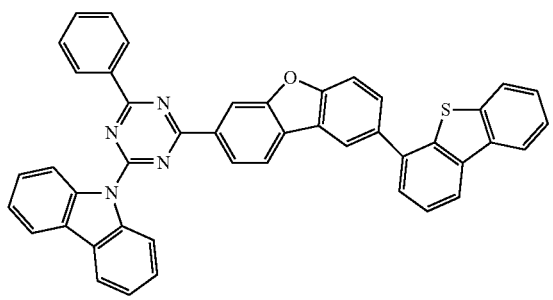
74
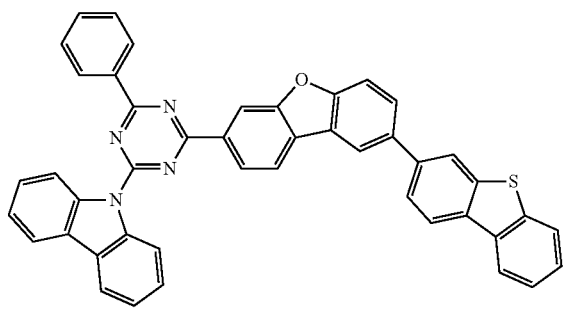
75
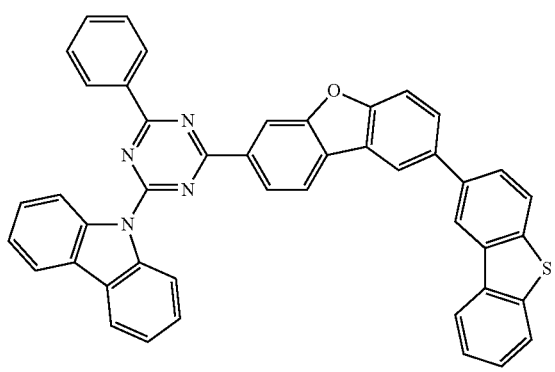
76
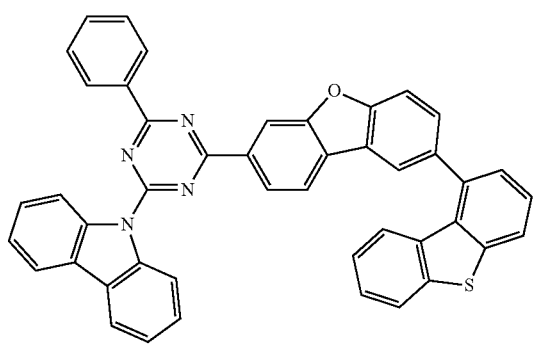

-continued
77
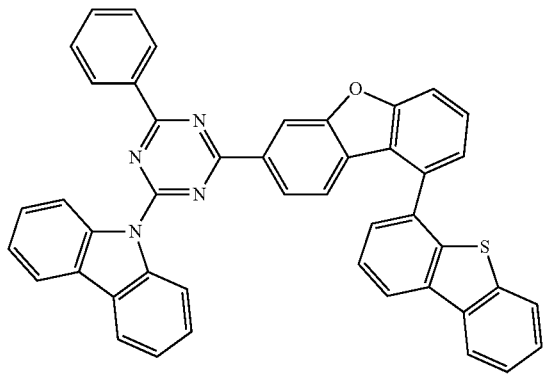
78
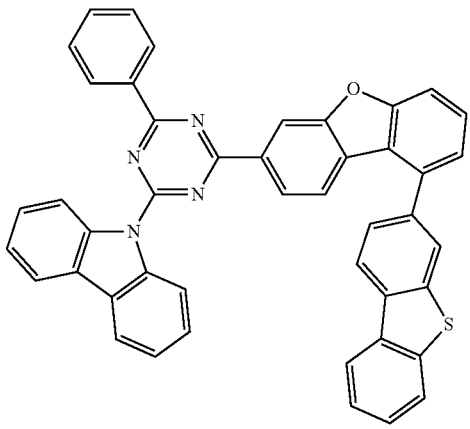
79
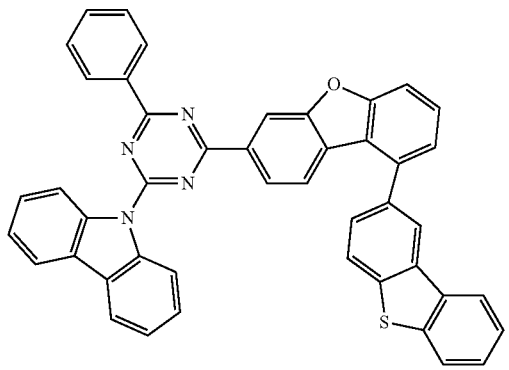
80
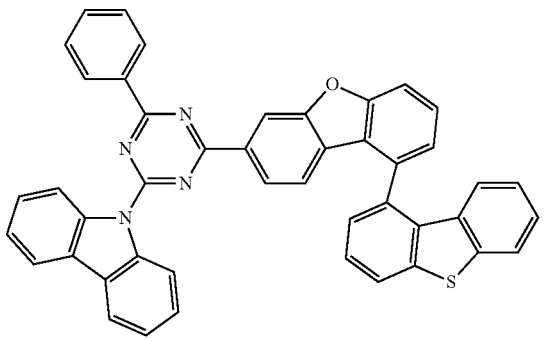
81
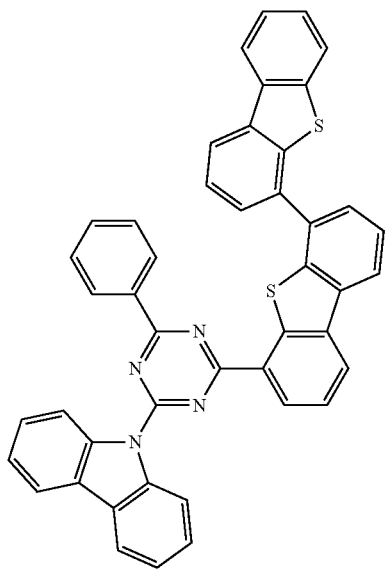
82
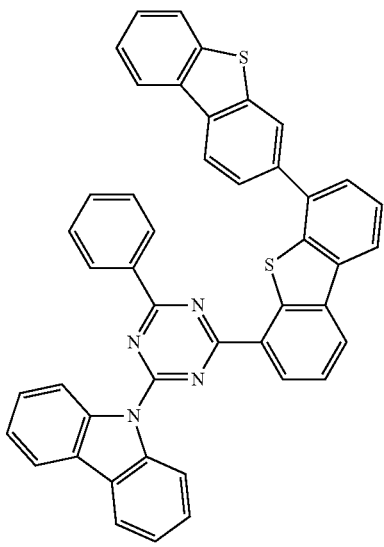

-continued
83
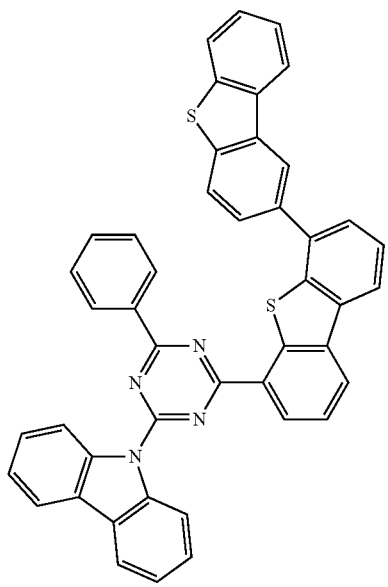
84
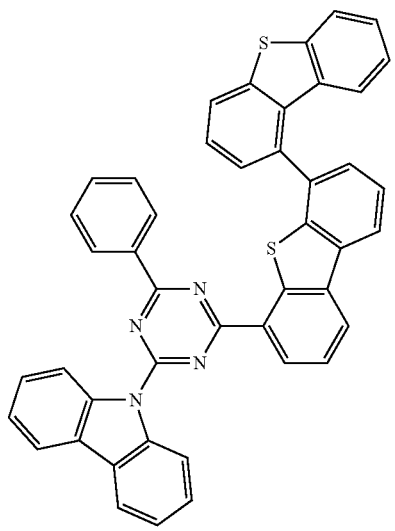
85
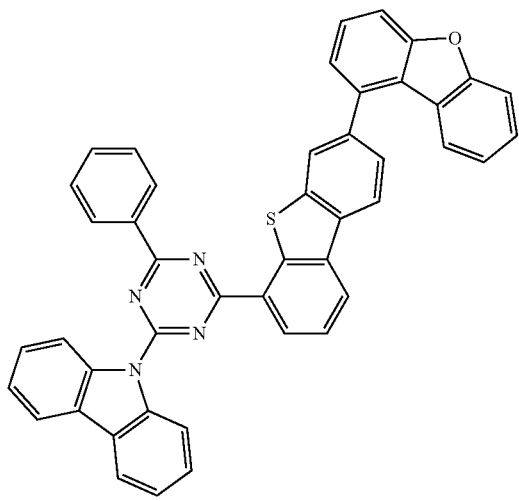
86
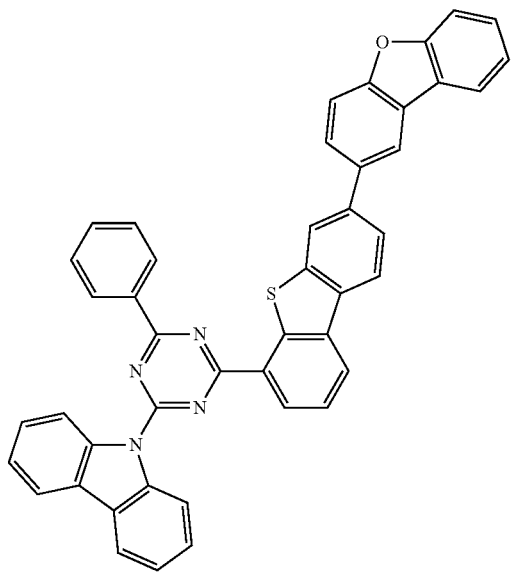

341                                                342
-continued
87
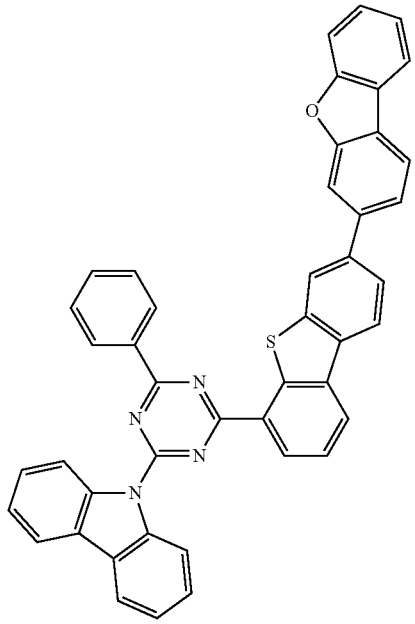
88
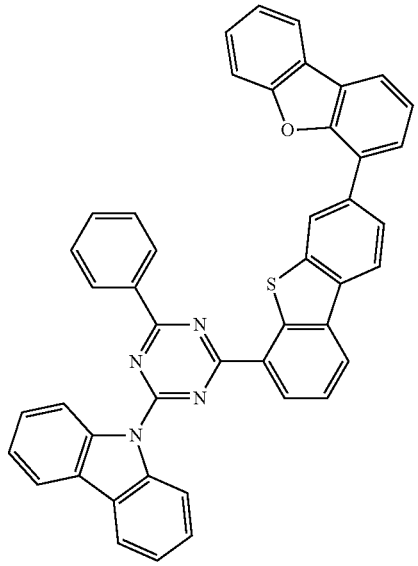
89
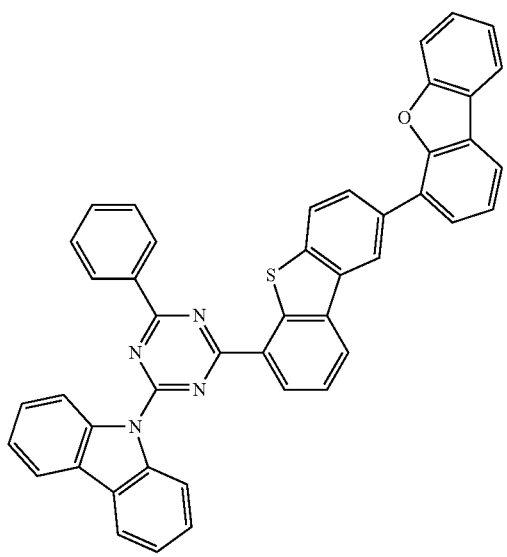
90
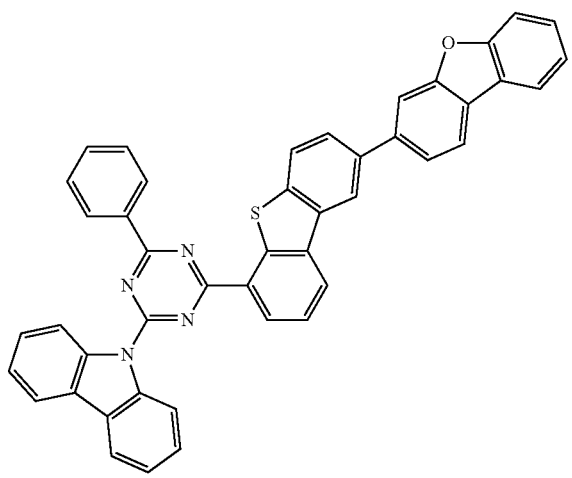
91
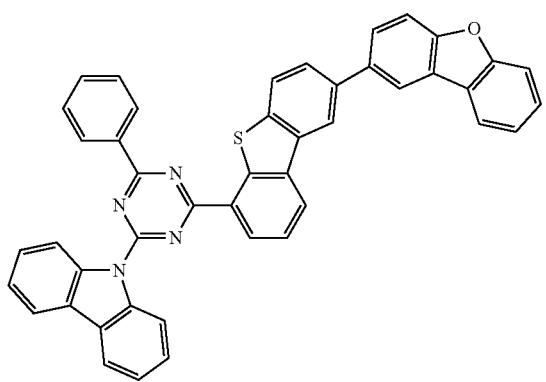
92
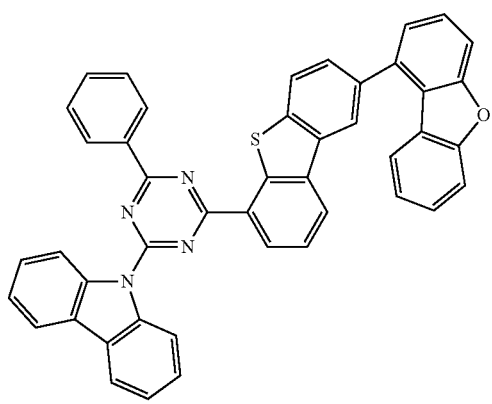

-continued
93
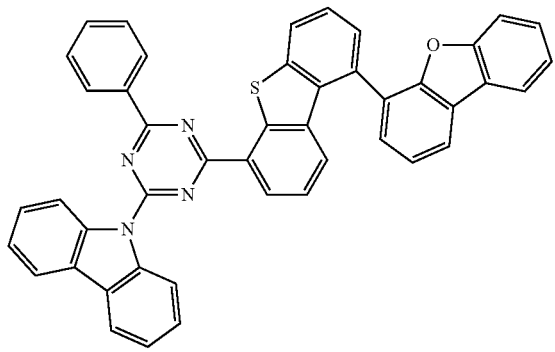
94
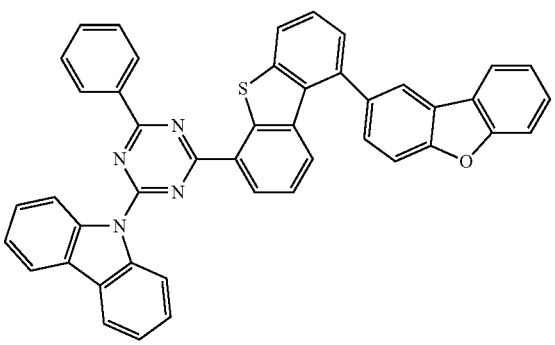
95
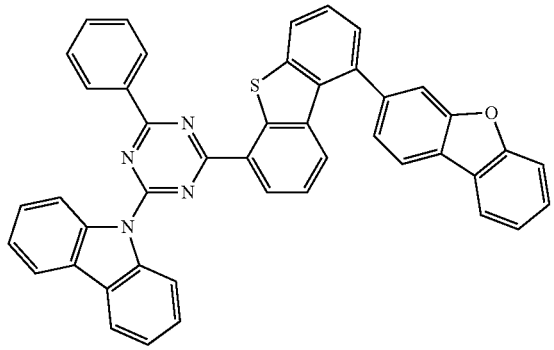
96
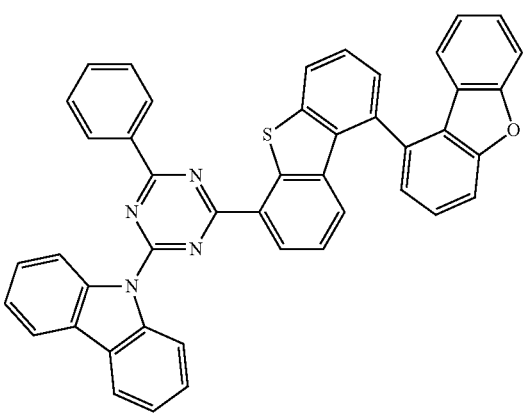
97
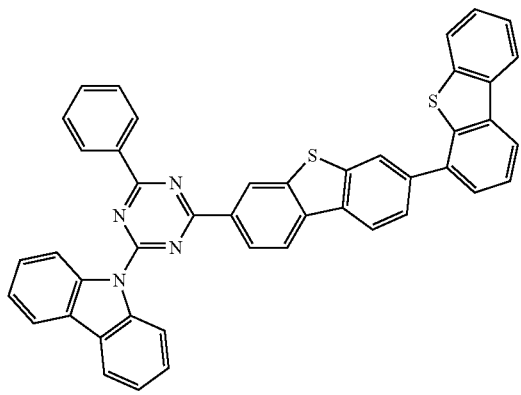
98
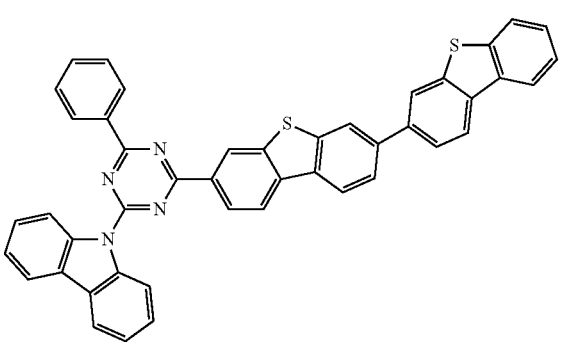
99
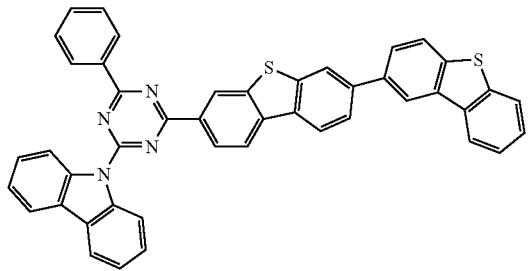
100
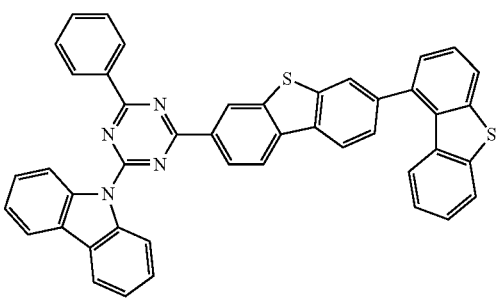

-continued
101
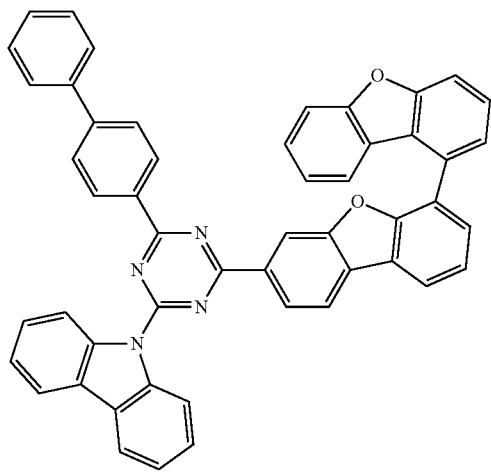
102
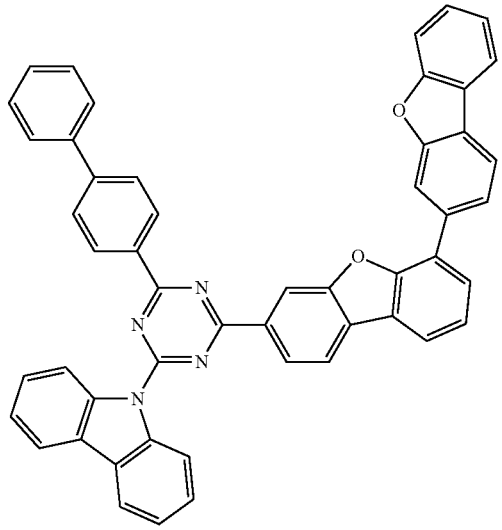
103
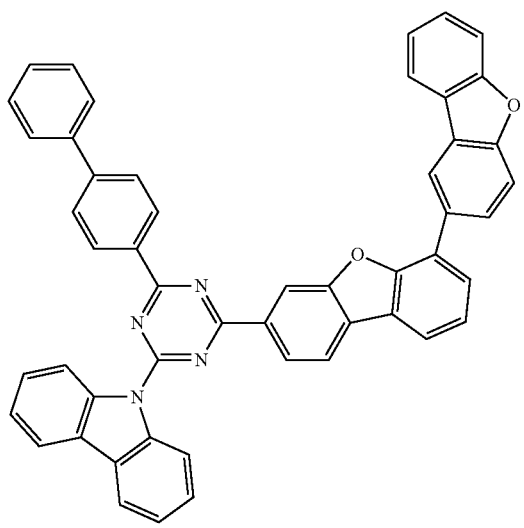
104
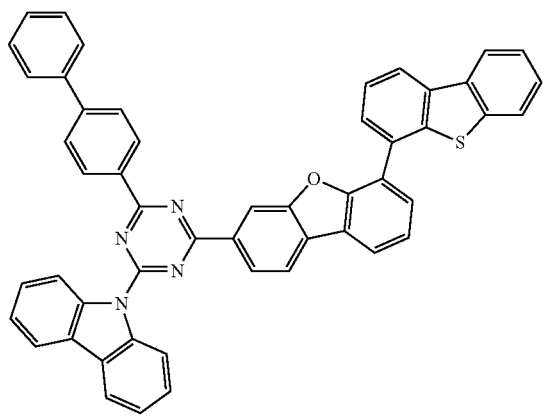
105
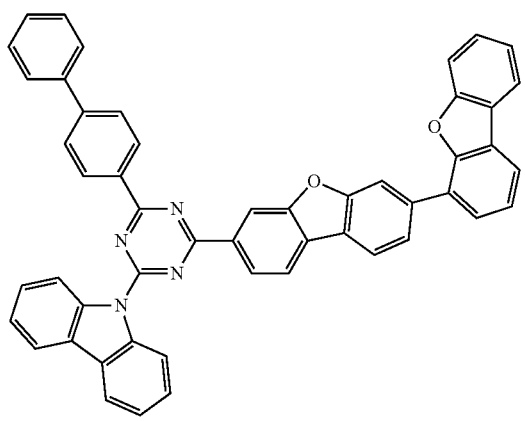
106
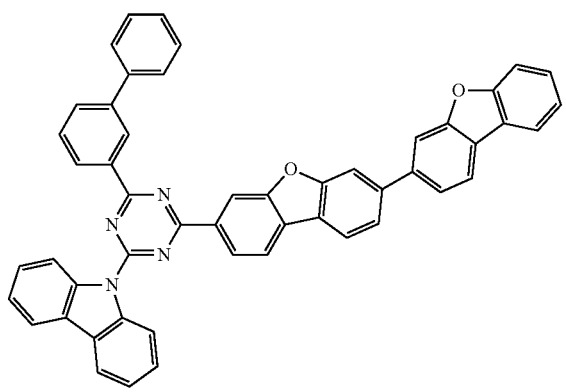

-continued
107
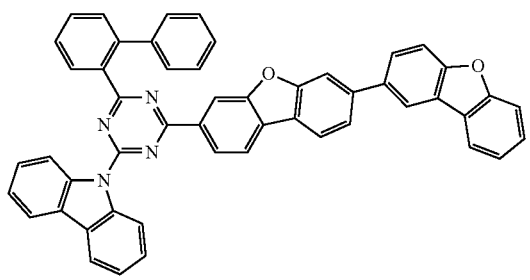
108
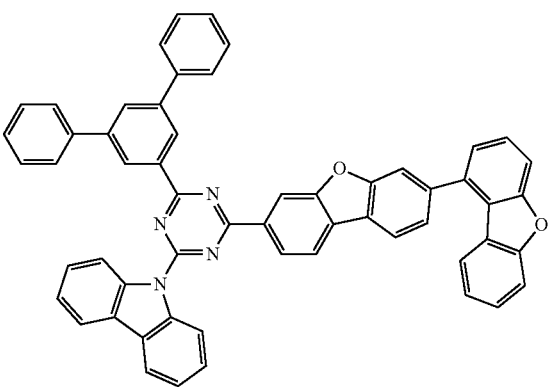
109
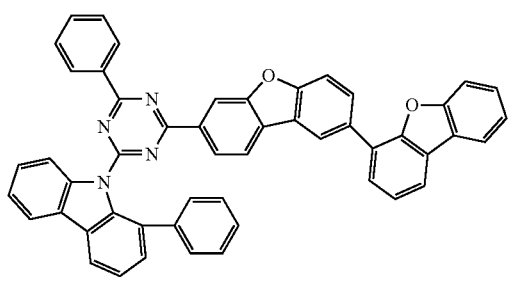
110
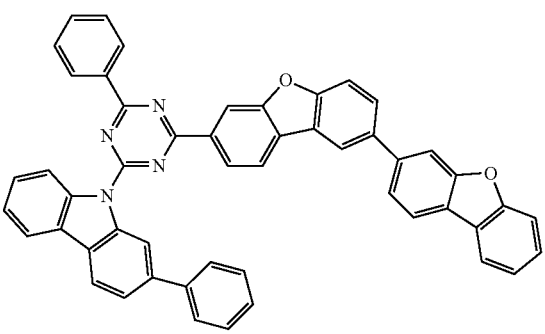
111
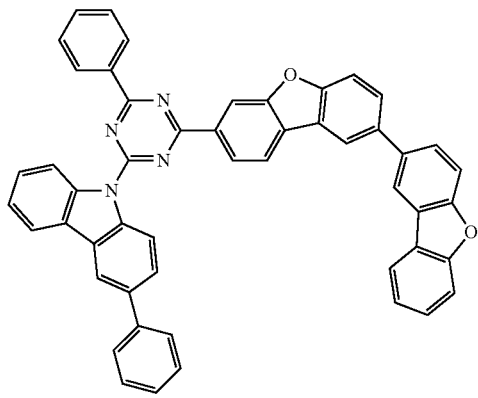
112
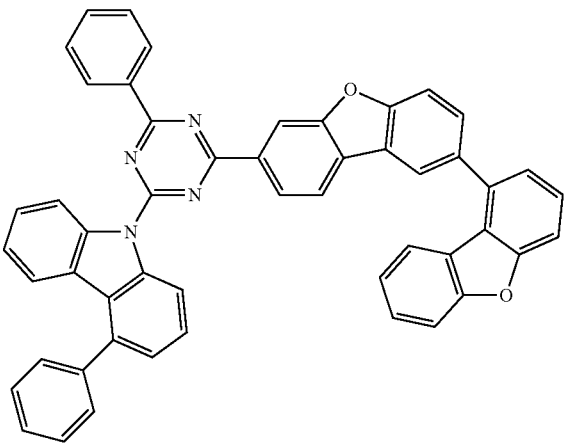
113
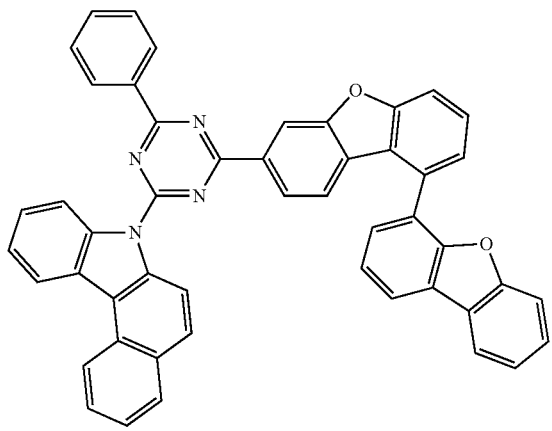
114
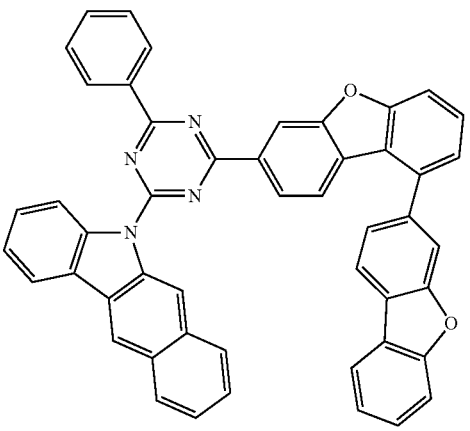

115
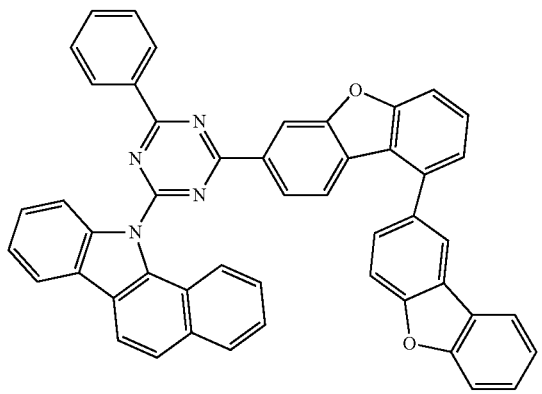
116
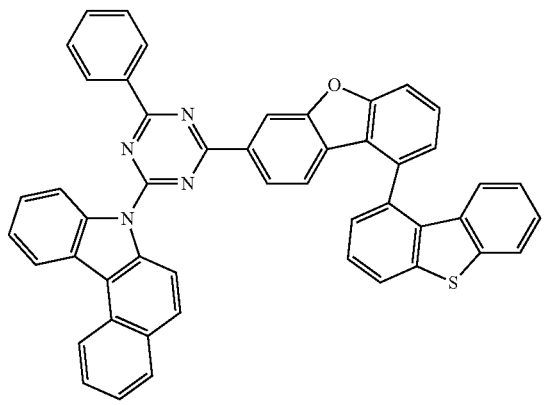
117
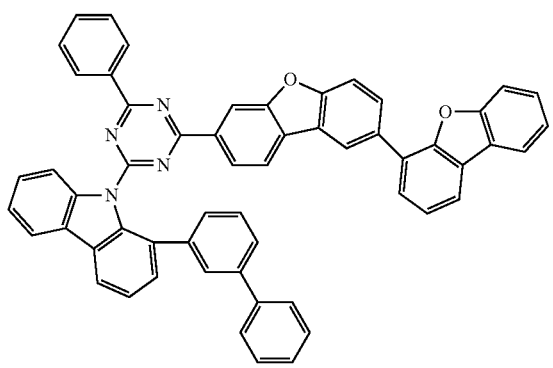
118
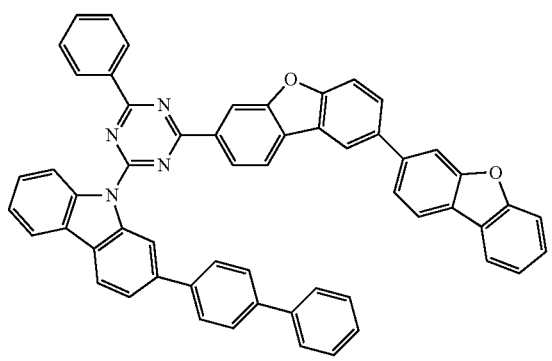
119
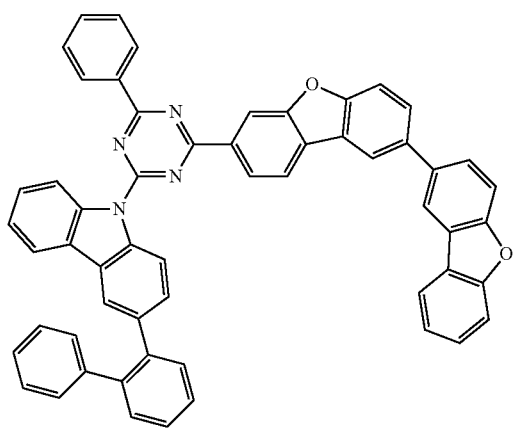
120
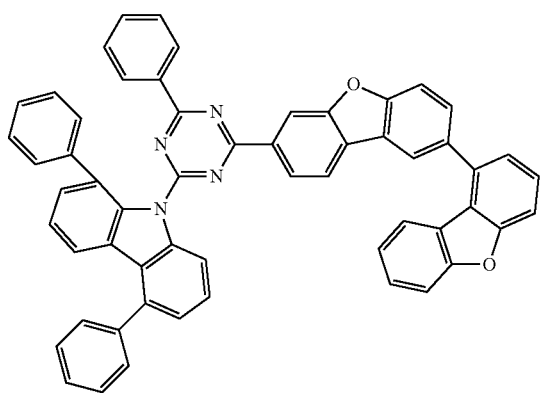

-continued
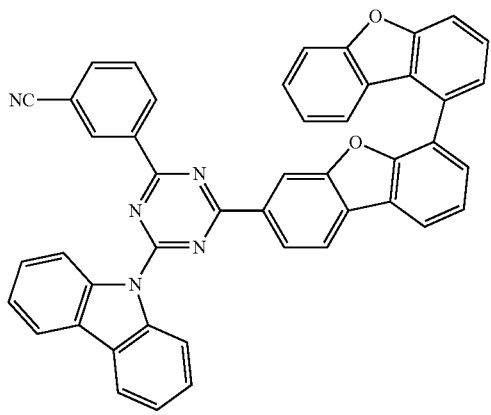
121
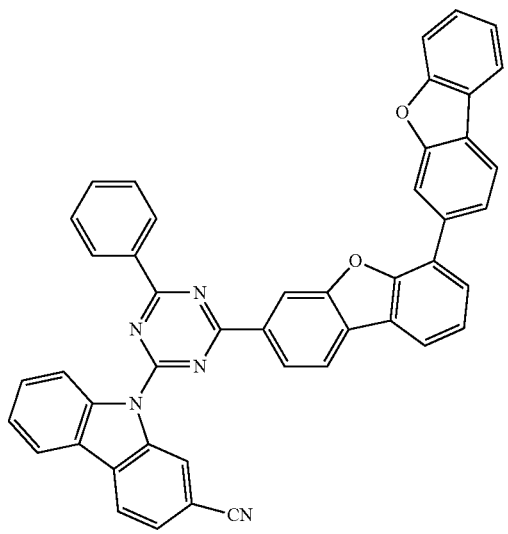
122
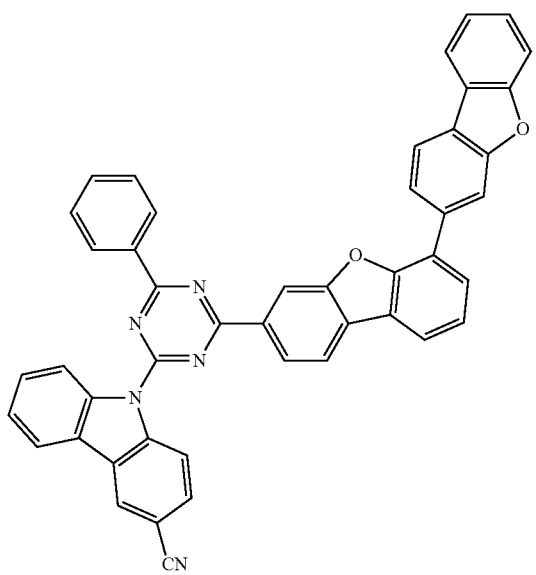
123
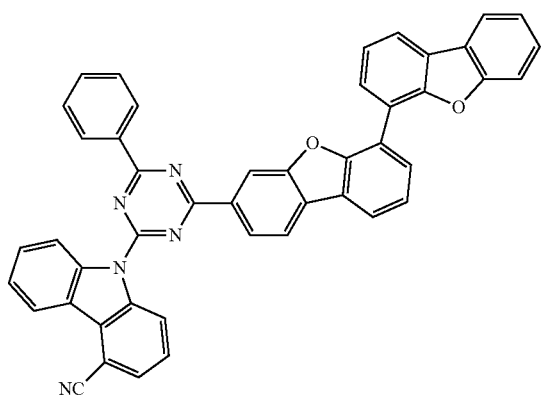
124
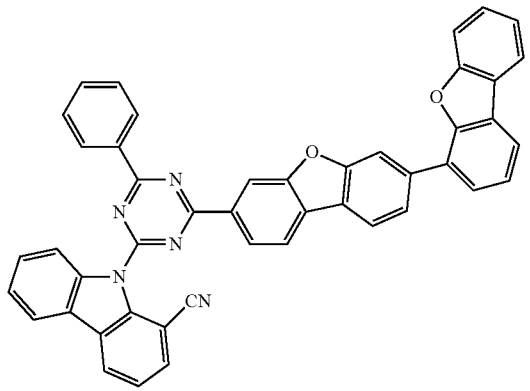
125
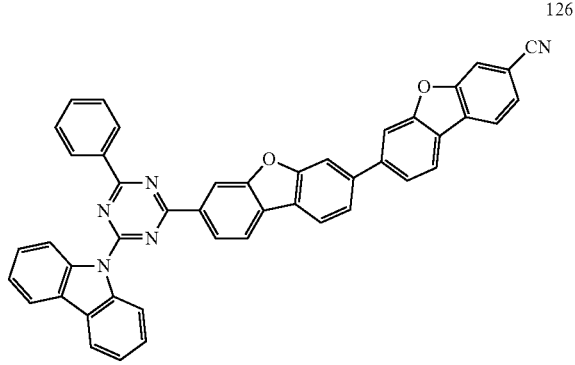
126

-continued
127
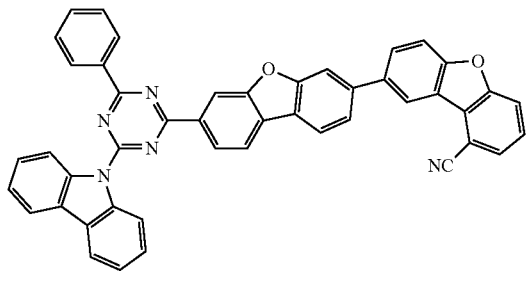
128
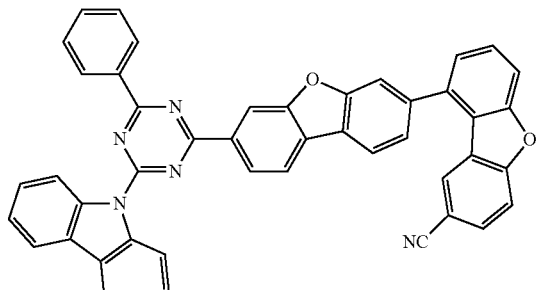
129
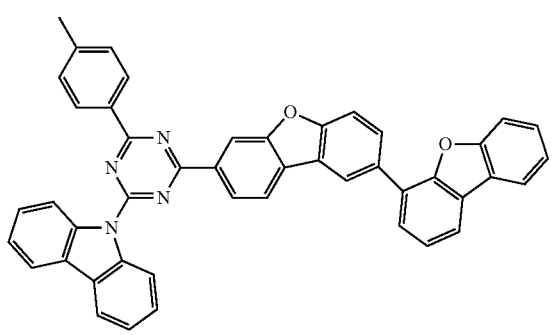
130
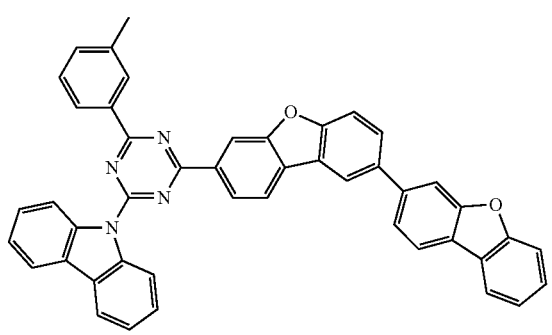
131
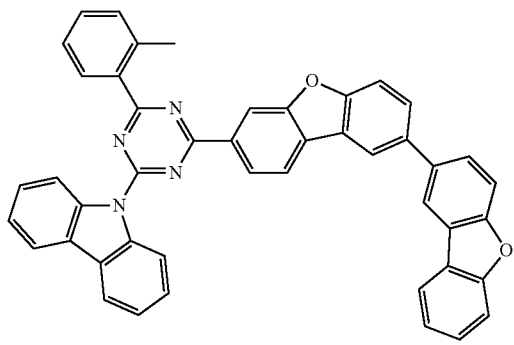
132
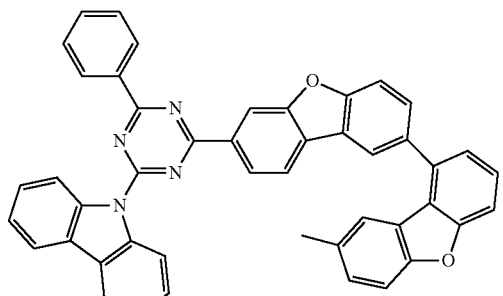
133
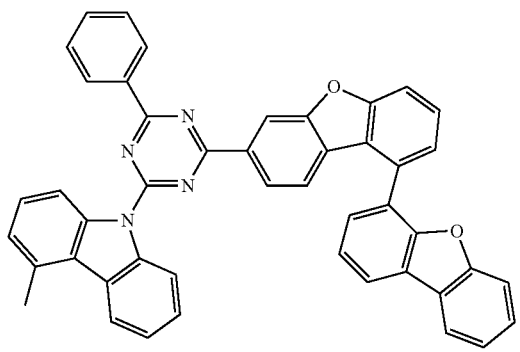
134
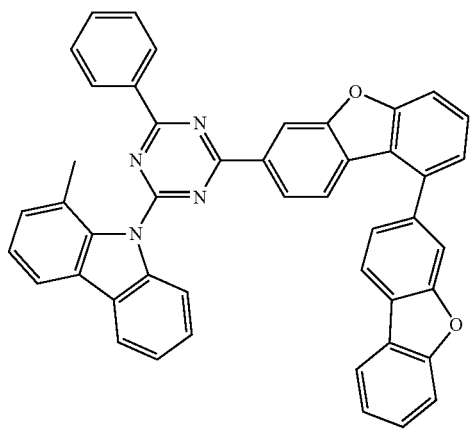

-continued
135
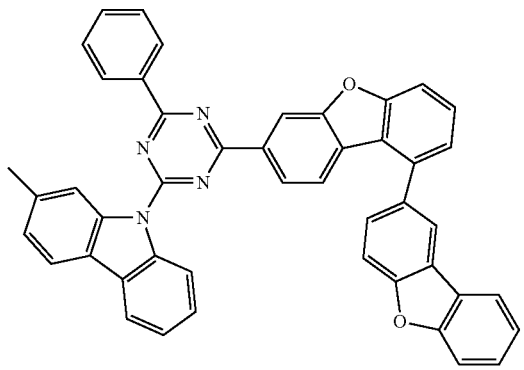
136
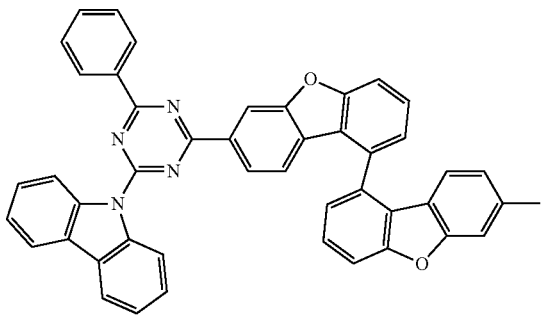
137
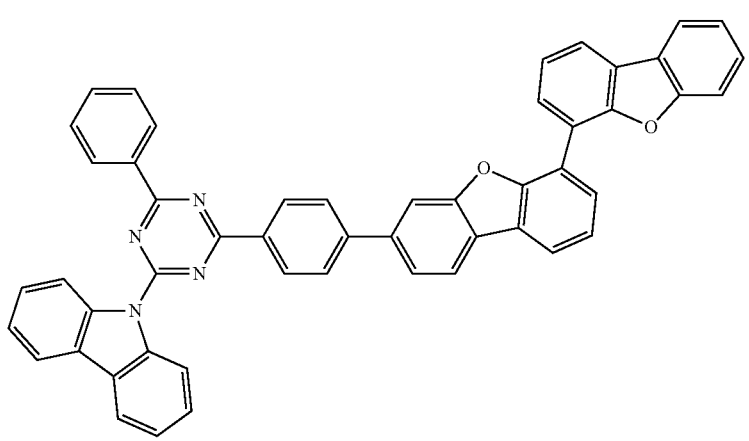
138
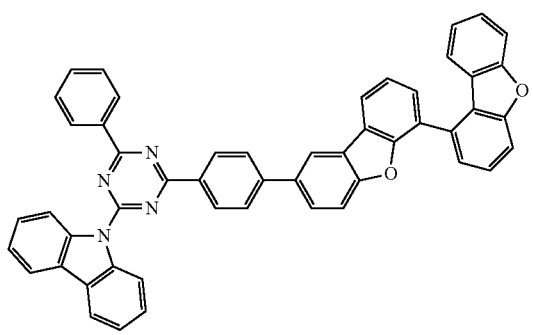
139
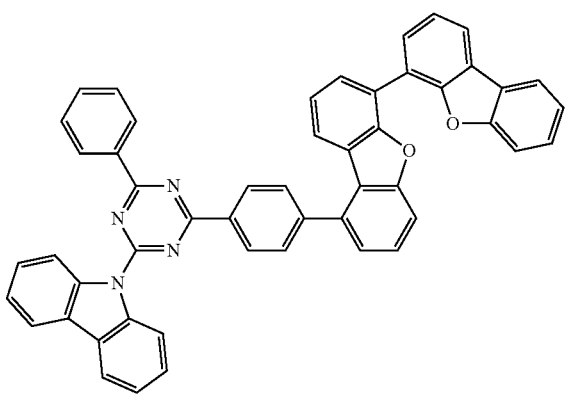

-continued
140
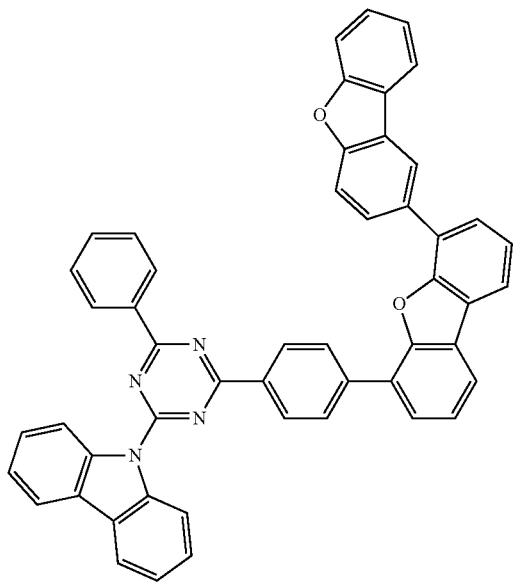
141
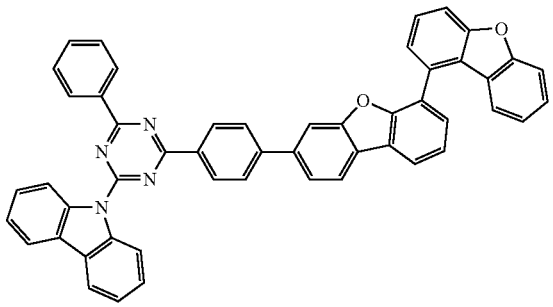
142
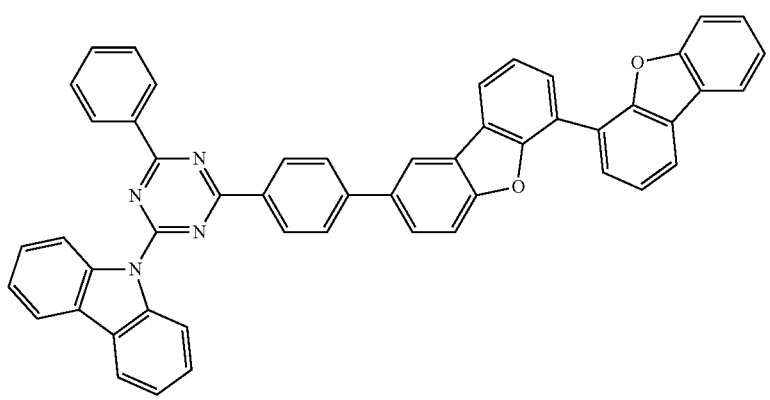
143
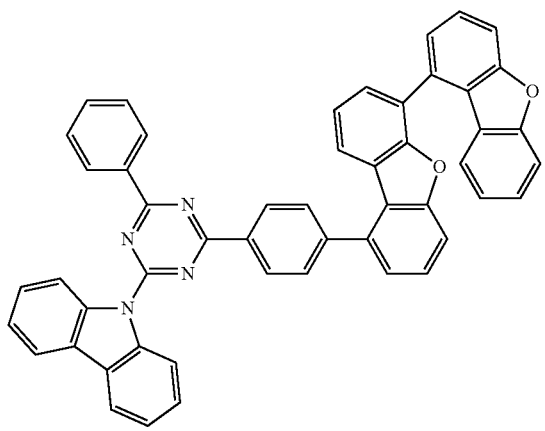
144
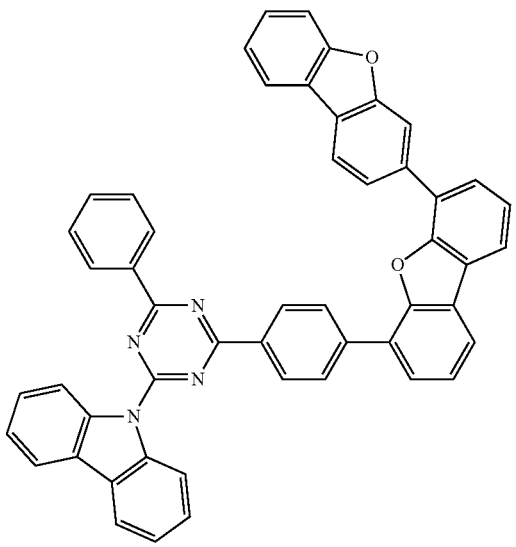

145
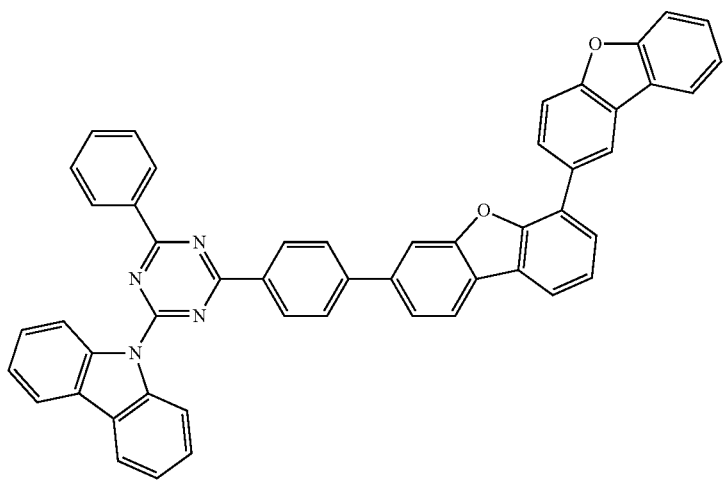
146
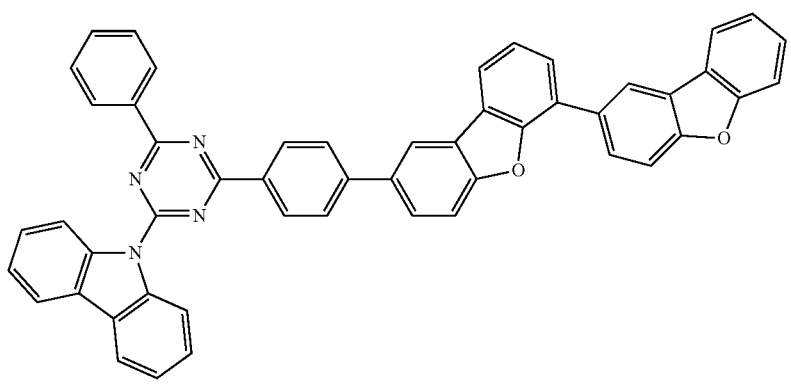
147
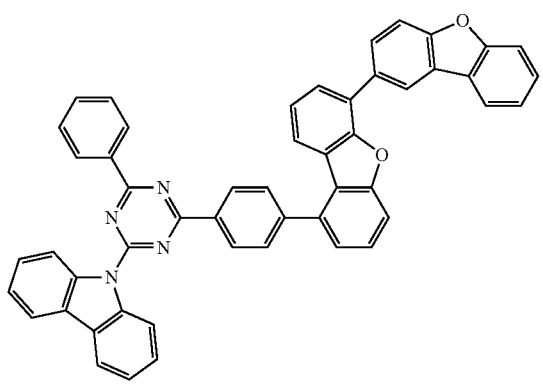
148
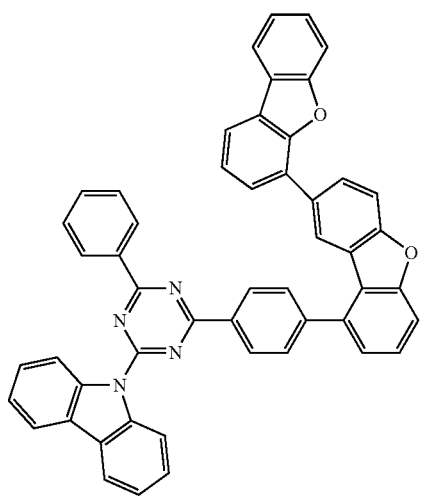

-continued
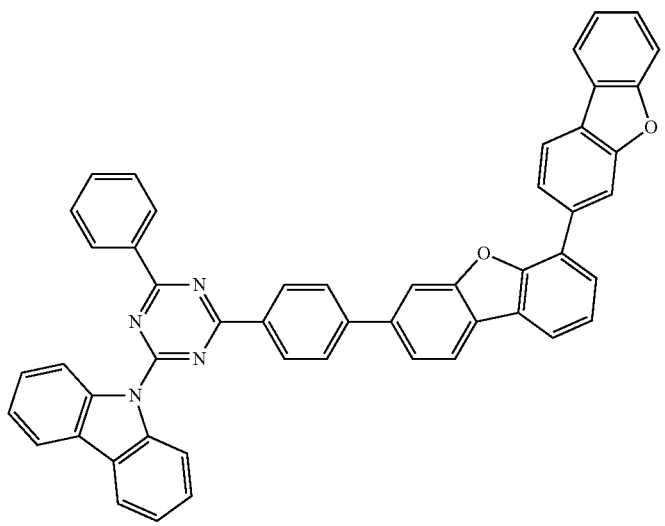
149
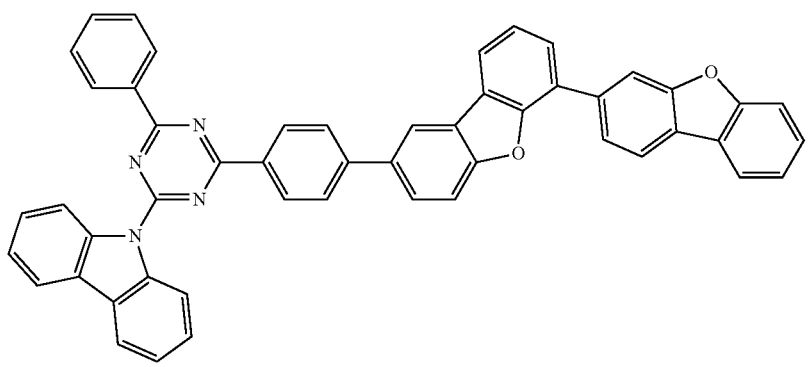
150
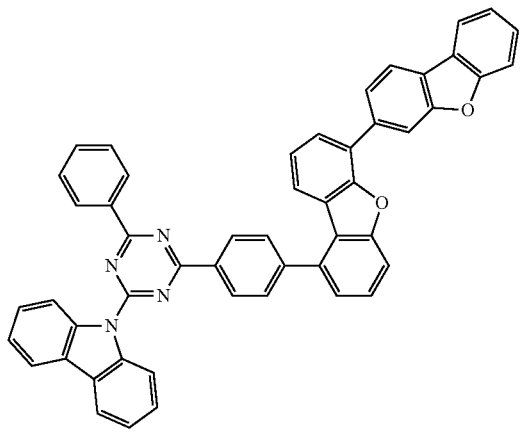
151
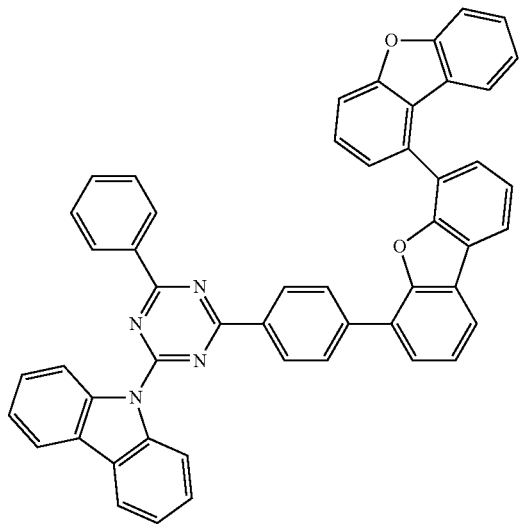
152

153
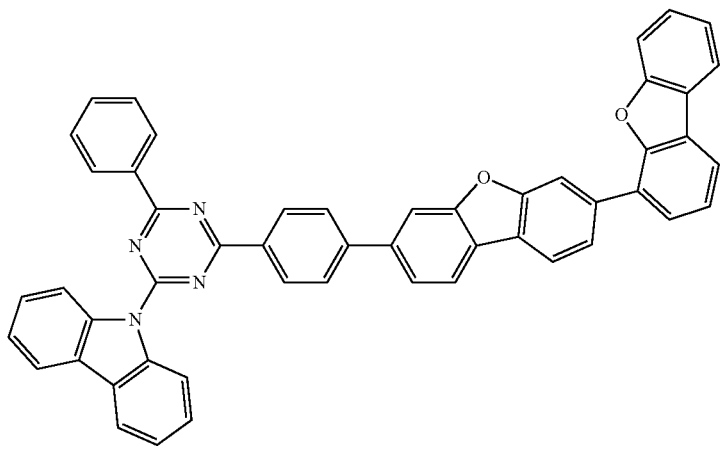
154
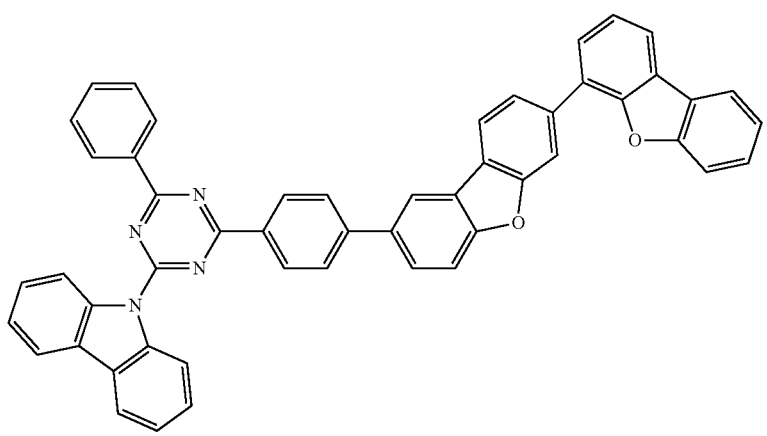
155
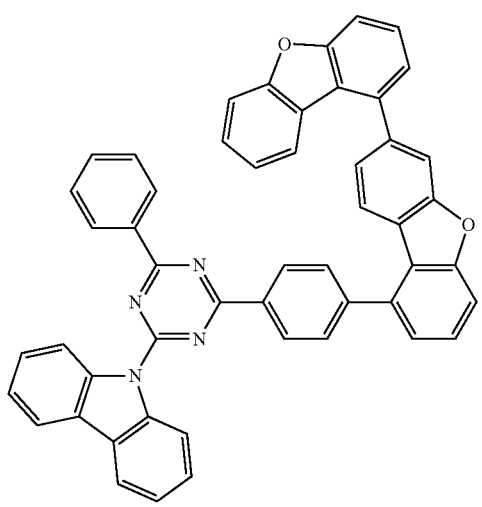
156
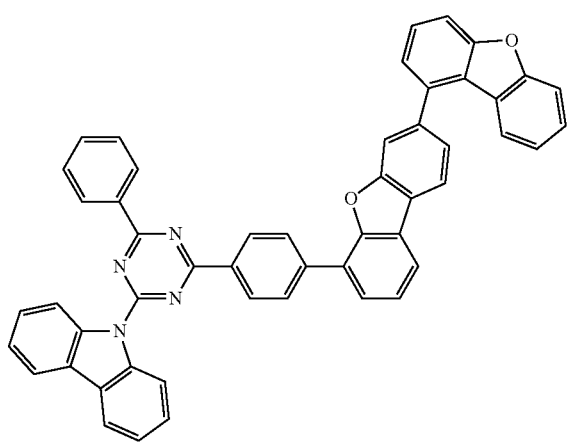

-continued
157
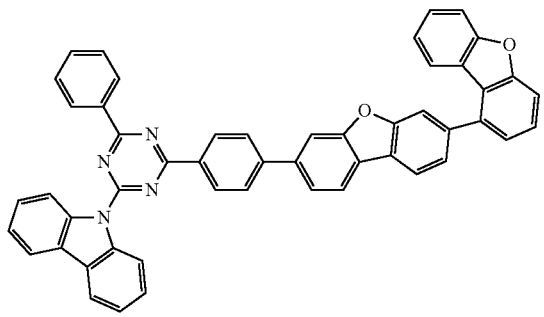
158
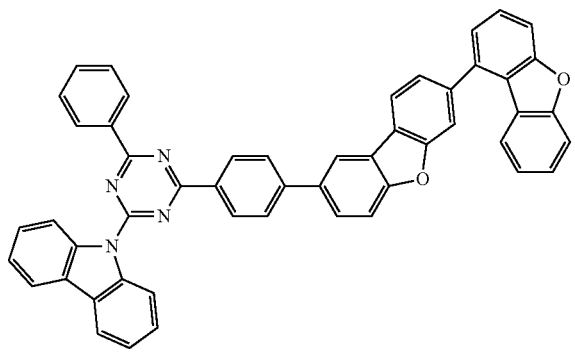
159
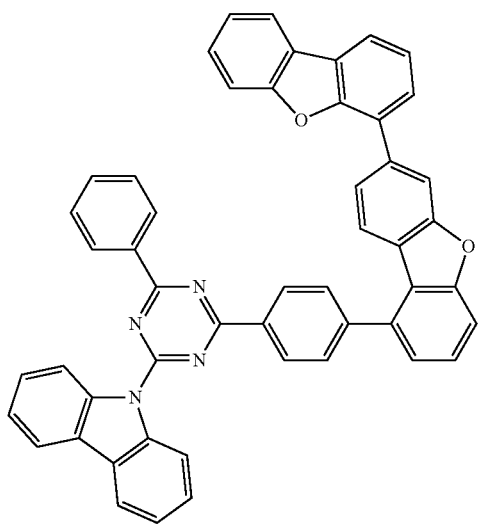
160
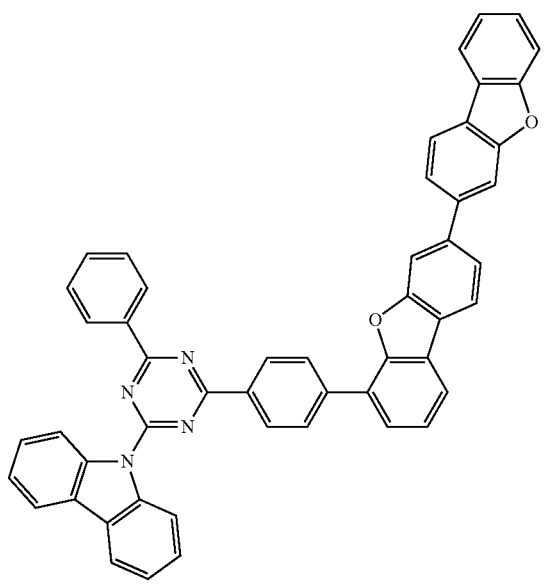
161
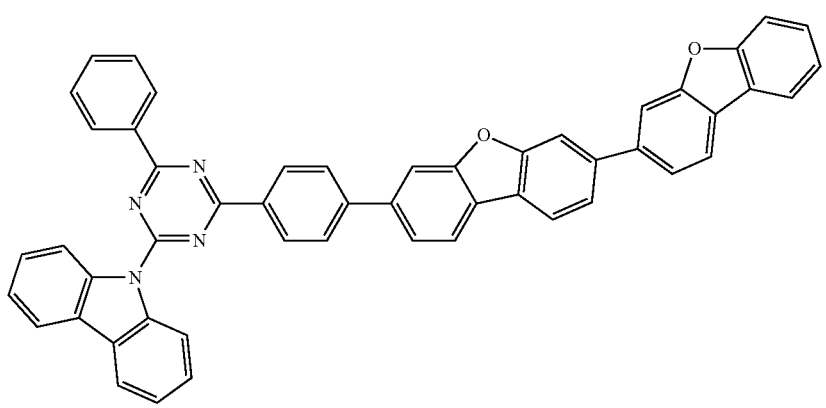

162
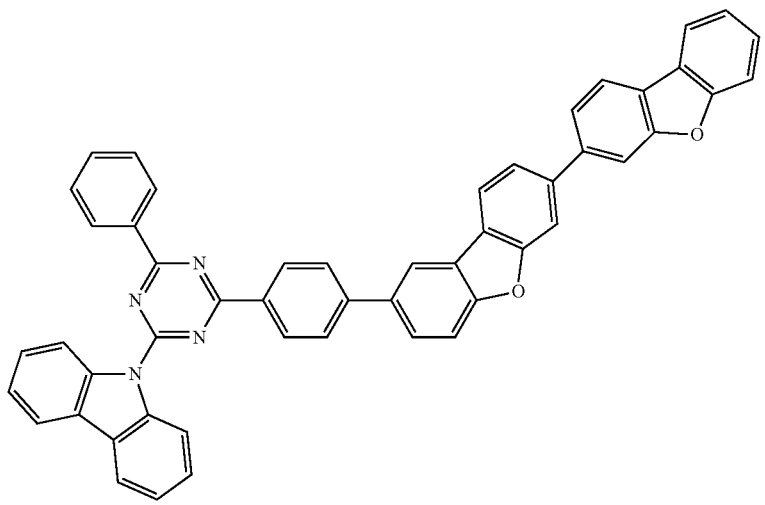
163
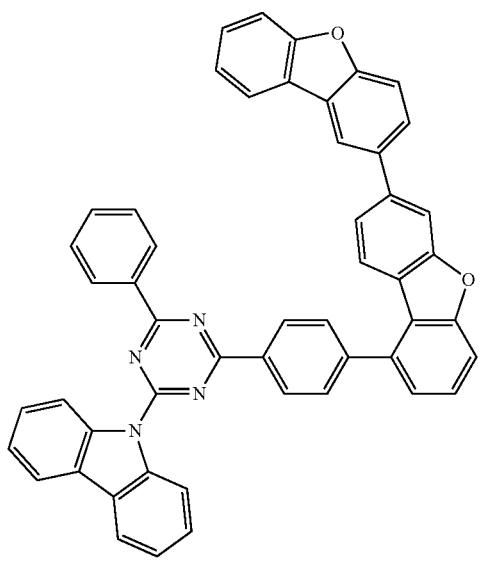
164
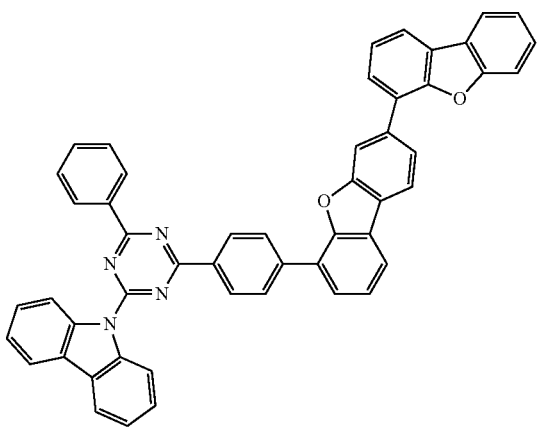
165
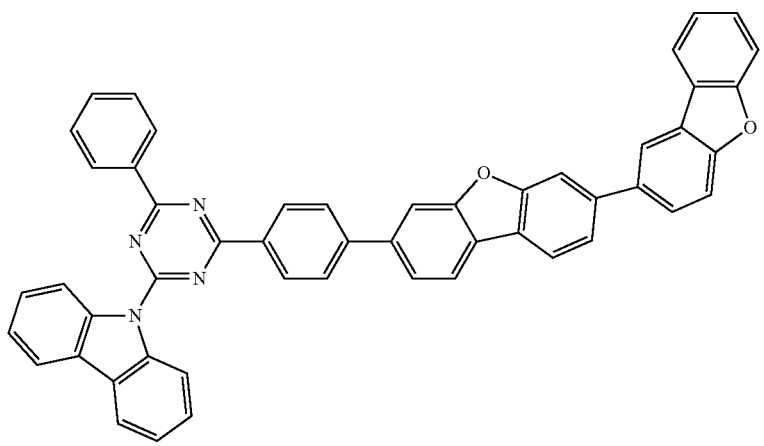

-continued
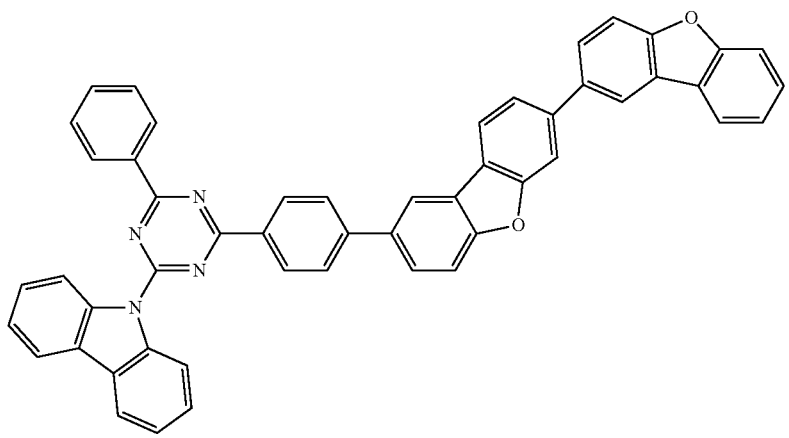
166
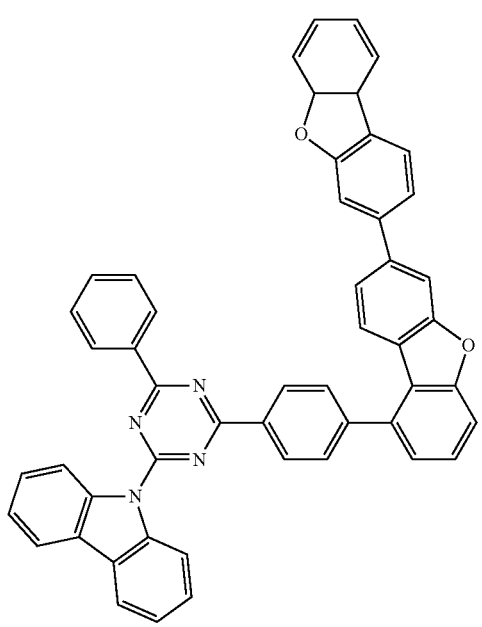
167
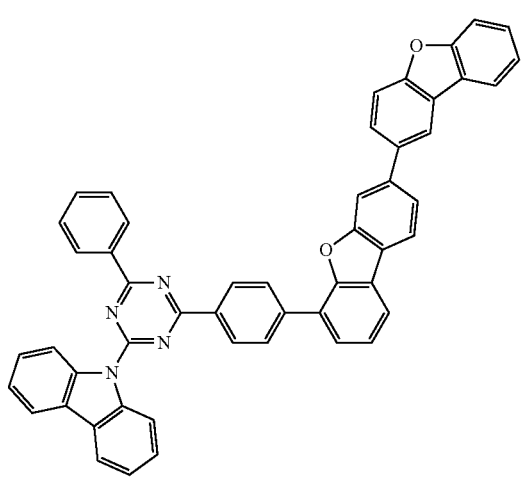
168
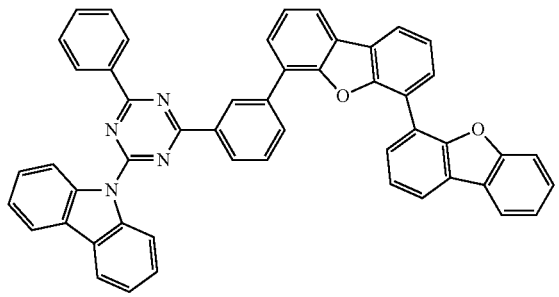
169
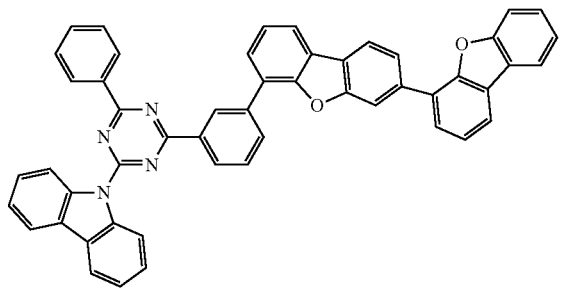
170

-continued
171 172
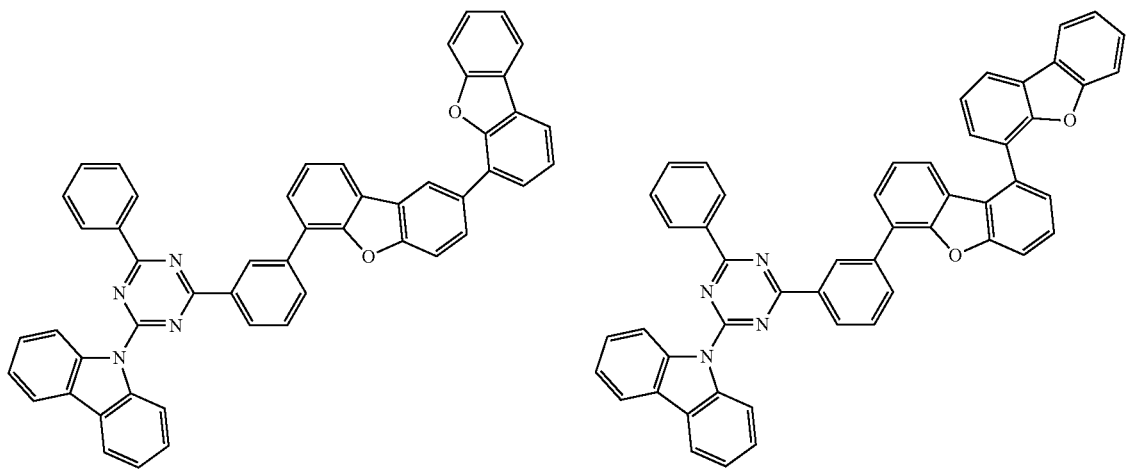
173 174
175 176
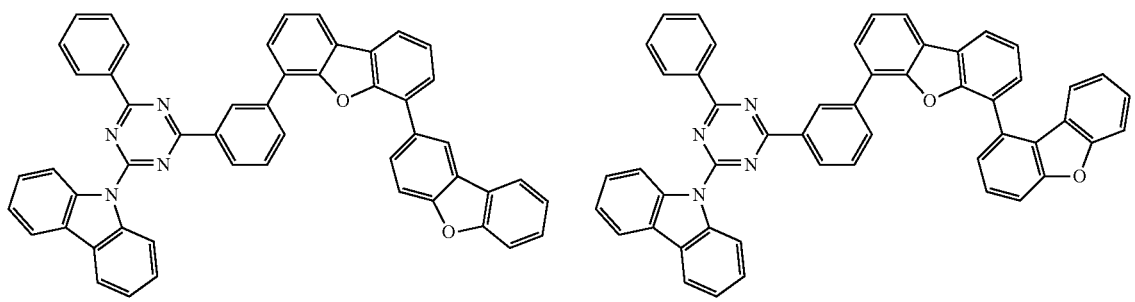
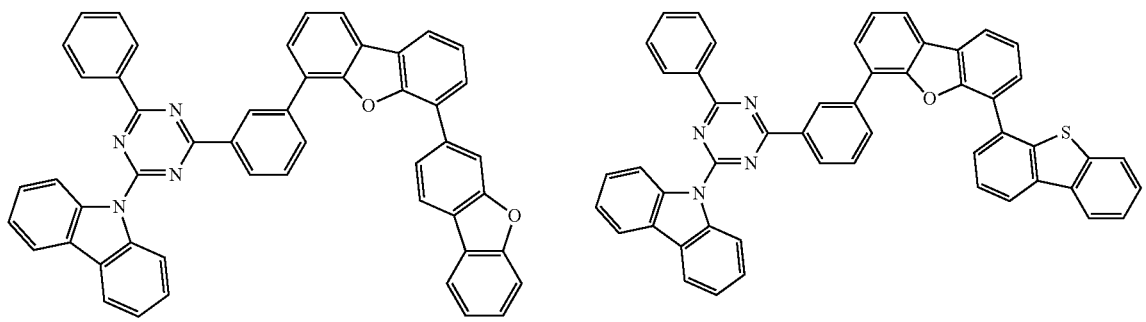
177 178
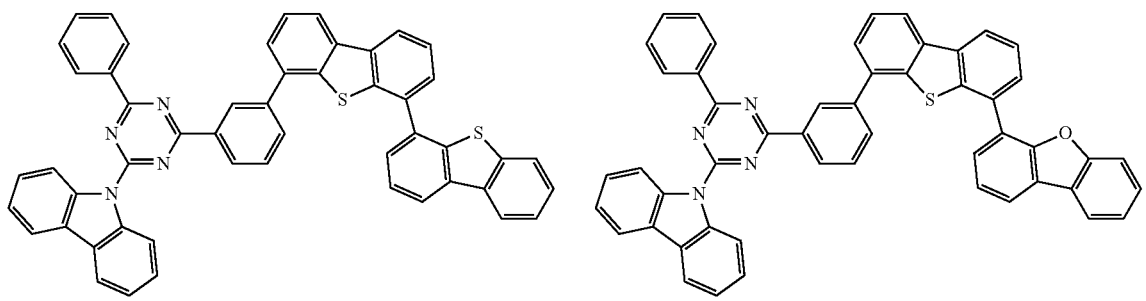

-continued
179
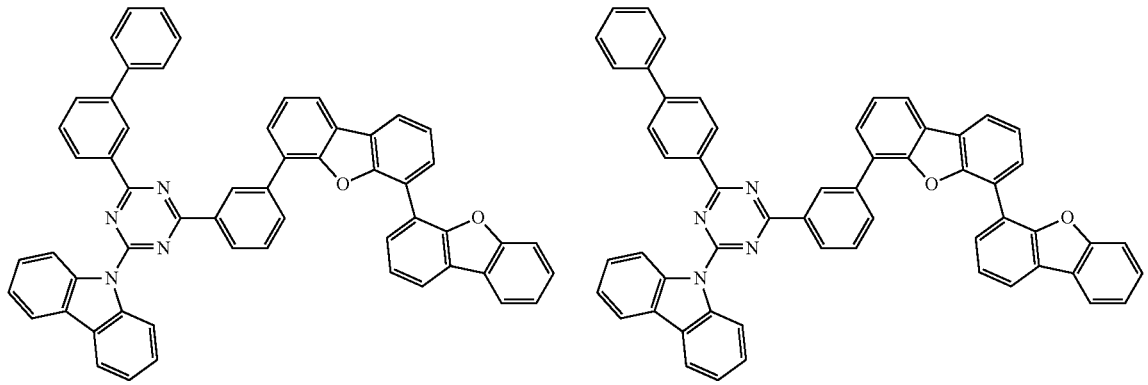
180
181
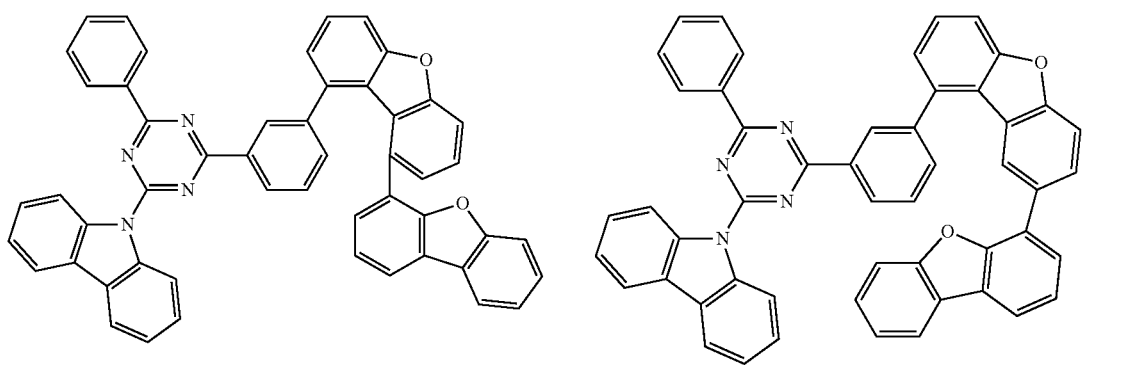
182
183
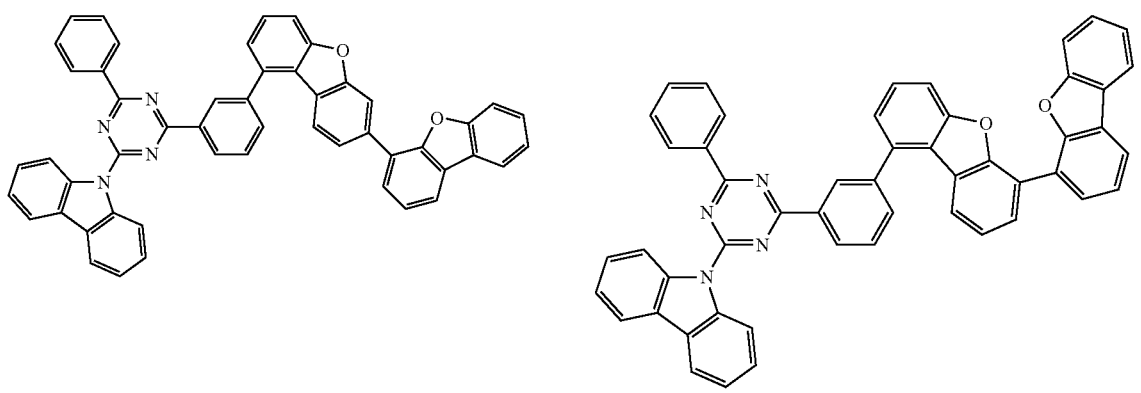
184
185
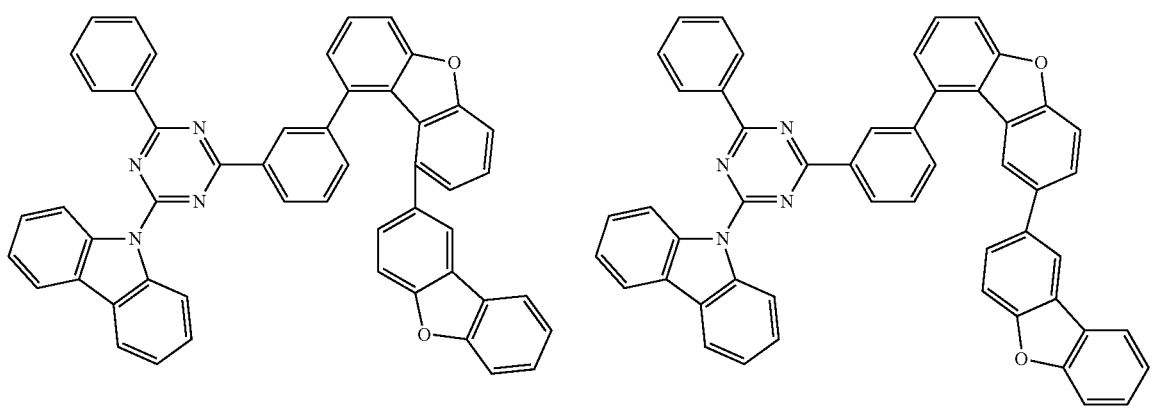
186

-continued
187
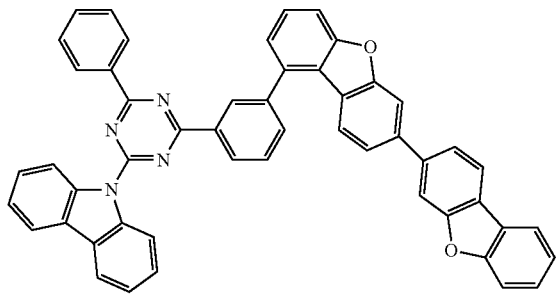
188
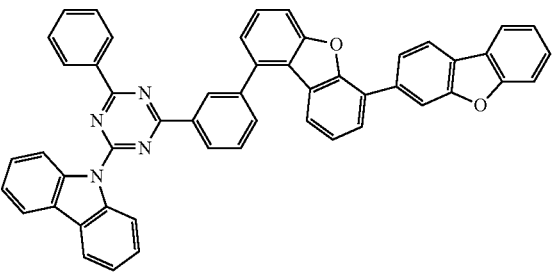
189
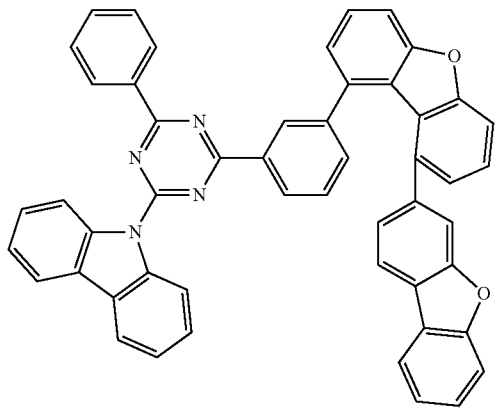
190
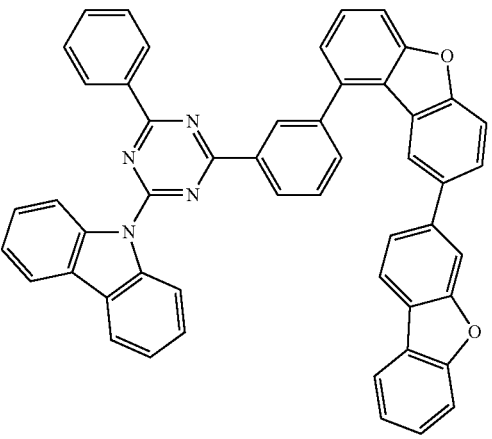
191
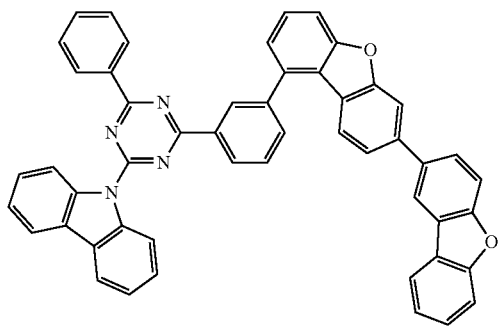
192
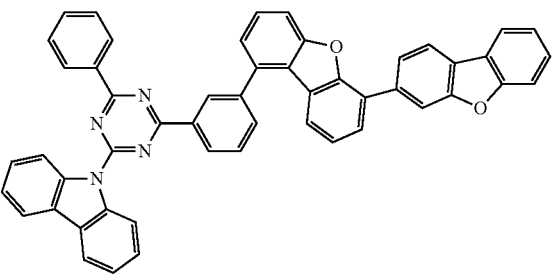
193
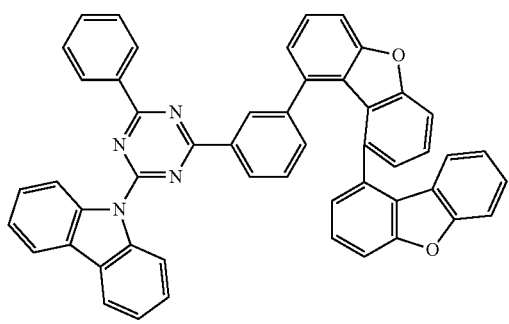
194
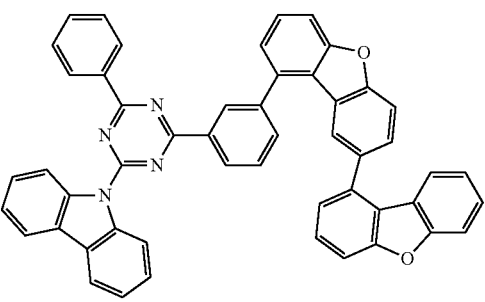

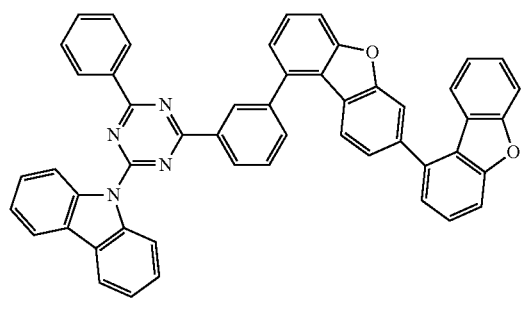
195
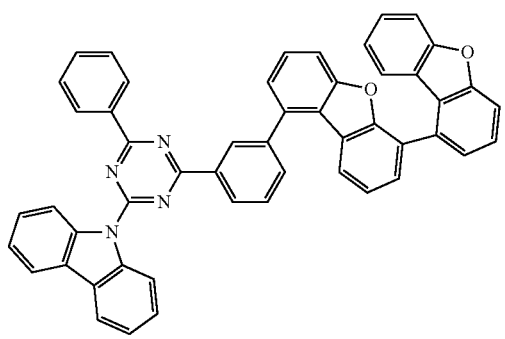
196
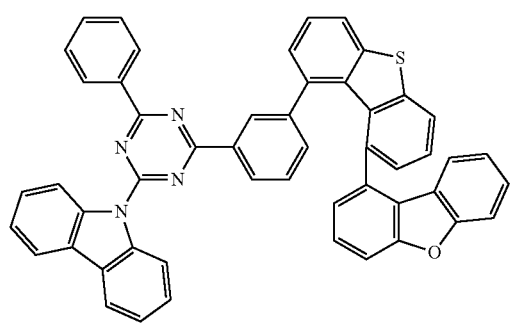
197
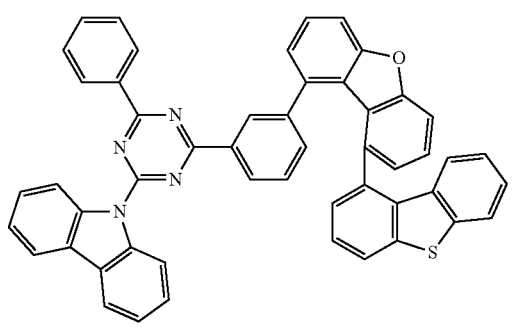
198
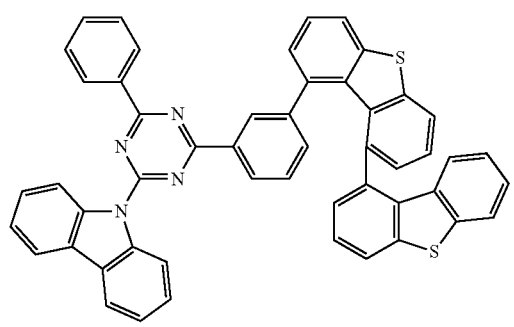
199
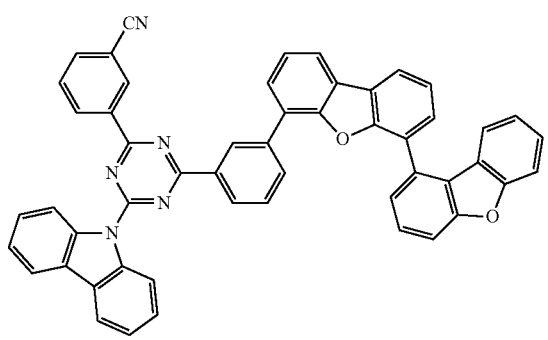
200
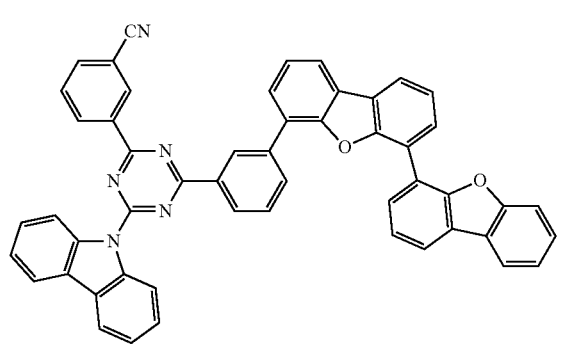
201
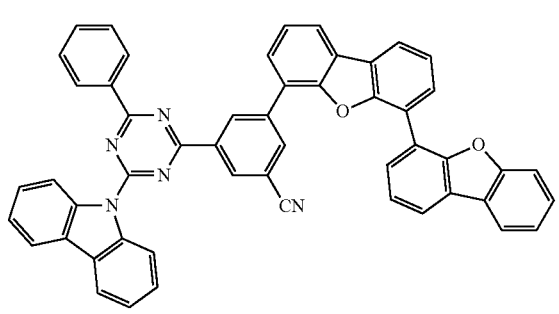
202

-continued

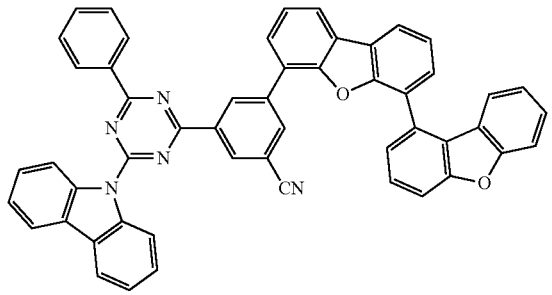
203

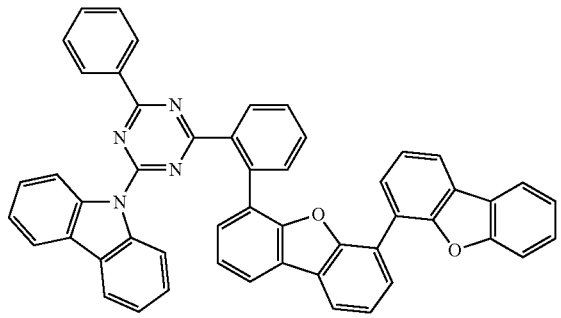
204

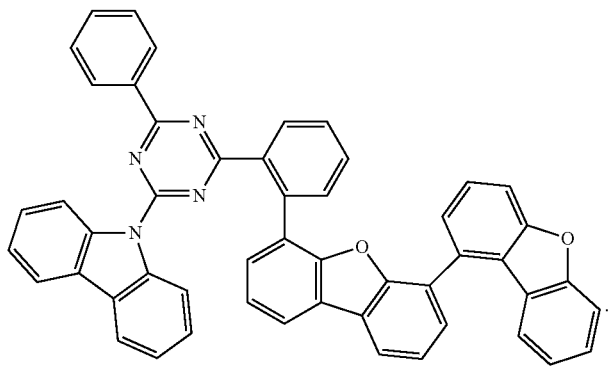
205

10. A composition for an organic optoelectronic device, the composition comprising a first compound and a second compound,
wherein:
the first compound is the compound as claimed in claim 1,
the second compound is represented by Chemical Formula 2; or a combination of Chemical Formula 3 and Chemical Formula 4:

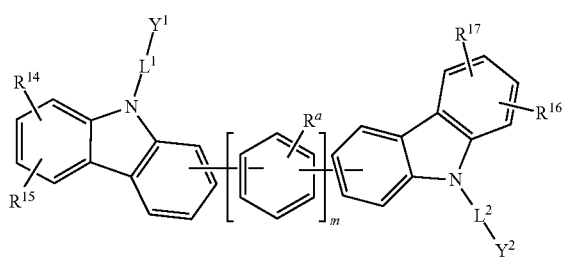
[Chemical Formula 2]

wherein, in Chemical Formula 2,
$Y^1$ and $Y^2$ are independently a substituted or unsubstituted C6 to C20 aryl group or a substituted or unsubstituted C2 to C30 heterocyclic group,
$L^1$ and $L^2$ are independently a single bond or a substituted or unsubstituted C6 to C20 arylene group,
$R^a$ and $R^{14}$ to $R^{17}$ are independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, and
m is an integer of 0 to 2;

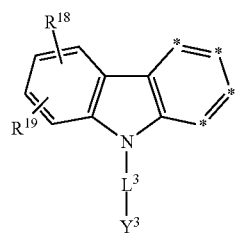
[Chemical Formula 3]

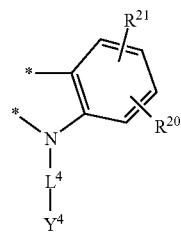
[Chemical Formula 4]

wherein, in Chemical Formulae 3 and 4,
$Y^3$ and $Y^4$ are independently a substituted or unsubstituted C6 to C20 aryl group, or a substituted or unsubstituted C2 to C30 heterocyclic group,
two adjacent *s of Chemical Formula 3 are linked at *s of Chemical Formula 4,
the other *s of Chemical Formula 3 not linked to Chemical Formula 4 are independently C-$L^a$-$R^b$,
$L^a$, $L^3$, and $L^4$ are independently a single bond or a substituted or unsubstituted C6 to C20 arylene group, and
$R^b$ and $R^{18}$ to $R^{21}$ are independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

11. The composition as claimed in claim 10, wherein:

the second compound is represented by Chemical Formula 2, and the second compound represented by Chemical Formula 2 is represented by Chemical Formula 2-8:

[Chemical Formula 2-8]

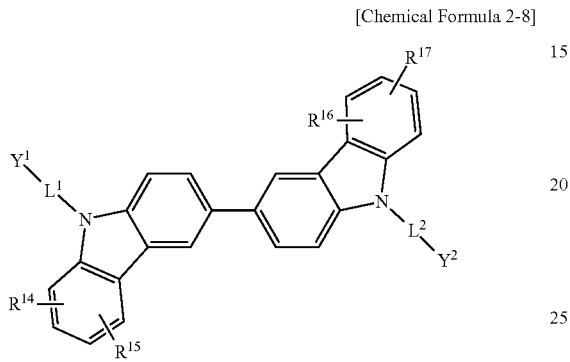

wherein, in Chemical Formula 2-8, $R^{14}$ to $R^{17}$ are independently hydrogen or a substituted or unsubstituted C6 to C12 aryl group, and moieties including *-L-Y and *-$L^2$-$Y^2$ are independently a moiety of Group II:

[Group II]

B-1

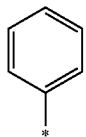

B-2

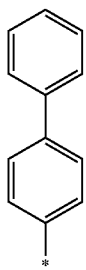

B-3

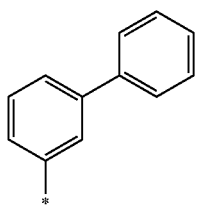

B-4

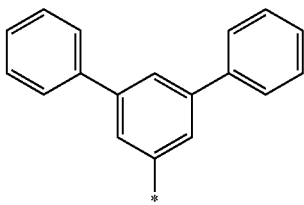

B-5

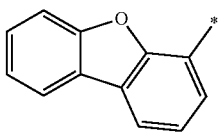

B-6

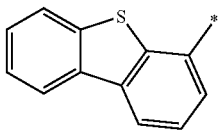

B-7

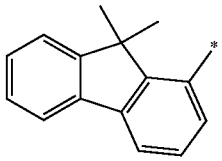

B-8

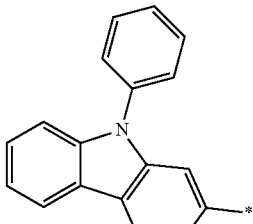

B-9

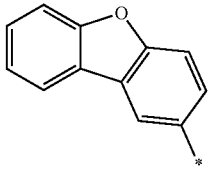

B-10

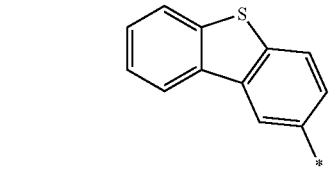

B-11

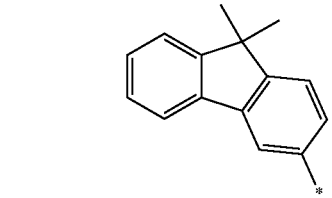

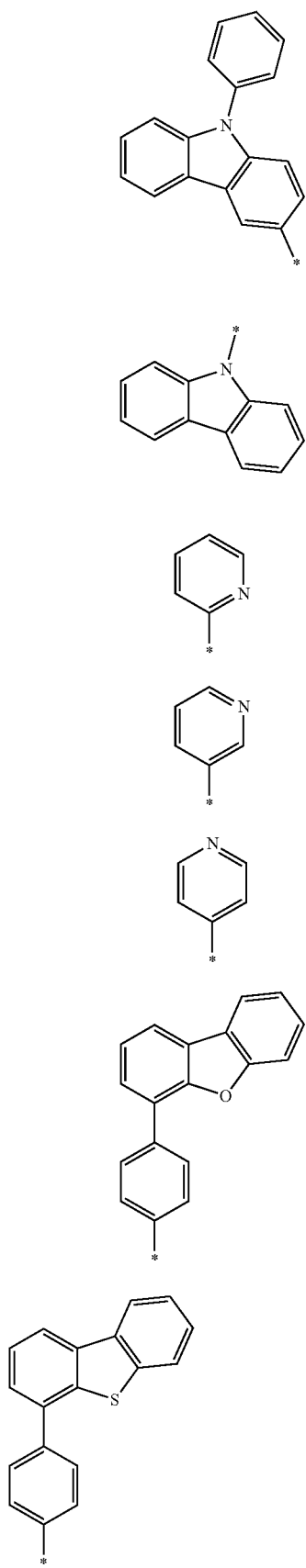
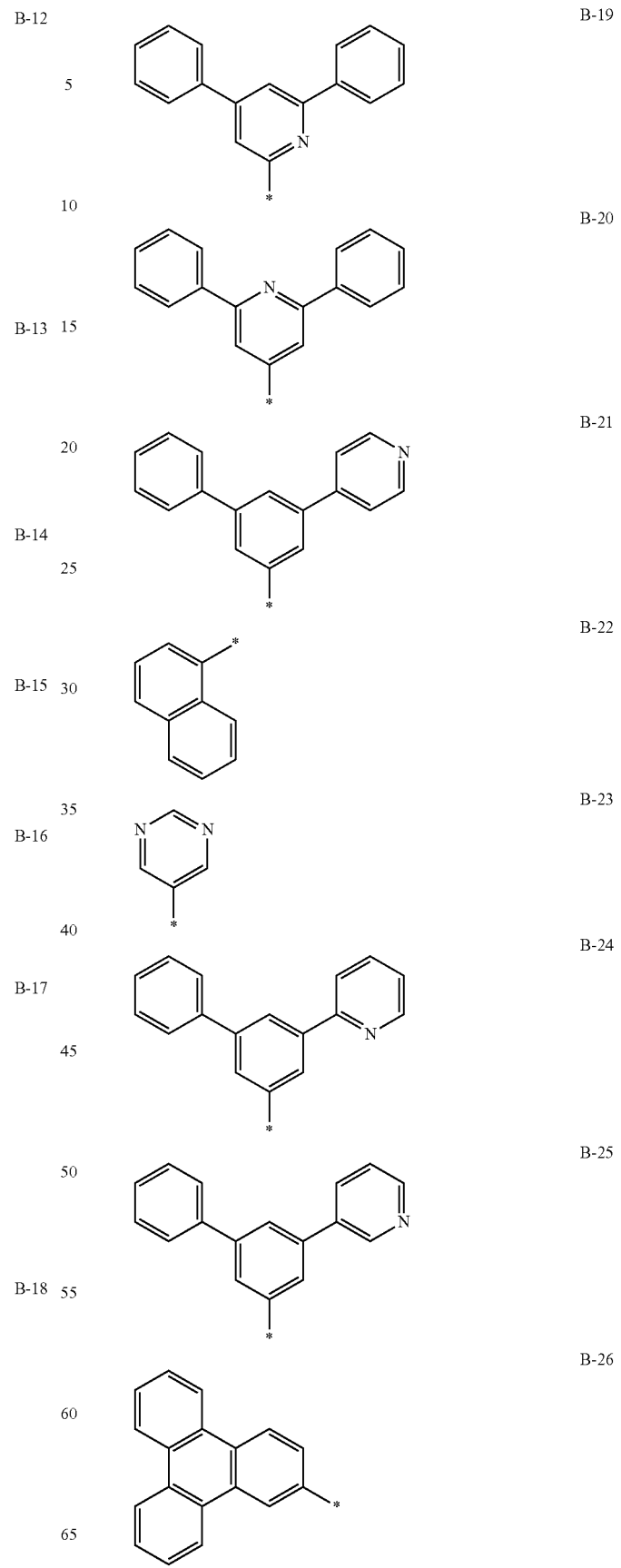

-continued

B-27

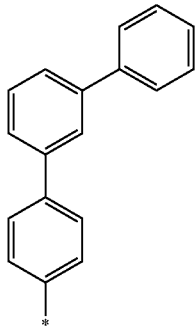

B-28

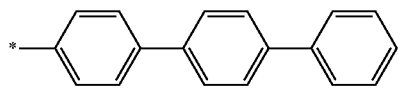

B-29

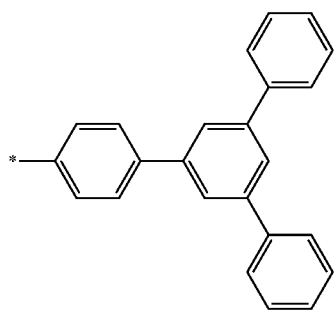

in which * is a linking point to N.

12. The composition as claimed in claim 11, wherein moieties including *-L¹-Y¹ and *-L²-Y² of Chemical Formula 2-8 are independently B-1, B-2, B-3, B-19, or B-26 of Group II.

13. The composition as claimed in claim 10, wherein:

the second compound is represented by a combination of Chemical Formula 3 and Chemical Formula 4, and the second compound represented by represented by a combination of Chemical Formula 3 and Chemical Formula 4 is represented by Chemical Formula 3A, Chemical Formula 3C, or Chemical Formula 3D:

[Chemical Formula 3A]

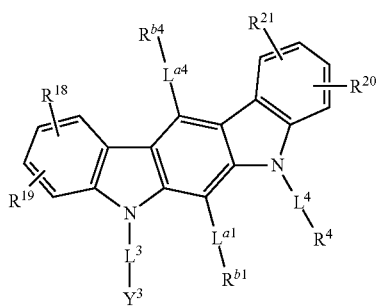

[Chemical Formula 3C]

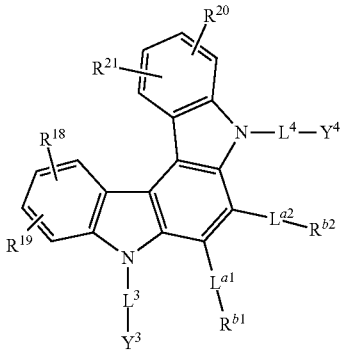

[Chemical Formula 3D]

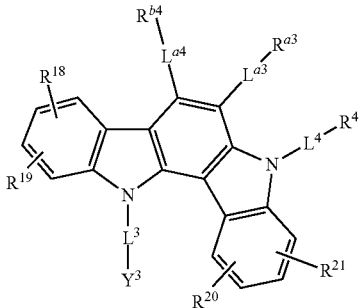

wherein, in Chemical Formula 3A, Chemical Formula 3C, and Chemical Formula 3D, $Y^3$ and $Y^4$ are independently a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, $L^3$, $L^4$, $L^{a1}$, to $L^{a4}$ are independently a single bond or a substituted or unsubstituted C6 to C20 arylene group, and $R^{b1}$ to $R^{b4}$ and $R^{18}$ to $R^{21}$ are independently hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

14. An organic optoelectronic device, comprising:
an anode and a cathode facing each other,
at least one organic layer between the anode and the cathode,
wherein the at least one organic layer includes the compound as claimed in claim 1.

15. The organic optoelectronic device as claimed in claim 14, wherein:
the at least one organic layer includes a light emitting layer, and
the light emitting layer includes the compound.

16. A display device comprising the organic optoelectronic device as claimed in claim 15.

17. An organic optoelectronic device, comprising:
an anode and a cathode facing each other,
at least one organic layer between the anode and the cathode, wherein the at least one organic layer includes the composition as claimed in claim 10.

18. The organic optoelectronic device as claimed in claim 17, wherein:
the at least one organic layer includes a light emitting layer, and
the light emitting layer includes the composition.

19. A display device comprising the organic optoelectronic device as claimed in claim 18.

* * * * *